(12) United States Patent
Kato et al.

(10) Patent No.: US 8,426,406 B2
(45) Date of Patent: Apr. 23, 2013

(54) GLUCOCORTICOID RECEPTOR AGONIST COMPRISING 2,2,4-TRIMETHYL-6-PHENYL-1,2-DIHYDROQUINOLINE DERIVATIVES HAVING SUBSTITUTED OXY GROUP

(75) Inventors: Masatomo Kato, Ikoma (JP); Miwa Takai, Ikoma (JP); Takahiro Matsuyama, Ikoma (JP); Tatsuji Kurose, Ikoma (JP); Yumi Hagiwara, Ikoma (JP); Mamoru Matsuda, Ikoma (JP); Toshiyuki Mori, Ikoma (JP); Kenji Imoto, Ikoma (JP); Atsuyoshi Dota, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 191 days.

(21) Appl. No.: 12/992,237

(22) PCT Filed: May 12, 2009

(86) PCT No.: PCT/JP2009/058801
§ 371 (c)(1),
(2), (4) Date: Jan. 31, 2011

(87) PCT Pub. No.: WO2009/139361
PCT Pub. Date: Nov. 19, 2009

(65) Prior Publication Data
US 2011/0118260 A1 May 19, 2011

(30) Foreign Application Priority Data
May 12, 2008 (JP) .................. 2008-124714

(51) Int. Cl.
*A61K 31/5377* (2006.01)
*A61K 31/47* (2006.01)
*A61K 31/4709* (2006.01)
*A61K 31/506* (2006.01)

(52) U.S. Cl.
USPC ......... 514/235.2; 514/311; 514/314; 514/256

(58) Field of Classification Search ............... 514/235.2, 514/311, 314, 256
See application file for complete search history.

(56) References Cited

U.S. PATENT DOCUMENTS
5,688,808 A  11/1997  Jones et al.
5,688,810 A  11/1997  Jones et al.
(Continued)

FOREIGN PATENT DOCUMENTS
CN  101535267  6/2009
CN  101535266  9/2009
(Continued)

OTHER PUBLICATIONS

Office Action (Documentary Conclusion on Defining of the State of Art) dated Mar. 10, 2012, issued in the Georgia Patent Application No. AP 2009 012027, and an English Translation thereof. (15 pages).
Sougou Rinsyou, 54(7), 1951-2076, 2005, 3 pages.
International Search Report (PCT/ISA/210) dated Jun. 16, 2009.
Written Opinion (PCT/ISA/237) dated Jun. 16, 2009.
Supplementary European Search Report dated Nov. 28, 2011, issued in the corresponding European Patent Application No. 09746568.6-2123.
Chinese Office Action mailed on Nov. 30, 2012, in corresponding Chinese Patent Application 200980127298.X.

*Primary Examiner* — Jennifer M Kim
(74) *Attorney, Agent, or Firm* — Buchanan Ingersoll & Rooney PC

(57) ABSTRACT

The present invention is related to glucocorticoid receptor agonists comprised of a compound represented by formula (1) which is 2,2,4-trimethyl-6-phenyl-1,2-dihydroquinoline derivative or a salt thereof and novel pharmacological effects of the glucocorticoid receptor agonists. In the formula (1), $R^1$ represents formula (2a), (3a), (4a) or (5a); R2 represents —(CO)—R8, —(CO)O—R9, or the like; $R^2$—O— is substituted at the 4- or -5-position of benzene ring A; $R^3$ represents a lower alkyl group; $R^4$, $R^5$, $R^6$ or $R^7$ represents a halogen atom, a lower alkyl group which may have a substituent, or the like; m, n, p or q represents 0, 1 or the like; $R^8$, $R^9$ or the like represents a lower alkyl group which may have a substituent, a lower alkenyl group, or the like.

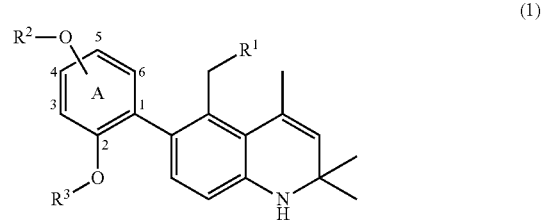

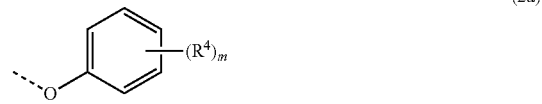

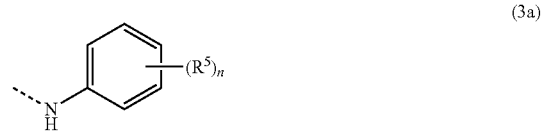

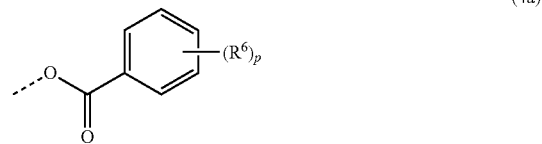

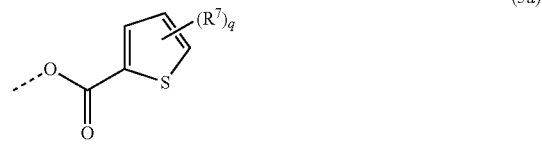

17 Claims, No Drawings

U.S. PATENT DOCUMENTS

| | | | |
|---|---|---|---|
| 5,693,646 A | 12/1997 | Jones et al. | |
| 5,693,647 A | 12/1997 | Jones et al. | |
| 5,696,127 A | 12/1997 | Jones et al. | |
| 5,696,130 A | 12/1997 | Jones et al. | |
| 5,696,133 A | 12/1997 | Jones et al. | |
| 5,994,544 A | 11/1999 | Jones et al. | |
| 6,093,821 A | 7/2000 | Jones et al. | |
| 6,121,450 A | 9/2000 | Jones et al. | |
| 6,448,405 B1 | 9/2002 | Jones et al. | |
| 6,696,459 B1 | 2/2004 | Jones et al. | |
| 6,858,627 B2 | 2/2005 | Bekkali et al. | |
| 8,017,775 B2 * | 9/2011 | Matsuda et al. | 546/18 |
| 2004/0014741 A1 | 1/2004 | Liu et al. | |
| 2004/0116455 A1 | 6/2004 | Bekkali et al. | |
| 2004/0186132 A1 | 9/2004 | Jones et al. | |
| 2007/0072908 A1 | 3/2007 | Yamamoto et al. | |
| 2007/0254917 A1 | 11/2007 | Higuchi et al. | |
| 2008/0064720 A1 | 3/2008 | Lassoie et al. | |
| 2009/0298826 A1 | 12/2009 | Matsuda et al. | |
| 2009/0298827 A1 | 12/2009 | Matsuda et al. | |
| 2009/0326009 A1 | 12/2009 | Matsuda et al. | |
| 2010/0056504 A1 | 3/2010 | Matsuda et al. | |
| 2010/0105681 A1 | 4/2010 | Lassoie et al. | |

FOREIGN PATENT DOCUMENTS

| | | |
|---|---|---|
| CN | 101605762 | 12/2009 |
| EP | 1 944 290 A1 | 7/2008 |
| EP | 2 085 387 A1 | 8/2009 |
| EP | 2 085 388 A1 | 8/2009 |
| EP | 2 085 389 A1 | 8/2009 |
| JP | 10-510840 A | 10/1998 |
| JP | 2002-193955 A | 7/2002 |
| RU | 2004135304 A | 7/2005 |
| RU | 2315041 C2 | 1/2008 |
| RU | 2008114369 A | 10/2009 |
| RU | 2383539 C2 | 3/2010 |
| RU | 2009122375 A | 12/2010 |
| WO | WO 96/19458 A2 | 6/1996 |
| WO | WO 2004/018429 A2 | 3/2004 |
| WO | WO 2006/019716 A1 | 2/2006 |
| WO | WO 2007/032556 A1 | 3/2007 |
| WO | WO 2008/059865 A1 | 5/2008 |
| WO | WO 2008/059866 A1 | 5/2008 |
| WO | WO 2008/059867 A1 | 5/2008 |
| WO | WO 2008/111632 A1 | 9/2008 |

* cited by examiner

GLUCOCORTICOID RECEPTOR AGONIST COMPRISING 2,2,4-TRIMETHYL-6-PHENYL-1,2-DIHYDROQUINOLINE DERIVATIVES HAVING SUBSTITUTED OXY GROUP

TECHNICAL FIELD

The present invention relates to glucocorticoid receptor agonist comprising 2,2,4-trimethyl-6-phenyl-1,2-dihydroquinoline derivatives having substituted oxy group which are useful as pharmaceuticals. The glucocorticoid receptor agonists of this invention are useful as a preventive or a therapeutic agent for inflammatory diseases or immune diseases, especially as a preventive or a therapeutic agent for ocular inflammatory diseases or dermatitis.

BACKGROUND ART

A glucocorticoid receptor is a 94 kDa ligand-activated intracellular transcriptional factor that is a member of the nuclear receptor superfamily. This receptor is known to affect the regulation of the metabolism of carbohydrates, proteins, fats and the like, suppression of the immune or inflammatory responses, activation of the central nervous system, regulation of cardiovascular function, and basal and stress-related homeostasis and the like due to its transcriptional regulatory action (SOUGOU RINSYOU, 54(7), 1951-2076 (2005), JP-A-2002-193955).

Such drugs which bind to a glucocorticoid receptor have an action of glucocorticoid receptor agonist or glucocorticoid receptor antagonist. However these actions are entirely different and it is determined which action the drugs show by the slight difference of the chemical structures of them.

As typical glucocorticoid receptor agonists, glucocorticoid receptor agonists synthesized in the living body such as cortisol and corticosterone, synthetic glucocorticoid receptor agonists such as dexamethasone, prednisone and prednisolone are known (JP-A-2002-193955). These glucocorticoid receptor agonists are generally called steroids due to having a steroid structure and are applied to the treatment of various diseases.

However, there are some cases that these steroids produce the side effects such as steroid peptic ulcer, steroid purpura, steroid pancreatitis, steroid diabetes, steroid cataract, steroid-induced glaucoma by the use of them (IGAKU DAIJITEN, NANZANDO, The 17th edition, 1038-1040). Therefore to prevent these side effects, it is hoped to create the drug which does not have a steroid structure.

On the other hand, compounds having a 1,2-dihydroquinoline structure are disclosed as glucocorticoid receptor modulators in WO 2004/018429, JP-T-10-0510840, WO 2006/019716 and the like. The range of the compounds disclosed in WO 2004/018429, JP-T-10-0510840, WO 2006/019716 is very wide and they have various chemical structures, and as one of those, the compounds having a 1,2-dihydroquinoline structure are disclosed. However, among those, there is no concrete disclosure that the compound having what kinds of chemical structures have the glucocorticoid receptor agonist action, that is, whether 2,2,4-trimethyl-6-phenyl-1,2-dihydroquinoline derivatives having substituted oxy group have the glucocorticoid receptor agonist action.

DISCLOSURE OF THE INVENTION

Problems to be Solved

It is a very interesting subject to find a new pharmacological action of 2,2,4-trimethyl-6-phenyl-1,2-dihydroquinoline derivatives having substituted oxy group.

Means of Solving Problems

The present inventors conducted the studies of finding a new pharmacological action of 2,2,4-trimethyl-6-phenyl-1,2-dihydroquinoline derivatives having substituted oxy group, and as a result, succeeded in finding that 2,2,4-trimethyl-6-phenyl-1,2-dihydroquinoline derivatives having substituted oxy group showed the excellent agonist activity to glucocorticoid receptor and are useful as a preventive or a therapeutic agent for inflammatory diseases.

In addition, 2,2,4-trimethyl-6-phenyl-1,2-dihydroquinoline derivatives having substituted oxy group showed an excellent inhibitory effect (inhibitory effect of the vascular hyper-permeability, inhibitory effect of choroidal vascularization, improvement effect of cornea disorder, respectively) on ocular inflammatory diseases models (choroidal neovascularization (CNV) model in rats or corneal disorder model in rat) by eye drops administration.

Furthermore, these derivatives also showed an excellent inhibitory effect for the vascular hyper-permeability in an atopic dermatitis model on mice and it was found that these derivatives are useful especially to a preventive or a therapeutic agent for the ocular inflammatory diseases or dermatitis, then the invention was achieved.

2,2,4-Trimethyl-6-phenyl-1,2-dihydroquinoline derivatives having substituted oxy group in this invention mean the compounds represented by formula (1), and the salts thereof (hereinafter referred to as "the present compound"), and the glucocorticoid receptor agonist comprising the present compound and the medical composition comprising at least a glucocorticoid receptor agonist as an active ingredient are this invention, preferably a preventive or a therapeutic agent comprising at least a glucocorticoid receptor agonist as an active ingredient for inflammatory diseases, more preferably a preventive or a therapeutic agent comprising at least a glucocorticoid receptor agonist as an active ingredient for ocular inflammatory diseases or dermatitis.

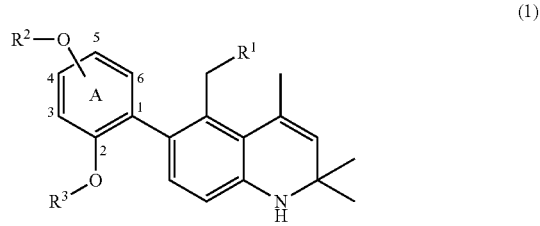

[$R^1$ represents formula (2a), (3a), (4a) or (5a);

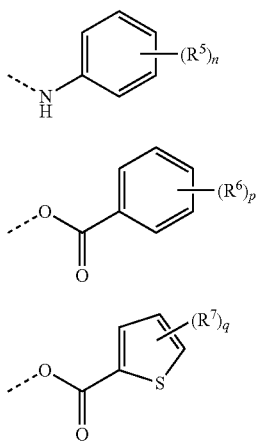

R² represents —(O)—R⁸, —(O)O—R⁹, —(SO)—R¹⁰, —(SO₂)—R¹¹ or —(CO)NR¹²R¹³;

R²—O— is substituted at the 4- or 5-position of benzene ring A;

R³ represents a lower alkyl group;

R⁴, R⁵, R⁶ or R⁷ represents a halogen atom, a lower alkyl group which may have a substituent, a lower alkenyl group, a lower alkynyl group, a lower alkoxy group, a nitro group or a formyl group;

m, n, p or q represents 0, 1 or 2;

in the case where m, n, p or q represents 2, each R⁴, R⁵, R⁶ or R⁷ may be the same or different;

R⁸, R⁹, R¹⁰ or R¹¹ represents a lower alkyl group which may have a substituent, a lower alkenyl group, a lower cycloalkyl group, an aryl group which may have a substituent or a heterocyclic group which may have a substituent;

R¹² and R¹³ may be the same or different and represent a hydrogen atom, a lower alkyl group which may have a substituent, an aryl group which may have a substituent or heterocyclic group. Hereinafter the same shall apply.]

Hereinafter, definitions of terms and phrases (atoms, groups and the like) used in this specification will be described in detail. In addition, a desirable range and the particularly desirable range of each definition is applied when the definition of terms and phrases is applied by the definition of another terms and phrases.

The "halogen atom" refers to a fluorine, chlorine, bromine or iodine atom.

The "lower alkyl group" refers to a straight chain or branched alkyl group having 1 to 8 carbon atoms, preferably 1 to 6. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower alkenyl group" refers to a straight chain or branched alkenyl group having 2 to 8 carbon atoms, preferably 2 to 6. Specific examples thereof include vinyl, propenyl, butenyl, pentenyl, hexenyl, heptenyl, octenyl, isopropenyl, 2-methyl-1-propenyl and 2-methyl-2-butenyl groups and the like.

The "lower alkynyl group" refers to a straight chain or branched alkynyl group having 2 to 8 carbon atoms, preferably 2 to 6. Specific examples thereof include ethynyl, propynyl, butynyl, pentynyl, hexynyl, heptynyl, octynyl, isobutynyl and isopentynyl groups and the like.

The "lower cycloalkyl group" refers to a cycloalkyl group having 3 to 10 carbon atoms, preferably 3 to 8. Specific examples thereof include cyclopropyl, cyclobutyl, cyclopentyl, cyclohexyl, cycloheptyl, cyclooctyl, cyclononanyl and cyclodecanyl groups.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl and phenanthryl groups and the like, especially preferably phenyl group.

The "heterocyclic ring" refers to a saturated or unsaturated monocyclic heterocyclic ring having one or a plurality of heteroatoms selected from a nitrogen atom, an oxygen atom and a sulfur atom in the ring (preferred, having one or two heteroatoms in the ring, and a saturated or unsaturated monocyclic 5 or 6 membered heterocyclic ring having 3 to 5 carbon atoms), or a bicyclic or tricyclic condensed polycyclic heterocyclic ring (preferred, having one or two heteroatoms in the ring, and a bicyclic or tricyclic condensed polycyclic heterocyclic ring having 7 to 13 carbon atoms).

Specific examples of the "saturated monocyclic heterocyclic ring" include pyrrolidine, pyrazolidine, imidazolidine, triazolidine, piperidine, hexahydropyridazine, hexahydropyrimidine, piperazine, homopiperidine and homopiperazine rings and the like having at least a nitrogen atom in the ring, tetrahydrofuran and tetrahydropyran rings and the like having at least an oxygen atom in the ring, tetrahydrothiophene and tetrahydrothiopyran rings and the like having at least a sulfur atom in the ring, oxazolidine, isoxazolidine and morpholine rings and the like having at least a nitrogen atom and an oxygen atom in the ring, and thiazolidine, isothiazolidine and thiomorpholine rings and the like having at least a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole, or perimidine rings and the like.

Specific examples of the "unsaturated monocyclic heterocyclic ring" include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having at least a nitrogen atom in the ring, dihydrofuran, furan, dihydropyran and pyran rings and the like having at least an oxygen atom in the ring, dihydrothiophene, thiophene, dihydrothiopyran and thiopyran rings and the like having at least a sulfur atom in the ring, dihydrooxazole, oxazole, dihydroisoxazole, isoxazole, dihydrooxazine and oxazine rings and the like having at least a nitrogen atom and an oxygen atom in the ring, dihydrothiazole, thiazole, dihydroisothiazole, isothiazole, dihydrothiazine and thiazine rings and the like having at least a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzothiazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, β-carboline, phenanthridine, acridine, phenanthroline, phenazine, phenothiazine or phenoxazine rings and the like.

Among the above "heterocyclic ring", piperidine, morpholine, imidazole, pyridine, furan, thiophen, oxazole or thiazole is preferable.

The "heterocyclic group" refers to a residue formed by removing a hydrogen atom from heterocyclic ring mentioned the above.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "lower alkylthio group" refers to a group formed by replacing the hydrogen atom of a mercapto group with a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio and isopentylthio groups and the like.

The "lower alkylcarbonyl group" refers to a group formed by replacing the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups and the like.

The "lower alkoxycarbonyl group" refers to a group formed by replacing the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentoxycarbonyl groups and the like.

The "lower alkylcarbonyloxy group" refers to a group formed by replacing the hydrogen atom of a hydroxy group with a lower alkylcarbonyl group. Specific examples thereof include methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, n-octylcarbonyloxy, isopropylcarbonyloxy, isobutylcarbonyloxy, sec-butylcarbonyloxy, tert-butylcarbonyloxy and isopentylcarbonyloxy groups and the like.

The "lower alkyl group which may have a substituent", refer to a "lower alkyl group" which may have one or a plurality of substituents selected from the following $\alpha^1$ group, preferred one or a plurality of substituents selected from the following $\alpha^2$ group.

[$\alpha^1$ group]

A halogen atom, a lower cycloalkyl group, an aryl group, a heterocyclic group, a lower alkoxy group and —NR$^a$R$^b$.

[$\alpha^2$ group]

A halogen atom, an aryl group, a heterocyclic group, a lower alkoxy group and —NR$^a$R$^b$.

The "aryl group which may have a substituent" and/or "heterocyclic group which may have a substituent" refer to a "aryl group" and/or "heterocyclic group" which may have one or a plurality of substituents selected from the following $\beta^1$ group, preferred one or a plurality of substituents selected from the following $\beta^2$ group.

[$\beta^1$ group]

A halogen atom, a lower alkyl group, a hydroxy group, a lower alkoxy group, a mercapto group, a lower alkylthio group, a formyl group, a lower alkylcarbonyl group, a carboxy group, a lower alkoxycarbonyl group, a lower alkylcarbonyloxy group, a nitro group and a cyano group.

[$\beta^2$ group]

A halogen atom, a lower alkyl group, a lower alkoxy group, a lower alkylthio group, a lower alkylcarbonyl group, a lower alkoxycarbonyl group, a lower alkylcarbonyloxy group, a nitro group and a cyano group.

$R^a$ and $R^b$ in the above "—NR$^a$R$^b$" may be the same or different and represent a substituent selected from the following $\gamma^1$ group, preferably the following $\gamma^2$ group.

[$\gamma^1$ group]

A hydrogen atom, a lower alkyl group and a lower alkoxycarbonyl group.

[$\gamma^2$ group]

A hydrogen atom and a lower alkyl group.

The term "a plurality of groups" as used in this invention means that each group may be the same or different and stands for 2 or more but not more than the number of groups which can be introduced into substitutable position(s), and the number is preferably 2 or 3, and 2 is particularly preferable.

Further, in this invention, a hydrogen atom and a halogen atom are also included in the concept of the "group".

The "glucocorticoid receptor agonist" as used in this invention refers to an agonist that exhibits a full agonistic action or a partial agonistic action by binding to the glucocorticoid receptor.

The "preventive or therapeutic agent" as used in this invention means the medicines for the prevention and/or the treatment of diseases.

As a medicinal usage of the "glucocorticoid receptor agonist" in this invention, there is especially no limitation as long as the disease is the one which the glucocorticoid receptor agonist is effective as a preventive or a therapeutic agent, and generally it is possible to apply to all of the disease that can be treated by the glucocorticosteroids For example, endocrine diseases such as chronic adrenocortical dysfunction (primary, secondary, pituitary, iatrogenic), acute adrenocortical dysfunction (adrenal crisis), adrenogenital syndrome, subacute thyroiditis, thyrotoxicosis syndrome [thyroid (poisoning) crisis], malignant exophthalmus due to thyroid disease, isolated ACTH deficiancy, idiopathic hypoglycemia; collagenosis such as lupus erythematosus (systemic and chronic discoid), systemic angitis (including aortitis syndrome, periarteritis nodosa, polyarteritis, Wegener's granulomatosis), multiple myositis (dermatomyositis), scleroderma; kidney diseases such as nephrosis, nephrotic syndrome; heart diseases such as congestive heart failure; Allergic diseases such as bronchial asthma, asthmatic bronchitis (including infantile asthmatic bronchitis), allergy and poisoning caused by medicine or other chemical substances (including drug rash, toxicoderma), serum sickness; blood diseases such as purpura (thrombocytopenic and non-thrombocytopenic), aplastic anemia, leukemia (including acute leukemiam, acute inversion of chronic myeloid leukemia, chronic lymphatic leukemia, leukemia cutis), hemolytic anemia, granulocytopenia; digestive apparatus diseases such as ulcerative colitis, regional enteritis, the improvement of physical status of serious illness hectic diseases (including the cancer end and sprue); liver diseases such as fulminant hepatitis, bile stagnation type acute hepatitis, chronic hepatitis, cirrhosis; pulmonary diseases such as sarcoidosis, diffuse interstitial pneumonia (including the pulmonary fibrosis, the radiation pneumonitis); serious infection; tuberculous diseases such as pulmonary tuberculosis, tuberculous meningitis, tuberculous pleurisy, tuberculous peritonitis, tuberculous pericarditis; neural diseases such as encephalomyelitis (including encephalitis, myelitis), peripheral neuritis (including Guillain-Barré syndrome), myotonia, myasthenia gravis, multiple sclerosis (including neuromyelitis optica), chorea minor, paralysis of facial nerve, arachonoid of spinal cord retinitis; malignant tumors such as malignant lymphoma (lymphosarcomatosis, reticulosarcomatosis, Hodgkin's disease, cutaneous reticulosis, mycosis fungoides) and similar disease (closely related diseases), acidophilic granuloma, relapse metastasis of breast cancer; digestive symptom (nausea, vomitus) by administering of an anti-malignant tumor agent (such as cisplatin); surgical diseases such as resection of adrenal gland, surgical invasion to the patient of adrenocortical hypofunction, lung edema after invading, transplant of organ or tissue, ophidiasis or insect venom (including serious sting), unidentified fervescence; obstetrics and gynecology diseases such as adhesion prevention after oviduct orthopedic surgery; urology diseases such as prostatic cancer, priapism; otorhinolaryngology diseases such as acute or chronic tympanitis, exudative tympanitis, tubal stenosis, Meniere's disease and Meniere's syndrome, acute sensorineural deafness, vasomotor rhinitis, allergic rhinitis, pollinosis (hay fever), progressives malignes Granulom, pharyngitis, laryngeal edema, follow-up treatment after otorhinolarygological surgical operation, dysosmia, acute or chronic (replicate) sialadenitis; oral surgery diseases such as inveterate stomatitis, glossitis; rheumatic diseases such as rheumatic fever (including rheumatic carditis), polymyalgia rheumatica, ankylosing spondylitis (rheumatoid spondylitis); the following infalammatory diseases, and the like are enumerated.

The "inflammatory disease" in this invention is not particularly limited as long as it is a disease with an inflammation. For example, diseases such as inflammatory bone-joint disorder, ocular inflammatory disease, asthma, bronchitis, rhinitis, dermatitis, inflammatory bowel disease and the like, preferably inflammatory bone-joint disorder, ocular inflammatory disease and dermatitis are enumerated.

At this time, the "inflammatory bone-joint disorder" is not particularly limited as long as it is a disease in the joint with an inflammation.

For example, rheumatoid arthritis, juvenile rheumatoid arthritis (including Still's disease), osteoarthritis, osteoporosis, spondylarthritis and the like are enumerated, preferably rheumatoid arthritis or osteoarthritis is enumerated.

The "ocular inflammatory disease" is not particularly limited as long as it is a disease in the eye with an inflammation. For example, as for inflammatory diseases of anterior segment of eyeball, keratitis, keratoconjunctivitis, conjunctivitis, blepharitis, dry eye syndrome (it is also called "dry eye"), allergic conjunctivitis, anterior uveitis, inflammation on anterior segment of eyeball after operation and inflammation by rejection of eye organization transplant and the like, preferably dry eye syndrome (it is also called "dry eye") and allergic conjunctivitis are enumerated. As for inflammatory diseases of posterior segment of eyeball, age-related macular degeneration (early age-related macular degeneration, dry type age-related macular degeneration and/or wet type age-related macular degeneration), diabetic retinopathy, diabetic macular edema, neovascular maculopathy, spasmodic epimacular membrane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury, inflammation on posterior segment of eyeball after operation, retinitis, uveitis, scleritis, optic neuritis and the like, preferably age-related macular degeneration (early age-related macular degeneration, dry type age-related macular degeneration and/or wet type age-related macular degeneration), diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury, retinitis and the like, especially preferably age-related macular degeneration, diabetic retinopathy and diabetic macular edema are enumerated.

Furthermore there "dermatitis" in this invention is not particularly limited as long as it is a disease on cutis with an inflammation. For example, eczema/deramatitis (acute eczema, subacute eczema, chronic eczema, contact dermatitis, mummular eczema, autosensitized dermatitis, atopic dermatitis, eczema infantum, lichen simplex chronicus vidal, other neurodermatitis, seborrheic dermatitis, keratoderma, keratodermia tylodes Palmaris progressiva, other hand/finger dermatitis, genital/anal eczema, pinna or external auditory meatus eczema/deramatitis, eczema, ermatitis and so on around nasal vestibule and nasal ala), prurigo (including Infantile strophulus, lichen urticatus, Urticaria persistens), urticaria, psoriasis and parapsoriasis (psoriasis vulgaris (severe case), psoriasis arthropathica, psoriatic erythroderma, pustular psoriasis, acrodermatitis, impetigo nerpetiformis, Reiter's syndrome), pustulosis palmoplantaris, lichen planus, benigns, erythema (erythema exsudativum multiforme, erythema nodosum), anaphylactoid purpura (allergic, Schonlein, Henoch), Weber-Christian disease, oculomncocutaneous syndrome (ectdermosis erosiva pluriorificialis, Stevens-Johnson syndrome, dermatostomatitis, Fuck's syndrome, Behcet's disease, Lipschutz' acute vulvae ulcer), Reynaud disease, alopecia greata, pemphigus (pemphigus vulgaris, pemphigus foliaceus, Senear-Usher syndrome, pemphigus vegetans), Duhring's dermatitis herpetiformis (including pemphigoid, prurigo gestationis), epidermolysis bullosa hereditaria, herpes zoster, erythroderma (includingpityriasis rubra hebra), lupus miliaris disseminatus faciei, allergic angitis and the related diseases (including pityriasis lichenoides et varioliformis acute), ulcerative chronic pyoderma, sclerema neonatorum and the like, Preferably eczema/deramatitis, prurigo, urticaria, psoriasis and parapsoriasis or atopic dermatitis, especially preferably atopic dermatitis are enumerated.

The "immune disease" in this prevention is not particularly limited as long as it is a disease with an immunity, especially "autoimmune disease" is enumerated.

The "salt" of the present compound is not particularly limited as long as it is a pharmaceutically acceptable salt. Examples thereof include salts with an inorganic acid such as hydrochloric acid, hydrobromic acid, hydroiodic acid, nitric acid, sulfuric acid, phosphoric acid or the like; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid, sulfosalicylic acid or the like; quaternary ammonium salts with methyl bromide, methyl iodide or the like; salts with a halogen ion such as a bromine ion, a chlorine ion, an iodine ion or the like; salts with an alkali metal such as lithium, sodium, potassium or the like; salts with an alkaline earth metal such as calcium, magnesium or the like; salts with a metal such as iron, zinc or the like; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine or the like.

In the case that there are geometrical isomers or optical isomers in the present compound, these isomers are also included in the scope of the present invention. Furthermore, the present compound may form a hydrate or solvate.

In the case that there are tautomers in the present compound, these tautomers are also included in the scope of the present invention.

In the case where there are polymorphism and polymorphism group (polymorphism system) in the present compound, these polymorphism and polymorphism group (polymorphism system) are also included in the scope of the present invention.

"Polymorphism group (polymorphism system)" herein means each crystal form in each step where the crystal form changes depending on conditions and states (the states also include a state of drug formulation) of manufacture, crystallization and preservation and the like, and the entire process.

(A) Examples of the present compound include compounds in which the respective groups are groups as defined below and salts thereof in the present compound represented by the general formula (1) and salts thereof.

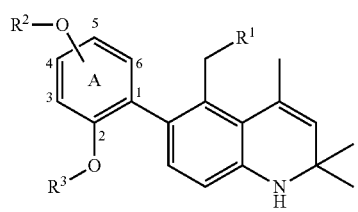
(1)

(A1) $R^1$ represents formula (2a), (3a), (4a) or (5a); and/or

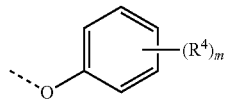
(2a)

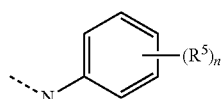
(3a)

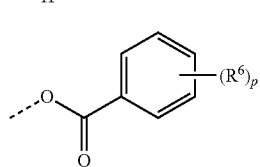
(4a)

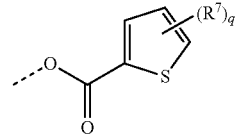
(5a)

(A2) $R^2$ represents —(CO)—$R^8$, —(CO)O—$R^9$, —(SO)—$R^{10}$, —(SO$_2$)—$R^{11}$ or —(CO)NR$^{12}$R$^{13}$; and/or (A3) $R^2$—O— is substituted at the 4- or -5-position of benzene ring A; and/or (A4) $R^3$ represents a lower alkyl group; and/or (A5) $R^4$, $R^5$, $R^6$ or $R^7$ represents a halogen atom, a lower alkyl group which may have a substituent, a lower alkenyl group, a lower alkynyl group, a lower alkoxy group, a nitro group or a formyl group; and/or (A6) m, n, p or q represents 0, 1 or 2; and/or (A7) in the case where m, n, p or q is 2, each $R^4$, $R^5$, $R^6$ or $R^7$ may be the same or different; and/or (A8) $R^8$, $R^9$, $R^{10}$ or $R^{11}$ represents a lower alkyl group which may have a substituent, a lower alkenyl group, a lower cycloalkyl group, an aryl group which may have a substituent, or a heterocyclic group which may have a substituent; and/or (A9) $R^{12}$ and $R^{13}$ may be the same or different and represent a hydrogen atom, a lower alkyl group which may have a substituent, an aryl group which may have a substituent or heterocyclic group.

That is, in the compounds represented by the general formula (1) and salts thereof, examples include compounds that comprise one or a combination of two or more selected from the above (A1), (A2), (A3), (A4), (A5), (A6), (A7), (A8) and (A9), and salts thereof.

(B) Preferred examples of the present compound include compounds in which the respective groups are groups as defined below and salts thereof in the compounds represented by the general formula (1) and salts thereof.

(B1) $R^1$ represents formula (2a), (3a), (4a) or (5a); and/or

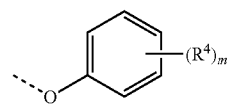
(2a)

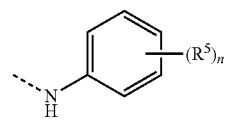
(3a)

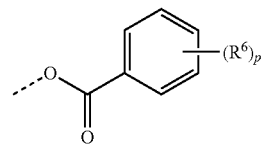
(4a)

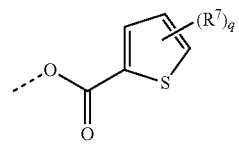
(5a)

(B2) $R^2$ represents —(CO)—$R^8$, —(CO)O—$R^9$, —(SO)—$R^{10}$, —(SO$_2$)—$R^{11}$ or —(CO)NR$^{12}$R$^{13}$; and/or (B3) $R^2$—O— is substituted at the 4- or -5-position of benzene ring A; and/or (B4) $R^3$ represents a lower alkyl group; and/or (B5) $R^4$ represents a halogen atom, a lower alkyl group, a lower alkoxy group or a nitro group; and/or (B6) $R^5$ represents a halogen atom, a lower alkyl group or a lower alkoxy group; and/or (B7) $R^6$ represents a halogen atom, a lower alkyl group or a lower alkoxy group; and/or (B8) $R^7$ represents a halogen atom or a lower alkyl group; and/or (B9) m, n or p represents 1 or 2; and/or (B10) in the case where m, n or p is 2, each $R^4$, $R^5$ or $R^6$ may be the same or different; and/or (B11) q represents 1; and/or (B12) $R^8$ represents a lower alkyl group which may have a substituent, a lower alkenyl group, a lower cycloalkyl group, an aryl group which may have a substituent or a heterocyclic group which may have a substituent; and/or (B13) $R^9$ represents a lower alkyl group which may have a substituent or an aryl group which may have a substituent; and/or (B14) $R^{10}$ or $R^{11}$ represents a lower alkyl group which may have a substituent or a lower cycloalkyl group; and/or (B15) $R^{12}$ and $R^{13}$ may be the same or different and represent a hydrogen atom, a lower alkyl group which may have a substituent, an aryl group which may have a substituent or heterocyclic group.

That is, in the compounds represented by the general formula (1) and salts thereof, examples include compounds that comprise one or a combination of two or more selected from the above (B1), (B2), (B3), (B4), (B5), (B6), (B7), (B8), (B9), (B10), (B11), (B12), (B13), (B14) and (B15), and salts thereof.

(C) Preferred examples of $R^1$ in the present compound include the compound in which $R^1$ represents formula (2a-1), (2a-2), (2a-3), (3a-1), (3a-2), (4a-1), (4a-2), (4a-3), (5a-1) or (5a-2),

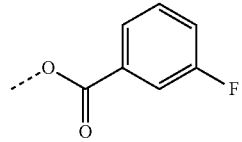
(2a-1)

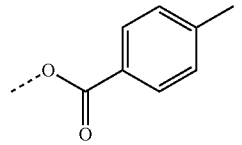
(2a-2)

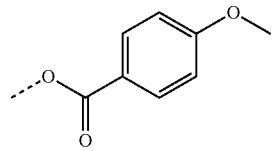
(2a-3)

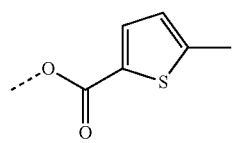
(3a-1)

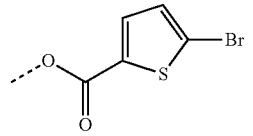
(3a-2)

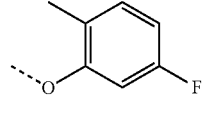
(4a-1)

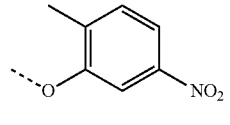
(4a-2)

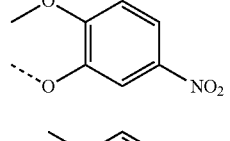
(4a-3)

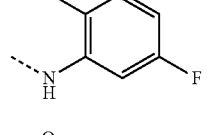
(5a-1)

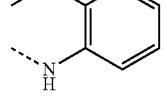
(5a-2)

more preferred examples of $R^1$ include the compound in which $R^1$ represents formula (2a-1), (2a-2), (2a-3), (3a-1), (3a-2), (4a-2) or (5a-1).

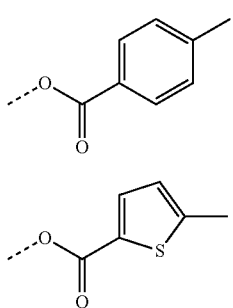

(4a-2)

(5a-1)

The compounds which satisfy this condition (C) and the above conditions (A) and/or (B), and salts thereof are especially preferable.

(D) Preferred examples of $R^2$ in the present compound include the compound in which $R^2$ represents —(CO)—$R^8$, —(SO$_2$)—$R^{11}$ or —(CO)NR$^{12}$R$^{13}$, more preferred examples include the compound in which $R^2$ represents —(CO)—$R^8$ or —(SO$_2$)—$R^{11}$, and furthermore preferred examples include the compound in which $R^2$ represents include —(CO)—$R^8$.

The compounds which satisfy this condition (D) and the above conditions (A) and/or (B), and salts thereof are especially preferable.

(E) Preferred examples of $R^3$ in the present compound include the compound in which $R^3$ represents a methyl group.

The compounds which satisfy this condition (E) and the above conditions (A) and/or (B), and salts thereof are especially preferable.

(F) Preferred examples of the substitution position of $R^2$—O— in the present compound include the case in which $R^2$—O—is substituted at the 4-position of benzene ring A.

The compounds which satisfy this condition (F) and the above conditions (A) and/or (B), and a salt thereof are especially preferable.

(G) Preferred specific examples of the present compound include the following compounds and salts thereof.

6-[4-(Furan-2-ylcarbonyloxy)-2-methoxyphenyl]-5-(2-methoxyphenylaminomethyl)-2,2,4-trimethyl-1,2-dihydroquinoline,
5-(5-Fluoro-2-methylphenoxymethyl)-6-[2-methoxy-4-(2-methoxybenzoyloxy)phenyl]-2,2,4-trimethyl-1,2-dihydroquinoline,
6-[4-(2-Chlorobenzoyloxy)-2-methoxyphenyl]-5-(5-fluoro-2-methylphenoxymethyl)-2,2,4-trimethyl-1,2-dihydroquinoline,
5-(5-Fluoro-2-methylphenoxymethyl)-6-[2-methoxy-4-(pyridin-3-ylcarbonyloxy)phenyl]-2,2,4-trimethyl-1,2-dihydroquinoline,
6-(4-Butyryloxy-2-methoxyphenyl)-5-(5-fluoro-2-methylphenoxymethyl)-2,2,4-trimethyl-1,2-dihydroquinoline,
5-(5-Fluoro-2-methylphenoxymethyl)-6-[2-methoxy-4-(thiophen-3-ylcarbonyloxy)phenyl]-2,2,4-trimethyl-1,2-dihydroquinoline,
5-(5-Fluoro-2-methylphenoxymethyl)-6-[4-(furan-2-ylcarbonyl oxy)-2-methoxyphenyl]-2,2,4-trimethyl-1,2-dihydroquinoline,
5-(5-Fluoro-2-methylphenoxymethyl)-6-(4-isobutyryloxy-2-methoxyphenyl)-2,2,4-trimethyl-1,2-dihydroquinoline,
5-(5-Fluoro-2-methylphenoxymethyl)-6-(2-methoxy-4-phenylacetoxyphenyl)-2,2,4-trimethyl-1,2-dihydroquinoline,
5-(5-Fluoro-2-methylphenoxymethyl)-6-[5-(furan-2-ylcarbonyl oxy)-2-methoxyphenyl]-2,2,4-trimethyl-1,2-dihydroquinoline,
5-(5-Fluoro-2-methylphenoxymethyl)-6-(2-methoxy-5-propionyl oxyphenyl)-2,2,4-trimethyl-1,2-dihydroquinoline,
5-(5-Fluoro-2-methylphenoxymethyl)-6-[2-methoxy-5-(pyridin-3-ylcarbonyloxy)phenyl]-2,2,4-trimethyl-1,2-dihydroquinoline,
5-(5-Fluoro-2-methylphenoxymethyl)-6-[4-(furan-3-ylcarbonyl oxy)-2-methoxyphenyl]-2,2,4-trimethyl-1,2-dihydroquinoline,
5-(5-Fluoro-2-methylphenoxymethyl)-6-[2-methoxy-4-(pyridin-4-ylcarbonyloxy)phenyl]-2,2,4-trimethyl-1,2-dihydroquinoline,
6-[4-(2-Acetoxybenzoyloxy)-2-methoxyphenyl]-5-(5-fluoro-2-m ethylphenoxymethyl)-2,2,4-trimethyl-1,2-dihydroquinoline,
5-(5-Fluoro-2-methylphenoxymethyl)-6-[2-methoxy-4-(2-methylthiobenzoyloxy)phenyl]-2,2,4-trimethyl-1,2-dihydroquinoline,
5-(5-Fluoro-2-methylphenoxymethyl)-6-[2-methoxy-4-(thiazol-4-ylcarbonyloxy)phenyl]-2,2,4-trimethyl-1,2-dihydroquinoline,
6-[4-(2-Fluorobenzoyloxy)-2-methoxyphenyl]-5-(5-fluoro-2-methylphenoxymethyl)-2,2,4-trimethyl-1,2-dihydroquinoline,
5-(5-Fluoro-2-methylphenoxymethyl)-6-[2-methoxy-4-(5-methyl furan-2-ylcarbonyloxy)phenyl]-2,2,4-trimethyl-1,2-dihydroquinoline,
5-(5-Fluoro-2-methylphenoxymethyl)-6-[2-methoxy-4-(2-methyl pyridin-3-ylcarbonyloxy)phenyl]-2,2,4-trimethyl-1,2-dihydro quinoline,
5-(5-Fluoro-2-methylphenoxymethyl)-6-[2-methoxy-4-(3-methoxylcarbonylbenzoyloxy)phenyl]-2,2,4-trimethyl-1,2-dihydroquinoline,
5-(5-Fluoro-2-methylphenoxymethyl)-6-[2-methoxy-4-(6-methyl pyridin-3-ylcarbonyloxy)phenyl]-2,2,4-trimethyl-1,2-dihydroquinoline,
5-(5-Fluoro-2-methylphenoxymethyl)-6-[2-methoxy-4-(3-methyl furan-2-ylcarbonyloxy)phenyl]-2,2,4-trimethyl-1,2-dihydroquinoline,
6-(4-t-Butylcarbonyloxy-2-methoxyphenyl)-5-(5-fluoro-2-methylphenoxymethyl)-2,2,4-trimethyl-1,2-dihydroquinoline,
6-[4-(2-Chloropyridin-4-ylcarbonyloxy)-2-methoxyphenyl]-5-(5-fluoro-2-methylphenoxymethyl)-2,2,4-trimethyl-1,2-dihydro quinoline,
5-(5-Fluoro-2-methylphenoxymethyl)-6-[4-(3-fluoropyridin-4-ylcarbonyloxy)-2-methoxyphenyl]-2,2,4-trimethyl-1,2-dihydro quinoline,
6-[2-Methoxy-4-(pyridin-3-ylcarbonyloxy)phenyl]-5-(2-methyl-5-nitrophenoxymethyl)-2,2,4-trimethyl-1,2-dihydroquinoline
5-(2-Methoxy-5-nitrophenoxymethyl)-6-[2-methoxy-4-(thiophen-3-ylcarbonyloxy)phenyl]-2,2,4-trimethyl-1,2-dihydroquinoline,
6-[2-Methoxy-4-(2-methylpyridin-3-ylcarbonyloxy)phenyl]-5-(2-methoxyphenylaminomethyl)-2,2,4-trimethyl-1,2-dihydroquinoline,
6-(4-Benzoyloxy-2-methoxyphenyl)-5-(2-methoxyphenylaminomethyl)-2,2,4-trimethyl-1,2-dihydroquinoline,
6-[4-(Furan-3-ylcarbonyloxy)-2-methoxyphenyl]-5-(2-methoxyphenylaminomethyl)-2,2,4-trimethyl-1,2-dihydroquinoline,
5-(2-Methoxyphenylaminomethyl)-6-[2-methoxy-4-(pyridin-3-yl carbonyloxy)phenyl]-2,2,4-trimethyl-1,2-dihydroquinoline,
6-[4-(2-Chlorobenzoyloxy)-2-methoxyphenyl]-5-(5-fluoro-2-methylphenylaminomethyl)-2,2,4-trimethyl-1,2-dihydroquinoline, 6-[4-(2-Chlorobenzoyloxy)-2-methoxyphenyl]-5-(2-methoxyphen ylaminomethyl)-2,2,4-trimethyl-1,2-dihydroquinoline, 6-[4-(2-Fluorobenzoyloxy)-2-methoxyphenyl]-5-(2-methoxyphen ylaminomethyl)-2,2,4-trimethyl-1,2-dihydroquinoline, 5-(2-Methoxyphenylaminomethyl)-6-[2-methoxy-4-(pyridin-4-yl carbonyloxy)phenyl]-2,2,4-trimethyl-1,2-dihydroquinoline, 5-(2-Methoxyphenylaminomethyl)-6-[2-methoxy-4-(thiophen-2-yl-carbonyloxy)phenyl]-2,2,4-trimethyl-1,2-dihydroquinoline, 5-(5-Fluoro-2-methylphenylaminomethyl)-6-[2-methoxy-4-(pyri din-3-ylcarbonyloxy)phenyl]-2,2,4-trimethyl-1,2-dihydroquinoline, 5-(5-Fluoro-2-methylphenylaminomethyl)-6-[4-(furan-2-ylcarbonyloxy)-2-methoxyphenyl]-2,2,4-trimethyl-1,2-dihydroquinoline, 6-[2-Methoxy-4-(3-methoxycarbonylbenzoyloxy)phenyl]-5-(2-methoxyphenylaminomethyl)-2,2,4-trimethyl-1,2-dihydroquinoline, 6-[4-(4-Fluorobenzoyloxy)-2-methoxyphenyl]-5-(2-methoxyphenylaminomethyl)-2,2,4-trimethyl-1,2-dihydroquinoline, 6-[2-Methoxy-4-(2-methylthiobenzoyloxy)phenyl]-5-(2-methoxy phenylaminomethyl)-2,2,4-trimethyl-1,2-dihydroquinoline, 6-[2-Methoxy-4-(3-methylfuran-2-ylcarbonyloxy)phenyl]-5-(2-methoxyphenylaminomethyl)-2,2,4-trimethyl-1,2-dihydroquinoline, 6-[2-Methoxy-4-(2-methoxypyridin-3-ylcarbonyloxy)phenyl]-5-(2-methoxyphenylaminomethyl)-2,2,4-trimethyl-1,2-dihydroquinoline, 5-(5-Fluoro-2-methylphenylaminomethyl)-6-[2-methoxy-4-(pyridin-4-ylcarbonyloxy)phenyl]-2,2,4-trimethyl-1,2-dihydroquinoline, 5-(5-Fluoro-2-methylphenylaminomethyl)-6-[2-methoxy-4-(2-methylpyridin-3-ylcarbonyloxy)phenyl]-2,2,4-trimethyl-1,2-dihydroquinoline, 5-(5-Fluoro-2-methylphenylaminomethyl)-6-[2-methoxy-4-(2-methoxypyridin-3-ylcarbonyloxy)phenyl]-2,2,4-trimethyl-1,2-dihydroquinoline, 5-(5-Fluoro-2-methylphenylaminomethyl)-6-[2-methoxy-4-(3-methylfuran-2-ylcarbonyloxy)phenyl]-2,2,4-trimethyl-1,2-dihydroquinoline, 6-[2-Methoxy-4-(6-methylpyridin-3-ylcarbonyloxy)phenyl]-5-(5-methylthiophen-2-ylcarbonyloxymethyl)-2,2,4-trimethyl-1,2-dihydroquinoline, 5-(4-Methylbenzoyloxymethyl)-6-[2-methoxy-4-(pyridin-3-ylcarbonyloxy)phenyl]-2,2,4-trimethyl-1,2-dihydroquinoline, 6-[2-Methoxy-4-(2-methoxybenzoyloxy)phenyl]-5-(5-methylthio phen-2-ylcarbonyloxymethyl)-2,2,4-trimethyl-1,2-dihydroquinoline, 6-[2-Methoxy-4-(pyridin-3-ylcarbonyloxy)phenyl]-5-(5-methylthiophen-2-ylcarbonyloxymethyl)-2,2,4-trimethyl-1,2-dihydro quinoline, 6-[4-(Furan-2-ylcarbonyloxy)-2-methoxyphenyl]-5-(5-methylthiophen-2-ylcarbonyloxymethyl)-2,2,4-trimethyl-1,2-dihydroquinoline, 6-[4-(2-Chlorobenzoyloxy)-2-methoxyphenyl]-5-(5-methylthiophen-2-ylcarbonyloxymethyl)-2,2,4-trimethyl-1,2-dihydroquinoline, 6-[4-(4-Chlorobenzoyloxy)-2-methoxyphenyl]-5-(5-methylthiophen-2-ylcarbonyloxymethyl)-2,2,4-trimethyl-1,2-dihydroquinoline, 6-(4-Benzoyloxy-2-methoxyphenyl)-5-(5-methylthiophen-2-ylcarbonyloxymethyl)-2,2,4-trimethyl-1,2-dihydroquinoline, 6-[2-Methoxy-4-(2-methylbenzoyloxy)phenyl]-5-(5-methylthiophen-2-ylcarbonyloxymethyl)-2,2,4-trimethyl-1,2-dihydroquinoline, 6-[4-(2-Fluorobenzoyloxy)-2-methoxyphenyl]-5-(5-methylthiophen-2-ylcarbonyloxymethyl)-2,2,4-trimethyl-1,2-dihydroquinoline, 6-[2-Methoxy-4-(thiophen-3-ylcarbonyloxy)phenyl]-5-(5-methylthiophen-2-ylcarbonyloxymethyl)-2,2,4-trimethyl-1,2-dihydroquinoline, 6-[4-(Furan-3-ylcarbonyloxy)-2-methoxyphenyl]-5-(5-methylthiophen-2-ylcarbonyloxymethyl)-2,2,4-trimethyl-1,2-dihydroquinoline, 6-[2-Methoxy-4-(2-methylthiobenzoyloxy)phenyl]-5-(5-methylthiophen-2-ylcarbonyloxymethyl)-2,2,4-trimethyl-1,2-dihydroquinoline, 6-[2-Methoxy-4-(2-methylpyridin-3-ylcarbonyloxy)phenyl]-5-(5-methylthiophen-2-ylcarbonyloxymethyl)-2,2,4-trimethyl-1,2-dihydroquinoline, 6-[2-Methoxy-4-(thiazol-4-ylcarbonyloxy)phenyl]-5-(5-methyl thiophen-2-ylcarbonyloxymethyl)-2,2,4-trimethyl-1,2-dihydro quinoline, 6-[2-Methoxy-4-(pyridin-4-ylcarbonyloxy)phenyl]-5-(5-methyl thiophen-2-ylcarbonyloxymethyl)-2,2,4-trimethyl-1,2-dihydro quinoline, 5-(4-Methoxybenzoyloxymethyl)-6-[2-methoxy-4-(pyridin-3-ylcarbonyloxy)phenyl]-2,2,4-trimethyl-1,2-dihydroquinoline, 5-(5-Bromothiophen-2-ylcarbonyloxymethyl)-6-[2-methoxy-4-(pyridin-3-ylcarbonyloxy)phenyl]-2,2,4-trimethyl-1,2-dihydroquinoline, 5-(5-Bromothiophen-2-ylcarbonyloxymethyl)-6-[4-(furan-2-ylcarbonyloxy)-2-methoxyphenyl]-2,2,4-trimethyl-1,2-dihydroquinoline, 6-(4-Isopropylcarbonyloxy-2-methoxyphenyl)-5-(5-methylthiophen-2-ylcarbonyloxymethyl)-2,2,4-trimethyl-1,2-dihydroquinoline, 6-[4-(2-Acetoxybenzoyloxy)-2-methoxyphenyl]-5-(5-methylthiophen-2-ylcarbonyloxymethyl)-2,2,4-trimethyl-1,2-dihydroquinoline, 6-[2-Methoxy-4-(2-methoxypyridin-3-ylcarbonyloxy)phenyl]-5-(5-methylthiophen-2-ylcarbonyloxymethyl)-2,2,4-trimethyl-1,2-dihydroquinoline, 6-[4-(4-Fluorobenzoyloxy)-2-methoxyphenyl]-5-(5-methylthiophen-2-ylcarbonyloxymethyl)-2,2,4-trimethyl-1,2-dihydroquinoline, 6-[2-Methoxy-4-(2-nitrobenzoyloxy)phenyl]-5-(5-methylthiophen-2-ylcarbonyloxymethyl)-2,2,4-trimethyl-1,2-dihydroquinoline, 6-[2-Methoxy-4-(3-methylfuran-2-ylcarbonyloxy)phenyl]-5-(5-methylthiophen-2-ylcarbonyloxymethyl)-2,2,4-trimethyl-1,2-dihydroquinoline, 5-(5-Fluoro-2-methylphenoxymethyl)-6-(2-methoxy-4-propylsulfonyloxyphenyl)-2,2,4-trimethyl-1,2-dihydroquinoline, 6-(4-Ethylsulfonyloxy-2-methoxyphenyl)-5-(5-fluoro-2-methyl phenoxymethyl)-2,2,4-trimethyl-1,2-dihydroquinoline, 5-(5-Fluoro-2-methylphenoxymethyl)-6-(4-isopropylsulfonyloxy-2-methoxyphenyl)-2,2,4-trimethyl-1,2-dihydroquinoline, 6-(4-Butylsulfonyloxy-2-methoxyphenyl)-5-(5-fluoro-2-methyl phenoxymethyl)-2,2,4-trimethyl-1,2-dihydroquinoline, 6-(4-Cyclopropylsulfonyloxy-2-methoxyphenyl)-5-(2-methoxy-5-nitrophenoxymethyl)-2,2,4-trimethyl-1,2-dihydroquinoline,
6-(4-Ethylsulfonyloxy-2-methoxyphenyl)-5-(2-methyl-5-nitrophenoxymethyl)-2,2,4-trimethyl-1,2-dihydroquinoline,
6-(2-Methoxy-4-propylsulfonyloxyphenyl)-5-(2-methyl-5-nitro phenoxymethyl)-2,2,4-trimethyl-1,2-dihydroquinoline,
6-(4-Cyclopropylsulfonyloxy-2-methoxyphenyl)-5-(5-fluoro-2-methylphenoxymethyl)-2,2,4-trimethyl-1,2-dihydroquinoline,
5-(2-Methoxyphenylaminomethyl)-6-(2-methoxy-4-propylsulfonyloxyphenyl)-2,2,4-trimethyl-1,2-dihydroquinoline,
6-(2-Methoxy-4-methylsulfonyloxyphenyl)-5-(2-methoxyphenylaminomethyl)-2,2,4-trimethyl-1,2-dihydroquinoline,
5-(5-Fluoro-2-methylphenylaminomethyl)-6-(2-methoxy-4-propylsulfonyloxyphenyl)-2,2,4-trimethyl-1,2-dihydroquinoline,
6-[2-Methoxy-4-(3,3,3-trifluoropropylsulfonyloxy)phenyl]-5-(5-methylthiophen-2-ylcarbonyloxymethyl)-2,2,4-trimethyl-1,2-dihydroquinoline,
6-(2-Methoxy-4-propylsulfonyloxyphenyl)-5-(5-methylthiophen-2-ylcarbonyloxymethyl)-2,2,4-trimethyl-1,2-dihydroquinoline,
6-(4-Isopropylsulfonyloxy-2-methoxyphenyl)-5-(5-methylthiophen-2-ylcarbonyloxymethyl)-2,2,4-trimethyl-1,2-dihydroquinoline,
6-(4-Cyclopentylsulfonyloxy-2-methoxyphenyl)-5-(5-methylthiophen-2-ylcarbonyloxymethyl)-2,2,4-trimethyl-1,2-dihydroquinoline,
6-(4-Ethylsulfonyloxy-2-methoxyphenyl)-5-(5-methylthiophen-2-ylcarbonyloxymethyl)-2,2,4-trimethyl-1,2-dihydroquinoline,
6-(4-Cyclopropylsulfonyloxy-2-methoxyphenyl)-5-(5-methylthiophen-2-ylcarbonyloxymethyl)-2,2,4-trimethyl-1,2-dihydroquinoline,
6-(4-Dimethylaminocarbonyloxy-2-methoxyphenyl)-5-(5-fluoro-2-methylphenoxymethyl)-2,2,4-trimethyl-1,2-dihydroquinoline,
6-[4-[N-(2-Dimethylaminoethyl)-N-ethylaminocarbonyloxy]-2-methoxyphenyl]-5-(5-fluoro-2-methylphenoxymethyl)-2,2,4-trim ethyl-1,2-dihydroquinoline,
6-[2-Methoxy-4-(morpholin-4-ylcarbonyloxy)phenyl]-5-(5-methylthiophen-2-ylcarbonyloxymethyl)-2,2,4-trimethyl-1,2-dihydroquinoline,
6-[4-(4-Chlorophenylaminocarbonyloxy)-2-methoxyphenyl]-5-(5-methylthiophen-2-ylcarbonyloxymethyl)-2,2,4-trimethyl-1,2-dihydroquinoline,
5-(5-Fluoro-2-methylphenoxymethyl)-6-[2-methoxy-4-(morpholin-4-ylcarbonyloxy)phenyl]-2,2,4-trimethyl-1,2-dihydroquinoline,
6-(4-Dimethylaminocarbonyloxy-2-methoxyphenyl)-5-(2-methyl-5-nitrophenoxymethyl)-2,2,4-trimethyl-1,2-dihydroquinoline,
6-[2-Methoxy-4-(morpholin-4-ylcarbonyloxy)phenyl]-5-(2-methoxyphenylaminomethyl)-2,2,4-trimethyl-1,2-dihydroquinoline,
6-(4-Dimethylaminocarbonyloxy-2-methoxyphenyl)-5-(5-methylthiophen-2-ylcarbonyloxymethyl)-2,2,4-trimethyl-1,2-dihydroquinoline.

The present compound can be synthesized according to the following procedures. The individual concrete preparation procedures are explained in detail in the section of "Production Examples" in Examples. These examples are intended to make the present invention more clearly understandable, and do not limit the scope of the present invention. In the following synthetic routes, the hal represents a halogen atom and the fmoc represents a 9-fluorenylmethoxycarbonyl group.

The present compound (I)-(a) (the compound in which $R^2$ is —(CO)—$R^8$ in the general formula (1)), the present compound (I)-(b) (the compound in which $R^2$ is —(CO)O—$R^9$ in the general formula (1)), the present compound (I)-(c) (the compound in which $R^2$ is —(SO$_2$)—$R^{11}$ in the general formula (1)), the present compound (I)-(d) (the compound in which $R^2$ is —(CO)NR$^{12}$R$^{13}$ in the general formula (1)), can be synthesized according to the synthetic route 1. Namely, the compound (I)-(a), (I)-(b), (I)-(c), and (I)-(d) can be given by the reaction of the compound (II) with a corresponding acid halide (III), (IV), (V), and (VI) in an organic solvent such as methylene dichloride, pyridine, tetrahydrofuran (hereinafter referred to as THF), N, N-dimethylformamide (hereinafter referred to as DMF) in the presence of a base such as triethylamine, diisopropylethylamine (hereinafter referred to as DIEA) at 0° C. to 100° C. for 10 minutes to 2 days.

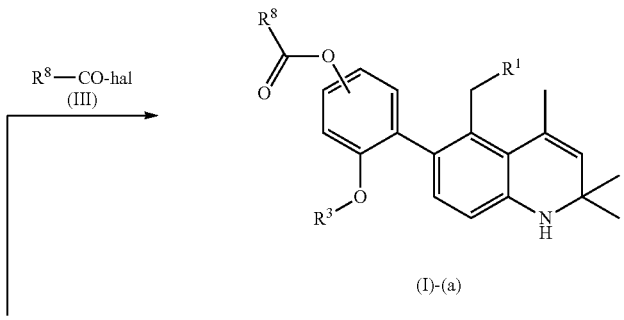

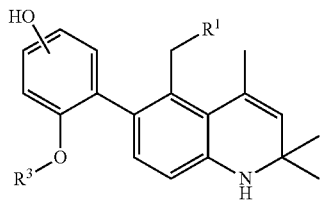

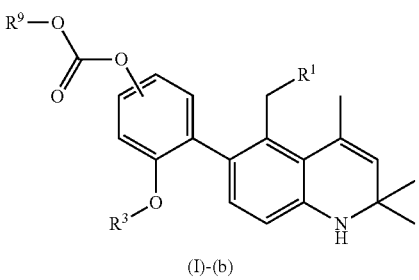

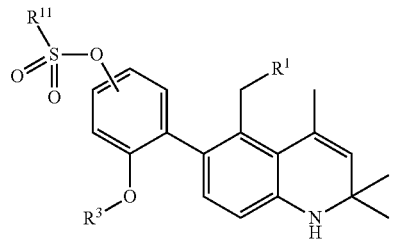

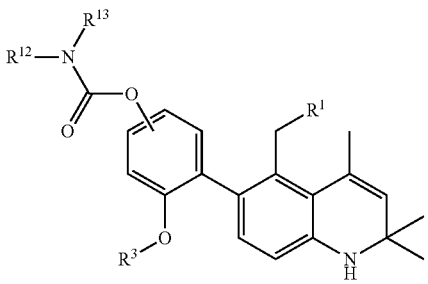

Synthetic Route 1

The present compound (I)-(a) (the compound in which $R^2$ is —(CO)—$R^8$ in the general formula (1)) can be also synthesized according to the synthetic route 2. Namely, the compound (I)-(a) can be given by the reaction of the compound (II) with a corresponding carboxylic acid (VII) in an organic solvent such as methylene dichloride, DMF in the presence of a base such as triethylamine, DIEA and a condensation agent such as N,N'-dicyclohexylcarbodiimide, O-(7-azabenzotriazol-1-yl)-N,N,N',N'-tetramethyluronium hexafluorophosphate at 0° C. to room temperature for 30 minutes to 3 days.

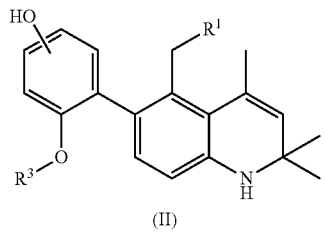

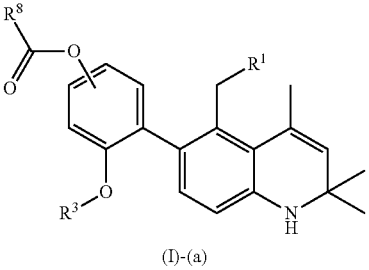

Synthetic Route 2

The present compound (I)-(d) (the compound in which $R^2$ is —(CO)$NR^{12}R^{13}$ in the general formula (1)) can be also synthesized according to the synthetic route 3. Namely, the compound (I)-(d) can be given by the reaction of the compound (II) with 1,1'-carbonyldiimidazole (hereinafter referred to as CDI) in an organic solvent such as methylene dichloride, THF in the presence of a catalyst such as 4-dimethylaminopyridine at room temperature to 50° C. for 30 minutes to 12 hours followed by the reaction with a corresponding amine (VIII) at room temperature to 100° C. for 30 minutes to 5 hours.

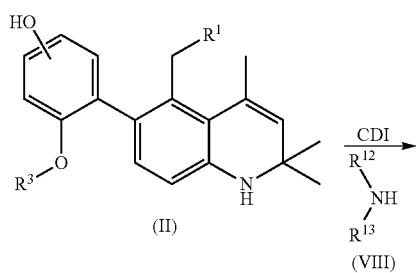

Synthetic Route 3

The present compound (I)-(e) (the compound in which $R^2$ is —(CO)$NR^{12}R^{13}$, $R^{13}$ is a hydrogen atom in the general formula (1)) can be synthesized according to the synthetic route 4. Namely, the compound (I)-(e) can be given by the reaction of the compound (II) with a corresponding isocyanate (IX) in an organic solvent such as methylene dichloride, THF, DMF in the presence of a base such as triethylamine, DIEA at 0° C. to room temperature for 30 minutes to 1 day.

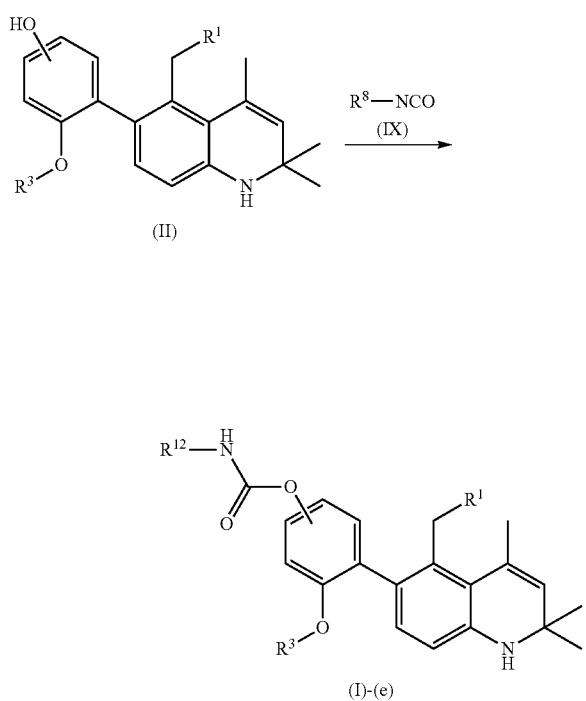

Synthetic Route 4

The present compound (I)-(f) (the compound in which $R^1$ is (3a) in the general formula (1)) can be also synthesized according to the synthetic route 5. Namely, after the introduction of $R^2$ to compound (X) according to the synthetic route 1 to 4, the present compound (I)-(f) can be given by the treatment in an organic solvent such as DMF, methylene dichloride in the presence of a base such as piperidine at 0° C. to 50° C. for 5 minutes to 24 hours.

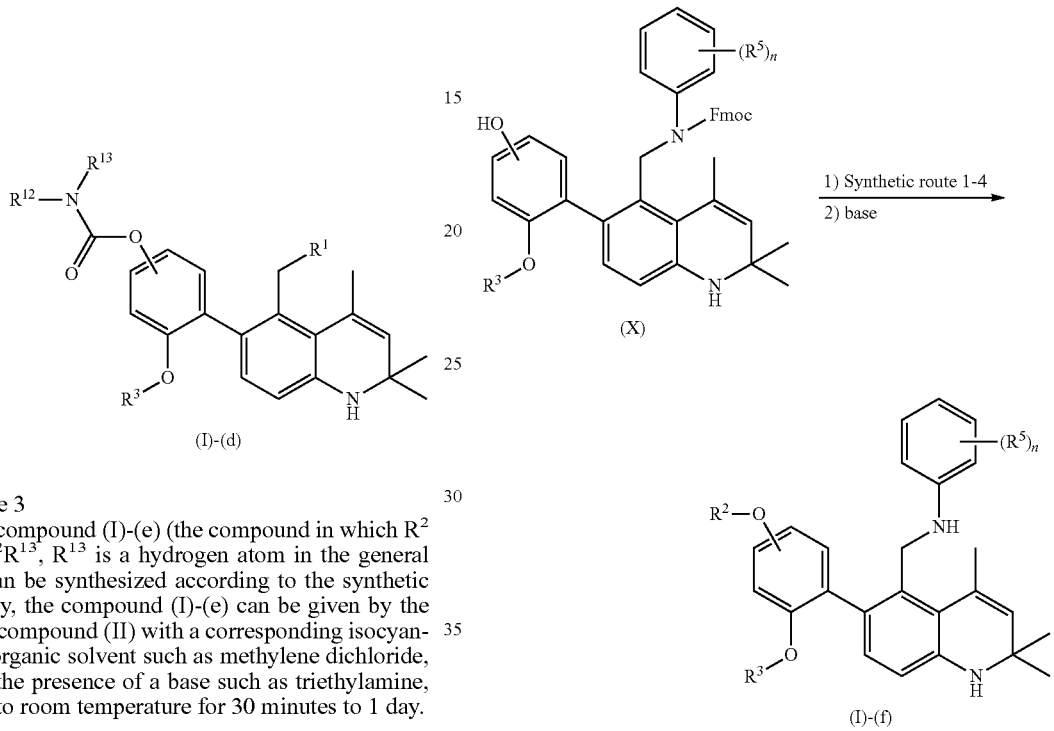

Synthetic Route 5

The compound (II)-(a) (the compounds in which $R^1$ is (2a) in the compound (II)), the compound (II)-(b) (the compounds in which $R^1$ is (3a) in the compound (II)), the compound (II)-(c) (the compounds in which $R^1$ is (4a) in the compound (II)), and the compound (II)-(d) (the compounds in which $R^1$ is (5a) in the compound (II)) can be synthesized according to the synthetic route 6. Namely, the compounds (XII) can be given by the reaction of the compound (XI) with methanesulfonyl chloride in an organic solvent such as methylene dichloride, DMF in the presence of a base such as triethylamine, DIEA at 0° C. to room temperature for 30 minutes to 3 days. The compound (XVII)-(a)~(XVII)-(d) can be given by the reaction of the obtained compound (XII) with a corresponding phenol (XIII), aniline (XIV), benzoic acid (XV), or thiophenecarboxylic acid (XVI) in an organic solvent such as DMF, methylene dichloride in the presence of a base such as potassium carbonate, DIEA, sodium hydride at 50° C. to 100° C. for 1 hour to 2 days. The compound (II)-(a)~(II)-(d) can be given by the treatment of the obtained compound (XVII)-(a)~(XVII)-(d) in an organic solvent such as methylene dichloride, 1,4-dioxane in the presence of an acid such as hydrogen chloride, trifluoroacetic acid at 0° C. to room temperature for 1 hour to 2 days.

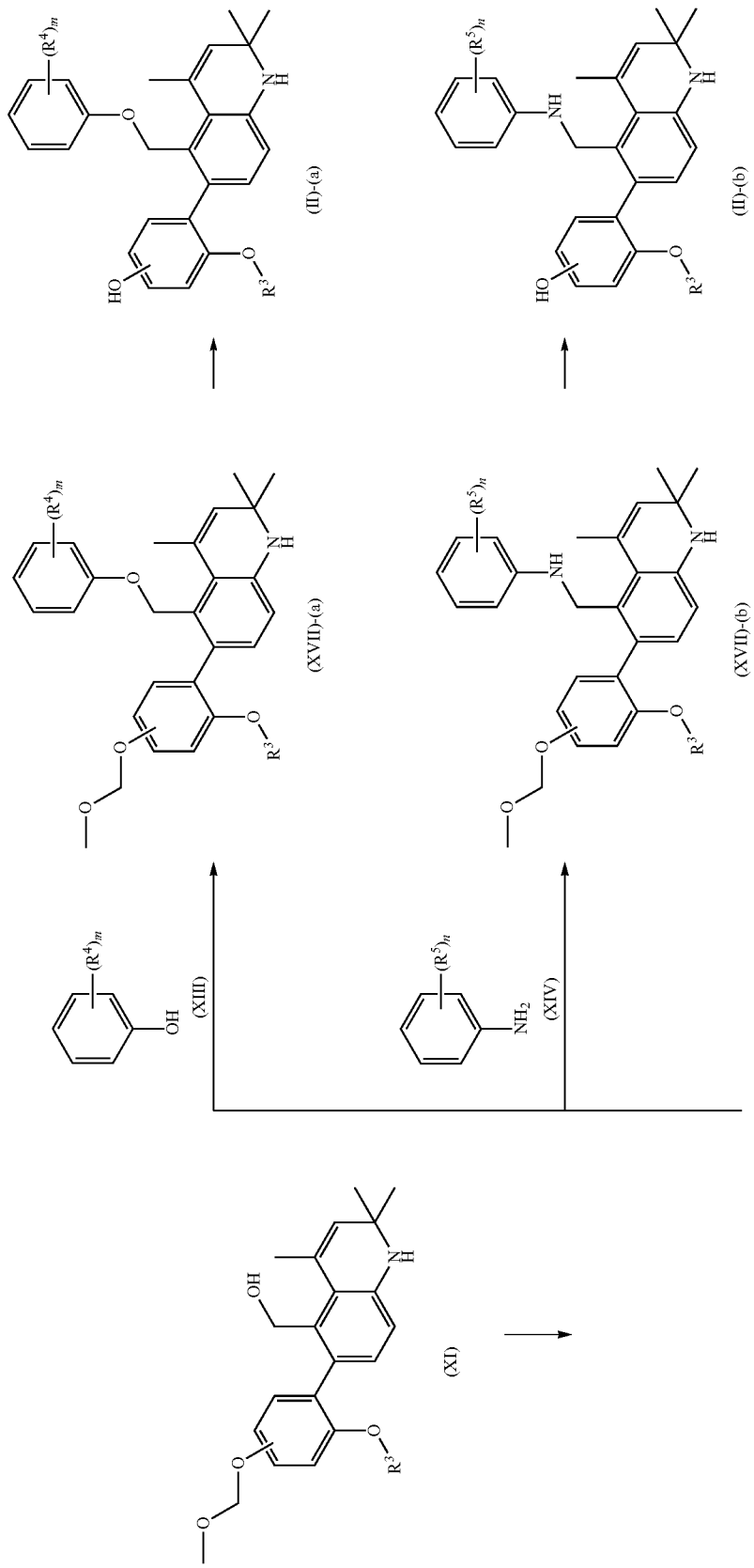

-continued
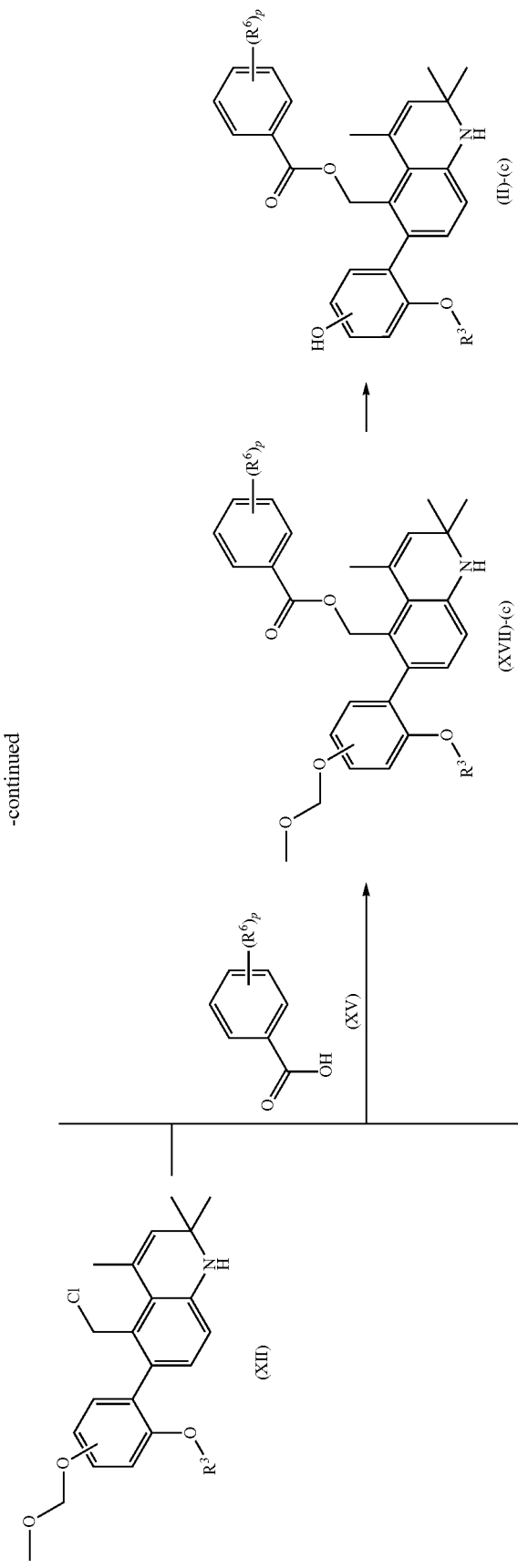
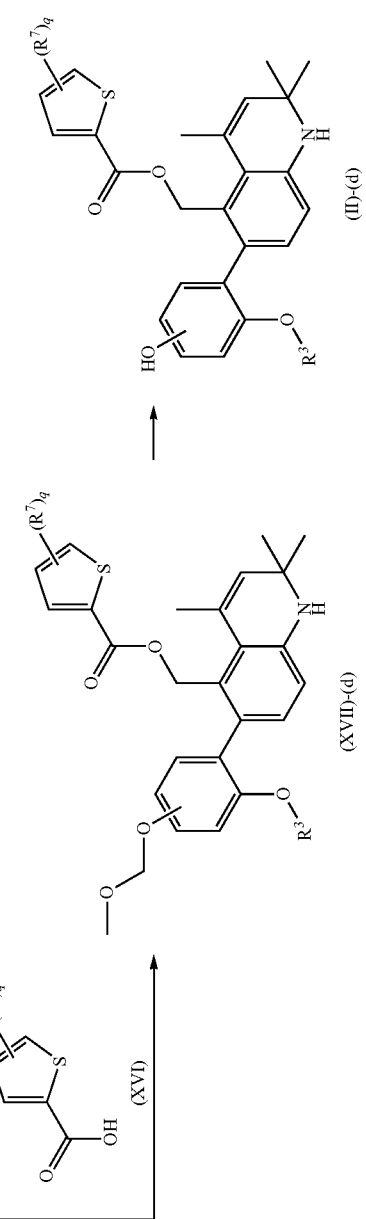

Synthetic Route 6

The compound (II)-(a) (the compounds in which $R^1$ is (2a) in the compound (II)), the compound (II)-(c) (the compounds in which $R^1$ is (4a) in the compound (II)), and the compound (II)-(d) (the compounds in which $R^1$ is (5a) in the compound (II)) can be also synthesized according to the synthetic route 7. Namely, the compounds (XVII)-(a), (XVII)-(c), and (XVII)-(d) can be given by the reaction of the compound (XI) with a corresponding phenol (XIII), benzoic acid (XV), or thiophenecarboxylic acid (XVI) in an organic solvent such as benzene, THF in the presence of a phosphine such as triphenylphosphine, tributylphospine and a reagent such as diethylazodicarboxylate, diisopropylazodicarboxylate, 1,1'-(azodicarbonyl)dipiperidine at room temperature for 1 hour to 2 days. The compound (II)-(a), (II)-(c), and (II)-(d) can be given by the treatment of the obtained compound (XVII)-(a), (XVII)-(c), and (XVII)-(d) in an organic solvent such as methylene dichloride, 1,4-dioxane in the presence of an acid such as hydrogen chloride, trifluoroacetic acid at 0° C. to room temperature for 1 hour to 2 days.

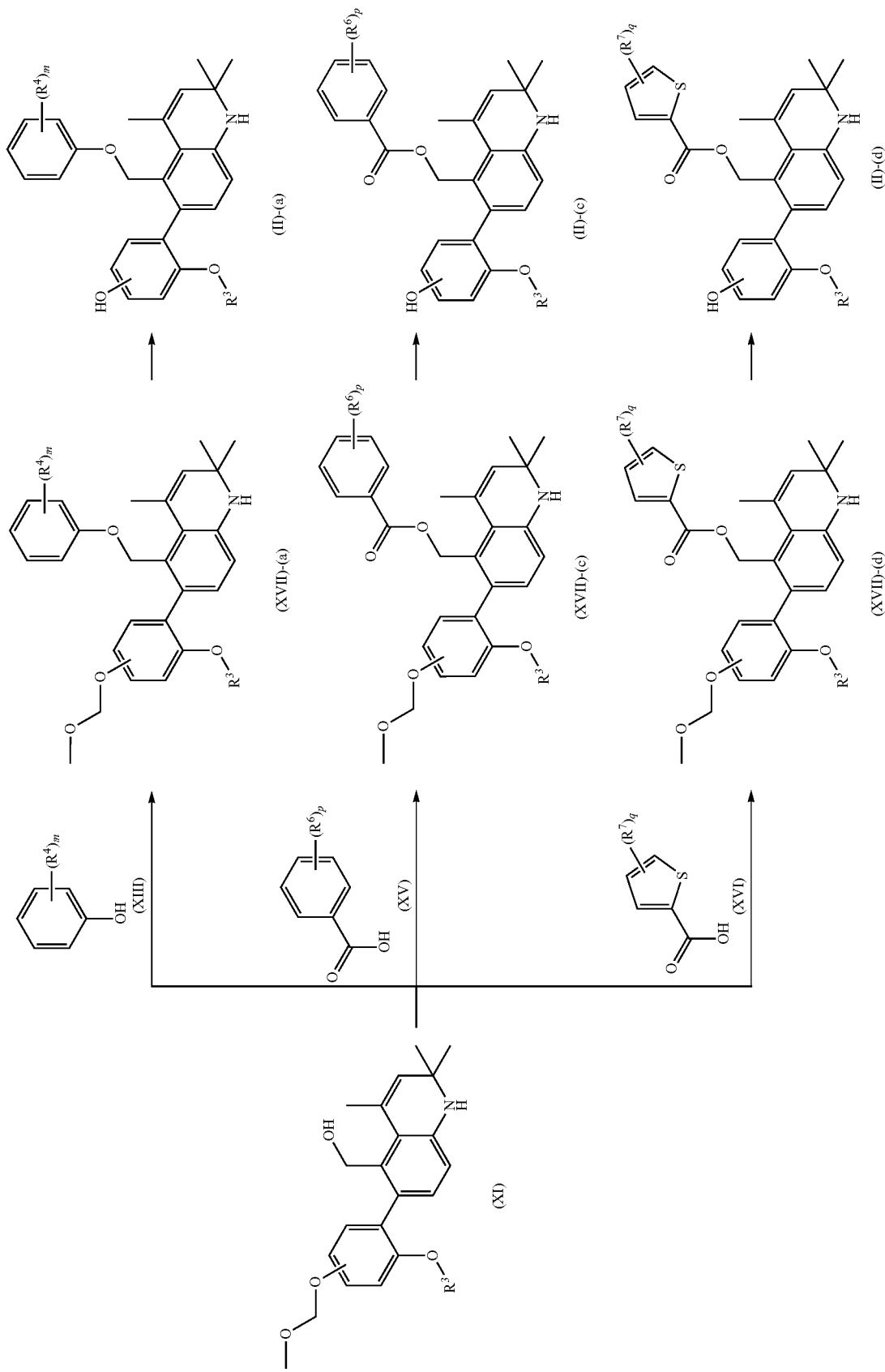

Synthetic Route 7

The compound (X) can be synthesized according to the synthetic route 8. Namely, the compound (X) can be given by the reaction of the compound (II)-(b) with 9-fluorenyl-methoxycarbonyl chloride in a solvent such as 1,4-dioxane, water in the presence of a base such as sodium hydrogen carbonate at 0° C. to 50° C. for 1 hour to 24 hours.

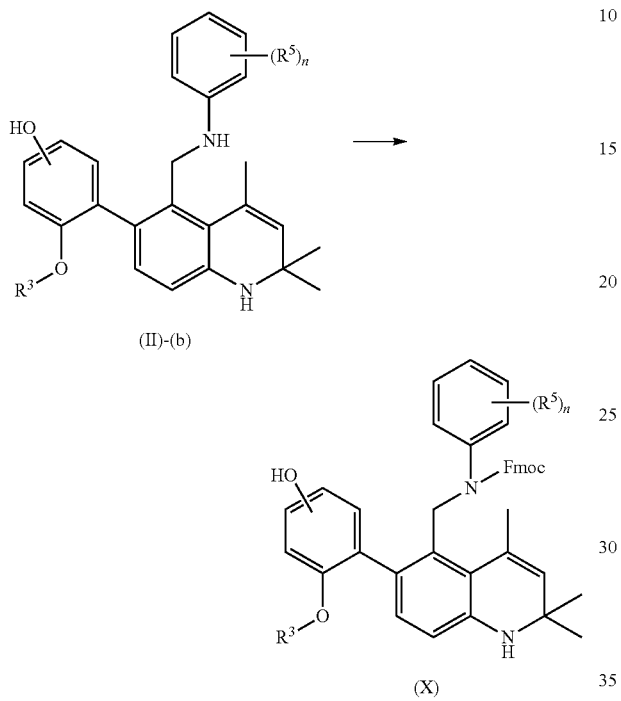

Synthetic Route 8

The compound (XI) can be synthesized according to the synthetic route 9. Namely, the compound (XX) can be given by the reaction of a boronic acid (XVIII) with a halide or triflate (XIX) in a solvent such as DMF, ethanol, toluene, water in the presence of a base such as cesium carbonate, sodium carbonate, potassium phosphate and a catalyst such as bis(triphenylphosphine)palladium (II) dichloride, tetrakis (triphenylphosphine) palladium (0) at 50° C. to 120° C. for 12 hours to 2 days. The compound (XXI) can be given by the treatment of the obtained compound (XX) in a solvent such as methylene dichloride, THF in the presence of an acid such as boron tribromide, hydrogen chloride at −78° C. to room temperature for 1 hour to 1 day. The compound (XXII) can be given by the treatment of the obtained compound (XXI) under hydrogen atmosphere in an organic solvent such as methanol, ethanol, 1,4-dioxane, THF in the presence of a catalyst such as palladium carbon, platinum dioxide at room temperature for 2 hours to 2 days. The compound (XXIII) can be given by the treatment of the obtained compound (XXII) in acetone in the presence of iodine at 80° C. to 130° C. for 24 hours to 5 days. The compound (XXIV) can be given by the reaction of the obtained compound (XXIII) with chlorodimethylether in an organic solvent such as methylene dichloride, DMF in the presence of a base such as potassium carbonate, triethylamine, DIEA. The compound (XXV) can be given by the treatment of the obtained compound (XXIV) in an organic solvent such as diethyl ether, THF in the presence of a reducing agent such as lithium aluminium hydride at 0° C. to 50° C. for 1 hour to 1 day. The compound (XI) can be given by the reaction of the obtained compound (XXV) with a corresponding halide (XXVI) in an organic solvent such as DMF, ethanol in the presence of a base such as potassium carbonate, DIEA at room temperature to 100° C. for 1 hour to 24 hours.

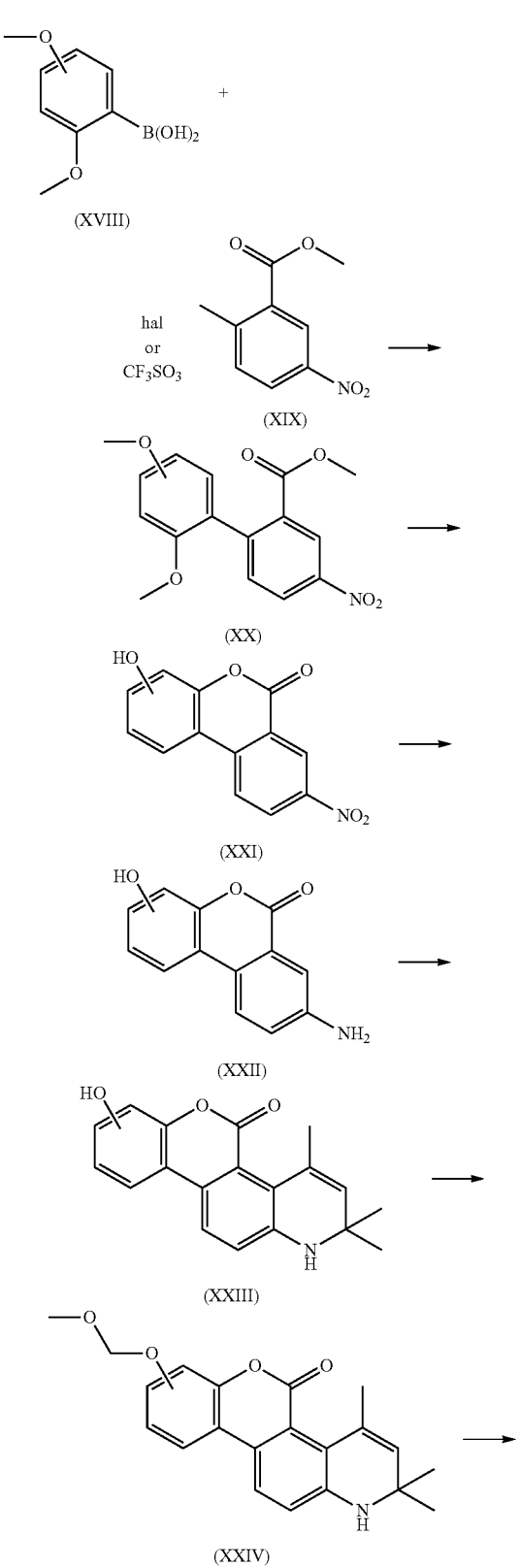

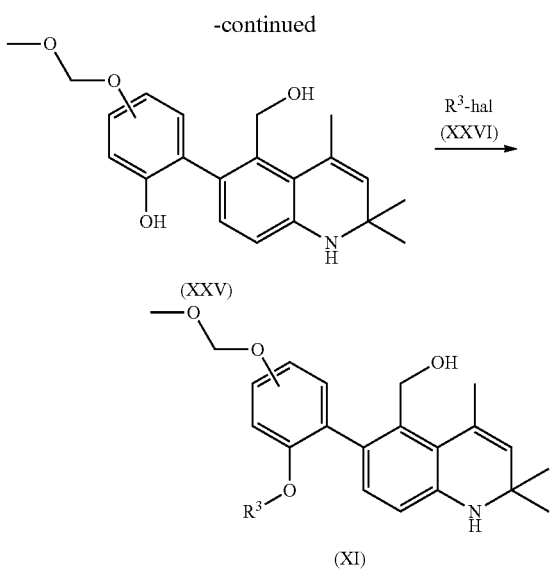

Synthetic Route 9

A detailed explanation of this matter will be described in the section of "Pharmacological Test" in Examples described below. At first, in order to investigate the binding activity of the present compound to the glucocorticoid receptor (hereinafter referred to as "GR"), receptor competitor assay was carried out by a fluorescence polarization method by using a GR competitor assay kit (manufactured by Invitrogen, cat No. P2816). As a result, the present compound showed more than 64% of GR binding ratio to GR.

Next, in order to evaluate the effect as a GR agonist of the present compound, the inhibitory effect on IL-6 production in human corneal epithelical cell line stimulated by Lipopolysaccharide (hereinafter referred to as "LPS" was investigated. As a result, the present compound showed an excellent inhibitory effect on IL-6 production, that is, the present compound has a GR agonistic effect and is useful as the preventive or therapeutic agent of the inflammatory diseases.

Further, in order to evaluate the possibility of the present compound as a therapeutic agent for the inflammatory diseases of anterior segment of eyeball by eye drops administration, the inhibitory effect on the dye leakage in the allergic conjunctiviitis model in mice and the improvement effect on the corneal disorder in the corneal disorder model in rats were investigated. As a result, the present compound showed the inhibitory effect on the vascular hyper-permeability and the improvement effect on the corneal disorder. That is, the present compound is useful as a preventive or therapeutic agent for the inflammatory diseases of anterior segment of eyeball, especially as a preventive or therapeutic agent for allergic conjunctivitis and dry eye syndrome (it is also called "dry eye").

Furthermore, in order to evaluate the possibility of the present compound as a preventive or therapeutic agent for the inflammatory diseases of posterior segment of eyeball, the inhibitory effect on the choroidal neovascularization in choroidal neovascularization model in rats by eye drops administration was investigated. As a result, the present compound showed the inhibitory effect on neovascularization. That is, the present compound is useful as a preventive and therapeutic agent for the inflammatory diseases of posterior segment of eyeball, especially as a preventive and therapeutic agent for retinal diseases such as age-related macular degeneration, diabetic retinopathy.

In addition, in order to evaluate the possibility of the present compound as a preventive or therapeutic agent for the dermatitis, the inhibitory effect on the vascular hyper-permeability in atopic dermatitis model in mice by topical instillation was investigated. As a result, the present compound also showed the inhibitory effect on the vascular hyper-permeability in this model. That is, the present compound is useful as a preventive and therapeutic agent for the dermatitis, especially as a preventive and therapeutic agent for atopic dermatitis.

As the results of the above pharmaceutical tests, the present compound is useful as a GR agonist, as a pharmaceutical composition comprising at least one of the GR agonists as an active ingredient, as a preventive or therapeutic agent for inflammatory or immune diseases comprising at least one of the GR agonists as an active ingredient, as a preventive or therapeutic agent for ocular inflammatory diseases or dermatitis comprising at least one of the GR agonists as an active ingredient, and the like.

The present compound can be administered either orally or parenterally. Examples of the dosage form include a tablet, a capsule, a granule, a powder, an injection, an eye drop, a suppository, percutaneous absorption preparation, an ointment, an aerosol (including an inhalation) and the like and such a preparation can be prepared using a commonly used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polysorbate 80, polyoxy 40 stearate or polyoxyethylene hydrogenated castor oil 60; a stabilizer such as sodium citrate or sodium edetate; a preservative such as benzalkonium chloride, paraben, benzothonium chloride, p-hydroxybenzoate ester, sodium benzoate or chlorobutanol; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The dose of the present compound can be appropriately selected depending on the kinds of the symptoms, age, dosage form or the like. For example, in the case of an oral preparation, it can be administered in an amount of generally 0.01 to 1000 mg, preferably 1 to 100 mg per day in a single dose or several divided doses. Further, in the case of an eye drop, a preparation containing the present compound at a concentration of generally 0.0001% to 10% (w/v), preferably 0.01% to 5% (w/v) can be administered in a single dose or several divided doses.

Advantage of the Invention

This invention provides the glucocorticoid receptor agonists comprising the present compound which are useful as medicines, the pharmaceutical composition comprising at least one of the glucocorticoid receptor agonists as an active ingredient, the preventive and the therapeutic agent for inflammatory disease comprising at least one of the glucocorticoid receptor agonists as an active ingredient, and the preventive and the therapeutic agent for ocular inflammatory diseases or dermatitis at least one of the glucocorticoid receptor agonists as an active ingredient.

Especially, the glucocorticoid receptor agonists in this prevention are useful for the ocular inflammatory diseases or dermatitis, and useful as a preventive or therapeutic agent for inflammatory disease on anterior ocular segment such as keratitis, keratoconjunctivitis, conjunctivitis, blepharitis, dry eye syndrome (it is also called "dry eye"), allergic conjunctivitis, anterior uveitis, inflammation on anterior ocular segment after operation and inflammation by rejection of eye organization transplant; the inflammatory disease on posterior ocular segment such as age-related macular degeneration, diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury, retinitis, uvetis, scleritis, optic neuritis; and/or the dermatitis such as eczema/deramatitis, prurigo, urticaria, psoriasis and parapsoriasis, atopic dermatitis.

MODE FOR CARRYING OUT THE INVENTION

Hereinafter, Production Examples of the present compound, Preparation Examples and results of Pharmacological Test will be described. However, these examples are described for the purpose of understanding the present invention better and are not meant to limit the scope of the present invention.

PRODUCTION EXAMPLES

Reference Example 1

5-Hydroxymethyl-6-(2-methoxy-4-methoxymethoxyphenyl)-2,2,4-trimethyl-1,2-dihydroquinoline (Reference Compound No. 1-1)

Methyl 2-(2,4-dimethoxyphenyl)-5-nitrobenzoate (Reference Compound No. 1-1-(1))

A mixture of 2,4-dimethoxyphenylboronic acid (25.0 g, 137 mmol), methyl 2-bromo-5-nitrobenzoate (35.7 g, 137 mmol), cesium carbonate (89.4 g, 274 mmol) and bis(triphenylphosphine)palladium (II) dichloride (4.81 g, 6.85 mmol) was suspended in N, N-dimethylformamide (450 mL), and then stirred under argon atmosphere at 80° C. overnight. After cooling down, ethyl acetate (200 mL), diethylether (400 mL) and water (1000 mL) were added thereto, and then separated. The water layer was extracted with a mixed solvent of ethyl acetate (150 mL)-diethylether (150 mL) (twice). The organic layer was combined and washed with water (500 mL, 3 times) and saturated brine (500 mL) successively, dried over anhydrous magnesium sulfate, and then the solvent was removed under reduced pressure to give the titled reference compound as a brown oil.
(Quantitative)

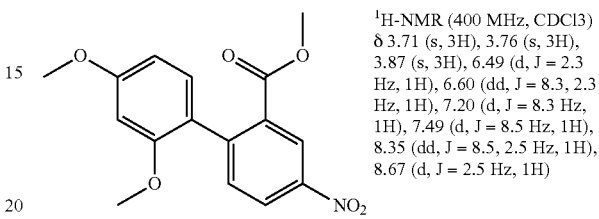

$^1$H-NMR (400 MHz, CDCl3) δ 3.71 (s, 3H), 3.76 (s, 3H), 3.87 (s, 3H), 6.49 (d, J = 2.3 Hz, 1H), 6.60 (dd, J = 8.3, 2.3 Hz, 1H), 7.20 (d, J = 8.3 Hz, 1H), 7.49 (d, J = 8.5 Hz, 1H), 8.35 (dd, J = 8.5, 2.5 Hz, 1H), 8.67 (d, J = 2.5 Hz, 1H)

3-Hydroxy-8-nitrobenzo[c]chromen-6-one (Reference Compound No. 1-1-(2))

A solution of methyl 2-(2,4-dimethoxyphenyl)-5-nitrobenzoate (Reference Compound No. 1-1-(1), 43.5 g, 137 mmol) in anhydrous methylene dichloride (250 mL) was cooled to −78° C., boron tribromide (96.2 g, 384 mmol) was added dropwise thereto, and then the mixture was stirred at room temperature for 1 hour. The mixture was cooled to −50° C. and methanol (300 mL) was added thereto. The precipitates were filtered with methanol to give the titled reference compound (18.0 g) as a yellow solid. (Yield 51%)

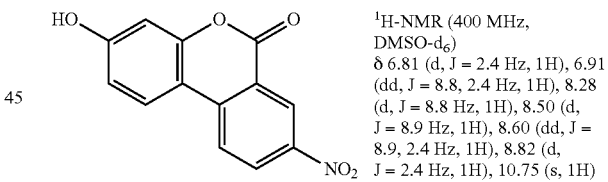

$^1$H-NMR (400 MHz, DMSO-d$_6$)
δ 6.81 (d, J = 2.4 Hz, 1H), 6.91 (dd, J = 8.8, 2.4 Hz, 1H), 8.28 (d, J = 8.8 Hz, 1H), 8.50 (d, J = 8.9 Hz, 1H), 8.60 (dd, J = 8.9, 2.4 Hz, 1H), 8.82 (d, J = 2.4 Hz, 1H), 10.75 (s, 1H)

8-Amino-3-hydroxybenzo[c]chromen-6-one (Reference Compound No. 1-1-(3))

3-Hydroxy-8-nitrobenzo[c]chromen-6-one (Reference Compound No. 1-1-(2), 52.01 g, 202 mmol) was dissolved in methanol (150 mL)-N,N-dimethylformamide (600 mL), 10% palladium on charcoal (5.00 g) was added thereto, and then the reaction mixture was stirred under hydrogen atmosphere (3 kgf/cm$^2$) at room temperature overnight. After the unsoluble materials were filtered, the methanol was removed under reduced pressure. Water (2 L) was added to the residue. The precipitated solid was filtered and dried at 90° C. under reduced pressure to give the titled reference compound (44.02 g) as a pale yellow solid.

8-Hydroxy-2,2,4-trimethyl-1,2-dihydro-6-oxa-1-azachrysen-5-one (Reference Compound No. 1-1-(4))

In a pressure tube, 8-amino-3-hydroxybenzo[c]chromen-6-one (Reference Compound No. 1-1-(3), 40.0 g, 176 mmol) was dissolved in acetone (440 mL)-N-methylpyrrolidone (240 mL), iodine (17.9 g, 70.5 mmol) was added thereto, the pressure tube was sealed, and then the reaction mixture was stirred at 110° C. for 3 days. After cooling down, acetone was removed under reduced pressure. To the obtained residue, ethyl acetate (700 mL), hexane (150 mL) and 1% aqueous sodium thiosulfate solution (700 mL) was added thereto and the mixture was separated. The water layer was extracted with a mixed solvent of ethyl acetate (250 mL)-hexane (50 mL) (3 times). The organic layer was combined and washed with water (500 mL, 3 times) and saturated brine (500 mL) successively, dried over anhydrous magnesium sulfate, and then the solvent was removed under reduced pressure. To the obtained residue, chloroform (150 mL) was added and the unsoluble materials were filtered. After the filtrate was concentrated, the residue was purified by silica gel column chromatography (hexane-ethyl acetate) to give the titled reference compound (26.0 g) as a yellow solid. (Yield 48%)

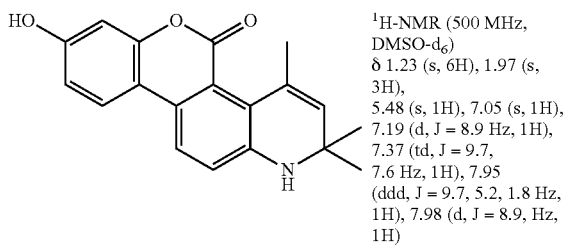

$^1$H-NMR (500 MHz, DMSO-$d_6$)
δ 1.23 (s, 6H), 1.97 (s, 3H), 5.48 (s, 1H), 7.05 (s, 1H), 7.19 (d, J = 8.9 Hz, 1H), 7.37 (td, J = 9.7, 7.6 Hz, 1H), 7.95 (ddd, J = 9.7, 5.2, 1.8 Hz, 1H), 7.98 (d, J = 8.9, Hz, 1H)

8-Methoxymethoxy-2,2,4-trimethyl-1,2-dihydro-6-oxa-1-azachrysen-5-one (Reference Compound No. 1-1-(5))

A mixture of 8-hydroxy-2,2,4-trimethyl-1,2-dihydro-6-oxa-1-azachrysen-5-one (Reference Compound No. 1-1-(4), 1.00 g, 3.25 mmol), chlorodimethylether (420 μL, 5.53 mmol) and potassium carbonate (1.35 g, 9.77 mmol) was suspended in anhydrous N,N-dimethylformamide (15 mL) and stirred at 50° C. overnight. After cooling down, ethyl acetate (100 mL) and diethylether (100 mL) were added thereto. The whole was washed with water (150 mL, 100 mL) and saturated brine (100 mL) successively, dried over anhydrous magnesium sulfate, and then the solvent was removed under reduced pressure. The obtained residue was purified by silica gel column chromatography (hexane-ethyl acetate) to give the titled reference compound (747 mg) as a yellow solid. (Yield 66%)

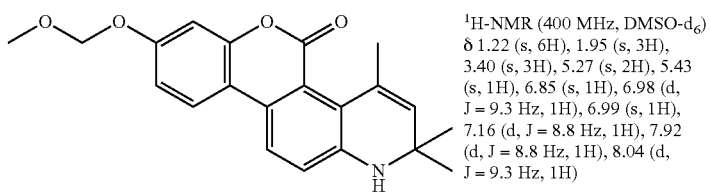

$^1$H-NMR (400 MHz, DMSO-$d_6$)
δ 1.22 (s, 6H), 1.95 (s, 3H), 3.40 (s, 3H), 5.27 (s, 2H), 5.43 (s, 1H), 6.85 (s, 1H), 6.98 (d, J = 9.3 Hz, 1H), 6.99 (s, 1H), 7.16 (d, J = 8.8 Hz, 1H), 7.92 (d, J = 8.8 Hz, 1H), 8.04 (d, J = 9.3 Hz, 1H)

6-(2-Hydroxy-4-methoxymethoxyphenyl)-5-hydroxymethyl-2,2,4-trimethyl-1,2-dihydroquinoline (Reference Compound No. 1-1-(6))

Lithium aluminum hydride (167 mg, 4.40 mmol) was suspended in anhydrous tetrahydrofuran (3 mL). A solution of 8-methoxymethoxy-2,2,4-trimethyl-1,2-dihydro-6-oxa-1-azachrysen-5-one (Reference Compound No. 1-1-(5), 744.1 mg, 2.12 mmol) in anhydrous tetrahydrofuran (10 mL) was added dropwise at 0° C., the reaction mixture was stirred at the same temperature for 30 minutes. Ethyl acetate (2 mL) and water (1 mL) were added to the reaction mixture successively, and then ethyl acetate (150 mL) was added thereto. 1N aqueous HCl solution (6 mL) was added, the mixture was washed with water (100 mL, twice) and saturated brine (50 mL) successively, and then dried over anhydrous magnesium sulfate. The solvent was removed under reduced pressure to give the titled reference compound (750.6 mg) as a pale yellow amorphous product. (Quantitative)

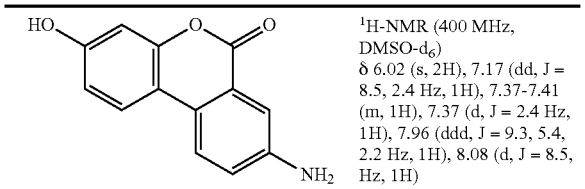

$^1$H-NMR (400 MHz, DMSO-$d_6$)
δ 6.02 (s, 2H), 7.17 (dd, J = 8.5, 2.4 Hz, 1H), 7.37-7.41 (m, 1H), 7.37 (d, J = 2.4 Hz, 1H), 7.96 (ddd, J = 9.3, 5.4, 2.2 Hz, 1H), 8.08 (d, J = 8.5, Hz, 1H)

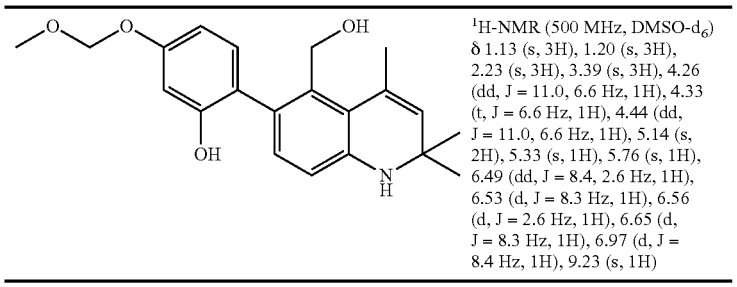

| | ¹H-NMR (500 MHz, DMSO-d$_6$) δ 1.13 (s, 3H), 1.20 (s, 3H), 2.23 (s, 3H), 3.39 (s, 3H), 4.26 (dd, J = 11.0, 6.6 Hz, 1H), 4.33 (t, J = 6.6 Hz, 1H), 4.44 (dd, J = 11.0, 6.6 Hz, 1H), 5.14 (s, 2H), 5.33 (s, 1H), 5.76 (s, 1H), 6.49 (dd, J = 8.4, 2.6 Hz, 1H), 6.53 (d, J = 8.3 Hz, 1H), 6.56 (d, J = 2.6 Hz, 1H), 6.65 (d, J = 8.3 Hz, 1H), 6.97 (d, J = 8.4 Hz, 1H), 9.23 (s, 1H) |
|---|---|

5-Hydroxymethyl-6-(2-methoxy-4-methoxymethoxyphenyl)-2,2,4-trimethyl-1,2-dihydroquinoline (Reference Compound No. 1-1)

A mixture of 6-(2-hydroxy-4-methoxymethoxyphenyl)-5-hydroxymethyl-2,2,4-trimethyl-1,2-dihydroquinoline (Reference Compound No. 1-1-(6), 746.1 mg, 2.10 mmol), methyl iodide (131 μL, 2.10 mmol) and potassium carbonate (582 mg, 4.21 mmol) was suspended in anhydrous N, N-dimethylformamide (10 mL) and stirred at 50° C. for 1 hour. After cooling down, the mixture was diluted with ethyl acetate (50 mL) and diethylether (50 mL). The mixture was washed with water (100 mL, twice) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (513.2 mg) as a colorless solid. (Yield 66%)

Reference Example 2

5-Chloromethyl-6-(2-methoxy-4-methoxymethoxyphenyl)-2,2,4-trimethyl-1,2-dihydroquinoline (Reference Compound No. 2)

5-Hydroxymethyl-6-(2-methoxy-4-methoxymethoxyphenyl)-2,2,4-trimethyl-1,2-dihydroquinoline (Reference Compound No. 1-1, 1.02 g, 2.76 mmol) was dissolved in anhydrous methylene dichloride (10 mL), and then triethylamine (0.490 mL, 3.52 mmol) and methanesulfonyl chloride (231 μL, 2.98 mmol) were added successively. The reaction mixture was stirred at room temperature for 5 hours. Chloroform (50 mL) and water (50 mL) were added to the reaction mixture and separated. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (515 mg) as an orange amorphous product. (Yield 49%)

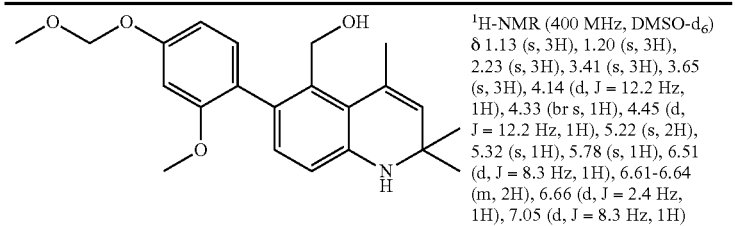

| | ¹H-NMR (400 MHz, DMSO-d$_6$) δ 1.13 (s, 3H), 1.20 (s, 3H), 2.23 (s, 3H), 3.41 (s, 3H), 3.65 (s, 3H), 4.14 (d, J = 12.2 Hz, 1H), 4.33 (br s, 1H), 4.45 (d, J = 12.2 Hz, 1H), 5.22 (s, 2H), 5.32 (s, 1H), 5.78 (s, 1H), 6.51 (d, J = 8.3 Hz, 1H), 6.61-6.64 (m, 2H), 6.66 (d, J = 2.4 Hz, 1H), 7.05 (d, J = 8.3 Hz, 1H) |
|---|---|

Using available compounds, the following Reference Compound No. 1-2 was obtained by a method similar to that of Reference Compound No. 1-1.

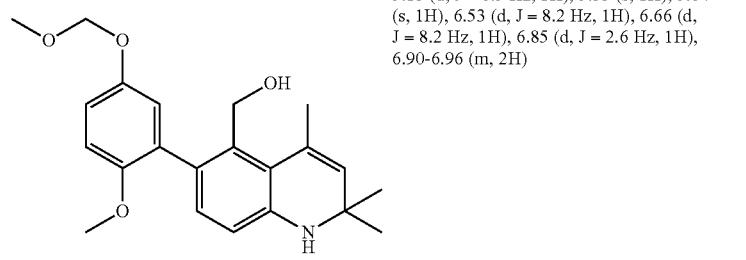

| 5-Hydroxymethyl-6-(2-methoxy-5-methoxymethoxyphenyl)-2,2,4-trimethyl-1,2-dihydroquinoline (Reference Compound No. 1-2) | ¹H-NMR (400 MHz, DMSO-d$_6$) δ 1.13 (s, 3H), 1.21 (s, 3H), 2.24 (s, 3H), 3.38 (s, 3H), 3.62 (s, 3H), 4.15 (dd, J = 12.2, 4.7 Hz, 1H), 4.38 (t, J = 4.7 Hz, 1H), 4.47 (dd, J = 12.2, 4.7 Hz, 1H), 5.11 (d, J = 6.5 Hz, 1H), 5.13 (d, J = 6.5 Hz, 1H), 5.33 (s, 1H), 5.84 (s, 1H), 6.53 (d, J = 8.2 Hz, 1H), 6.66 (d, J = 8.2 Hz, 1H), 6.85 (d, J = 2.6 Hz, 1H), 6.90-6.96 (m, 2H) |
|---|---|

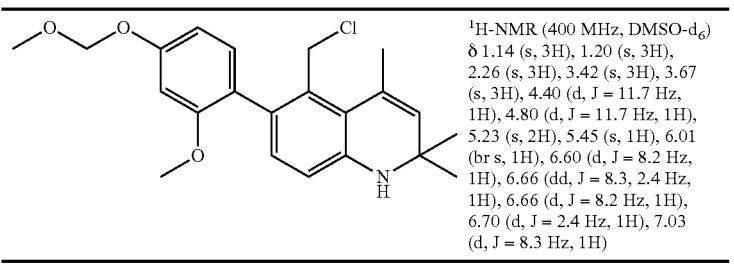

¹H-NMR (400 MHz, DMSO-d₆) δ 1.14 (s, 3H), 1.20 (s, 3H), 2.26 (s, 3H), 3.42 (s, 3H), 3.67 (s, 3H), 4.40 (d, J = 11.7 Hz, 1H), 4.80 (d, J = 11.7 Hz, 1H), 5.23 (s, 2H), 5.45 (s, 1H), 6.01 (br s, 1H), 6.60 (d, J = 8.2 Hz, 1H), 6.66 (dd, J = 8.3, 2.4 Hz, 1H), 6.66 (d, J = 8.2 Hz, 1H), 6.70 (d, J = 2.4 Hz, 1H), 7.03 (d, J = 8.3 Hz, 1H)

Reference Example 3

5-(5-Fluoro-2-methylphenoxymethyl)-6-(2-methoxy-4-methoxymethoxyphenyl)-2,2,4-trimethyl-1,2-dihydroquinoline (Reference Compound No. 3-1)

5-Hydroxymethyl-6-(2-methoxy-4-methoxymethoxyphenyl)-2,2,4-trimethyl-1,2-dihydroquinoline (Reference Compound No. 1-1, 511.7 mg, 1.39 mmol), 5-fluoro-2-methylphenol (182 μL, 1.67 mmol), tri-n-butylphosphine (521 μL, 2.09 mmol), and 1,1'-(azodicarbonyl) dipiperidine (526 mg, 2.08 mmol) were dissolved in anhydrous benzene (8 mL), and then the mixture was stirred under argon atmosphere at room temperature for 1 hour. Hexane (15 mL) was added to the reaction mixture, and the unsoluble materials were filtered. The filtrate was concentrated under reduced pressure and the residue was purified by silica gel column chromatography (hexane-ethyl acetate) to give the titled reference compound (411.4 mg) as a colorless amorphous product. (Yield 62%)

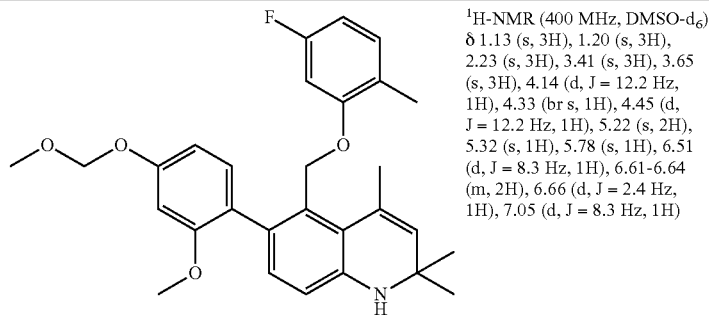

¹H-NMR (400 MHz, DMSO-d₆) δ 1.13 (s, 3H), 1.20 (s, 3H), 2.23 (s, 3H), 3.41 (s, 3H), 3.65 (s, 3H), 4.14 (d, J = 12.2 Hz, 1H), 4.33 (br s, 1H), 4.45 (d, J = 12.2 Hz, 1H), 5.22 (s, 2H), 5.32 (s, 1H), 5.78 (s, 1H), 6.51 (d, J = 8.3 Hz, 1H), 6.61-6.64 (m, 2H), 6.66 (d, J = 2.4 Hz, 1H), 7.05 (d, J = 8.3 Hz, 1H)

Using Reference Compound No. 1-1 or 1-2, the following Reference Compounds (No. 3-2~3-9) were obtained by a method similar to that of Reference Compound No. 3-1.

5-(5-Fluoro-2-methylphenoxymethyl)-6-(2-methoxy-5-methoxymethoxyphenyl)-2,2,4-trimethyl-1,2-dihydroquinoline (Reference Compound No. 3-2)

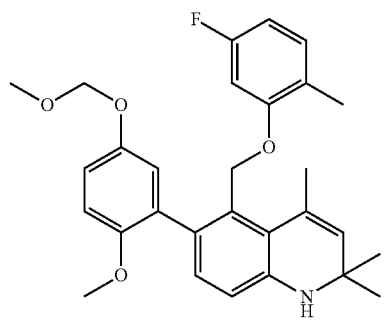

¹H-NMR (500 MHz, DMSO-d₆) δ 1.05 (s, 3H), 1.15 (s, 3H), 2.02 (s, 3H), 2.08 (s, 3H), 3.29 (s, 3H), 3.67 (s, 3H), 4.62 (d, J = 12.1 Hz, 1H), 5.02 (d, J = 6.7 Hz, 1H), 5.06 (d, J = 6.7 Hz, 1H), 5.10 (d, J = 12.1 Hz, 1H), 5.39 (s, 1H), 6.02 (s, 1H), 6.35 (dd, J = 11.6, 2.4 Hz, 1H), 6.52 (td, J = 8.4, 2.4 Hz, 1H), 6.63 (d, J = 8.2 Hz, 1H), 6.79 (d, J = 8.2 Hz, 1H), 6.86 (d, J = 2.7 Hz, 1H), 6.95 (dd, J = 8.9, 2.7 Hz, 1H), 6.97 (d, J = 8.9 Hz, 1H), 7.02-7.05 (m, 1H)

| | |
|---|---|
| 6-(2-Methoxy-4-methoxymethoxy-phenyl)-5-(2-methyl-5-nitro-phenoxymethyl)-2,2,4-trimethyl-1,2-dihydroquinoline (Reference Compound No. 3-3) 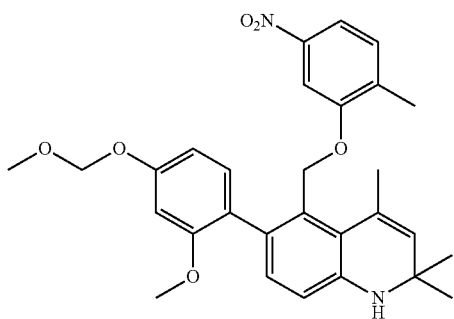 | $^1$H-NMR (400 MHz, DMSO-$d_6$) δ 0.87 (s, 3H), 1.17 (s, 3H), 2.13 (s, 3H), 2.18 (s, 3H), 3.39 (s, 3H), 3.72 (s, 3H), 4.79 (d, J = 12.7 Hz, 1H), 5.21 (s, 2H), 5.31 (d, J = 12.7 Hz, 1H), 5.38 (s, 1H), 5.97 (s, 1H), 6.59 (d, J = 8.2 Hz, 1H), 6.65 (dd, J = 8.2, 2.4 Hz, 1H), 6.70 (d, J = 2.4 Hz, 1H), 6.76 (d, J = 8.2 Hz, 1H), 7.12 (d, J = 2.1 Hz, 1H), 7.17 (d, J = 8.2 Hz, 1H), 7.32 (d, J = 8.7 Hz, 1H), 7.62 (dd, J = 8.7, 2.1 Hz, 1H) |
| 6-(2-Methoxy-4-methoxymethoxy-phenyl)-5-(2-methoxy-5-nitro-phenoxymethyl)-2,2,4-trimethyl-1,2-dihydroquinoline (Reference Compound No. 3-4) 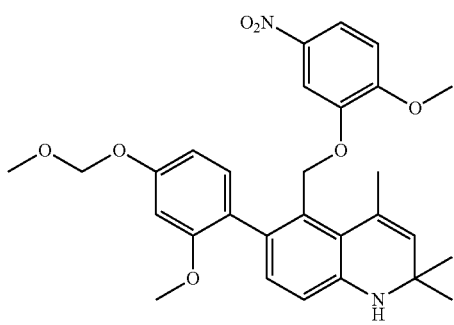 | $^1$H-NMR (400 MHz, DMSO-$d_6$) δ 1.01 (s, 3H), 1.17 (s, 3H), 2.14 (s, 3H), 3.67 (s, 3H), 3.82 (s, 3H), 3.90 (s, 3H), 4.67 (d, J = 12.1 Hz, 1H), 5.17 (s, 2H), 5.25 (d, J = 12.1 Hz, 1H), 5.38 (s, 1H), 5.96 (s, 1H), 6.54 (dd, J = 8.4, 2.3 Hz, 1H), 6.59 (d, J = 8.1 Hz, 1H), 6.64 (d, J = 2.3 Hz, 1H), 6.72 (d, J = 8.1 Hz, 1H), 7.04 (d, J = 8.4 Hz, 1H), 7.08 (d, J = 8.9 Hz, 1H), 7.28 (d, J = 2.7 Hz, 1H), 7.80 (dd, J = 8.9, 2.7 Hz, 1H) |
| 6-(2-Methoxy-4-methoxymethoxy-phenyl)-5-(4-methylbenzoyloxy-methyl)-2,2,4-trimethyl-1,2-dihydroquinoline (Reference Compound No. 3-5) 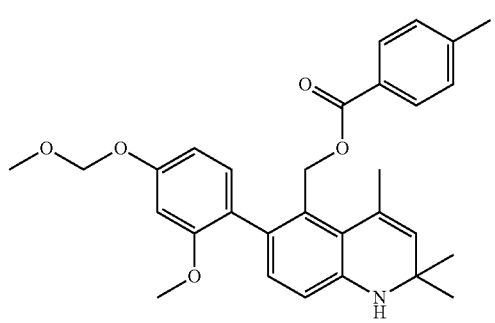 | $^1$H-NMR (400 MHz, DMSO-$d_6$) δ 1.14 (s, 3H), 1.23 (s, 3H), 2.07 (s, 3H), 2.35 (s, 3H), 3.39 (s, 3H), 3.64 (s, 3H), 4.97 (d, J = 12.8 Hz, 1H), 5.20 (d, J = 12.8 Hz, 1H), 5.20 (s, 2H), 5.44 (s, 1H), 6.05 (s, 1H), 6.58 (dd, J = 8.3, 2.3 Hz, 1H), 6.65 (d, J = 8.2 Hz, 1H), 6.66 (d, J = 2.3 Hz, 1H), 6.75 (d, J = 8.2 Hz, 1H), 7.04 (d, J = 8.3 Hz, 1H), 7.27 (d, J = 7.9 Hz, 2H), 7.71 (d, J = 7.9 Hz, 2H) |

| | |
|---|---|
| 6-(2-Methoxy-4-methoxymethoxy-phenyl)-5-(5-methylthiophen-2-ylcarbonyloxymethyl)-2,2,4-trimethyl-1,2-dihydroquinoline (Reference Compound No. 3-6)<br/>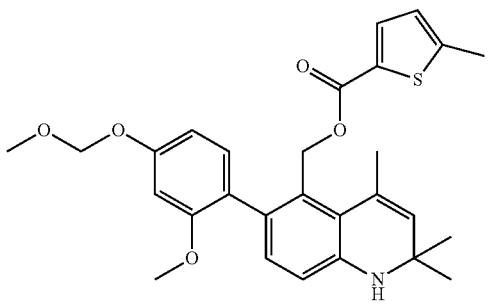 | $^1$H-NMR (400 MHz, DMSO-d$_6$) δ 1.14 (s, 3H), 1.21 (s, 3H), 2.07 (s, 3H), 2.47 (s, 3H), 3.40 (s, 3H), 3.64 (s, 3H), 4.90 (d, J = 12.7 Hz, 1H), 5.16 (d, J = 12.7 Hz, 1H), 5.21 (s, 2H), 5.43 (s, 1H), 6.04 (s, 1H), 6.59 (dd, J = 8.3, 2.4 Hz, 1H), 6.64 (d, J = 8.3 Hz, 1H), 6.67 (d, J = 2.4 Hz, 1H), 6.73 (d, J = 8.3 Hz, 1H), 6.88 (dd, J = 3.7, 1.1 Hz, 1H), 7.02 (d, J = 8.3 Hz, 1H), 7.47 (d, J = 3.7 Hz, 1H) |
| 5-(3-Fluorobenzoyloxymethyl)-6-(2-methoxy-4-methoxymethoxy-phenyl)-2,2,4-trimethyl-1,2-dihydroquinoline (Reference Compound No. 3-7)<br/>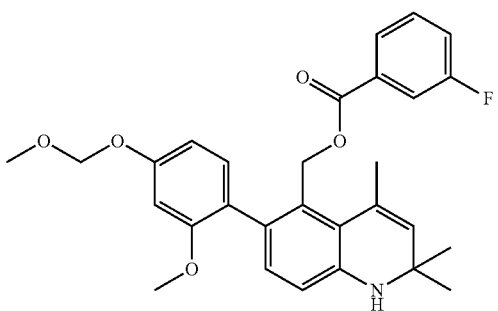 | $^1$H-NMR (500 MHz, DMSO-d$_6$) δ 1.13 (s, 3H), 1.23 (s, 3H), 2.09 (s, 3H), 3.40 (s, 3H), 3.65 (s, 3H), 5.05 (d, J = 12.8 Hz, 1H), 5.20 (s, 2H), 5.25 (d, J = 12.8 Hz, 1H), 5.46 (s, 1H), 6.07 (s, 1H), 6.59 (dd, J = 8.2, 2.4 Hz, 1H), 6.65 (d, J = 8.1 Hz, 1H), 6.67 (d, J = 2.4 Hz, 1H), 6.75 (d, J = 8.1 Hz, 1H), 7.04 (d, J = 8.2 Hz, 1H), 7.47-7.57 (m, 3H), 7.66 (dt, J = 7.6, 1.4 Hz, 1H) |
| 5-(5-Bromothiophen-2-ylcarbonyloxymethyl)-6-(2-methoxy-4-methoxymethoxyphenyl)-2,2,4-trimethyl-1,2-dihydroquinoline (Reference Compound No. 3-8)<br/>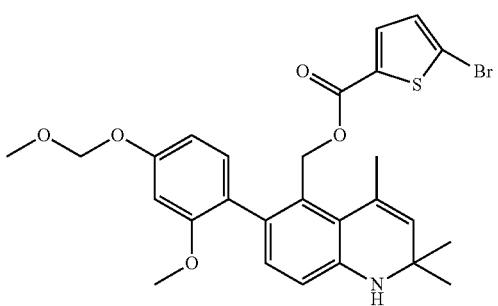 | $^1$H-NMR (400 MHz, DMSO-d$_6$) δ 1.12 (s, 3H), 1.22 (s, 3H), 2.08 (s, 3H), 3.40 (s, 3H), 3.65 (s, 3H), 4.97 (d, J = 12.9 Hz, 1H), 5.20 (d, J = 12.9 Hz, 1H), 5.21 (s, 2H), 5.45 (s, 1H), 6.06 (s, 1H), 6.59 (dd, J = 8.3, 2.3 Hz, 1H), 6.64 (d, J = 8.2 Hz, 1H), 6.67 (d, J = 2.3 Hz, 1H), 6.74 (d, J = 8.2 Hz, 1H), 7.03 (d, J = 8.3 Hz, 1H), 7.33 (d, J = 4.0 Hz, 1H), 7.49 (d, J = 4.0 Hz, 1H) |

| | |
|---|---|
| 5-(4-Methoxybenzoyloxymethyl)-6-(2-methoxy-4-methoxymethoxyphenyl)-2,2,4-trimethyl-1,2-dihydroquinoline (Reference Compound No. 3-9) 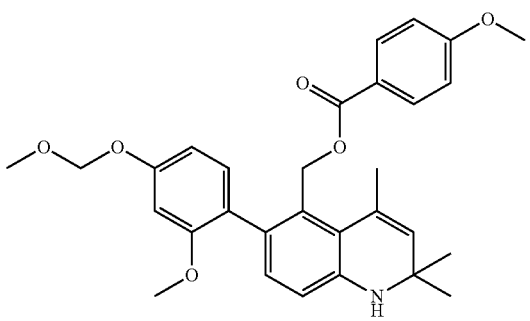 | $^1$H-NMR (400 MHz, DMSO-d$_6$) δ 1.14 (s, 3H), 1.23 (s, 3H), 2.07 (s, 3H), 3.40 (s, 3H), 3.64 (s, 3H), 3.81 (s, 3H), 4.95 (d, J = 12.9 Hz, 1H), 5.18 (d, J = 12.9 Hz, 1H), 5.20 (s, 2H), 5.44 (s, 1H), 6.05 (br s, 1H), 6.59 (dd, J = 8.3, 2.3 Hz, 1H), 6.64 (d, J = 8.1 Hz, 1H), 6.66 (d, J = 2.3 Hz, 1H), 6.74 (d, J = 8.1 Hz, 1H), 6.99 (d, J = 8.9 Hz, 2H), 7.04 (d, J = 8.3 Hz, 1H), 7.77 (d, J = 8.9 Hz, 2H) |

Reference Example 4

6-(2-Methoxy-4-methoxymethoxyphenyl)-5-(2-methoxyphenylaminomethyl)-2,2,4-trimethyl-1,2-dihydroquinoline (Reference Compound No. 4-1)

A mixture of 5-chloromethyl-6-(2-methoxy-4-methoxymethoxyphenyl)-2,2,4-trimethyl-1,2-dihydroquinoline (Reference Compound No. 2, 262 mg, 0.675 mmol), 2-methoxyaniline (84 μL, 0.74 mmol) and potassium carbonate (151 mg, 1.09 mmol) was suspended in anhydrous N,N-dimethylformamide (4 mL) and the suspension was stirred at 80° C. overnight. After cooling down, ethyl acetate (20 mL) and water (20 mL) were added to the reaction mixture and separated. The organic layer was washed with saturated brine (20 mL), dried over anhydrous magnesium sulfate, and then the solvent was removed under reduced pressure. The obtained residue was purified by silica gel column chromatography (hexane-ethyl acetate) to give the titled reference compound (196 mg) as a yellow amorphous product. (Yield 61%)

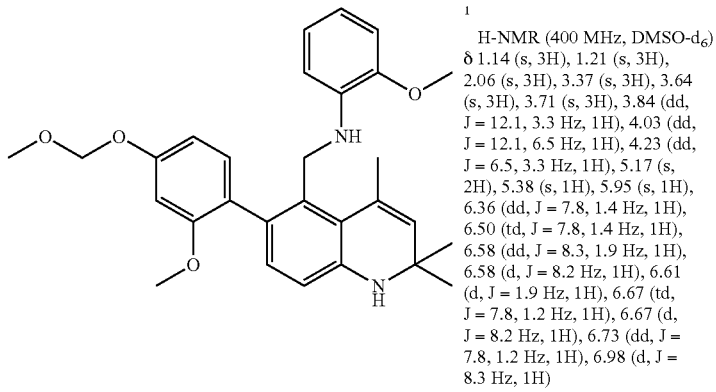

$^1$H-NMR (400 MHz, DMSO-d$_6$) δ 1.14 (s, 3H), 1.21 (s, 3H), 2.06 (s, 3H), 3.37 (s, 3H), 3.64 (s, 3H), 3.71 (s, 3H), 3.84 (dd, J = 12.1, 3.3 Hz, 1H), 4.03 (dd, J = 12.1, 6.5 Hz, 1H), 4.23 (dd, J = 6.5, 3.3 Hz, 1H), 5.17 (s, 2H), 5.38 (s, 1H), 5.95 (s, 1H), 6.36 (dd, J = 7.8, 1.4 Hz, 1H), 6.50 (td, J = 7.8, 1.4 Hz, 1H), 6.58 (dd, J = 8.3, 1.9 Hz, 1H), 6.58 (d, J = 8.2 Hz, 1H), 6.61 (d, J = 1.9 Hz, 1H), 6.67 (td, J = 7.8, 1.2 Hz, 1H), 6.67 (d, J = 8.2 Hz, 1H), 6.73 (dd, J = 7.8, 1.2 Hz, 1H), 6.98 (d, J = 8.3 Hz, 1H)

Using Reference Compound No. 2, the following Reference Compound No. 4-2 was obtained by a method similar to that of Reference Compound No. 4-1.

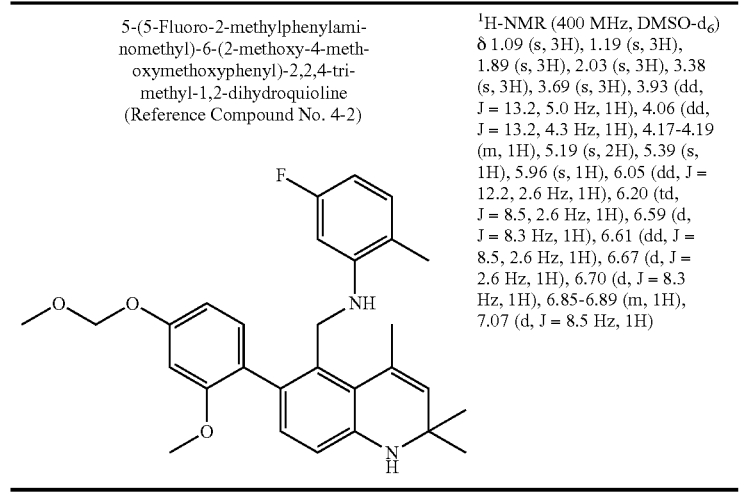

| 5-(5-Fluoro-2-methylphenylaminomethyl)-6-(2-methoxy-4-methoxymethoxyphenyl)-2,2,4-trimethyl-1,2-dihydroquioline (Reference Compound No. 4-2) | $^1$H-NMR (400 MHz, DMSO-$d_6$) δ 1.09 (s, 3H), 1.19 (s, 3H), 1.89 (s, 3H), 2.03 (s, 3H), 3.38 (s, 3H), 3.69 (s, 3H), 3.93 (dd, J = 13.2, 5.0 Hz, 1H), 4.06 (dd, J = 13.2, 4.3 Hz, 1H), 4.17-4.19 (m, 1H), 5.19 (s, 2H), 5.39 (s, 1H), 5.96 (s, 1H), 6.05 (dd, J = 12.2, 2.6 Hz, 1H), 6.20 (td, J = 8.5, 2.6 Hz, 1H), 6.59 (d, J = 8.3 Hz, 1H), 6.61 (dd, J = 8.5, 2.6 Hz, 1H), 6.67 (d, J = 2.6 Hz, 1H), 6.70 (d, J = 8.3 Hz, 1H), 6.85-6.89 (m, 1H), 7.07 (d, J = 8.5 Hz, 1H) |

Reference Example 5

5-(5-Fluoro-2-methylphenoxymethyl)-6-(4-hydroxy-2-methoxyphenyl)-2,2,4-trimethyl-1,2-dihydroquinoline (Reference Compound No. 5-1)

5-(5-Fluoro-2-methylphenoxymethyl)-6-(2-methoxy-4-methoxymethoxyphenyl)-2,2,4-trimethyl-1,2-dihydroquinoline (Reference Compound No. 3-1, 424 mg, 0.888 mmol) was dissolved in 1,4-dioxane (5 mL), 4N HCl/1,4-dioxane solution (666 μL) was added thereto, and then the mixture was stirred at room temperature overnight. The mixture was diluted with ethyl acetate (150 mL). The mixture was washed with water (100 mL, twice) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (241.7 mg) as a colorless solid. (Yield 63%)

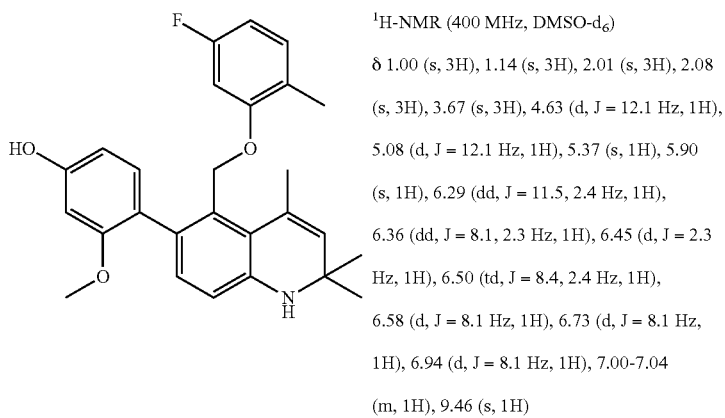

$^1$H-NMR (400 MHz, DMSO-$d_6$)

δ 1.00 (s, 3H), 1.14 (s, 3H), 2.01 (s, 3H), 2.08 (s, 3H), 3.67 (s, 3H), 4.63 (d, J = 12.1 Hz, 1H), 5.08 (d, J = 12.1 Hz, 1H), 5.37 (s, 1H), 5.90 (s, 1H), 6.29 (dd, J = 11.5, 2.4 Hz, 1H), 6.36 (dd, J = 8.1, 2.3 Hz, 1H), 6.45 (d, J = 2.3 Hz, 1H), 6.50 (td, J = 8.4, 2.4 Hz, 1H), 6.58 (d, J = 8.1 Hz, 1H), 6.73 (d, J = 8.1 Hz, 1H), 6.94 (d, J = 8.1 Hz, 1H), 7.00-7.04 (m, 1H), 9.46 (s, 1H)

Using any compounds among Reference Compounds No. 3-2~3-9 and 4-1~4-2, the following Reference Compounds (No. 5-2~5-11) were obtained by a method similar to that of Reference Compound No. 5-1.

5-(5-Fluoro-2-methylphenoxymethyl)-6-(5-hydroxy-2-methoxyphenyl)-2,2,4-trimethyl-1,2-dihydroquinoline (Reference Compound No. 5-2)

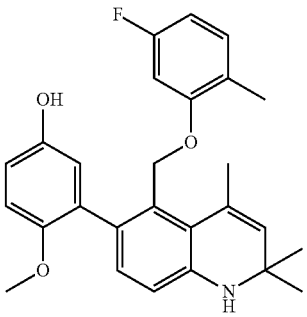

$^1$H-NMR (400 MHz, DMSO-d$_6$) δ 1.02 (s, 3H), 1.15 (s, 3H), 2.01 (s, 3H), 2.06 (s, 3H), 3.61 (s, 3H), 4.65 (d, J = 12.2 Hz, 1H), 5.10 (d, J = 12.2 Hz, 1H), 5.38 (s, 1H), 5.99 (s, 1H), 6.33 (dd, J = 11.5, 2.4 Hz, 1H), 6.51 (td, J = 8.4, 2.4 Hz, 1H), 6.59 (d, J = 2.9 Hz, 1H), 6.61 (d, J = 8.3 Hz, 1H), 6.67 (dd, J = 8.8, 2.9 Hz, 1H), 6.75 (d, J = 8.3 Hz, 1H), 6.85 (d, J = 8.8 Hz, 1H), 7.00-7.04 (m, 1H), 8.93(s, 1H)

6-(4-Hydroxy-2-methoxyphenyl)-5-(2-methyl-5-nitrophenoxymethyl)-2,2,4-trimethyl-1,2-dihydroquinoline (Reference Compound No. 5-3)

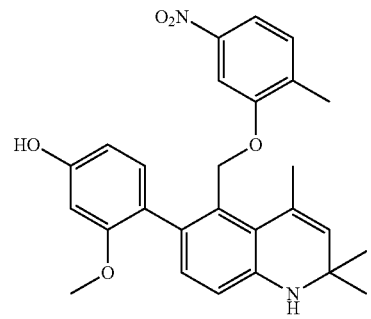

$^1$H-NMR (400 MHz, DMSO-d$_6$) δ 0.85 (s, 3H), 1.17 (s, 3H), 2.13 (s, 3H), 2.18 (s, 3H), 3.68 (s, 3H), 4.79 (d, J = 12.5 Hz, 1H), 5.30 (d, J = 12.5 Hz, 1H), 5.37 (s, 1H), 5.92 (s, 1H), 6.40 (dd, J = 8.2, 2.3 Hz, 1H), 6.46 (d, J = 2.3 Hz, 1H), 6.57 (d, J = 8.3 Hz, 1H), 6.74 (d, J = 8.3 Hz, 1H), 7.05 (d, J = 8.2 Hz, 1H), 7.11 (d, J = 2.3 Hz, 1H), 7.32 (d, J = 8.3 Hz, 1H), 7.62 (dd, J = 8.3, 2.3 Hz, 1H), 9.50 (s, 1H)

6-(4-Hydroxy-2-methoxyphenyl)-5-(2-methoxy-5-nitrophenoxymethyl)-2,2,4-trimethyl-1,2-dihydroquinoline (Reference Compound No. 5-4)

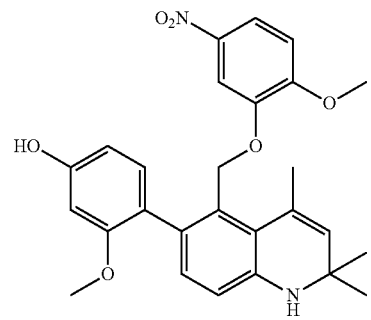

$^1$H-NMR (400 MHz, CDCl$_3$) δ 0.98 (s, 3H), 1.17 (s, 3H), 2.13 (s, 3H), 3.63 (s, 3H), 3.82 (s, 3H), 4.67 (d, J = 12.0 Hz, 1H), 5.24 (d, J = 12.0 Hz, 1H), 5.36 (s, 1H), 5.90 (s, 1H), 6.28 (dd, J = 8.3, 2.2 Hz, 1H), 6.40 (d, J = 2.2 Hz, 1H), 6.58 (d, J = 8.2 Hz, 1H), 6.71 (d, J = 8.2 Hz, 1H), 6.94 (d, J = 8.3 Hz, 1H), 7.08 (d, J = 9.2 Hz, 1H), 7.28 (d, J = 2.8 Hz, 1H), 7.79 (dd, J = 9.2, 2.8 Hz, 1H), 9.40 (s, 1H)

| | |
|---|---|
| 6-(4-Hydroxy-2-methoxyphenyl)-5-(4-methylbenzoyloxymethyl)-2,2,4-trimethyl-1,2-dihydroquinoline (Reference Compound No. 5-5)<br />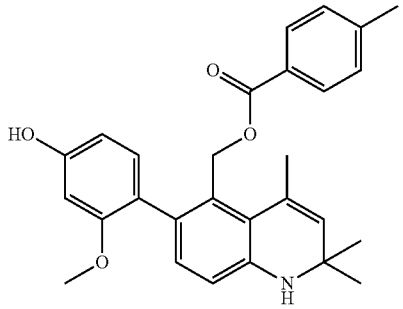 | $^1$H-NMR (500 MHz, DMSO-d$_6$) δ 1.15 (s, 3H), 1.22 (s, 3H), 2.06 (s, 3H), 2.35 (s, 3H), 3.60 (s, 3H), 4.96 (d, J = 12.7 Hz, 1H), 5.19 (d, J = 12.7 Hz, 1H), 5.43 (s, 1H), 6.00 (s, 1H), 6.31 (dd, J = 8.2, 2.4 Hz, 1H), 6.41 (d, J = 2.4 Hz, 1H), 6.63 (d, J = 8.2 Hz, 1H), 6.73 (d, J = 8.2 Hz, 1H), 6.89 (d, J = 8.2 Hz, 1H), 7.27 (d, J = 8.1 Hz, 2H), 7.72 (d, J = 8.1 Hz, 2H), 9.42 (s, 1H) |
| 6-(4-Hydroxy-2-methoxyphenyl)-5-(5-methylthiophen-2-ylcarbonyloxymethyl)-2,2,4-trimethyl-1,2-dihydroquinoline (Reference Compound No. 5-6)<br />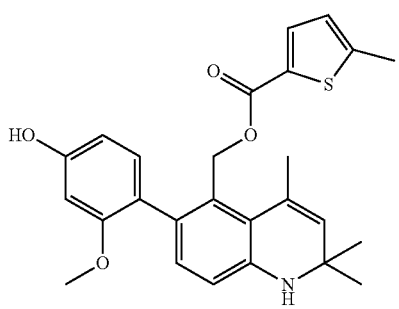 | $^1$H-NMR (500 MHz, DMSO-d$_6$) δ 1.14 (s, 3H), 1.21 (s, 3H), 2.06 (s, 3H), 2.47 (s, 3H), 3.60 (s, 3H), 4.89 (d, J = 12.7 Hz, 1H), 5.15 (d, J = 12.7 Hz, 1H), 5.42 (s, 1H), 5.99 (s, 1H), 6.31 (dd, J = 8.1, 2.1 Hz, 1H), 6.42 (d, J = 2.1 Hz, 1H), 6.62 (d, J = 8.2 Hz, 1H), 6.72 (d, J = 8.2 Hz, 1H), 6.88 (d, J = 8.1 Hz, 1H), 6.88 (dd, J = 3.7, 1.1 Hz, 1H), 7.47 (d, J = 3.7 Hz, 1H), 9.43 (s, 1H) |
| 5-(3-Fluorobenzoyloxymethyl)-6-(4-hydroxy-2-methoxyphenyl)-2,2,4-trimethyl-1,2-dihydroquinoline (Reference Compound No. 5-7)<br />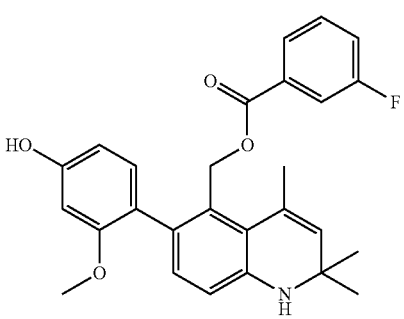 | $^1$H-NMR (500 MHz, DMSO-d$_6$) δ 1.13 (s, 3H), 1.23 (s, 3H), 2.07 (s, 3H), 3.60 (s, 3H), 5.03 (d, J = 12.8 Hz, 1H), 5.23 (d, J = 12.8 Hz, 1H), 5.45 (s, 1H), 6.03 (s, 1H), 6.32 (dd, J = 8.1, 2.4 Hz, 1H), 6.42 (d, J = 2.4 Hz, 1H), 6.64 (d, J = 8.1 Hz, 1H), 6.74 (d, J = 8.1 Hz, 1H), 6.90 (d, J = 8.1 Hz, 1H), 7.48-7.57 (m, 3H), 7.66-7.67 (m, 1H), 9.43 (s, 1H) |

| | |
|---|---|
| 5-(5-Bromothiophen-2-ylcarbonyloxymethyl)-6-(4-hydroxy-2-methoxyphenyl)-2,2,4-trimethyl-1,2-dihydroquinoline (Reference Compound No. 5-8)<br>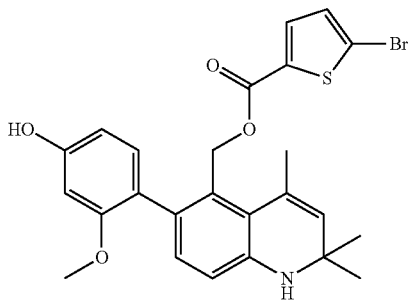 | $^1$H-NMR (400 MHz, DMSO-d$_6$) δ 1.13 (s, 3H), 1.21 (s, 3H), 2.06 (s, 3H), 3.60 (s, 3H), 4.95 (d, J = 12.6 Hz, 1H), 5.18 (d, J = 12.6 Hz, 1H), 5.44 (s, 1H), 6.02 (s, 1H), 6.32 (dd, J = 8.1, 2.3 Hz, 1H), 6.41 (d, J = 2.3 Hz, 1H), 6.63 (d, J = 8.3 Hz, 1H), 6.72 (d, J = 8.3 Hz, 1H), 6.88 (d, J = 8.1 Hz, 1H), 7.33 (d, J = 4.0 Hz, 1H), 7.49 (d, J = 4.0 Hz, 1H), 9.44 (s, 1H) |
| 6-(4-Hydroxy-2-methoxyphenyl)-5-(4-methoxybenzoyloxymethyl)-2,2,4-trimethyl-1,2-dihydroquinoline (Reference Compound No. 5-9)<br>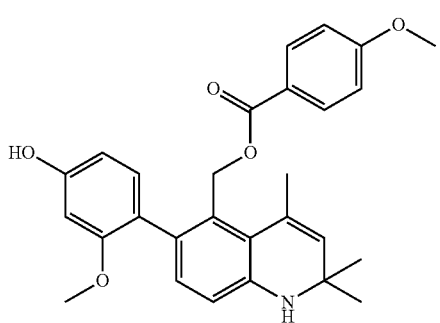 | $^1$H-NMR (500 MHz, DMSO-d$_6$) δ 1.15 (s, 3H), 1.22 (s, 3H), 2.06 (s, 3H), 3.60 (s, 3H), 3.81 (s, 3H), 4.94 (d, J = 12.7 Hz, 1H), 5.16 (d, J = 12.7 Hz, 1H), 5.43 (s, 1H), 5.99 (s, 1H), 6.31 (dd, J = 8.0, 2.2 Hz, 1H), 6.41 (d, J = 2.2 Hz, 1H), 6.63 (d, J = 8.2 Hz, 1H), 6.73 (d, J = 8.2 Hz, 1H), 6.89 (d, J = 8.0 Hz, 1H), 6.99 (dt, J = 9.2, 2.2 Hz, 2H), 7.78 (dt, J = 9.2, 2.2 Hz, 2H), 9.41 (s, 1H) |

| Compound | NMR |
|---|---|
| 6-(4-Hydroxy-2-methoxyphenyl)-5-(2-methoxyphenylaminomethyl)-2,2,4-trimethyl-1,2-dihydroquioline (Reference Compound No. 5-10) 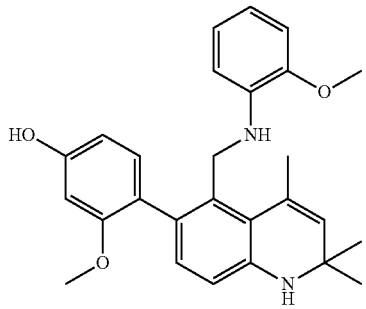 | $^1$H-NMR (500 MHz, DMSO-$d_6$) δ 1.13 (s, 3H), 1.21 (s, 3H), 2.06 (s, 3H), 3.59 (s, 3H), 3.71 (s, 3H), 3.83 (dd, J = 12.2, 3.4 Hz, 1H), 4.02 (dd, J = 12.2, 6.7 Hz, 1H), 4.23 (dd, J = 6.7, 3.4 Hz, 1H), 5.37 (s, 1H), 5.90 (s, 1H), 6.31 (dd, J = 8.2, 2.2 Hz, 1H), 6.35 (dd, J = 7.7, 1.6 Hz, 1H), 6.36 (d, J = 2.2 Hz, 1H), 6.50 (td, J = 7.7, 1.6 Hz, 1H), 6.56 (d, J = 8.1 Hz, 1H), 6.66 (d, J = 8.1 Hz, 1H), 6.68 (td, J = 7.7, 1.2 Hz, 1H), 6.73 (dd, J = 7.7, 1.2 Hz, 1H), 6.84 (d, J = 8.2 Hz, 1H), 9.36 (s, 1H) |
| 5-(5-Fluoro-2-methylphenylaminomethyl)-6-(4-hydroxy-2-methoxyphenyl)-2,2,4-trimethyl-1,2-dihydroquioline (Reference Compound No. 5-11) 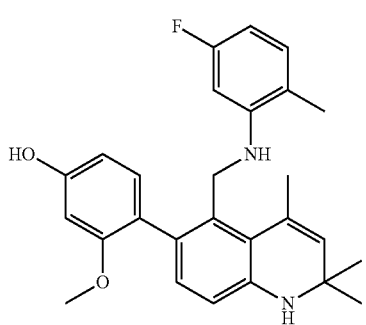 [SMILES: COc1cc(O)ccc1-c1ccc2c(c1COc1cc(F)ccc1C)C(C)=CC(C)(C)N2] | $^1$H-NMR (400 MHz, DMSO-$d_6$) δ 1.09 (s, 3H), 1.19 (s, 3H), 1.89 (s, 3H), 2.04 (s, 3H), 3.65 (s, 3H), 3.93 (dd, J = 13.3, 6.7 Hz, 1H), 4.02-4.07 (m, 1H), 4.14-4.17 (m, 1H), 5.39 (s, 1H), 5.93 (s, 1H), 6.06 (dd, J = 12.1, 2.5 Hz, 1H), 6.20 (td, J = 8.4, 2.5 Hz, 1H), 6.35 (dd, J = 8.1, 2.2 Hz, 1H), 6.42 (d, J = 2.2 Hz, 1H), 6.57 (d, J = 8.2 Hz, 1H), 6.69 (d, J = 8.2 Hz, 1H), 6.86-6.89 (m, 1H), 6.93 (d, J = 8.1 Hz, 1H), 9.41 (s, 1H) |

Reference Example 6

6-(4-Hydroxy-2-methoxyphenyl)-5-[N-(2-methoxyphenyl)-N-(9-fluorenylmethoxycarbonyl)aminomethyl]-2,2,4-trimethyl-1,2-dihydroquinoline (Reference Compound No. 6)

6-(4-Hydroxy-2-methoxyphenyl)-5-(2-methoxyphenylaminomethyl)-2,2,4-trimethyl-1,2-dihydroquinoline (Reference Compound No. 5-10, 37.7 mg, 0.0876 mmol) and sodium hydrogen carbonate (9.5 mg, 0.113 mmol) were dissolved in 1,4-dioxane (0.5 mL)-water (0.5 mL), and then 9-fluorenylmethoxycarbonyl chloride (25.6 mg, 0.0990 mmol) was added thereto under ice cooling. After the reaction mixture was stirred at room temperature for 3 hours, it was diluted with ethyl acetate (10 mL). The mixture was washed with 1N aqueous HCl solution (10 mL), water (10 mL) and saturated brine (10 mL) successively, dried over anhydrous magnesium sulfate, and then the solvent was removed under reduced pressure. The obtained residue was purified by silica gel column chromatography (hexane-ethyl acetate) to give the titled reference compound (19.7 mg) as a colorless amorphous product. (Yield 34%)

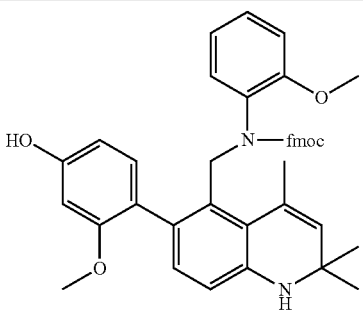

$^1$H-NMR (400 MHz, DMSO-$d_6$) δ 1.22 (s, 3H), 1.28 (s, 3H), 2.20 (s, 3H), 3.29 (s, 3H), 3.61 (s, 3H), 3.89 (s, 2H), 5.30 (d, J = 14.3 Hz, 1H), 5.45 (s, 1H), 5.81 (d, J = 14.3 Hz, 1H), 5.85 (s, 1H), 6.22 (dd, J = 8.2, 2.1 Hz, 1H), 6.34-6.35 (m, 2H), 6.43 (d, J = 8.3 Hz, 1H), 6.63-6.65 (m, 2H), 6.87-6.91 (m, 3H), 7.09-7.25 (m, 4H), 7.31-7.35 (m, 2H), 7.79 (d, J = 7.6 Hz, 2H), 9.32 (s, 1H)

Example 1

6-(4-Benzoyloxy-2-methoxyphenyl)-5-(5-fluoro-2-methylphenoxymethyl)-2,2,4-trimethyl-1,2-dihydroquinoline (Compound No. 1-1)

5-(5-Fluoro-2-methylphenoxymethyl)-6-(4-hydroxy-2-methoxyphenyl)-2,2,4-trimethyl-1,2-dihydroquinoline (Reference Compound No. 5-1, 25.5 mg, 0.588 mmol) was dissolved in anhydrous tetrahydrofuran (0.5 mL), then triethylamine (19.7 μL, 0.141 mmol) and benzoyl chloride (8.2 μL, 0.071 mmol) were added thereto. The reaction mixture was stirred at room temperature for 30 minutes. The mixture was diluted with ethyl acetate (100 mL). The mixture was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (26.7 mg) as a colorless solid. (Yield 63%)

6-[4-(Furan-2-ylcarbonyloxy)-2-methoxyphenyl]-5-(2-methoxy phenylaminomethyl)-2,2,4-trimethyl-1,2-dihydroquinoline (Compound No. 1-3)

6-(4-Hydroxy-2-methoxyphenyl)-5-[N-(2-methoxyphenyl)-N-(9-fluorenylmethoxycarbonyl)aminomethyl]-2,2,4-trimethyl-1,2-dihydroquinoline (Reference Compound No.

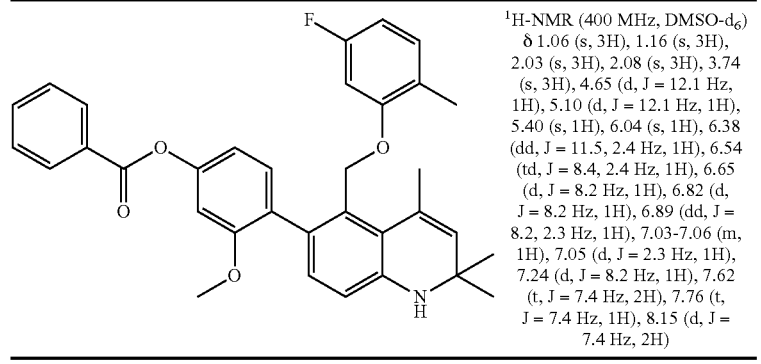

$^1$H-NMR (400 MHz, DMSO-$d_6$) δ 1.06 (s, 3H), 1.16 (s, 3H), 2.03 (s, 3H), 2.08 (s, 3H), 3.74 (s, 3H), 4.65 (d, J = 12.1 Hz, 1H), 5.10 (d, J = 12.1 Hz, 1H), 5.40 (s, 1H), 6.04 (s, 1H), 6.38 (dd, J = 11.5, 2.4 Hz, 1H), 6.54 (td, J = 8.4, 2.4 Hz, 1H), 6.65 (d, J = 8.2 Hz, 1H), 6.82 (d, J = 8.2 Hz, 1H), 6.89 (dd, J = 8.2, 2.3 Hz, 1H), 7.03-7.06 (m, 1H), 7.05 (d, J = 2.3 Hz, 1H), 7.24 (d, J = 8.2 Hz, 1H), 7.62 (t, J = 7.4 Hz, 2H), 7.76 (t, J = 7.4 Hz, 1H), 8.15 (d, J = 7.4 Hz, 2H)

6-(4-t-Butoxycarbonylaminoacetoxy-2-methoxyphenyl)-5-(5-fluoro-2-methylphenoxymethyl)-2,2,4-trimethyl-1,2-dihydroquinoline (Compound No. 1-2)

5-(5-Fluoro-2-methylphenoxymethyl)-6-(4-hydroxy-2-methoxyphenyl)-2,2,4-trimethyl-1,2-dihydroquinoline (Reference Compound No. 5-1, 30.2 mg, 0.070 mmol) and Boc-glycine (15.1 mg, 0.086 mmol) were dissolved in N,N-dimethylformamide (1 mL), N, N-diisopropylethylamine (31.4 μL, 0.18 mmol) and O-(7-azabenzotriazol-1-yl)-N,N,N',N'-tetramethyluronium hexafluorophosphate (35.4 mg, 0.093 mmol) were added thereto, and then the mixture was stirred at room temperature overnight. Ethyl acetate (10 mL) was added to the reaction mixture, then the mixture was washed with water (10 mL) and saturated brine (10 mL) successively. The organic layer was dried over anhydrous magnesium sulfate and the solvent was removed under reduced pressure. The obtained residue was purified by silica gel column chromatography (hexane-ethyl acetate) to give the titled compound (35.3 mg) as a colorless amorphous product. (Yield 86%)

6, 17.4 mg, 0.0267 mmol) was dissolved in methylene dichloride (0.5 mL), and then triethylamine (10 μL, 0.072 mmol) and 2-furoyl chloride (3.6 μL, 0.036 mmol) were added thereto successively. After the reaction mixture was stirred at room temperature for 3 hours, the reaction mixture was purified by silica gel column chromatography (hexane-ethyl acetate) to give a colorless amorphous product (15.6 mg). The obtained colorless amorphous product (11.8 mg) was dissolved in N,N-dimethylformamide (0.3 mL) and piperidine (15.6 μL, 0.158 mmol) was added thereto. After the reaction mixture was stirred at room temperature for 1 minute, it was diluted with ethyl acetate (10 mL). The reaction mixture was washed with water (10 mL) and saturated brine (10 mL) successively, dried over anhydrous magnesium sulfate, and then the solvent was removed under reduced pressure. The obtained residue was purified by silica gel column chromatography (hexane-ethyl acetate) to give the titled compound (6.0 mg) as a colorless solid. (Yield 76%)

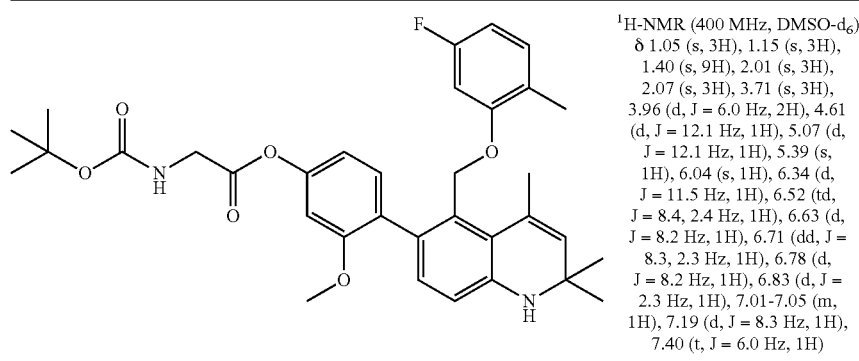

$^1$H-NMR (400 MHz, DMSO-$d_6$) δ 1.05 (s, 3H), 1.15 (s, 3H), 1.40 (s, 9H), 2.01 (s, 3H), 2.07 (s, 3H), 3.71 (s, 3H), 3.96 (d, J = 6.0 Hz, 2H), 4.61 (d, J = 12.1 Hz, 1H), 5.07 (d, J = 12.1 Hz, 1H), 5.39 (s, 1H), 6.04 (s, 1H), 6.34 (d, J = 11.5 Hz, 1H), 6.52 (td, J = 8.4, 2.4 Hz, 1H), 6.63 (d, J = 8.2 Hz, 1H), 6.71 (dd, J = 8.3, 2.3 Hz, 1H), 6.78 (d, J = 8.2 Hz, 1H), 6.83 (d, J = 2.3 Hz, 1H), 7.01-7.05 (m, 1H), 7.19 (d, J = 8.3 Hz, 1H), 7.40 (t, J = 6.0 Hz, 1H)

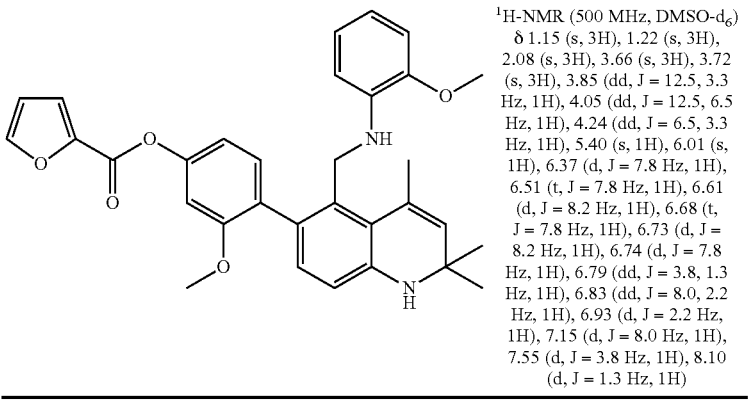

¹H-NMR (500 MHz, DMSO-d₆)
δ 1.15 (s, 3H), 1.22 (s, 3H), 2.08 (s, 3H), 3.66 (s, 3H), 3.72 (s, 3H), 3.85 (dd, J = 12.5, 3.3 Hz, 1H), 4.05 (dd, J = 12.5, 6.5 Hz, 1H), 4.24 (dd, J = 6.5, 3.3 Hz, 1H), 5.40 (s, 1H), 6.01 (s, 1H), 6.37 (d, J = 7.8 Hz, 1H), 6.51 (t, J = 7.8 Hz, 1H), 6.61 (d, J = 8.2 Hz, 1H), 6.68 (t, J = 7.8 Hz, 1H), 6.73 (d, J = 8.2 Hz, 1H), 6.74 (d, J = 7.8 Hz, 1H), 6.79 (dd, J = 3.8, 1.3 Hz, 1H), 6.83 (dd, J = 8.0, 2.2 Hz, 1H), 6.93 (d, J = 2.2 Hz, 1H), 7.15 (d, J = 8.0 Hz, 1H), 7.55 (d, J = 3.8 Hz, 1H), 8.10 (d, J = 1.3 Hz, 1H)

Using any compounds among Reference Compounds No. 5-1~5-11 and 6, the following Compounds (No. 1-4~1-175) were obtained by a method similar to those of Compounds No. 1-1~3.

5-(5-Fluoro-2-methylphenoxymethyl)-6-[2-methoxy-4-(4-methoxybenzoyloxy)phenyl]-2,2,4-trimethyl-1,2-dihydroquinoline (Compound No. 1-4)

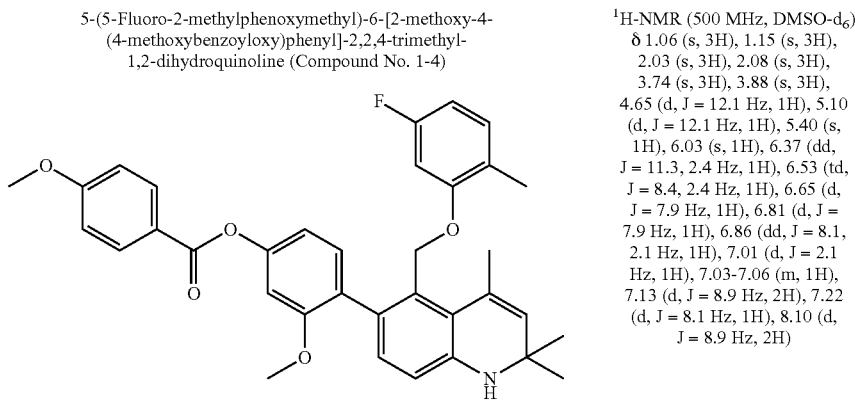

¹H-NMR (500 MHz, DMSO-d₆)
δ 1.06 (s, 3H), 1.15 (s, 3H), 2.03 (s, 3H), 2.08 (s, 3H), 3.74 (s, 3H), 3.88 (s, 3H), 4.65 (d, J = 12.1 Hz, 1H), 5.10 (d, J = 12.1 Hz, 1H), 5.40 (s, 1H), 6.03 (s, 1H), 6.37 (dd, J = 11.3, 2.4 Hz, 1H), 6.53 (td, J = 8.4, 2.4 Hz, 1H), 6.65 (d, J = 7.9 Hz, 1H), 6.81 (d, J = 7.9 Hz, 1H), 6.86 (dd, J = 8.1, 2.1 Hz, 1H), 7.01 (d, J = 2.1 Hz, 1H), 7.03-7.06 (m, 1H), 7.13 (d, J = 8.9 Hz, 2H), 7.22 (d, J = 8.1 Hz, 1H), 8.10 (d, J = 8.9 Hz, 2H)

5-(5-Fluoro-2-methylphenoxymethyl)-6-[2-methoxy-4-(3-methoxybenzoyloxy)phenyl]-2,2,4-trimethyl-1,2-dihydroquinoline (Compound No. 1-5)

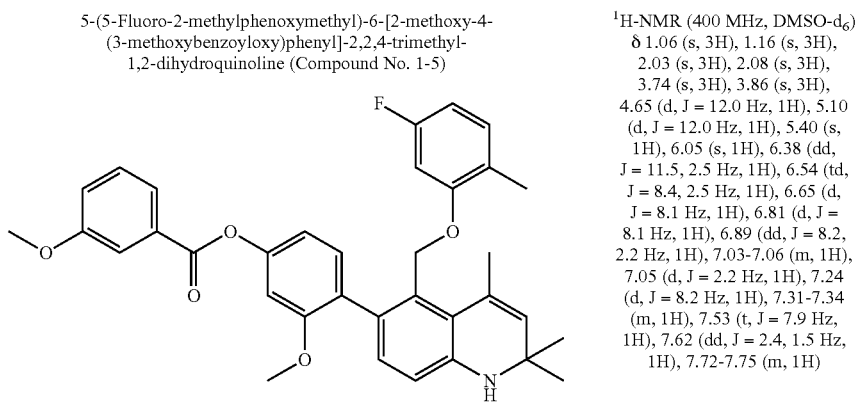

¹H-NMR (400 MHz, DMSO-d₆)
δ 1.06 (s, 3H), 1.16 (s, 3H), 2.03 (s, 3H), 2.08 (s, 3H), 3.74 (s, 3H), 3.86 (s, 3H), 4.65 (d, J = 12.0 Hz, 1H), 5.10 (d, J = 12.0 Hz, 1H), 5.40 (s, 1H), 6.05 (s, 1H), 6.38 (dd, J = 11.5, 2.5 Hz, 1H), 6.54 (td, J = 8.4, 2.5 Hz, 1H), 6.65 (d, J = 8.1 Hz, 1H), 6.81 (d, J = 8.1 Hz, 1H), 6.89 (dd, J = 8.2, 2.2 Hz, 1H), 7.03-7.06 (m, 1H), 7.05 (d, J = 2.2 Hz, 1H), 7.24 (d, J = 8.2 Hz, 1H), 7.31-7.34 (m, 1H), 7.53 (t, J = 7.9 Hz, 1H), 7.62 (dd, J = 2.4, 1.5 Hz, 1H), 7.72-7.75 (m, 1H)

5-(5-Fluoro-2-methylphenoxymethyl)-6-[2-methoxy-4-(2-methoxybenzoyloxy)phenyl]-2,2,4-trimethyl-1,2-dihydroquinoline (Compound No. 1-6)

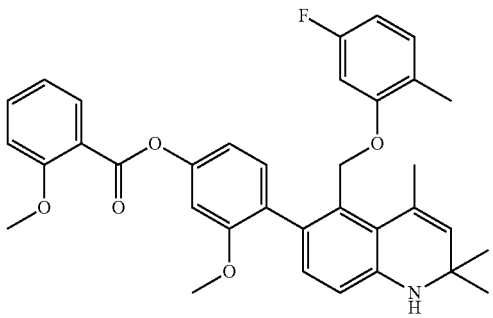 [SMILES: COc1ccccc1C(=O)Oc1ccc(-c2ccc3c(c2COc2cc(F)ccc2C)C(C)=CC(C)(C)N3)c(OC)c1]

¹H-NMR (400 MHz, DMSO-d₆) δ 1.05 (s, 3H), 1.15 (s, 3H), 2.03 (s, 3H), 2.08 (s, 3H), 3.74 (s, 3H), 3.88 (s, 3H), 4.65 (d, J = 12.1 Hz, 1H), 5.10 (d, J = 12.1 Hz, 1H), 5.40 (s, 1H), 6.03 (s, 1H), 6.37 (dd, J = 11.4, 2.6 Hz, 1H), 6.53 (td, J = 8.3, 2.4 Hz, 1H), 6.64 (d, J = 8.3 Hz, 1H), 6.81 (d, J = 8.3 Hz, 1H), 6.84 (dd, J = 8.3, 2.2 Hz, 1H), 6.98 (d, J = 2.2 Hz, 1H), 7.02-7.06 (m, 1H), 7.10 (t, J = 7.5 Hz, 1H), 7.23 (d, J = 8.3 Hz, 1H), 7.23 (d, J = 7.5 Hz, 1H), 7.64 (t, J = 7.5 Hz, 1H), 7.93 (d, J = 7.5 Hz, 1H)

6-[4-(2-Chlorobenzoyloxy)-2-methoxyphenyl]-5-(5-fluoro-2-methylphenoxymethyl)-2,2,4-trimethyl-1,2-dihydroquinoline (Compound No. 1-7)

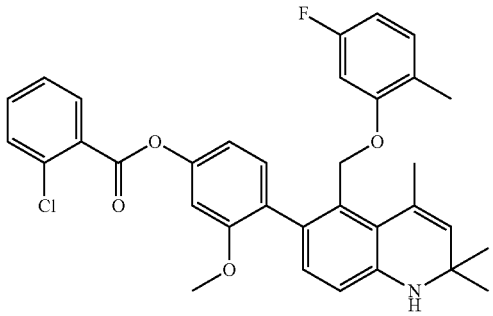

¹H-NMR (400 MHz, DMSO-d₆) δ 1.06 (s, 3H), 1.16 (s, 3H), 2.03 (s, 3H), 2.08 (s, 3H), 3.75 (s, 3H), 4.65 (d, J = 12.2 Hz, 1H), 5.10 (d, J = 12.2 Hz, 1H), 5.40 (s, 1H), 6.05 (s, 1H), 6.38 (dd, J = 11.5, 2.4 Hz, 1H), 6.53 (td, J = 8.4, 2.4 Hz, 1H), 6.65 (d, J = 8.3 Hz, 1H), 6.81 (d, J = 8.3 Hz, 1H), 6.91 (dd, J = 8.2, 2.2 Hz, 1H), 7.02-7.06 (m, 1H), 7.07 (d, J = 2.2 Hz, 1H), 7.25 (d, J = 8.2 Hz, 1H), 7.54-7.58 (m, 1H), 7.67-7.69 (m, 2H), 8.10-8.12 (m, 1H)

5-(5-Fluoro-2-methylphenoxymethyl)-6-[2-methoxy-4-(pyridin-3-ylcarbonyloxy)phenyl]-2,2,4-trimethyl-1,2-dihydroquinoline (Compound No. 1-8)

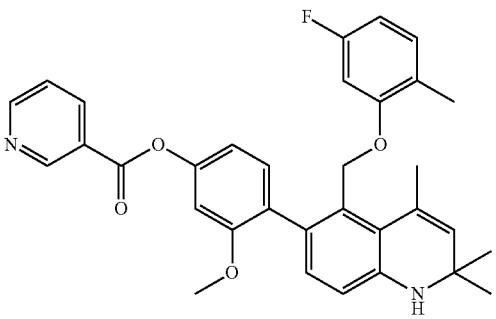 [SMILES: COc1cc(OC(=O)c2cccnc2)ccc1-c1ccc2c(c1COc1cc(F)ccc1C)C(C)=CC(C)(C)N2]

¹H-NMR (400 MHz, DMSO-d₆) δ 1.06 (s, 3H), 1.16 (s, 3H), 2.03 (s, 3H), 2.08 (s, 3H), 3.74 (s, 3H), 4.65 (d, J = 12.2 Hz, 1H), 5.10 (d, J = 12.2 Hz, 1H), 5.40 (s, 1H), 6.05 (s, 1H), 6.38 (dd, J = 11.4, 2.4 Hz, 1H), 6.54 (td, J = 8.4, 2.4 Hz, 1H), 6.65 (d, J = 8.3 Hz, 1H), 6.82 (d, J = 8.3 Hz, 1H), 6.93 (dd, J = 8.2, 2.2 Hz, 1H), 7.02-7.06 (m, 1H), 7.11 (d, J = 2.2 Hz, 1H), 7.25 (d, J = 8.2 Hz, 1H), 7.66 (ddd, J = 8.0, 4.9, 0.8 Hz, 1H), 8.48 (dt, J = 8.0, 2.0 Hz, 1H), 8.91 (dd, J = 4.9, 2.0 Hz, 1H), 9.27 (dd, J = 2.0, 0.8 Hz, 1H)

6-(4-Butyryloxy-2-methoxyphenyl)-5-(5-fluoro-2-methylphenoxymethyl)-2,2,4-trimethyl-1,2-dihydroquinoline (Compound No. 1-9)

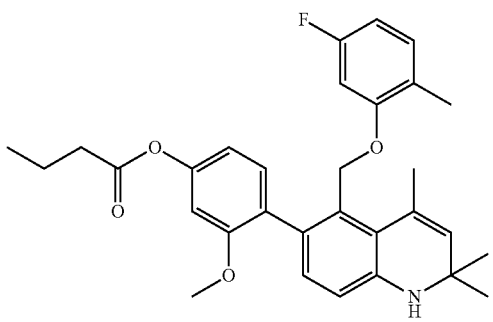

¹H-NMR (400 MHz, DMSO-d₆) δ 0.98 (t, J =7.3 Hz, 3H), 1.05 (s, 3H), 1.15 (s, 3H), 1.64-1.70 (m, 2H), 2.01 (s, 3H), 2.07 (s, 3H), 2.55 (t, J = 7.3 Hz, 2H), 3.71 (s, 3H), 4.61 (d, J = 12.2 Hz, 1H), 5.07 (d, J = 12.2 Hz, 1H), 5.39 (s, 1H), 6.03 (s, 1H), 6.34 (dd, J = 11.5, 2.4 Hz, 1H), 6.52 (td, J = 8.4, 2.4 Hz, 1H), 6.63 (d, J = 8.3 Hz, 1H), 6.71 (dd, J = 8.2, 2.2 Hz, 1H), 6.78 (d, J = 8.3 Hz, 1H), 6.84 (d, J = 2.2 Hz, 1H), 7.01-7.05 (m, 1H), 7.17 (d, J = 8.2 Hz, 1H)

| Compound | NMR |
|---|---|
| 6-(4-Acetoxy-2-methoxyphenyl)-5-(5-fluoro-2-methylphenoxymethyl)-2,2,4-trimethyl-1,2-dihydroquinoline (Compound No. 1-10)<br>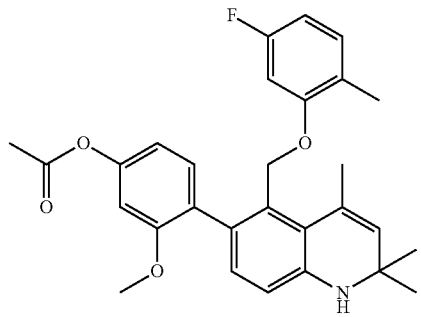 [SMILES: COc1cc(OC(C)=O)ccc1-c1ccc2c(c1COc1cc(F)ccc1C)C(C)=CC(C)(C)N2] | $^{1}$H-NMR (500 MHz, DMSO-$d_6$) δ 1.05 (s, 3H), 1.15 (s, 3H), 2.01 (s, 3H), 2.07 (s, 3H), 2.26 (s, 3H), 3.71 (s, 3H), 4.61 (d, J = 12.2 Hz, 1H), 5.07 (d, J = 12.2 Hz, 1H), 5.39 (s, 1H), 6.02 (s, 1H), 6.33 (dd, J = 11.6, 2.4 Hz, 1H), 6.52 (td, J = 8.4, 2.4 Hz, 1H), 6.63 (d, J = 8.1 Hz, 1H), 6.72 (dd, J = 8.2, 2.1 Hz, 1H), 6.78 (d, J = 8.1 Hz, 1H), 6.86 (d, J = 2.1 Hz, 1H), 7.02-7.05 (m, 1H), 7.17 (d, J = 8.2 Hz, 1H) |
| 5-(5-Fluoro-2-methylphenoxymethyl)-6-(2-methoxy-4-propionyloxyphenyl)-2,2,4-trimethyl-1,2-dihydroquinoline (Compound No. 1-11)<br>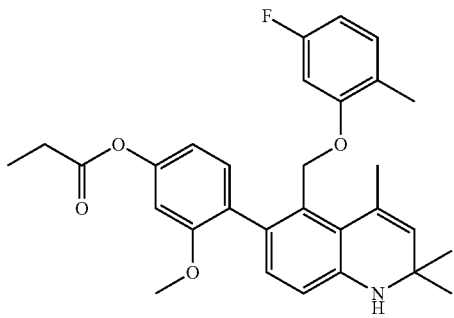 [SMILES: CCC(=O)Oc1ccc(-c2ccc3c(c2COc2cc(F)ccc2C)C(C)=CC(C)(C)N3)c(OC)c1] | $^{1}$H-NMR (400 MHz, DMSO-$d_6$) δ 1.05 (s, 3H), 1.14 (t, J = 7.5 Hz, 3H), 1.15 (s, 3H), 2.01 (s, 3H), 2.07 (s, 3H), 2.59 (q, J = 7.5 Hz, 2H), 3.71 (s, 3H), 4.61 (d, J = 12.1 Hz, 1H), 5.07 (d, J = 12.1 Hz, 1H), 5.39 (s, 1H), 6.03 (s, 1H), 6.34 (dd, J = 11.5, 2.4 Hz, 1H), 6.52 (td, J = 8.4, 2.4 Hz, 1H), 6.63 (d, J = 8.3 Hz, 1H), 6.72 (dd, J = 8.1, 2.2 Hz, 1H), 6.78 (d, J = 8.3 Hz, 1H), 6.85 (d, J = 2.2 Hz, 1H), 7.01-7.05 (m, 1H), 7.17 (d, J = 8.1 Hz, 1H) |
| 5-(5-Fluoro-2-methylphenoxymethyl)-6-[2-methoxy-4-(thiophen-3-ylcarbonyloxy)phenyl]-2,2,4-trimethyl-1,2-dihydroquinoline (Compound No. 1-12)<br>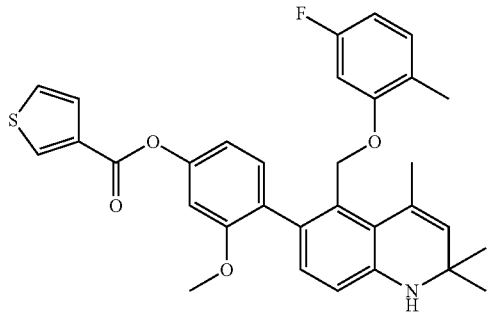 [SMILES: COc1cc(OC(=O)c2ccsc2)ccc1-c1ccc2c(c1COc1cc(F)ccc1C)C(C)=CC(C)(C)N2] | $^{1}$H-NMR (500 MHz, DMSO-$d_6$) δ 1.06 (s, 3H), 1.15 (s, 3H), 2.02 (s, 3H), 2.08 (s, 3H), 3.73 (s, 3H), 4.64 (d, J = 12.1 Hz, 1H), 5.09 (d, J = 12.1 Hz, 1H), 5.40 (s, 1H), 6.03 (s, 1H), 6.37 (dd, J = 11.3, 2.4 Hz, 1H), 6.53 (td, J = 8.4, 2.4 Hz, 1H), 6.64 (d, J = 8.2 Hz, 1H), 6.81 (d, J = 8.2 Hz, 1H), 6.86 (dd, J = 8.2, 2.2 Hz, 1H), 7.01 (d, J = 2.2 Hz, 1H), 7.03-7.06 (m, 1H), 7.22 (d, J = 8.2 Hz, 1H), 7.62 (dd, J = 5.0, 1.2 Hz, 1H), 7.75 (dd, J = 5.0, 3.0 Hz, 1H), 8.60 (dd, J = 3.0, 1.2 Hz, 1H) |
| 5-(5-Fluoro-2-methylphenoxymethyl)-6-[4-(furan-2-ylcarbonyloxy)-2-methoxyphenyl]-2,2,4-trimethyl-1,2-dihydroquinoline (Compound No. 1-13)<br>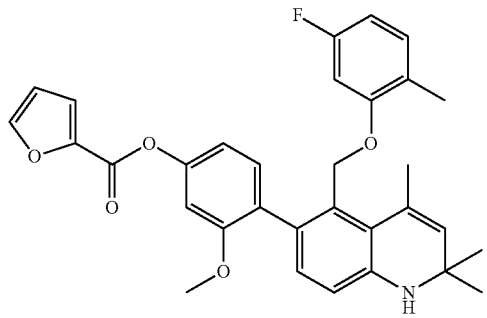 [SMILES: COc1cc(OC(=O)c2ccco2)ccc1-c1ccc2c(c1COc1cc(F)ccc1C)C(C)=CC(C)(C)N2] | $^{1}$H-NMR (500 MHz, DMSO-$d_6$) δ 1.06 (s, 3H), 1.15 (s, 3H), 2.02 (s, 3H), 2.08 (s, 3H), 3.73 (s, 3H), 4.64 (d, J = 12.1 Hz, 1H), 5.09 (d, J = 12.1 Hz, 1H), 5.40 (s, 1H), 6.03 (s, 1H), 6.37 (dd, J = 11.5, 2.4 Hz, 1H), 6.53 (td, J = 8.4, 2.4 Hz, 1H), 6.64 (d, J = 8.2 Hz, 1H), 6.80 (d, J = 8.2 Hz, 1H), 6.81 (dd, J = 3.6, 1.8 Hz, 1H), 6.86 (dd, J = 8.2, 2.2 Hz, 1H), 7.02 (d, J = 2.2 Hz, 1H), 7.02-7.05 (m, 1H), 7.22 (d, J = 8.2 Hz, 1H), 7.57 (d, J = 3.6 Hz, 1H), 8.11 (d, J = 1.8 Hz, 1H) |

5-(5-Fluoro-2-methylphenoxymethyl)-6-(4-isobutyryloxy-2-methoxyphenyl)-2,2,4-trimethyl-1,2-dihydroquinoline (Compound No. 1-14)

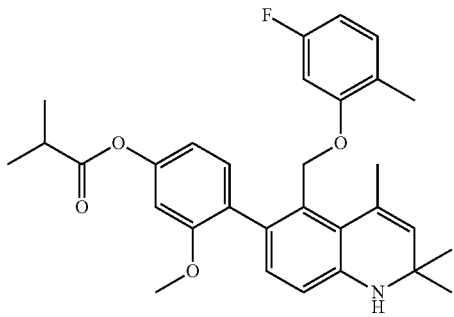 [SMILES: COc1cc(OC(=O)C(C)C)ccc1-c1ccc2c(c1COc1cc(F)ccc1C)C(C)=CC(C)(C)N2]

$^1$H-NMR (400 MHz, DMSO-d$_6$) δ 1.05 (s, 3H), 1.15 (s, 3H), 1.24 (d, J = 7.0 Hz, 6H), 2.01 (s, 3H), 2.07 (s, 3H), 2.81 (sept, J = 7.0 Hz, 1H), 3.72 (s, 3H), 4.61 (d, J = 12.1 Hz, 1H), 5.07 (d, J = 12.1 Hz, 1H), 5.39 (s, 1H), 6.03 (s, 1H), 6.35 (dd, J = 11.5, 2.5 Hz, 1H), 6.52 (td, J = 8.4, 2.5 Hz, 1H), 6.63 (d, J = 8.3 Hz, 1H), 6.71 (dd, J = 8.3, 2.2 Hz, 1H), 6.78 (d, J = 8.3 Hz, 1H), 6.83 (d, J = 2.2 Hz, 1H), 7.02-7.05 (m, 1H), 7.18 (d, J = 8.3 Hz, 1H)

5-(5-Fluoro-2-methylphenoxymethyl)-6-(2-methoxy-4-phenylacetoxyphenyl)-2,2,4-trimethyl-1,2-dihydroquinoline (Compound No. 1-15)

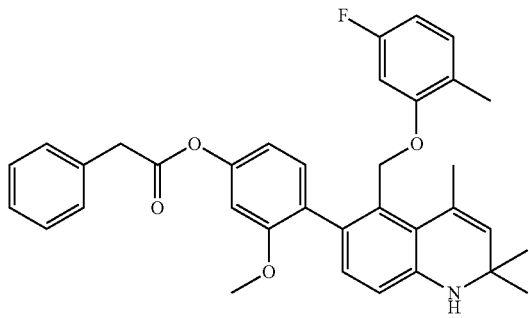

$^1$H-NMR (400 MHz, DMSO-d$_6$) δ 1.05 (s, 3H), 1.14 (s, 3H), 2.01 (s, 3H), 2.06 (s, 3H), 3.71 (s, 3H), 3.96 (s, 2H), 4.60 (d, J = 12.2 Hz, 1H), 5.06 (d, J = 12.2 Hz, 1H), 5.39 (s, 1H), 6.02 (s, 1H), 6.33 (dd, J = 11.5, 2.5 Hz, 1H), 6.52 (td, J = 8.4, 2.5 Hz, 1H), 6.62 (d, J = 8.2 Hz, 1H), 6.71 (dd, J = 8.1, 2.2 Hz, 1H), 6.77 (d, J = 8.2 Hz, 1H), 6.85 (d, J = 2.2 Hz, 1H), 7.01-7.04 (m, 1H), 7.17 (d, J = 8.1 Hz, 1H), 7.28-7.32 (m, 1H), 7.35-7.40 (m, 4H)

5-(5-Fluoro-2-methylphenoxymethyl)-6-[2-methoxy-5-(thiophen-3-ylcarbonyloxy)phenyl]-2,2,4-trimethyl-1,2-dihydroquinoline (Compound No. 1-16)

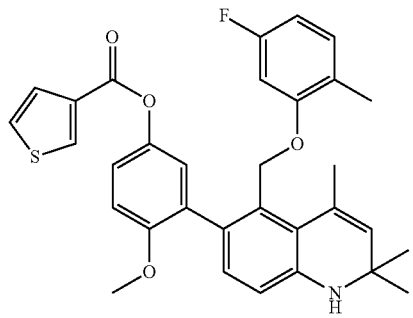 [SMILES: COc1ccc(OC(=O)c2ccsc2)cc1-c1ccc2c(c1COc1cc(F)ccc1C)C(C)=CC(C)(C)N2]

$^1$H-NMR (500 MHz, DMSO-d$_6$) δ 1.10 (s, 3H), 1.13 (s, 3H), 1.98 (s, 3H), 2.06 (s, 3H), 3.75 (s, 3H), 4.63 (d, J = 11.8 Hz, 1H), 5.09 (d, J = 11.8 Hz, 1H), 5.40 (s, 1H), 6.06 (s, 1H), 6.43 (dd, J = 11.3, 2.4 Hz, 1H), 6.52 (td, J = 8.4, 2.4 Hz, 1H), 6.64 (d, J = 8.2 Hz, 1H), 6.84 (d, J = 8.2 Hz, 1H), 6.97-7.00 (m, 1H), 7.05 (d, J = 2.9 Hz, 1H), 7.10 (d, J = 8.9 Hz, 1H), 7.18 (dd, J = 8.9, 2.9 Hz, 1H), 7.54 (dd, J = 5.1, 1.2 Hz, 1H), 7.73 (dd, J = 5.1, 3.0 Hz, 1H), 8.51 (dd, J = 3.0, 1.2 Hz, 1H)

5-(5-Fluoro-2-methylphenoxymethyl)-6-[5-(furan-2-ylcarbonyloxy)-2-methoxyphenyl]-2,2,4-trimethyl-1,2-dihydroquinoline (Compound No. 1-17)

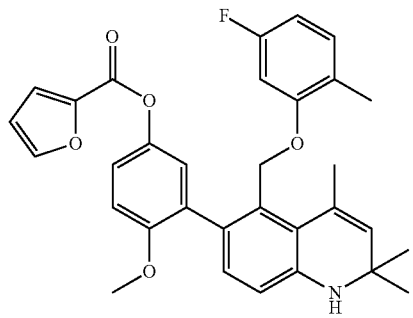 [SMILES: COc1ccc(OC(=O)c2ccco2)cc1-c1ccc2c(c1COc1cc(F)ccc1C)C(C)=CC(C)(C)N2]

$^1$H-NMR (400 MHz, DMSO-d$_6$) δ 1.10 (s, 3H), 1.13 (s, 3H), 1.99 (s, 3H), 2.06 (s, 3H), 3.75 (s, 3H), 4.64 (d, J = 12.3 Hz, 1H), 5.08 (d, J = 12.3 Hz, 1H), 5.40 (s, 1H), 6.07 (s, 1H), 6.42 (dd, J = 11.5, 2.5 Hz, 1H), 6.52 (td, J = 8.4, 2.5 Hz, 1H), 6.64 (d, J = 8.3 Hz, 1H), 6.79 (dd, J = 3.6, 1.7 Hz, 1H), 6.83 (d, J = 8.3 Hz, 1H), 6.97-7.00 (m, 1H), 7.06 (d, J = 2.9 Hz, 1H), 7.10 (d, J = 8.9 Hz, 1H), 7.19 (dd, J = 8.9, 2.9 Hz, 1H), 7.48 (dd, J = 3.6, 0.7 Hz, 1H), 8.08 (dd, J = 1.7, 0.7 Hz, 1H)

| 5-(5-Fluoro-2-methylphenoxymethyl)-6-(2-methoxy-5-propionyloxyphenyl)-2,2,4-trimethyl-1,2-dihydroquinoline (Compound No. 1-18) 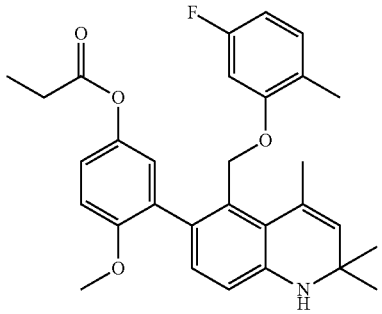 [SMILES: CCC(=O)Oc1ccc(OC)c(-c2ccc3c(c2COc2cc(F)ccc2C)C(C)=CC(C)(C)N3)c1] | $^1$H-NMR (500 MHz, DMSO-d$_6$) δ 1.09 (t, J = 7.5 Hz, 3H), 1.09 (s, 3H), 1.13 (s, 3H), 2.01 (s, 3H), 2.06 (s, 3H), 2.49-2.53 (m, 2H), 3.72 (s, 3H), 4.60 (d, J = 11.9 Hz, 1H), 5.07 (d, J = 11.9 Hz, 1H), 5.40 (s, 1H), 6.05 (s, 1H), 6.40 (dd, J = 11.5, 2.4 Hz, 1H), 6.53 (td, J = 8.4, 2.4 Hz, 1H), 6.64 (d, J = 8.2 Hz, 1H), 6.80 (d, J = 8.2 Hz, 1H), 6.92 (d, J = 2.4 Hz, 1H), 7.02-7.06 (m, 3H) |
|---|---|
| 5-(5-Fluoro-2-methylphenoxymethyl)-6-[2-methoxy-5-(pyridin-3-ylcarbonyloxy)phenyl]-2,2,4-trimethyl-1,2-dihydroquinoline (Compound No. 1-19) 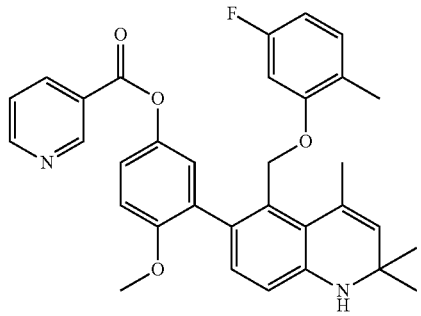 [SMILES: COc1ccc(OC(=O)c2cccnc2)cc1-c1ccc2c(c1COc1cc(F)ccc1C)C(C)=CC(C)(C)N2] | $^1$H-NMR (400 MHz, DMSO-d$_6$) δ 1.12 (s, 3H), 1.13 (s, 3H), 1.98 (s, 3H), 2.06 (s, 3H), 3.76 (s, 3H), 4.62 (d, J = 11.9 Hz, 1H), 5.09 (d, J = 11.9 Hz, 1H), 5.40 (s, 1H), 6.08 (s, 1H), 6.46 (dd, J = 11.5, 2.4 Hz, 1H), 6.52 (td, J = 8.4, 2.4 Hz, 1H), 6.65 (d, J = 8.2 Hz, 1H), 6.85 (d, J = 8.2 Hz, 1H), 6.94-6.98 (m, 1H), 7.13 (d, J = 2.9 Hz, 1H), 7.13 (d, J = 9.0 Hz, 1H), 7.25 (dd, J = 9.0, 2.9 Hz, 1H), 7.65 (ddd, J = 8.1, 4.9, 1.1 Hz, 1H), 8.38 (dt, J = 8.1, 1.9 Hz, 1H), 8.89 (dd, J = 4.9, 1.9 Hz, 1H), 9.18 (t, J = 1.1 Hz, 1H) |
| 6-(5-Butyryloxy-2-methoxyphenyl)-5-(5-fluoro-2-methylphenoxymethyl)-2,2,4-trimethyl-1,2-dihydroquinoline (Compound No. 1-20) 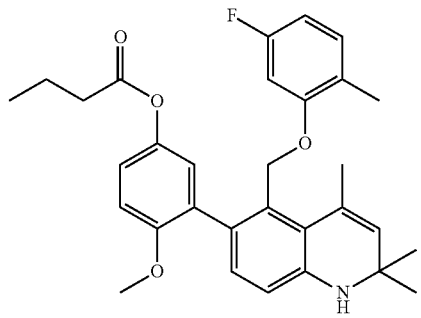 [SMILES: CCCC(=O)Oc1ccc(OC)c(-c2ccc3c(c2COc2cc(F)ccc2C)C(C)=CC(C)(C)N3)c1] | $^1$H-NMR (400 MHz, DMSO-d$_6$) δ 0.94 (t, J = 7.3 Hz, 3H), 1.09 (s, 3H), 1.14 (s, 3H), 1.57-1.66 (m, 2H), 2.01 (s, 3H), 2.06 (s, 3H), 2.49-2.52 (m, 2H), 3.72 (s, 3H), 4.59 (d, J = 12.0 Hz, 1H), 5.07 (d, J = 12.0 Hz, 1H), 5.40 (s, 1H), 6.06 (s, 1H), 6.40 (dd, J = 11.5, 2.4 Hz, 1H), 6.53 (td, J = 8.4, 2.4 Hz, 1H), 6.63 (d, J = 8.3 Hz, 1H), 6.80 (d, J = 8.3 Hz, 1H), 6.91 (d, J = 2.4 Hz, 1H), 7.01-7.07 (m, 3H) |
| 5-(5-Fluoro-2-methylphenoxymethyl)-6-(5-isobutyryloxy-2-methoxyphenyl)-2,2,4-trimethyl-1,2-dihydroquinoline (Compound No. 1-21) 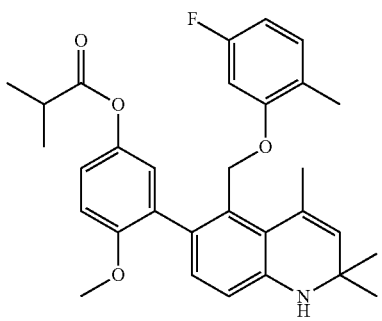 [SMILES: COc1ccc(OC(=O)C(C)C)cc1-c1ccc2c(c1COc1cc(F)ccc1C)C(C)=CC(C)(C)N2] | $^1$H-NMR (400 MHz, DMSO-d$_6$) δ 1.08 (s, 3H), 1.14 (s, 3H), 1.17 (d, J = 7.1 Hz, 6H), 2.01 (s, 3H), 2.06 (s, 3H), 2.73 (sept, J = 7.1 Hz, 1H), 3.72 (s, 3H), 4.57 (d, J = 11.9 Hz, 1H), 5.08 (d, J = 11.9 Hz, 1H), 5.40 (s, 1H), 6.06 (s, 1H), 6.40 (dd, J = 11.5, 2.4 Hz, 1H), 6.53 (td, J = 8.4, 2.4 Hz, 1H), 6.64 (d, J = 8.1 Hz, 1H), 6.80 (d, J = 8.1 Hz, 1H), 6.90 (d, J = 2.7 Hz, 1H), 7.01-7.07 (m, 3H) |

5-(5-Fluoro-2-methylphenoxymethyl)-6-[2-methoxy-4-(thiophen-2-ylcarbonyloxy)phenyl]-2,2,4-trimethyl-1,2-dihydroquinoline (Compound No. 1-22)

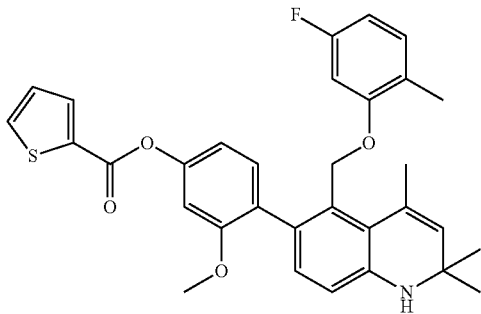

$^1$H-NMR (400 MHz, DMSO-d$_6$) δ 1.06 (s, 3H), 1.15 (s, 3H), 2.02 (s, 3H), 2.08 (s, 3H), 3.74 (s, 3H), 4.64 (d, J = 12.1 Hz, 1H), 5.09 (d, J = 12.1 Hz, 1H), 5.40 (s, 1H), 6.04 (s, 1H), 6.37 (dd, J = 11.5, 2.4 Hz, 1H), 6.53 (td, J = 8.4, 2.4 Hz, 1H), 6.64 (d, J = 8.3 Hz, 1H), 6.81 (d, J = 8.3 Hz, 1H), 6.88 (dd, J = 8.2, 2.2 Hz, 1H), 7.03 (d, J = 2.2 Hz, 1H), 7.02-7.06 (m, 1H), 7.23 (d, J = 8.2 Hz, 1H), 7.32 (dd, J = 5.0, 3.9 Hz, 1H), 8.03 (dd, J = 3.9, 1.3 Hz, 1H), 8.10 (dd, J = 5.0, 1.3 Hz, 1H)

5-(5-Fluoro-2-methylphenoxymethyl)-6-(2-methoxy-5-phenylacetoxyphenyl)-2,2,4-trimethyl-1,2-dihydroquinoline (Compound No. 1-23)

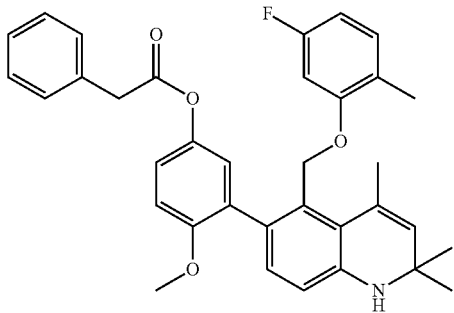 [SMILES: COc1ccc(OC(=O)Cc2ccccc2)cc1-c1ccc2c(c1COc1cc(F)ccc1C)C(C)=CC(C)(C)N2]

$^1$H-NMR (400 MHz, DMSO-d$_6$) δ 1.09 (s, 3H), 1.13 (s, 3H), 1.99 (s, 3H), 2.05 (s, 3H), 3.72 (s, 3H), 3.88 (s, 2H), 4.58 (d, J = 11.9 Hz, 1H), 5.06 (d, J = 11.9 Hz, 1H), 5.39 (s, 1H), 6.06 (s, 1H), 6.39 (dd, J = 11.5, 2.4 Hz, 1H), 6.53 (td, J = 8.5, 2.4 Hz, 1H), 6.63 (d, J = 8.3 Hz, 1H), 6.78 (d, J = 8.3 Hz, 1H), 6.90 (d, J = 2.0 Hz, 1H), 7.01-7.05 (m, 3H), 7.28-7.38 (m, 5H)

5-(5-Fluoro-2-methylphenoxymethyl)-6-[2-methoxy-4-(3-phenylpropionyloxy)phenyl]-2,2,4-trimethyl-1,2-dihydroquinoline (Compound No. 1-24)

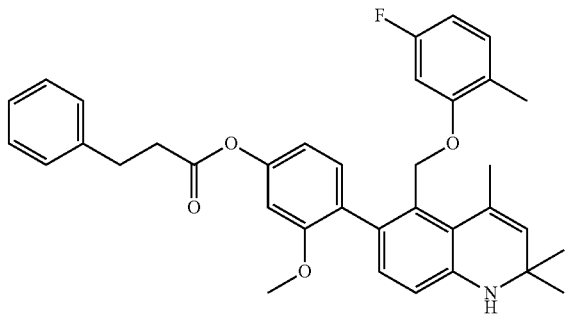 [SMILES: COc1cc(OC(=O)CCc2ccccc2)ccc1-c1ccc2c(c1COc1cc(F)ccc1C)C(C)=CC(C)(C)N2]

$^1$H-NMR (400 MHz, DMSO-d$_6$) δ 1.05 (s, 3H), 1.14 (s, 3H), 2.01 (s, 3H), 2.06 (s, 3H), 2.88-2.92 (m, 2H), 2.96-3.00 (m, 2H), 3.69 (s, 3H), 4.60 (d, J = 12.1 Hz, 1H), 5.06 (d, J = 12.1 Hz, 1H), 5.39 (s, 1H), 6.03 (s, 1H), 6.34 (dd, J = 11.5, 2.4 Hz, 1H), 6.52 (td, J = 8.4, 2.4 Hz, 1H), 6.63 (d, J = 8.2 Hz, 1H), 6.64 (dd, J = 8.1, 2.2 Hz, 1H), 6.73 (d, J = 2.2 Hz, 1H), 6.77 (d, J = 8.2 Hz, 1H), 7.01-7.05 (m, 1H), 7.16 (d, J = 8.1 Hz, 1H), 7.20-7.24 (m, 1H), 7.29-7.34 (m, 4H)

5-(5-Fluoro-2-methylphenoxymethyl)-6-[4-(furan-3-ylcarbonyloxy)-2-methoxyphenyl]-2,2,4-trimethyl-1,2-dihydroquinoline (Compound No. 1-25)

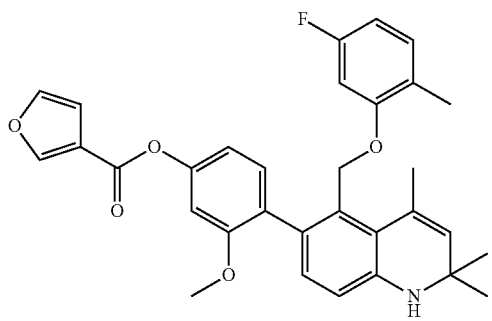 [SMILES: COc1cc(OC(=O)c2ccoc2)ccc1-c1ccc2c(c1COc1cc(F)ccc1C)C(C)=CC(C)(C)N2]

$^1$H-NMR (400 MHz, DMSO-d$_6$) δ 1.06 (s, 3H), 1.15 (s, 3H), 2.02 (s, 3H), 2.07 (s, 3H), 3.73 (s, 3H), 4.62 (d, J = 12.2 Hz, 1H), 5.08 (d, J = 12.2 Hz, 1H), 5.40 (s, 1H), 6.04 (s, 1H), 6.37 (dd, J = 11.5, 2.4 Hz, 1H), 6.53 (td, J = 8.4, 2.4 Hz, 1H), 6.64 (d, J = 8.2 Hz, 1H), 6.80 (d, J = 8.2 Hz, 1H), 6.84 (dd, J = 8.2, 2.2 Hz, 1H), 6.94 (dd, J = 1.7, 0.9 Hz, 1H), 6.98 (d, J = 2.2 Hz, 1H), 7.02-7.06 (m, 1H), 7.22 (d, J = 8.2 Hz, 1H), 7.92 (t, J = 1.7 Hz, 1H), 8.64 (dd, J = 1.7, 0.9 Hz, 1H)

5-(5-Fluoro-2-methylphenoxymethyl)-6-
[2-methoxy-4-(pyridin-2-ylcarbonyloxy)phenyl]-2,2,4-trimethyl-
1,2-dihydroquinoline (Compound No. 1-26)

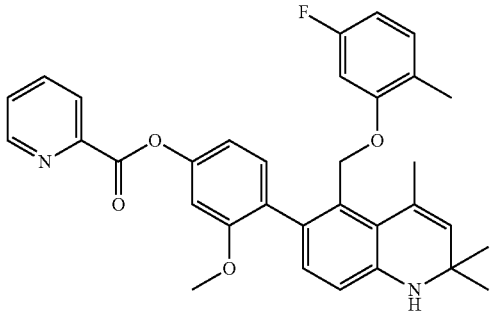 [SMILES: COc1cc(OC(=O)c2ccccn2)ccc1-c1ccc2c(c1COc1cc(F)ccc1C)C(C)=CC(C)(C)N2]

$^1$H-NMR (500 MHz, DMSO-d$_6$)
δ 1.06 (s, 3H), 1.16 (s, 3H),
2.03 (s, 3H), 2.08 (s, 3H),
3.74 (s, 3H), 4.66 (d, J = 12.2
Hz, 1H), 5.10 (d, J = 12.2 Hz,
1H), 5.40 (s, 1H), 6.04 (s,
1H), 6.38 (dd, J = 11.5, 2.4 Hz,
1H), 6.53 (td, J = 8.4, 2.4 Hz,
1H), 6.65 (d, J = 8.2 Hz, 1H),
6.82 (d, J = 8.2 Hz, 1H), 6.91
(dd, J = 8.2, 2.2 Hz, 1H),
7.03-7.06 (m, 1H), 7.06 (d,
J = 2.2 Hz, 1H), 7.25 (d, J = 8.2
Hz, 1H), 7.74 (ddd, J = 7.7,
4.7, 1.1 Hz, 1H), 8.09 (td,
J = 7.7, 1.7 Hz, 1H), 8.25 (dt,
J = 7.7, 1.1 Hz, 1H), 8.82 (ddd,
J = 4.7, 1.7, 1.1 Hz, 1H)

5-(5-Fluoro-2-methylphenoxymethyl)-6-[2-methoxy-5-
(thiophen-2-ylcarbonyloxy)phenyl]-2,2,4-trimethyl-
1,2-dihydroquinoline (Compound No. 1-27)

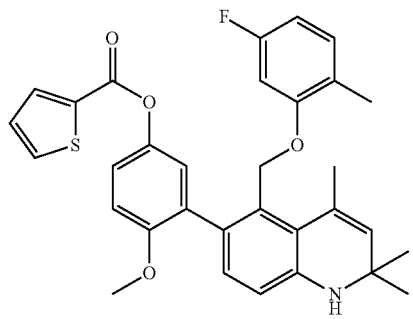

$^1$H-NMR (400 MHz, DMSO-d$_6$)
δ 1.11 (s, 3H), 1.13 (s, 3H),
1.99 (s, 3H), 2.06 (s, 3H),
3.75 (s, 3H), 4.61 (d, J = 12.4
Hz, 1H), 5.09 (d, J = 12.4 Hz,
1H), 5.40 (s, 1H), 6.07 (s,
1H), 6.44 (dd, J = 11.4, 2.5 Hz,
1H), 6.52 (td, J = 8.4, 2.5 Hz,
1H), 6.64 (d, J = 8.3 Hz, 1H),
6.84 (d, J = 8.3 Hz, 1H),
6.96-7.01 (m, 1H), 7.07 (d,
J = 2.9 Hz, 1H), 7.10 (d, J = 8.9
Hz, 1H), 7.20 (dd, J = 8.9, 2.9
Hz, 1H), 7.30 (dd, J = 5.0, 3.8
Hz, 1H), 7.94 (dd, J = 3.8, 1.3
Hz, 1H), 8.07 (dd, J = 5.0, 1.3
Hz, 1H)

5-(5-Fluoro-2-methylphenoxymethyl)-6-[5-(furan-
3-ylcarbonyloxy)-2-methoxyphenyl]-2,2,4-trimethyl-
1,2-dihydroquinoline (Compound No. 1-28)

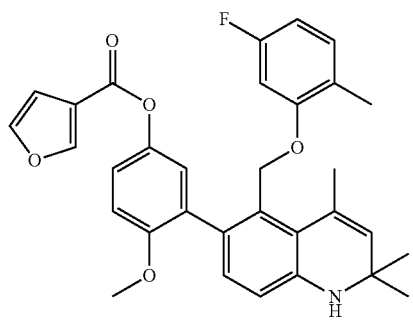 [SMILES: COc1ccc(OC(=O)c2ccoc2)cc1-c1ccc2c(c1COc1cc(F)ccc1C)C(C)=CC(C)(C)N2]

$^1$H-NMR (400 MHz, DMSO-d$_6$)
δ 1.10 (s, 3H), 1.13 (s, 3H),
1.99 (s, 3H), 2.06 (s, 3H),
3.74 (s, 3H), 4.63 (d, J = 12.4
Hz, 1H), 5.08 (d, J = 12.4 Hz,
1H), 5.40 (s, 1H), 6.07 (s,
1H), 6.42 (dd, J = 11.5, 2.5 Hz,
1H), 6.53 (td, J = 8.5, 2.5 Hz,
1H), 6.64 (d, J = 8.2 Hz, 1H),
6.83 (d, J = 8.2 Hz, 1H), 6.87
(dd, J = 1.7, 0.9 Hz, 1H),
6.98-7.01 (m, 1H), 7.04 (d,
J = 2.9 Hz, 1H), 7.10 (d, J = 9.0
Hz, 1H), 7.17 (dd, J = 9.0, 2.9
Hz, 1H), 7.89 (t, J = 1.7 Hz,
1H), 8.55 (dd, J = 1.7, 0.9 Hz,
1H)

5-(5-Fluoro-2-methylphenoxymethyl)-6-[2-methoxy-4-
(2-nitrobenzoyloxy)phenyl]-2,2,4-trimethyl-
1,2-dihydroquinoline (Compound No. 1-29)

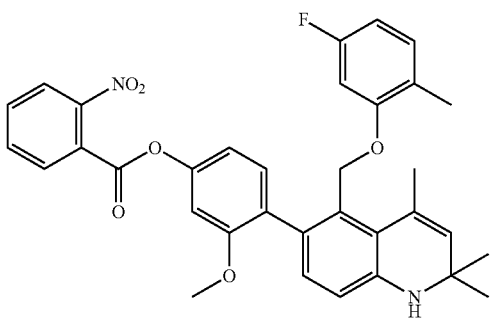 [SMILES: COc1cc(OC(=O)c2ccccc2[N+](=O)[O-])ccc1-c1ccc2c(c1COc1cc(F)ccc1C)C(C)=CC(C)(C)N2]

$^1$H-NMR (400 MHz, DMSO-d$_6$)
δ 1.06 (s, 3H), 1.15 (s, 3H),
2.02 (s, 3H), 2.07 (s, 3H),
3.75 (s, 3H), 4.64 (d, J = 12.2
Hz, 1H), 5.09 (d, J = 12.2 Hz,
1H), 5.40 (s, 1H), 6.06 (s,
1H), 6.38 (dd, J = 11.4, 2.3 Hz,
1H), 6.53 (td, J = 8.5, 2.3 Hz,
1H), 6.65 (d, J = 8.2 Hz, 1H),
6.81 (d, J = 8.2 Hz, 1H), 6.88
(dd, J = 8.3, 2.2 Hz, 1H), 7.02
(d, J = 2.2 Hz, 1H), 7.02-7.06
(m, 1H), 7.28 (d, J = 8.3 Hz,
1H), 7.92 (td, J = 7.7, 1.4 Hz,
1H), 7.96 (td, J = 7.7, 1.4 Hz,
1H), 8.13 (dd, J = 7.7, 1.4 Hz,
1H), 8.19 (dd, J = 7.7, 1.4 Hz,
1H)

5-(5-Fluoro-2-methylphenoxymethyl)-6-[2-methoxy-4-(3-nitrobenzoyloxy)phenyl]-2,2,4-trimethyl-1,2-dihydroquinoline (Compound No. 1-30)

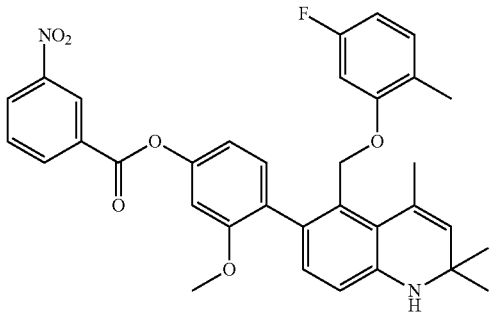 [SMILES: COc1cc(OC(=O)c2cccc([N+](=O)[O-])c2)ccc1-c1ccc2c(c1COc1cc(F)ccc1C)C(C)=CC(C)(C)N2]

$^1$H-NMR (400 MHz, DMSO-d$_6$) δ 1.06 (s, 3H), 1.16 (s, 3H), 2.03 (s, 3H), 2.08 (s, 3H), 3.75 (s, 3H), 4.65 (d, J = 12.1 Hz, 1H), 5.11 (d, J = 12.1 Hz, 1H), 5.41 (s, 1H), 6.06 (s, 1H), 6.39 (dd, J = 11.5, 2.4 Hz, 1H), 6.54 (td, J = 8.4, 2.4 Hz, 1H), 6.65 (d, J = 8.3 Hz, 1H), 6.82 (d, J = 8.3 Hz, 1H), 6.95 (dd, J = 8.3, 2.2 Hz, 1H), 7.03-7.07 (m, 1H), 7.13 (d, J = 2.2 Hz, 1H), 7.26 (d, J = 8.3 Hz, 1H), 7.93 (t, J = 7.9 Hz, 1H), 8.54-8.56 (m, 1H), 8.58-8.61 (m, 1H), 8.81 (t, J = 2.0 Hz, 1H)

5-(5-Fluoro-2-methylphenoxymethyl)-6-[2-methoxy-4-(4-nitrobenzoyloxy)phenyl]-2,2,4-trimethyl-1,2-dihydroquinoline (Compound No. 1-31)

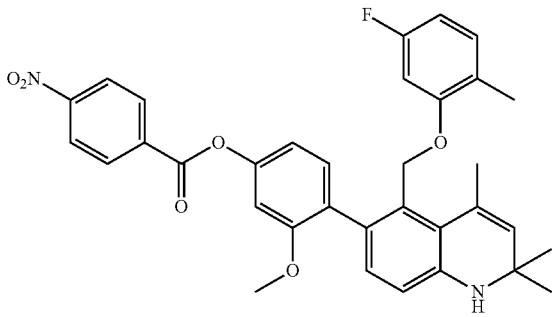 [SMILES: COc1cc(OC(=O)c2ccc([N+](=O)[O-])cc2)ccc1-c1ccc2c(c1COc1cc(F)ccc1C)C(C)=CC(C)(C)N2]

$^1$H-NMR (400 MHz, DMSO-d$_6$) δ 1.06 (s, 3H), 1.16 (s, 3H), 2.03 (s, 3H), 2.08 (s, 3H), 3.74 (s, 3H), 4.65 (d, J = 12.1 Hz, 1H), 5.10 (d, J = 12.1 Hz, 1H), 5.40 (s, 1H), 6.06 (s, 1H), 6.38 (dd, J = 11.4, 2.3 Hz, 1H), 6.54 (td, J = 8.4, 2.3 Hz, 1H), 6.65 (d, J = 8.3 Hz, 1H), 6.82 (d, J = 8.3 Hz, 1H), 6.95 (dd, J = 8.3, 2.2 Hz, 1H), 7.03-7.06 (m, 1H), 7.12 (d, J = 2.2 Hz, 1H), 7.26 (d, J = 8.3 Hz, 1H), 8.38 (d, J = 9.0 Hz, 2H), 8.43 (d, J = 9.0 Hz, 2H)

5-(5-Fluoro-2-methylphenoxymethyl)-6-(2-methoxy-4-methoxyacetoxyphenyl)-2,2,4-trimethyl-1,2-dihydroquinoline (Compound No. 1-32)

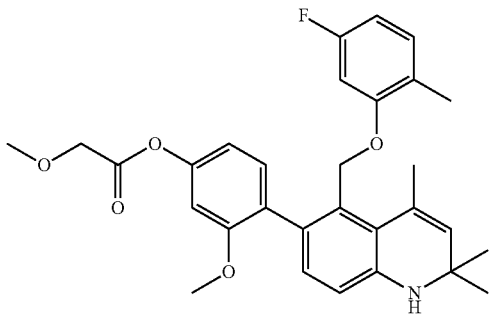

$^1$H-NMR (400 MHz, DMSO-d$_6$) δ 1.05 (s, 3H), 1.15 (s, 3H), 2.01 (s, 3H), 2.07 (s, 3H), 3.40 (s, 3H), 3.72 (s, 3H), 4.33 (s, 2H), 4.61 (d, J = 12.2 Hz, 1H), 5.07 (d, J = 12.2 Hz, 1H), 5.39 (s, 1H), 6.04 (s, 1H), 6.35 (dd, J = 11.5, 2.5 Hz, 1H), 6.52 (td, J = 8.4, 2.5 Hz, 1H), 6.63 (d, J = 8.4 Hz, 1H), 6.77 (dd, J = 8.1, 2.1 Hz, 1H), 6.78 (d, J = 8.4 Hz, 1H), 6.91 (d, J = 2.1 Hz, 1H), 7.01-7.05 (m, 1H), 7.19 (d, J = 8.1 Hz, 1H)

5-(5-Fluoro-2-methylphenoxymethyl)-6-[2-methoxy-4-(pyridin-4-ylcarbonyloxy)phenyl]-2,2,4-trimethyl-1,2-dihydroquinoline (Compound No. 1-33)

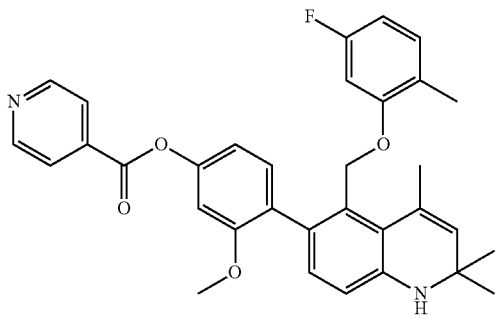

$^1$H-NMR (500 MHz, DMSO-d$_6$) δ 1.06 (s, 3H), 1.15 (s, 3H), 2.03 (s, 3H), 2.08 (s, 3H), 3.74 (s, 3H), 4.64 (d, J = 12.1 Hz, 1H), 5.10 (d, J = 12.1 Hz, 1H), 5.40 (s, 1H), 6.05 (s, 1H), 6.38 (dd, J = 11.3, 2.4 Hz, 1H), 6.54 (td, J = 8.4, 2.4 Hz, 1H), 6.65 (d, J = 8.2 Hz, 1H), 6.81 (d, J = 8.2 Hz, 1H), 6.93 (dd, J = 8.2, 2.4 Hz, 1H), 7.03-7.06 (m, 1H), 7.11 (d, J = 2.4 Hz, 1H), 7.25 (d, J = 8.2 Hz, 1H), 8.02 (d, J = 6.0 Hz, 2H), 8.89 (d, J = 6.0 Hz, 2H)

5-(5-Fluoro-2-methylphenoxymethyl)-6-[2-methoxy-5-(pyridin-2-ylcarbonyloxy)phenyl]-2,2,4-trimethyl-1,2-dihydroquinoline (Compound No. 1-34)

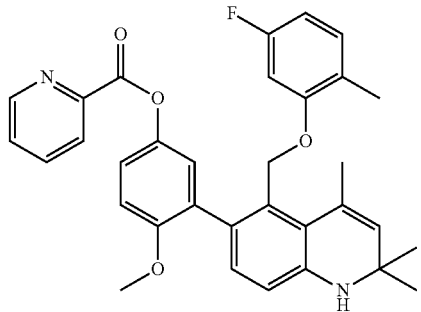 [SMILES: COc1ccc(OC(=O)c2ccccn2)cc1-c1ccc2c(c1COc1cc(F)ccc1C)C(C)=CC(C)(C)N2]

$^1$H-NMR (400 MHz, DMSO-d$_6$)
δ 1.10 (s, 3H), 1.13 (s, 3H), 1.98 (s, 3H), 2.06 (s, 3H), 3.76 (s, 3H), 4.67 (d, J = 12.0 Hz, 1H), 5.09 (d, J = 12.0 Hz, 1H), 5.40 (s, 1H), 6.08 (s, 1H), 6.43 (dd, J = 11.6, 2.4 Hz, 1H), 6.52 (td, J = 8.4, 2.4 Hz, 1H), 6.65 (d, J = 8.3 Hz, 1H), 6.85 (d, J = 8.3 Hz, 1H), 6.95-6.99 (m, 1H), 7.11 (d, J = 2.9 Hz, 1H), 7.13 (d, J = 9.0 Hz, 1H), 7.23 (dd, J = 9.0, 2.9 Hz, 1H), 7.73 (ddd, J = 7.7, 4.8, 1.1 Hz, 1H), 8.07 (td, J = 7.7, 1.7 Hz, 1H), 8.15 (dt, J = 7.7, 1.1 Hz, 1H), 8.80 (ddd, J = 4.8, 1.7, 1.1 Hz, 1H)

5-(5-Fluoro-2-methylphenoxymethyl)-6-[2-methoxy-5-(pyridin-4-ylcarbonyloxy)phenyl]-2,2,4-trimethyl-1,2-dihydroquinoline (Compound No. 1-35)

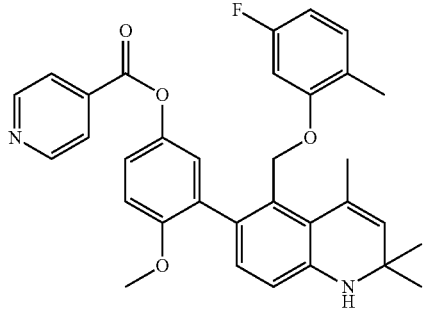 [SMILES: COc1ccc(OC(=O)c2ccncc2)cc1-c1ccc2c(c1COc1cc(F)ccc1C)C(C)=CC(C)(C)N2]

$^1$H-NMR (400 MHz, DMSO-d$_6$)
δ 1.12 (s, 3H), 1.13 (s, 3H), 1.98 (s, 3H), 2.06 (s, 3H), 3.76 (s, 3H), 4.61 (d, J = 11.8 Hz, 1H), 5.09 (d, J = 11.8 Hz, 1H), 5.40 (s, 1H), 6.09 (s, 1H), 6.45 (dd, J = 11.4, 2.4 Hz, 1H), 6.53 (td, J = 8.3, 2.4 Hz, 1H), 6.65 (d, J = 8.3 Hz, 1H), 6.85 (d, J = 8.3 Hz, 1H), 6.96-6.99 (m, 1H), 7.13 (d, J = 2.9 Hz, 1H), 7.13 (d, J = 9.0 Hz, 1H), 7.26 (dd, J = 9.0, 2.9 Hz, 1H), 7.92 (d, J = 6.1 Hz, 2H), 8.88 (d, J = 6.1 Hz, 2H)

6-[4-(2-Acetoxybenzoyloxy)-2-methoxyphenyl]-5-(5-fluoro-2-methylphenoxymethyl)-2,2,4-trimethyl-1,2-dihydroquinoline (Compound No. 1-36)

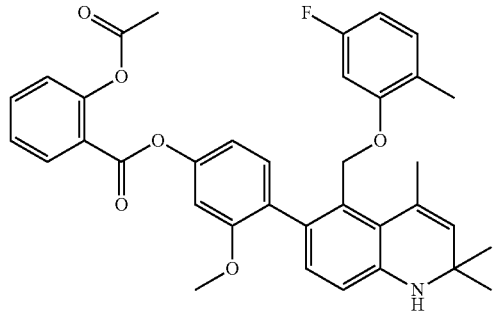 [SMILES: COc1cc(OC(=O)c2ccccc2OC(C)=O)ccc1-c1ccc2c(c1COc1cc(F)ccc1C)C(C)=CC(C)(C)N2]

$^1$H-NMR (500 MHz, CDCl$_3$)
δ 1.13 (s, 3H), 1.23 (s, 3H), 2.08 (s, 3H), 2.17 (s, 3H), 2.32 (s, 3H), 3.76 (s, 3H), 4.75 (d, J = 11.9 Hz, 1H), 5.12 (d, J = 11.9 Hz, 1H), 5.46 (s, 1H), 6.21 (dd, J = 11.0, 2.4 Hz, 1H), 6.43 (td, J = 8.4, 2.4 Hz, 1H), 6.59 (d, J = 8.1 Hz, 1H), 6.78 (d, J = 2.1 Hz, 1H), 6.81 (dd, J = 8.1, 2.1 Hz, 1H), 6.92 (d, J = 8.1 Hz, 1H), 6.93-6.95 (m, 1H), 7.19 (dd, J = 7.9, 1.4 Hz, 1H), 7.29 (d, J = 8.1 Hz, 1H), 7.40 (td, J = 7.9, 1.4 Hz, 1H), 7.65 (td, J = 7.9, 1.4 Hz, 1H), 8.24 (dd, J = 7.9, 1.4 Hz, 1H)

6-[4-(1-t-Butoxycarbonylpiperidin-4-ylcarbonyloxy)-2-methoxyphenyl]-5-(5-fluoro-2-methylphenoxymethyl)-2,2,4-trimethyl-1,2-dihydroquinoline (Compound No. 1-37)

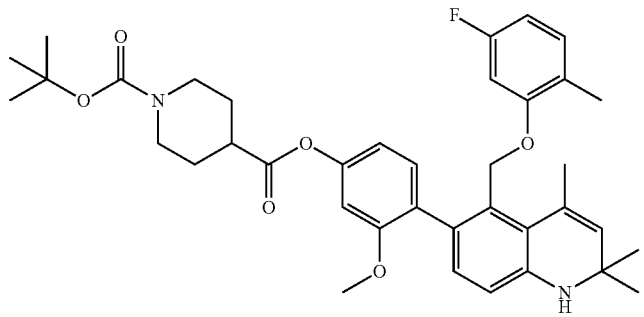 [SMILES: COc1cc(OC(=O)C2CCN(C(=O)OC(C)(C)C)CC2)ccc1-c1ccc2c(c1COc1cc(F)ccc1C)C(C)=CC(C)(C)N2]

$^1$H-NMR (400 MHz, DMSO-d$_6$)
δ 1.05 (s, 3H), 1.15 (s, 3H), 1.53-1.62 (m, 2H), 1.95-1.96 (m, 2H), 2.01 (s, 3H), 2.07 (s, 3H), 2.81-2.84 (m, 1H), 2.91-2.93 (m, 2H), 3.72 (s, 3H), 3.89-3.92 (m, 2H), 4.61 (d, J = 12.1 Hz, 1H), 5.07 (d, J = 12.1 Hz, 1H), 5.39 (s, 1H), 6.03 (s, 1H), 6.34 (dd, J = 11.5, 2.4 Hz, 1H), 6.52 (td, J = 8.4, 2.4 Hz, 1H), 6.63 (d, J = 8.1 Hz, 1H), 6.73 (dd, J = 8.3, 2.2 Hz, 1H), 6.78 (d, J = 8.1 Hz, 1H), 6.86 (d, J = 2.2 Hz, 1H), 7.01-7.05 (m, 1H), 7.18 (d, J = 8.3 Hz, 1H)

5-(5-Fluoro-2-methylphenoxymethyl)-6-[2-methoxy-4-(2-methylthiobenzoyloxy)phenyl]-2,2,4-trimethyl-1,2-dihydroquinoline (Compound No. 1-38)

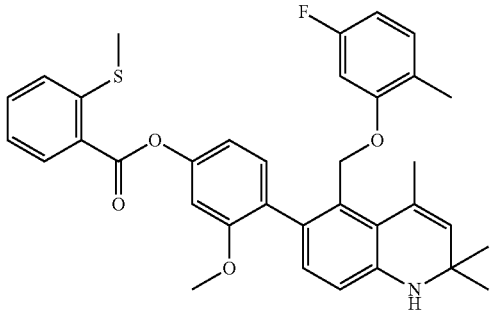 [SMILES: COc1cc(OC(=O)c2ccccc2SC)ccc1-c1ccc2c(c1COc1cc(F)ccc1C)C(C)=CC(C)(C)N2]

$^1$H-NMR (500 MHz, DMSO-d$_6$)
δ 1.06 (s, 3H), 1.15 (s, 3H), 2.03 (s, 3H), 2.08 (s, 3H), 2.47 (s, 3H), 3.74 (s, 3H), 4.66 (d, J = 12.2 Hz, 1H), 5.11 (d, J = 12.2 Hz, 1H), 5.40 (s, 1H), 6.04 (s, 1H), 6.38 (dd, J = 11.5, 2.4 Hz, 1H), 6.53 (td, J = 8.4, 2.4 Hz, 1H), 6.65 (d, J = 8.2 Hz, 1H), 6.81 (d, J = 8.2 Hz, 1H), 6.87 (dd, J = 8.0, 2.4 Hz, 1H), 7.02 (d, J = 2.4 Hz, 1H), 7.03-7.06 (m, 1H), 7.24 (d, J = 8.0 Hz, 1H), 7.31-7.35 (m, 1H), 7.47 (d, J = 7.9 Hz, 1H), 7.66-7.69 (m, 1H), 8.19 (dd, J = 7.6, 1.5 Hz, 1H)

6-[4-(1-t-Butoxycarbonylimidazol-4-ylcarbonyloxy)-2-methoxyphenyl]-5-(5-fluoro-2-methylphenoxymethyl)-2,2,4-trimethyl-1,2-dihydroquinoline (Compound No. 1-39)

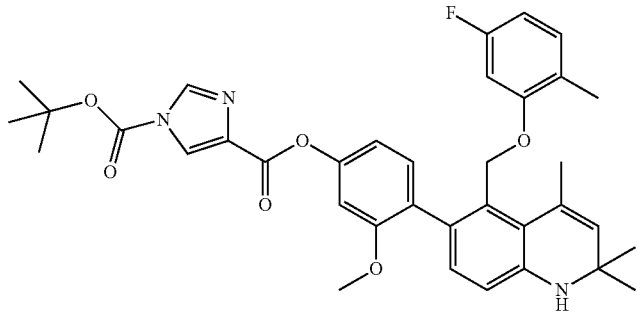 [SMILES: COc1cc(OC(=O)c2cn(C(=O)OC(C)(C)C)cn2)ccc1-c1ccc2c(c1COc1cc(F)ccc1C)C(C)=CC(C)(C)N2]

$^1$H-NMR (400 MHz, DMSO-d$_6$)
δ 1.06 (s, 3H), 1.15 (s, 3H), 1.61 (s, 9H), 2.02 (s, 3H), 2.08 (s, 3H), 3.73 (s, 3H), 4.63 (d, J = 12.1 Hz, 1H), 5.09 (d, J = 12.1 Hz, 1H), 5.40 (s, 1H), 6.05 (s, 1H), 6.37 (dd, J = 11.5, 2.4 Hz, 1H), 6.53 (td, J = 8.4, 2.4 Hz, 1H), 6.64 (d, J = 8.3 Hz, 1H), 6.81 (d, J = 8.3 Hz, 1H), 6.85 (dd, J = 8.3, 2.2 Hz, 1H), 6.99 (d, J = 2.2 Hz, 1H), 7.02-7.06 (m, 1H), 7.22 (d, J = 8.3 Hz, 1H), 8.37 (d, J = 1.2 Hz, 1H), 8.41 (d, J = 1.2 Hz, 1H)

5-(5-Fluoro-2-methylphenoxymethyl)-6-[2-methoxy-4-(thiazol-4-ylcarbonyloxy)phenyl]-2,2,4-trimethyl-1,2-dihydroquinoline (Compound No. 1-40)

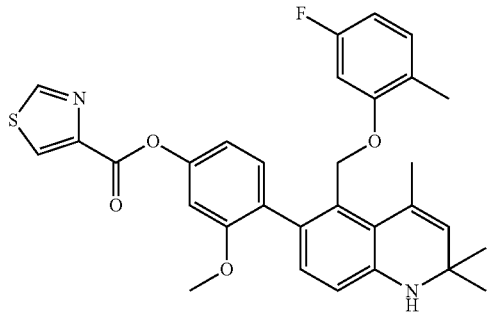

$^1$H-NMR (400 MHz, DMSO-d$_6$)
δ 1.06 (s, 3H), 1.15 (s, 3H), 2.02 (s, 3H), 2.08 (s, 3H), 3.74 (s, 3H), 4.64 (d, J = 12.1 Hz, 1H), 5.10 (d, J = 12.1 Hz, 1H), 5.40 (s, 1H), 6.05 (s, 1H), 6.37 (dd, J = 11.2, 2.5 Hz, 1H), 6.53 (td, J = 8.4, 2.5 Hz, 1H), 6.65 (d, J = 8.3 Hz, 1H), 6.82 (d, J = 8.3 Hz, 1H), 6.89 (dd, J = 6.3, 2.2 Hz, 1H), 7.02-7.06 (m, 1H), 7.04 (d, J = 2.2 Hz, 1H), 7.24 (d, J = 8.3 Hz, 1H), 8.88 (d, J = 1.9 Hz, 1H), 9.28 (d, J = 1.9 Hz, 1H)

5-(5-Fluoro-2-methylphenoxymethyl)-6-[2-methoxy-4-(thiazol-5-ylcarbonyloxy)phenyl]-2,2,4-trimethyl-1,2-dihydroquinoline (Compound No. 1-41)

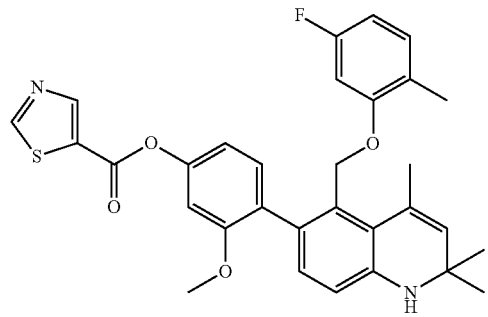

$^1$H-NMR (400 MHz, DMSO-d$_6$)
δ 1.06 (s, 3H), 1.15 (s, 3H), 2.02 (s, 3H), 2.07 (s, 3H), 3.74 (s, 3H), 4.63 (d, J = 12.2 Hz, 1H), 5.09 (d, J = 12.2 Hz, 1H), 5.40 (s, 1H), 6.06 (s, 1H), 6.38 (dd, J = 11.2, 2.5 Hz, 1H), 6.53 (td, J = 8.5, 2.5 Hz, 1H), 6.64 (d, J = 8.2 Hz, 1H), 6.81 (d, J = 8.2 Hz, 1H), 6.91 (dd, J = 8.2, 2.2 Hz, 1H), 7.02-7.06 (m, 1H), 7.08 (d, J = 2.2 Hz, 1H), 7.24 (d, J = 8.2 Hz, 1H), 8.76 (d, J = 0.7 Hz, 1H), 9.49 (d, J = 0.7 Hz, 1H)

5-(5-Fluoro-2-methylphenoxymethyl)-6-[2-methoxy-4-(oxazol-4-ylcarbonyloxy)phenyl]-2,2,4-trimethyl-1,2-dihydroquinoline (Compound No. 1-42)

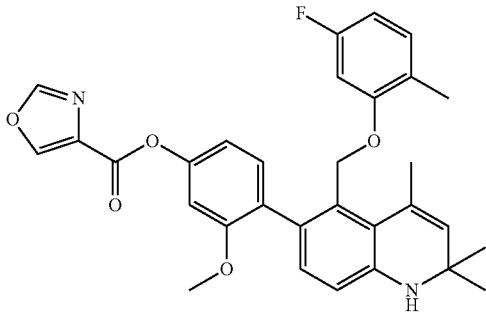 [SMILES: COc1cc(OC(=O)c2cocn2)ccc1-c1ccc2c(c1COc1cc(F)ccc1C)C(C)=CC(C)(C)N2]

$^1$H-NMR (400 MHz, DMSO-$d_6$) δ 1.06 (s, 3H), 1.15 (s, 3H), 2.02 (s, 3H), 2.08 (s, 3H), 3.73 (s, 3H), 4.63 (d, J = 12.4 Hz, 1H), 5.09 (d, J = 12.4 Hz, 1H), 5.40 (s, 1H), 6.06 (s, 1H), 6.37 (dd, J = 11.5, 2.4 Hz, 1H), 6.53 (td, J = 8.4, 2.4 Hz, 1H), 6.64 (d, J = 8.2 Hz, 1H), 6.81 (d, J = 8.2 Hz, 1H), 6.86 (dd, J = 8.2, 2.3 Hz, 1H), 7.01 (d, J = 2.3 Hz, 1H), 7.02-7.06 (m, 1H), 7.23 (d, J = 8.2 Hz, 1H), 8.67 (d, J = 1.0 Hz, 1H), 9.14 (d, J = 1.0 Hz, 1H)

5-(5-Fluoro-2-methylphenoxymethyl)-6-[2-methoxy-4-(5-methylthiophen-2-ylcarbonyloxy)phenyl]-2,2,4-trimethyl-1,2-dihydroquinoline (Compound No. 1-43)

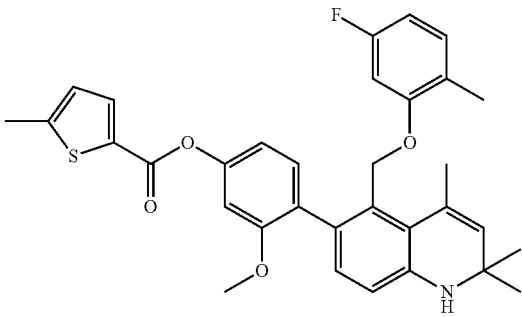

$^1$H-NMR (400 MHz, DMSO-$d_6$) δ 1.05 (s, 3H), 1.15 (s, 3H), 2.02 (s, 3H), 2.07 (s, 3H), 2.57 (s, 3H), 3.74 (s, 3H), 4.63 (d, J = 12.1 Hz, 1H), 5.09 (d, J = 12.1 Hz, 1H), 5.40 (s, 1H), 6.05 (s, 1H), 6.37 (dd, J = 11.4, 2.5 Hz, 1H), 6.53 (td, J = 8.4, 2.5 Hz, 1H), 6.64 (d, J = 8.3 Hz, 1H), 6.80 (d, J = 8.3 Hz, 1H), 6.85 (dd, J = 8.3, 2.4 Hz, 1H), 7.00 (d, J = 2.4 Hz, 1H), 7.02-7.06 (m, 2H), 7.22 (d, J = 8.3 Hz, 1H), 7.85 (d, J = 3.4 Hz, 1H)

6-[4-(3-Acetylbenzoyloxy)-2-methoxyphenyl]-5-(5-fluoro-2-methylphenoxymethyl)-2,2,4-trimethyl-1,2-dihydroquinoline (Compound No. 1-44)

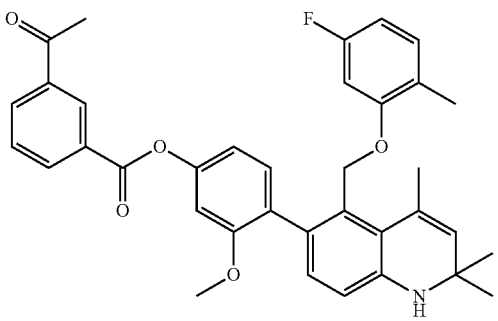 [SMILES: COc1cc(OC(=O)c2cccc(C(C)=O)c2)ccc1-c1ccc2c(c1COc1cc(F)ccc1C)C(C)=CC(C)(C)N2]

$^1$H-NMR (500 MHz, DMSO-$d_6$) δ 1.06 (s, 3H), 1.16 (s, 3H), 2.03 (s, 3H), 2.08 (s, 3H), 2.68 (s, 3H), 3.75 (s, 3H), 4.65 (d, J = 12.2 Hz, 1H), 5.11 (d, J = 12.2 Hz, 1H), 5.40 (s, 1H), 6.05 (s, 1H), 6.39 (dd, J = 11.3, 2.4 Hz, 1H), 6.54 (td, J = 8.4, 2.4 Hz, 1H), 6.65 (d, J = 8.1 Hz, 1H), 6.82 (d, J = 8.1 Hz, 1H), 6.93 (dd, J = 8.1, 2.1 Hz, 1H), 7.03-7.06 (m, 1H), 7.09 (d, J = 2.1 Hz, 1H), 7.25 (d, J = 8.1 Hz, 1H), 7.79 (t, J = 7.9 Hz, 1H), 8.32 (dt, J = 7.9, 1.5 Hz, 1H), 8.38 (dt, J = 7.9, 1.5 Hz, 1H), 8.68 (t, J = 1.5 Hz, 1H)

6-[4-(2-Fluorobenzoyloxy)-2-methoxyphenyl]-5-(5-fluoro-2-methylphenoxymethyl)-2,2,4-trimethyl-1,2-dihydroquinoline (Compound No. 1-45)

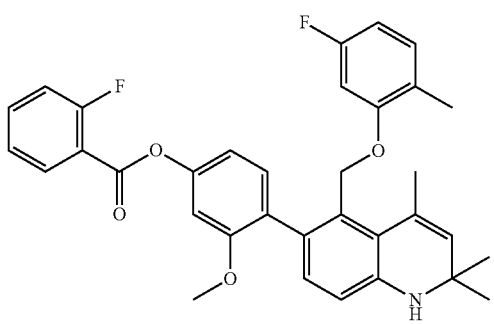 [SMILES: COc1cc(OC(=O)c2ccccc2F)ccc1-c1ccc2c(c1COc1cc(F)ccc1C)C(C)=CC(C)(C)N2]

$^1$H-NMR (400 MHz, DMSO-$d_6$) δ 1.06 (s, 3H), 1.15 (s, 3H), 2.03 (s, 3H), 2.08 (s, 3H), 3.74 (s, 3H), 4.65 (d, J = 12.1 Hz, 1H), 5.10 (d, J = 12.1 Hz, 1H), 5.40 (s, 1H), 6.05 (s, 1H), 6.38 (dd, J = 11.4, 2.4 Hz, 1H), 6.53 (td, J = 8.4, 2.4 Hz, 1H), 6.65 (d, J = 8.3 Hz, 1H), 6.81 (d, J = 8.3 Hz, 1H), 6.90 (dd, J = 8.2, 2.2 Hz, 1H), 7.02-7.06 (m, 1H), 7.06 (d, J = 2.2 Hz, 1H), 7.24 (d, J = 8.2 Hz, 1H), 7.41-7.47 (m, 2H), 7.76-7.81 (m, 1H), 8.12 (td, J = 7.8, 1.7 Hz, 1H)

| | |
|---|---|
| 6-[4-(3-Fluorobenzoyloxy)-2-methoxyphenyl]-5-(5-fluoro-2-methylphenoxymethyl)-2,2,4-trimethyl-1,2-dihydroquinoline (Compound No. 1-46)<br>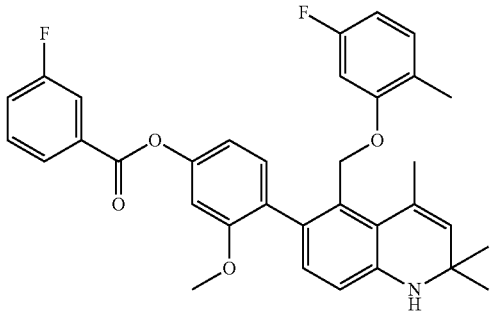 [SMILES: COc1cc(OC(=O)c2cccc(F)c2)ccc1-c1ccc2c(c1COc1cc(F)ccc1C)C(C)=CC(C)(C)N2] | $^1$H-NMR (400 MHz, DMSO-d$_6$) δ 1.06 (s, 3H), 1.16 (s, 3H), 2.03 (s, 3H), 2.08 (s, 3H), 3.74 (s, 3H), 4.64 (d, J = 12.2 Hz, 1H), 5.10 (d, J = 12.2 Hz, 1H), 5.40 (s, 1H), 6.06 (s, 1H), 6.38 (dd, J = 11.4, 2.5 Hz, 1H), 6.54 (td, J = 8.2, 2.5 Hz, 1H), 6.65 (d, J = 8.2 Hz, 1H), 6.81 (d, J = 8.2 Hz, 1H), 6.91 (dd, J = 8.2, 2.2 Hz, 1H), 7.02-7.06 (m, 1H), 7.08 (d, J = 2.2 Hz, 1H), 7.25 (d, J = 8.2 Hz, 1H), 7.63 (tdd, J = 8.5, 2.6, 1.2 Hz, 1H), 7.66-7.71 (m, 1H), 7.88-7.91 (m, 1H), 8.00 (dt, J = 7.5, 1.4 Hz, 1H) |
| 6-[4-(4-Fluorobenzoyloxy)-2-methoxyphenyl]-5-(5-fluoro-2-methylphenoxymethyl)-2,2,4-trimethyl-1,2-dihydroquinoline (Compound No. 1-47)<br>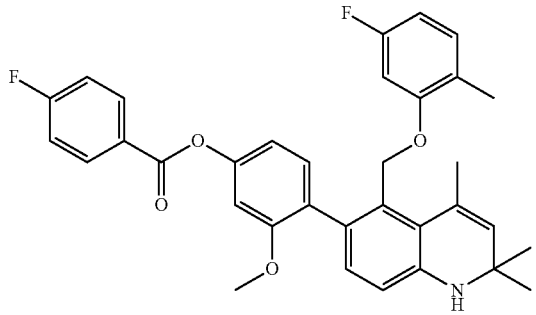 [SMILES: COc1cc(OC(=O)c2ccc(F)cc2)ccc1-c1ccc2c(c1COc1cc(F)ccc1C)C(C)=CC(C)(C)N2] | $^1$H-NMR (500 MHz, DMSO-d$_6$) δ 1.06 (s, 3H), 1.15 (s, 3H), 2.03 (s, 3H), 2.08 (s, 3H), 3.74 (s, 3H), 4.65 (d, J = 12.2 Hz, 1H), 5.10 (d, J = 12.2 Hz, 1H), 5.40 (s, 1H), 6.05 (s, 1H), 6.38 (dd, J = 11.3, 2.4 Hz, 1H), 6.54 (td, J = 8.4, 2.4 Hz, 1H), 6.65 (d, J = 8.2 Hz, 1H), 6.81 (d, J = 8.2 Hz, 1H), 6.89 (dd, J = 8.1, 2.1 Hz, 1H), 7.03-7.06 (m, 1H), 7.06 (d, J = 2.1 Hz, 1H), 7.24 (d, J = 8.1 Hz, 1H), 7.44-7.47 (m, 2H), 8.20-8.23 (m, 2H) |
| 5-(5-Fluoro-2-methylphenoxymethyl)-6-[2-methoxy-4-(5-methylfuran-2-ylcarbonyloxy)phenyl]-2,2,4-trimethyl-1,2-dihydroquinoline (Compound No. 1-48)<br>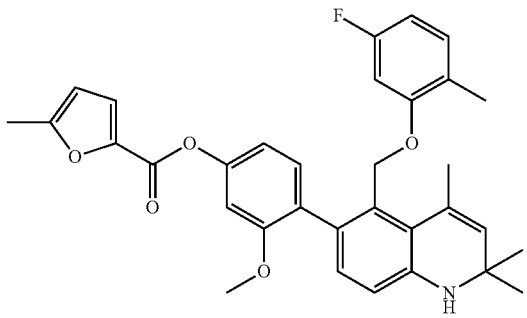 | $^1$H-NMR (400 MHz, DMSO-d$_6$) δ 1.06 (s, 3H), 1.15 (s, 3H), 2.02 (s, 3H), 2.07 (s, 3H), 2.42 (s, 3H), 3.73 (s, 3H), 4.63 (d, J = 12.0 Hz, 1H), 5.08 (d, J = 12.0 Hz, 1H), 5.40 (s, 1H), 6.04 (s, 1H), 6.37 (dd, J = 11.5, 2.4 Hz, 1H), 6.45 (d, J = 3.4 Hz, 1H), 6.53 (td, J = 8.4, 2.4 Hz, 1H), 6.64 (d, J = 8.1 Hz, 1H), 6.80 (d, J = 8.1 Hz, 1H), 6.84 (dd, J = 8.3, 2.3 Hz, 1H), 6.98 (d, J = 2.3 Hz, 1H), 7.02-7.06 (m, 1H), 7.21 (d, J = 8.3 Hz, 1H), 7.47 (d, J = 3.4 Hz, 1H) |
| 5-(5-Fluoro-2-methylphenoxymethyl)-6-[2-methoxy-4-(2-methylpyridin-3-ylcarbonyloxy)phenyl]-2,2,4-trimethyl-1,2-dihydroquinoline (Compound No. 1-49)<br>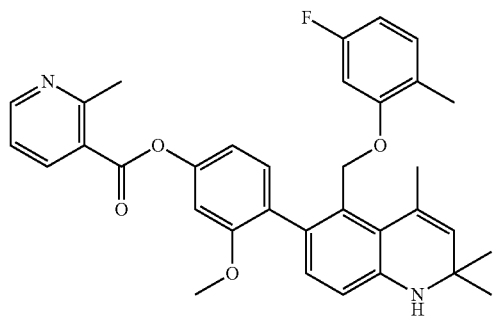 | $^1$H-NMR (400 MHz, DMSO-d$_6$) δ 1.06 (s, 3H), 1.15 (s, 3H), 2.03 (s, 3H), 2.08 (s, 3H), 2.80 (s, 3H), 3.75 (s, 3H), 4.65 (d, J = 12.1 Hz, 1H), 5.11 (d, J = 12.1 Hz, 1H), 5.40 (s, 1H), 6.06 (s, 1H), 6.38 (dd, J = 11.2, 2.4 Hz, 1H), 6.53 (td, J = 8.4, 2.4 Hz, 1H), 6.65 (d, J = 8.1 Hz, 1H), 6.81 (d, J = 8.1 Hz, 1H), 6.92 (dd, J = 8.2, 2.3 Hz, 1H), 7.03-7.06 (m, 1H), 7.09 (d, J = 2.3 Hz, 1H), 7.25 (d, J = 8.2 Hz, 1H), 7.47 (dd, J = 7.9, 4.7 Hz, 1H), 8.45 (dd, J = 7.9, 1.7 Hz, 1H), 8.72 (dd, J = 4.7, 1.7 Hz, 1H) |

5-(5-Fluoro-2-methylphenoxymethyl)-6-[2-methoxy-4-(pyridin-3-ylacetoxy)phenyl]-2,2,4-trimethyl-1,2-dihydroquinoline (Compound No. 1-50)

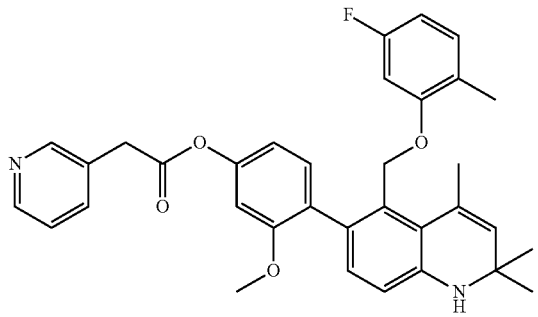 [SMILES: COc1cc(OC(=O)Cc2cccnc2)ccc1-c1ccc2c(c1COc1cc(F)ccc1C)C(C)=CC(C)(C)N2]

$^1$H-NMR (400 MHz, DMSO-d$_6$) δ 1.05 (s, 3H), 1.14 (s, 3H), 2.01 (s, 3H), 2.06 (s, 3H), 3.71 (s, 3H), 4.05 (s, 2H), 4.60 (d, J = 12.1 Hz, 1H), 5.07 (d, J = 12.1 Hz, 1H), 5.39 (s, 1H), 6.04 (s, 1H), 6.34 (dd, J = 11.5, 2.4 Hz, 1H), 6.52 (td, J = 8.5, 2.4 Hz, 1H), 6.62 (d, J = 8.2 Hz, 1H), 6.75 (dd, J = 8.2, 2.3 Hz, 1H), 6.78 (d, J = 8.2 Hz, 1H), 6.89 (d, J = 2.3 Hz, 1H), 7.01-7.05 (m, 1H), 7.18 (d, J = 8.2 Hz, 1H), 7.40 (dd, J = 7.8, 4.8 Hz, 1H), 7.47 (dt, J = 7.8, 2.0 Hz, 1H), 8.50 (dd, J = 4.8, 2.0 Hz, 1H), 8.59 (d, J = 2.0 Hz, 1H)

5-(5-Fluoro-2-methylphenoxymethyl)-6-[2-methoxy-4-(3-methylthiophen-2-ylcarbonyloxy)phenyl]-2,2,4-trimethyl-1,2-dihydroquinoline (Compound No. 1-51)

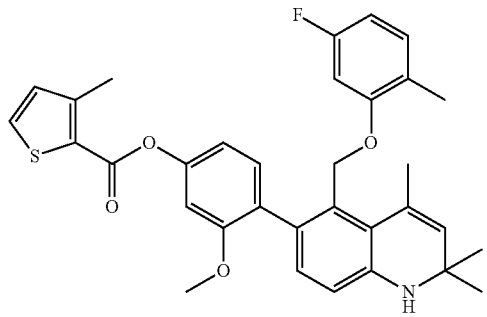

$^1$H-NMR (500 MHz, DMSO-d$_6$) δ 1.05 (s, 3H), 1.15 (s, 3H), 2.03 (s, 3H), 2.08 (s, 3H), 2.56 (s, 3H), 3.74 (s, 3H), 4.65 (d, J = 12.1 Hz, 1H), 5.10 (d, J = 12.1 Hz, 1H), 5.40 (s, 1H), 6.04 (s, 1H), 6.37 (dd, J = 11.5, 2.5 Hz, 1H), 6.53 (td, J = 8.4, 2.5 Hz, 1H), 6.64 (d, J = 8.2 Hz, 1H), 6.80 (d, J = 8.2 Hz, 1H), 6.85 (dd, J = 8.2, 2.2 Hz, 1H), 7.00 (d, J = 2.2 Hz, 1H), 7.03-7.06 (m, 1H), 7.17 (d, J = 5.1 Hz, 1H), 7.22 (d, J = 8.2 Hz, 1H), 7.93 (d, J = 5.1 Hz, 1H)

5-(5-Fluoro-2-methylphenoxymethyl)-6-[2-methoxy-4-(4-methylthiophen-2-ylcarbonyloxy)phenyl]-2,2,4-trimethyl-1,2-dihydroquinoline (Compound No. 1-52)

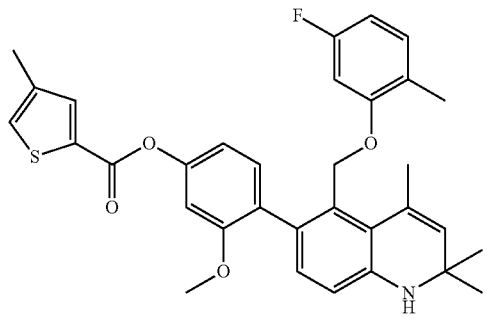

$^1$H-NMR (500 MHz, DMSO-d$_6$) δ 1.07 (s, 3H), 1.16 (s, 3H), 2.03 (s, 3H), 2.08 (s, 3H), 2.30 (s, 3H), 3.74 (s, 3H), 4.64 (d, J = 12.4 Hz, 1H), 5.10 (d, J = 12.4 Hz, 1H), 5.41 (s, 1H), 6.05 (s, 1H), 6.38 (dd, J = 11.3, 2.5 Hz, 1H), 6.54 (td, J = 8.5, 2.5 Hz, 1H), 6.65 (d, J = 8.2 Hz, 1H), 6.81 (d, J = 8.2 Hz, 1H), 6.87 (dd, J = 8.2, 2.2 Hz, 1H), 7.02 (d, J = 2.2 Hz, 1H), 7.04-7.07 (m, 1H), 7.23 (d, J = 8.2 Hz, 1H), 7.69-7.70 (m, 1H), 7.87 (d, J = 1.2 Hz, 1H)

6-[4-(4-Acetylbenzoyloxy)-2-methoxyphenyl]-5-(5-fluoro-2-methylphenoxymethyl)-2,2,4-trimethyl-1,2-dihydroquinoline (Compound No. 1-53)

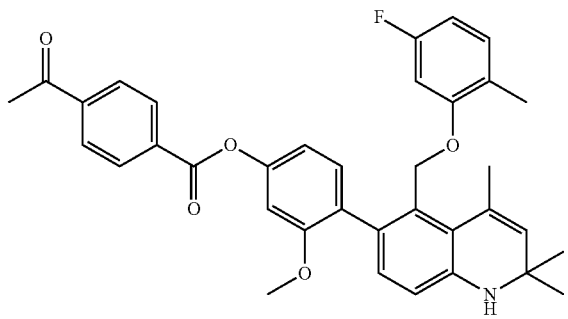 [SMILES: COc1cc(OC(=O)c2ccc(C(C)=O)cc2)ccc1-c1ccc2c(c1COc1cc(F)ccc1C)C(C)=CC(C)(C)N2]

$^1$H-NMR (400 MHz, DMSO-d$_6$) δ 1.06 (s, 3H), 1.16 (s, 3H), 2.03 (s, 3H), 2.08 (s, 3H), 2.67 (s, 3H), 3.74 (s, 3H), 4.65 (d, J = 12.2 Hz, 1H), 5.10 (d, J = 12.2 Hz, 1H), 5.40 (s, 1H), 6.06 (s, 1H), 6.38 (dd, J = 11.5, 2.4 Hz, 1H), 6.54 (td, J = 8.4, 2.4 Hz, 1H), 6.65 (d, J = 8.2 Hz, 1H), 6.82 (d, J = 8.2 Hz, 1H), 6.92 (dd, J = 8.3, 2.2 Hz, 1H), 7.03-7.07 (m, 1H), 7.09 (d, J = 2.2 Hz, 1H), 7.25 (d, J = 8.3 Hz, 1H), 8.14-8.17 (m, 2H), 8.25-8.28 (m, 2H)

5-(5-Fluoro-2-methylphenoxymethyl)-6-[2-methoxy-4-(3-methoxycarbonylbenzoyloxy)phenyl]-2,2,4-trimethyl-1,2-dihydroquinoline (Compound No. 1-54)

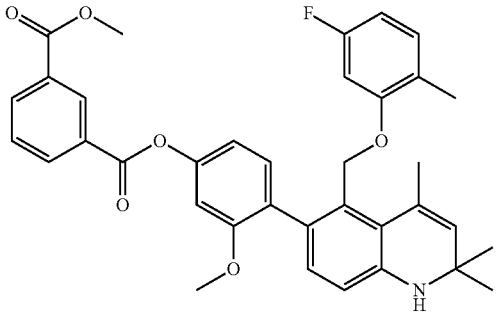 [SMILES: COC(=O)c1cccc(C(=O)Oc2ccc(-c3ccc4c(c3COc3cc(F)ccc3C)C(C)=CC(C)(C)N4)c(OC)c2)c1]

$^1$H-NMR (400 MHz, DMSO-d$_6$)
δ 1.06 (s, 3H), 1.16 (s, 3H), 2.03 (s, 3H), 2.08 (s, 3H), 3.74 (s, 3H), 3.92 (s, 3H), 4.65 (d, J = 12.2 Hz, 1H), 5.11 (d, J = 12.2 Hz, 1H), 5.40 (s, 1H), 6.06 (s, 1H), 6.39 (dd, J = 11.5, 2.4 Hz, 1H), 6.54 (td, J = 8.3, 2.4 Hz, 1H), 6.65 (d, J = 8.2 Hz, 1H), 6.82 (d, J = 8.2 Hz, 1H), 6.93 (dd, J = 8.2, 2.2 Hz, 1H), 7.03-7.06 (m, 1H), 7.10 (d, J = 2.2 Hz, 1H), 7.25 (d, J = 8.2 Hz, 1H), 7.79 (t, J = 7.9 Hz, 1H), 8.31 (dt, J = 7.9, 1.6 Hz, 1H), 8.40 (dt, J = 7.9, 1.6 Hz, 1H), 8.66 (t, J = 1.6 Hz, 1H)

5-(5-Fluoro-2-methylphenoxymethyl)-6-[2-methoxy-4-(6-methylpyridin-3-ylcarbonyloxy)phenyl]-2,2,4-trimethyl-1,2-dihydroquinoline (Compound No. 1-55)

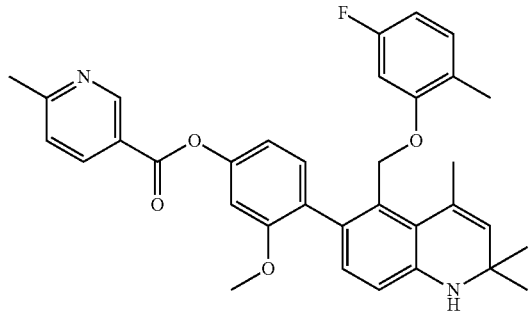

$^1$H-NMR (400 MHz, DMSO-d$_6$)
δ 1.06 (s, 3H), 1.16 (s, 3H), 2.03 (s, 3H), 2.08 (s, 3H), 2.61 (s, 3H), 3.74 (s, 3H), 4.64 (d, J = 12.2 Hz, 1H), 5.10 (d, J = 12.2 Hz, 1H), 5.40 (s, 1H), 6.05 (s, 1H), 6.38 (dd, J = 11.4, 2.4 Hz, 1H), 6.54 (td, J = 8.4, 2.4 Hz, 1H), 6.65 (d, J = 8.3 Hz, 1H), 6.82 (d, J = 8.3 Hz, 1H), 6.91 (dd, J = 8.1, 2.2 Hz, 1H), 7.03-7.06 (m, 1H), 7.08 (d, J = 2.2 Hz, 1H), 7.24 (d, J = 8.1 Hz, 1H), 7.51 (d, J = 8.1 Hz, 1H), 8.35 (dd, J = 8.1, 2.2 Hz, 1H), 9.14 (d, J = 2.2 Hz, 1H)

5-(5-Fluoro-2-methylphenoxymethyl)-6-[2-methoxy-4-(4-methylpyridin-3-ylcarbonyloxy)phenyl]-2,2,4-trimethyl-1,2-dihydroquinoline (Compound No. 1-56)

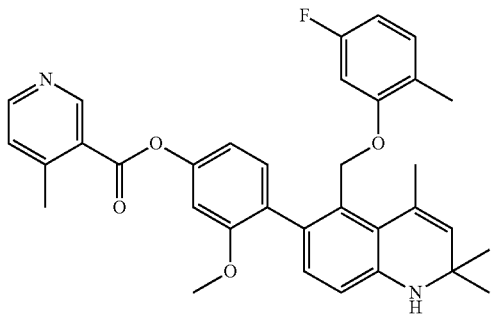 [SMILES: COc1cc(OC(=O)c2cnccc2C)ccc1-c1ccc2c(c1COc1cc(F)ccc1C)C(C)=CC(C)(C)N2]

$^1$H-NMR (500 MHz, DMSO-d$_6$)
δ 1.07 (s, 3H), 1.16 (s, 3H), 2.04 (s, 3H), 2.09 (s, 3H), 2.64 (s, 3H), 3.76 (s, 3H), 4.66 (d, J = 12.2 Hz, 1H), 5.11 (d, J = 12.2 Hz, 1H), 5.41 (s, 1H), 6.05 (s, 1H), 6.39 (dd, J = 11.3, 2.4 Hz, 1H), 6.54 (td, J = 8.4, 2.4 Hz, 1H), 6.66 (d, J = 8.1 Hz, 1H), 6.82 (d, J = 8.1 Hz, 1H), 6.95 (dd, J = 8.0, 2.2 Hz, 1H), 7.04-7.07 (m, 1H), 7.12 (d, J = 2.2 Hz, 1H), 7.26 (d, J = 8.0 Hz, 1H), 7.48 (d, J = 5.1 Hz, 1H), 8.69 (d, J = 5.1 Hz, 1H), 9.19 (s, 1H)

5-(5-Fluoro-2-methylphenoxymethyl)-6-[2-methoxy-4-(3-methylfuran-2-ylcarbonyloxy)phenyl]-2,2,4-trimethyl-1,2-dihydroquinoline (Compound No. 1-57)

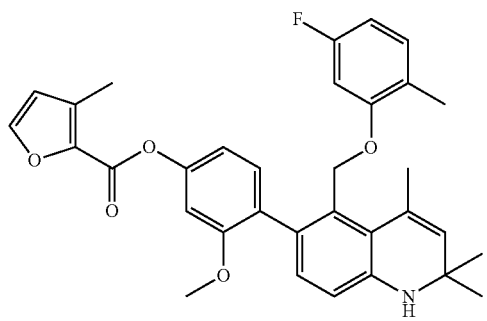

$^1$H-NMR (400 MHz, DMSO-d$_6$)
δ 1.05 (s, 3H), 1.15 (s, 3H), 2.02 (s, 3H), 2.08 (s, 3H), 2.38 (s, 3H), 3.73 (s, 3H), 4.65 (d, J = 12.2 Hz, 1H), 5.10 (d, J = 12.2 Hz, 1H), 5.40 (s, 1H), 6.05 (s, 1H), 6.37 (dd, J = 11.4, 2.5 Hz, 1H), 6.53 (td, J = 8.4, 2.5 Hz, 1H), 6.64 (d, J = 8.2 Hz, 1H), 6.70 (d, J = 1.7 Hz, 1H), 6.80 (d, J = 8.2 Hz, 1H), 6.86 (dd, J = 8.3, 2.2 Hz, 1H), 7.01 (d, J = 2.2 Hz, 1H), 7.02-7.06 (m, 1H), 7.22 (d, J = 8.3 Hz, 1H), 7.96 (d, J = 1.7 Hz, 1H)

6-(4-t-Butylcarbonyloxy-2-methoxyphenyl)-5-(5-fluoro-2-methylphenoxymethyl)-2,2,4-trimethyl-1,2-dihydroquinoline (Compound No. 1-58)

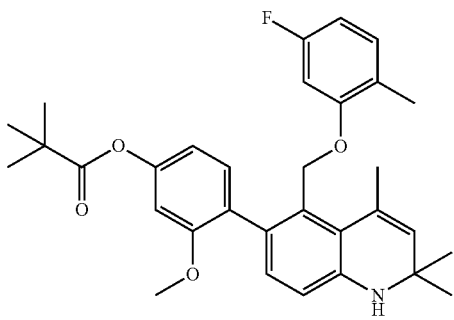 [SMILES: COc1cc(OC(=O)C(C)(C)C)ccc1-c1ccc2c(c1COc1cc(F)ccc1C)C(C)=CC(C)(C)N2]

$^{1}$H-NMR (500 MHz, DMSO-$d_6$) δ 1.05 (s, 3H), 1.15 (s, 3H), 1.31 (s, 9H), 2.02 (s, 3H), 2.06 (s, 3H), 3.73 (s, 3H), 4.61 (d, J = 12.2 Hz, 1H), 5.07 (d, J = 12.2 Hz, 1H), 5.39 (s, 1H), 6.03 (s, 1H), 6.35 (dd, J = 11.3, 2.4 Hz, 1H), 6.53 (td, J = 8.4, 2.4 Hz, 1H), 6.63 (d, J = 8.2 Hz, 1H), 6.69 (dd, J = 8.1, 2.3 Hz, 1H), 6.78 (d, J = 8.2 Hz, 1H), 6.81 (d, J = 2.3 Hz, 1H), 7.02-7.05 (m, 1H), 7.18 (d, J = 8.1 Hz, 1H)

5-(5-Fluoro-2-methylphenoxymethyl)-6-[2-methoxy-4-(2-methoxycarbonylbenzoyloxy)phenyl]-2,2,4-trimethyl-1,2-dihydroquinoline (Compound No. 1-59)

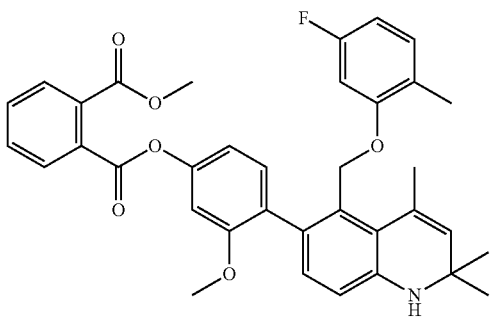 [SMILES: COC(=O)c1ccccc1C(=O)Oc1ccc(-c2ccc3c(c2COc2cc(F)ccc2C)C(C)=CC(C)(C)N3)c(OC)c1]

$^{1}$H-NMR (400 MHz, DMSO-$d_6$) δ 1.06 (s, 3H), 1.16 (s, 3H), 2.03 (s, 3H), 2.08 (s, 3H), 3.75 (s, 3H), 3.85 (s, 3H), 4.64 (d, J = 12.2 Hz, 1H), 5.09 (d, J = 12.2 Hz, 1H), 5.40 (s, 1H), 6.06 (s, 1H), 6.38 (dd, J = 11.5, 2.4 Hz, 1H), 6.53 (td, J = 8.3, 2.4 Hz, 1H), 6.62 (d, J = 8.3 Hz, 1H), 6.81 (d, J = 8.3 Hz, 1H), 6.89 (dd, J = 8.2, 2.2 Hz, 1H), 7.00 (d, J = 2.2 Hz, 1H), 7.02-7.06 (m, 1H), 7.26 (d, J = 8.2 Hz, 1H), 7.75-7.80 (m, 2H), 7.85-7.87 (m, 1H), 7.96-7.99 (m, 1H)

5-(5-Fluoro-2-methylphenoxymethyl)-6-[2-methoxy-4-(4-methoxycarbonylbenzoyloxy)phenyl]-2,2,4-trimethyl-1,2-dihydroquinoline (Compound No. 1-60)

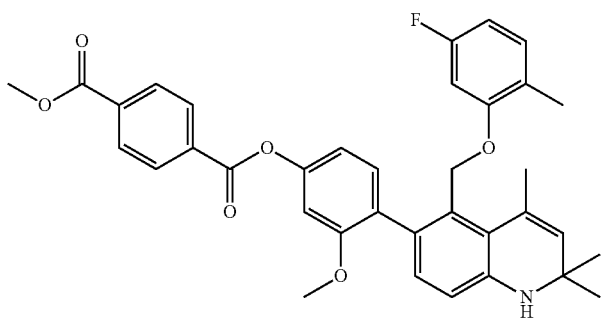

$^{1}$H-NMR (400 MHz, DMSO-$d_6$) δ 1.06 (s, 3H), 1.16 (s, 3H), 2.03 (s, 3H), 2.08 (s, 3H), 3.74 (s, 3H), 3.92 (s, 3H), 4.65 (d, J = 12.2 Hz, 1H), 5.10 (d, J = 12.2 Hz, 1H), 5.40 (s, 1H), 6.06 (s, 1H), 6.38 (dd, J = 11.5, 2.4 Hz, 1H), 6.54 (td, J = 8.3, 2.4 Hz, 1H), 6.65 (d, J = 8.3 Hz, 1H), 6.82 (d, J = 8.3 Hz, 1H), 6.93 (dd, J = 8.2, 2.2 Hz, 1H), 7.03-7.07 (m, 1H), 7.09 (d, J = 2.2 Hz, 1H), 7.25 (d, J = 8.2 Hz, 1H), 8.17 (d, J = 8.6 Hz, 2H), 8.28 (d, J = 8.6 Hz, 2H)

5-(5-Fluoro-2-methylphenoxymethyl)-6-[2-methoxy-4-(pyrimidin-5-ylcarbonyloxy)phenyl]-2,2,4-trimethyl-1,2-dihydroquinoline (Compound No. 1-61)

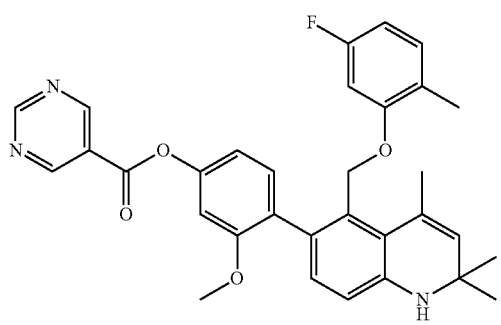 [SMILES: COc1cc(OC(=O)c2cncnc2)ccc1-c1ccc2c(c1COc1cc(F)ccc1C)C(C)=CC(C)(C)N2]

$^{1}$H-NMR (500 MHz, DMSO-$d_6$) δ 1.07 (s, 3H), 1.16 (s, 3H), 2.03 (s, 3H), 2.08 (s, 3H), 3.74 (s, 3H), 4.64 (d, J = 12.1 Hz, 1H), 5.09 (d, J = 12.1 Hz, 1H), 5.41 (s, 1H), 6.06 (s, 1H), 6.39 (dd, J = 11.3, 2.5 Hz, 1H), 6.54 (td, J = 8.3, 2.5 Hz, 1H), 6.65 (d, J = 8.2 Hz, 1H), 6.82 (d, J = 8.2 Hz, 1H), 6.95 (dd, J = 8.2, 2.2 Hz, 1H), 7.03-7.06 (m, 1H), 7.13 (d, J = 2.2 Hz, 1H), 7.26 (d, J = 8.2 Hz, 1H), 9.44 (s, 2H), 9.51 (s, 1H)

| | |
|---|---|
| 6-[4-(3-Chlorothiophen-2-ylcarbonyloxy)-2-methoxyphenyl]-5-(5-fluoro-2-methylphenoxymethyl)-2,2,4-trimethyl-1,2-dihydroquinoline (Compound No. 1-62)<br />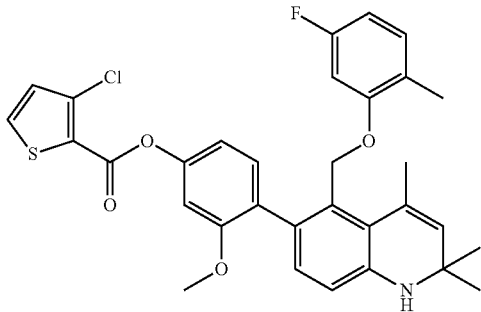 | $^1$H-NMR (400 MHz, DMSO-d$_6$) δ 1.05 (s, 3H), 1.15 (s, 3H), 2.02 (s, 3H), 2.07 (s, 3H), 3.74 (s, 3H), 4.64 (d, J = 12.3 Hz, 1H), 5.10 (d, J = 12.3 Hz, 1H), 5.40 (s, 1H), 6.05 (s, 1H), 6.37 (dd, J = 11.4, 2.4 Hz, 1H), 6.53 (td, J = 8.4, 2.4 Hz, 1H), 6.64 (d, J = 8.2 Hz, 1H), 6.80 (d, J = 8.2 Hz, 1H), 6.88 (dd, J = 8.2, 2.3 Hz, 1H), 7.02-7.06 (m, 1H), 7.04 (d, J = 2.3 Hz, 1H), 7.23 (d, J = 8.2 Hz, 1H), 7.36 (d, J = 5.1 Hz, 1H), 8.15 (d, J = 5.1 Hz, 1H) |
| 6-[4-(5-Chlorothiophen-2-ylcarbonyloxy)-2-methoxyphenyl]-5-(5-fluoro-2-methylphenoxymethyl)-2,2,4-trimethyl-1,2-dihydroquinoline (Compound No. 1-63)<br />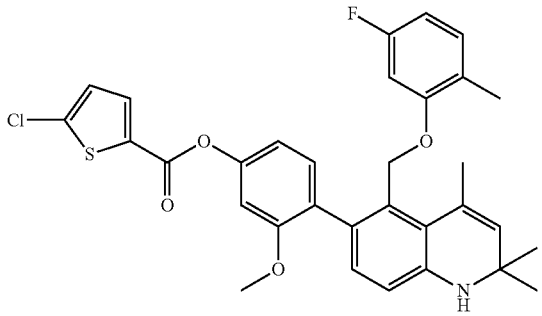 | $^1$H-NMR (400 MHz, DMSO-d$_6$) δ 1.06 (s, 3H), 1.16 (s, 3H), 2.02 (s, 3H), 2.07 (s, 3H), 3.73 (s, 3H), 4.62 (d, J = 12.1 Hz, 1H), 5.08 (d, J = 12.1 Hz, 1H), 5.40 (s, 1H), 6.05 (s, 1H), 6.37 (dd, J = 11.5, 2.4 Hz, 1H), 6.53 (td, J = 8.4, 2.4 Hz, 1H), 6.64 (d, J = 8.2 Hz, 1H), 6.80 (d, J = 8.2 Hz, 1H), 6.88 (dd, J = 8.1, 2.2 Hz, 1H), 7.02-7.06 (m, 1H), 7.04 (d, J = 2.2 Hz, 1H), 7.23 (d, J = 8.1 Hz, 1H), 7.39 (d, J = 4.2 Hz, 1H), 7.93 (d, J = 4.2 Hz, 1H) |
| 6-[4-(5-Bromofuran-2-ylcarbonyloxy)-2-methoxyphenyl]-5-(5-fluoro-2-methylphenoxymethyl)-2,2,4-trimethyl-1,2-dihydroquinoline (Compound No. 1-64)<br />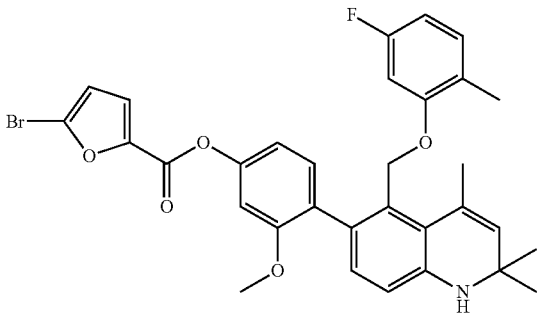 [SMILES: COc1cc(OC(=O)c2ccc(Cl)s2)ccc1-c1ccc2c(c1COc1cc(F)ccc1C)C(C)=CC(C)(C)N2] | $^1$H-NMR (400 MHz, DMSO-d$_6$) δ 1.06 (s, 3H), 1.15 (s, 3H), 2.02 (s, 3H), 2.07 (s, 3H), 3.73 (s, 3H), 4.62 (d, J = 12.1 Hz, 1H), 5.08 (d, J = 12.2 Hz, 1H), 5.40 (s, 1H), 6.05 (s, 1H), 6.37 (dd, J = 11.4, 2.5 Hz, 1H), 6.53 (td, J = 8.4, 2.5 Hz, 1H), 6.64 (d, J = 8.2 Hz, 1H), 6.80 (d, J = 8.2 Hz, 1H), 6.87 (dd, J = 8.3, 2.3 Hz, 1H), 6.97 (d, J = 3.7 Hz, 1H), 7.02-7.06 (m, 1H), 7.03 (d, J = 2.3 Hz, 1H), 7.22 (d, J = 8.3 Hz, 1H), 7.61 (d, J = 3.7 Hz, 1H) |
| 5-(5-Fluoro-2-methylphenoxymethyl)-6-[2-methoxy-4-(5-nitrofuran-2-ylcarbonyloxy)phenyl]-2,2,4-trimethyl-1,2-dihydroquinoline (Compound No. 1-65)<br />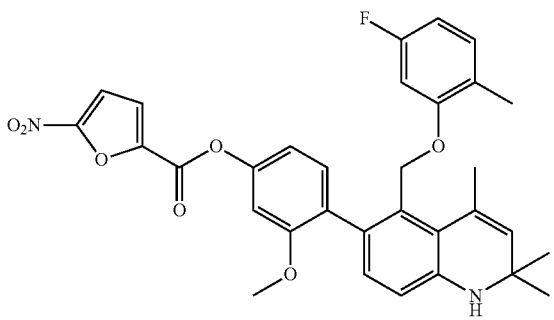 [SMILES: COc1cc(OC(=O)c2ccc([N+](=O)[O-])o2)ccc1-c1ccc2c(c1COc1cc(F)ccc1C)C(C)=CC(C)(C)N2] | $^1$H-NMR (400 MHz, DMSO-d$_6$) δ 1.07 (s, 3H), 1.16 (s, 3H), 2.02 (s, 3H), 2.08 (s, 3H), 3.74 (s, 3H), 4.63 (d, J = 12.2 Hz, 1H), 5.09 (d, J = 12.2 Hz, 1H), 5.40 (s, 1H), 6.06 (s, 1H), 6.38 (dd, J = 11.2, 2.5 Hz, 1H), 6.54 (td, J = 8.4, 2.5 Hz, 1H), 6.65 (d, J = 8.2 Hz, 1H), 6.81 (d, J = 8.2 Hz, 1H), 6.93 (dd, J = 8.2, 2.2 Hz, 1H), 7.02-7.06 (m, 1H), 7.09 (d, J = 2.2 Hz, 1H), 7.26 (d, J = 8.2 Hz, 1H), 7.84 (d, J = 3.9 Hz, 1H), 7.89 (d, J = 3.9 Hz, 1H) |

6-[4-(2-Chloro-6-methylpyridin-4-ylcarbonyloxy)-2-methoxyphenyl]-5-(5-fluoro-2-methylphenoxymethyl)-2,2,4-trimethyl-1,2-dihydroquinoline (Compound No. 1-66)

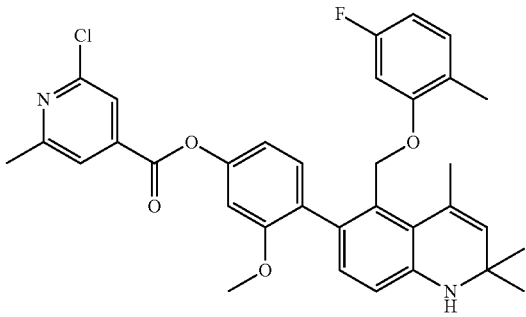

$^1$H-NMR (400 MHz, DMSO-d$_6$) δ 1.07 (s, 3H), 1.17 (s, 3H), 2.02 (s, 3H), 2.08 (s, 3H), 2.60 (s, 3H), 3.73 (s, 3H), 4.62 (d, J = 12.0 Hz, 1H), 5.09 (d, J = 12.0 Hz, 1H), 5.40 (s, 1H), 6.06 (s, 1H), 6.38 (dd, J = 11.4, 2.3 Hz, 1H), 6.54 (td, J = 8.4, 2.3 Hz, 1H), 6.65 (d, J = 8.3 Hz, 1H), 6.81 (d, J = 8.3 Hz, 1H), 6.94 (dd, J = 8.3, 2.3 Hz, 1H), 7.02-7.07 (m, 1H), 7.11 (d, J = 2.3 Hz, 1H), 7.26 (d, J = 8.3 Hz, 1H), 7.88 (d, J = 1.0 Hz, 1H), 7.93 (d, J = 1.0 Hz, 1H)

6-[4-(3-Chloropyridin-4-ylcarbonyloxy)-2-methoxyphenyl]-5-(5-fluoro-2-methylphenoxymethyl)-2,2,4-trimethyl-1,2-dihydroquinoline (Compound No. 1-67)

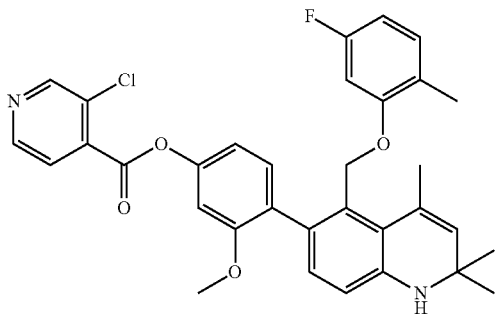 [SMILES: COc1cc(OC(=O)c2ccncc2Cl)ccc1-c1ccc2c(c1COc1cc(F)ccc1C)C(C)=CC(C)(C)N2]

$^1$H-NMR (400 MHz, DMSO-d$_6$) δ 1.07 (s, 3H), 1.16 (s, 3H), 2.03 (s, 3H), 2.08 (s, 3H), 3.74 (s, 3H), 4.63 (d, J = 12.1 Hz, 1H), 5.09 (d, J = 12.1 Hz, 1H), 5.41 (s, 1H), 6.06 (s, 1H), 6.38 (dd, J = 11.4, 2.4 Hz, 1H), 6.54 (td, J = 8.4, 2.4 Hz, 1H), 6.65 (d, J = 8.2 Hz, 1H), 6.81 (d, J = 8.2 Hz, 1H), 6.95 (dd, J = 8.3, 2.2 Hz, 1H), 7.03-7.07 (m, 1H), 7.13 (d, J = 2.2 Hz, 1H), 7.26 (d, J = 8.3 Hz, 1H), 8.03 (dd, J = 5.0, 1.8 Hz, 1H), 8.10 (dd, J = 1.8, 0.7 Hz, 1H), 8.72 (dd, J = 5.0, 0.7 Hz, 1H)

6-[4-(2-Chloropyridin-4-ylcarbonyloxy)-2-methoxyphenyl]-5-(5-fluoro-2-methylphenoxymethyl)-2,2,4-trimethyl-1,2-dihydroquinoline (Compound No. 1-68)

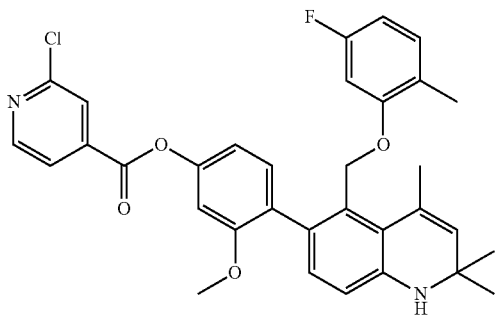 [SMILES: COc1cc(OC(=O)c2ccnc(Cl)c2)ccc1-c1ccc2c(c1COc1cc(F)ccc1C)C(C)=CC(C)(C)N2]

$^1$H-NMR (400 MHz, DMSO-d$_6$) δ 1.06 (s, 3H), 1.16 (s, 3H), 2.03 (s, 3H), 2.08 (s, 3H), 3.75 (s, 3H), 4.64 (d, J = 12.0 Hz, 1H), 5.10 (d, J = 12.0 Hz, 1H), 5.40 (s, 1H), 6.06 (s, 1H), 6.38 (dd, J = 11.5, 2.4 Hz, 1H), 6.53 (td, J = 8.5, 2.4 Hz, 1H), 6.65 (d, J = 8.2 Hz, 1H), 6.82 (d, J = 8.2 Hz, 1H), 6.95 (dd, J = 8.2, 2.2 Hz, 1H), 7.02-7.06 (m, 1H), 7.11 (d, J = 2.2 Hz, 1H), 7.27 (d, J = 8.2 Hz, 1H), 8.06 (d, J = 4.9 Hz, 1H), 8.79 (d, J = 4.9 Hz, 1H), 8.91 (s, 1H)

5-(5-Fluoro-2-methylphenoxymethyl)-6-[4-(3-fluoropyridin-4-ylcarbonyloxy)-2-methoxyphenyl]-2,2,4-trimethyl-1,2-dihydroquinoline (Compound No. 1-69)

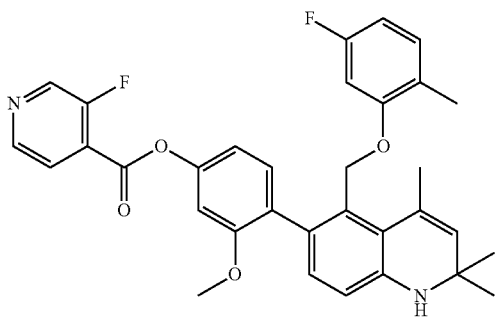 [SMILES: COc1cc(OC(=O)c2ccncc2F)ccc1-c1ccc2c(c1COc1cc(F)ccc1C)C(C)=CC(C)(C)N2]

$^1$H-NMR (400 MHz, DMSO-d$_6$) δ 1.06 (s, 3H), 1.16 (s, 3H), 2.03 (s, 3H), 2.08 (s, 3H), 3.74 (s, 3H), 4.64 (d, J = 12.2 Hz, 1H), 5.10 (d, J = 12.2 Hz, 1H), 5.40 (s, 1H), 6.06 (s, 1H), 6.38 (dd, J = 11.5, 2.4 Hz, 1H), 6.53 (td, J = 8.3, 2.4 Hz, 1H), 6.65 (d, J = 8.2 Hz, 1H), 6.82 (d, J = 8.2 Hz, 1H), 6.94 (dd, J = 8.2, 2.3 Hz, 1H), 7.02-7.06 (m, 1H), 7.11 (d, J = 2.3 Hz, 1H), 7.26 (d, J = 8.2 Hz, 1H), 8.03-8.05 (m, 1H), 8.70 (d, J = 4.9 Hz, 1H), 8.88 (d, J = 2.2 Hz, 1H)

| | |
|---|---|
| 6-(4-Butyryloxy-2-methoxyphenyl)-5-(2-methyl-5-nitrophenoxymethyl)-2,2,4-trimethyl-1,2-dihydroquinoline (Compound No. 1-70)<br />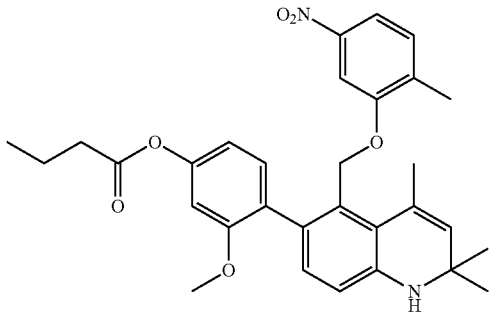 [SMILES: CCCC(=O)Oc1ccc(-c2ccc3c(c2COc2cc([N+](=O)[O-])ccc2C)C(C)=CC(C)(C)N3)c(OC)c1] | ¹H-NMR (500 MHz, DMSO-D₆) δ 0.90 (s, 3H), 0.98 (t, J = 7.5 Hz, 3H), 1.18 (s, 3H), 1.63-1.69 (m, 2H), 2.12 (s, 3H), 2.18 (s, 3H), 2.56 (t, J = 7.2 Hz, 2H), 3.73 (s, 3H), 4.77 (d, J = 12.5 Hz, 1H), 5.30 (d, J = 12.5 Hz, 1H), 5.40 (s, 1H), 6.04 (s, 1H), 6.62 (d, J = 8.2 Hz, 1H), 6.75 (dd, J = 8.2, 2.1 Hz, 1H), 6.79 (d, J = 8.2 Hz, 1H), 6.85 (d, J = 2.1 Hz, 1H), 7.14 (d, J = 2.1 Hz, 1H), 7.27 (d, J = 8.2 Hz, 1H), 7.33 (d, J = 8.1 Hz, 1H), 7.63 (dd, J = 8.1, 2.1 Hz, 1H) |
| 6-[2-Methoxy-4-(2-methoxybenzoyloxy)phenyl]-5-(2-methyl-5-nitrophenoxymethyl)-2,2,4-trimethyl-1,2-dihydroquinoline (Compound No. 1-71)<br />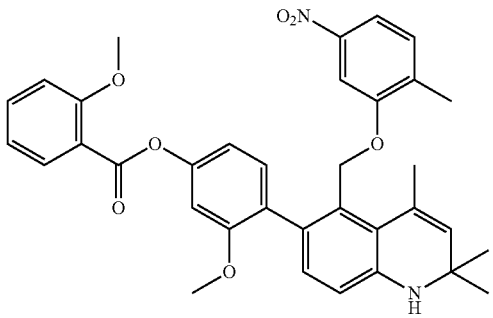 [SMILES: COc1ccccc1C(=O)Oc1ccc(-c2ccc3c(c2COc2cc([N+](=O)[O-])ccc2C)C(C)=CC(C)(C)N3)c(OC)c1] | ¹H-NMR (500 MHz, DMSO-D₆) δ 0.90 (s, 3H), 1.19 (s, 3H), 2.13 (s, 3H), 2.19 (s, 3H), 3.76 (s, 3H), 3.88 (s, 3H), 4.81 (d, J = 12.7 Hz, 1H), 5.34 (d, J = 12.7 Hz, 1H), 5.40 (s, 1H), 6.05 (s, 1H), 6.63 (d, J = 8.2 Hz, 1H), 6.82 (d, J = 8.2 Hz, 1H), 6.88 (dd, J = 8.2, 2.3 Hz, 1H), 6.99 (d, J = 2.3 Hz, 1H), 7.11 (t, J = 7.5 Hz, 1H), 7.17 (d, J = 2.0 Hz, 1H), 7.24 (d, J = 8.6 Hz, 1H), 7.32 (d, J = 8.2 Hz, 1H), 7.34 (d, J = 7.9 Hz, 1H), 7.63-7.66 (m, 2H), 7.93 (dd, J = 7.9, 2.0 Hz, 1H) |
| 6-[2-Methoxy-4-(pyridin-3-ylcarbonyloxy)phenyl]-5-(2-methyl-5-nitrophenoxymethyl)-2,2,4-trimethyl-1,2-dihydroquinoline (Compound No. 1-72)<br />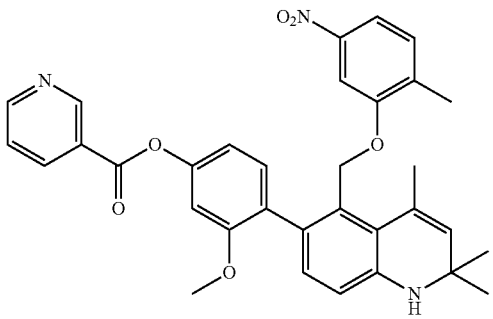 [SMILES: COc1cc(OC(=O)c2cccnc2)ccc1-c1ccc2c(c1COc1cc([N+](=O)[O-])ccc1C)C(C)=CC(C)(C)N2] | ¹H-NMR (400 MHz, DMSO-D₆) δ 0.91 (s, 3H), 1.19 (s, 3H), 2.14 (s, 3H), 2.19 (s, 3H), 3.76 (s, 3H), 4.81 (d, J = 12.5 Hz, 1H), 5.33 (d, J = 12.5 Hz, 1H), 5.41 (s, 1H), 6.07 (s, 1H), 6.64 (d, J = 8.2 Hz, 1H), 6.83 (d, J = 8.2 Hz, 1H), 6.97 (dd, J = 8.3, 2.2 Hz, 1H), 7.11 (d, J = 2.2 Hz, 1H), 7.18 (d, J = 2.2 Hz, 1H), 7.34 (d, J = 8.3 Hz, 1H), 7.34 (d, J = 8.3 Hz, 1H), 7.63-7.68 (m, 2H), 8.48 (dt, J = 8.1, 2.0 Hz, 1H), 8.91 (dd, J = 4.8, 2.0 Hz, 1H), 9.28 (dd, J = 2.0, 0.7 Hz, 1H) |
| 6-[4-(Furan-2-ylcarbonyloxy)-2-methoxyphenyl]-5-(2-methyl-5-nitrophenoxymethyl)-2,2,4-trimethyl-1,2-dihydroquinoline (Compound No. 1-73)<br />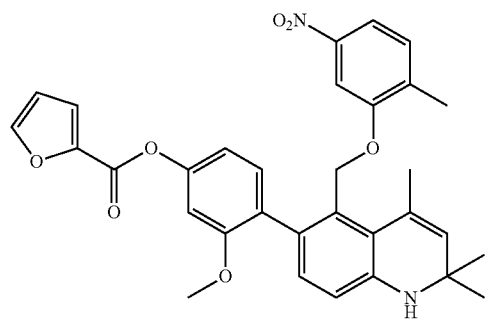 [SMILES: COc1cc(OC(=O)c2ccco2)ccc1-c1ccc2c(c1COc1cc([N+](=O)[O-])ccc1C)C(C)=CC(C)(C)N2] | ¹H-NMR (500 MHz, DMSO-D₆) δ 0.91 (s, 3H), 1.19 (s, 3H), 2.13 (s, 3H), 2.19 (s, 3H), 3.75 (s, 3H), 4.80 (d, J = 12.7 Hz, 1H), 5.32 (d, J = 12.7 Hz, 1H), 5.41 (s, 1H), 6.06 (s, 1H), 6.63 (d, J = 8.6 Hz, 1H), 6.81 (dd, J = 3.4, 1.8 Hz, 1H), 6.82 (d, J = 8.6 Hz, 1H), 6.90 (dd, J = 8.2, 2.2 Hz, 1H), 7.03 (d, J = 2.2 Hz, 1H), 7.17 (d, J = 2.1 Hz, 1H), 7.32 (d, J = 8.2 Hz, 1H), 7.34 (d, J = 8.2 Hz, 1H), 7.57 (dd, J = 3.4, 0.8 Hz, 1H), 7.64 (dd, J = 8.2, 2.1 Hz, 1H), 8.11 (dd, J = 1.8, 0.8 Hz, 1H) |

6-[4-(2-Chlorobenzoyloxy)-2-methoxyphenyl]-5-(2-methoxy-5-nitrophenoxymethyl)-2,2,4-trimethyl-1,2-dihydroquinoline (Compound No. 1-74)

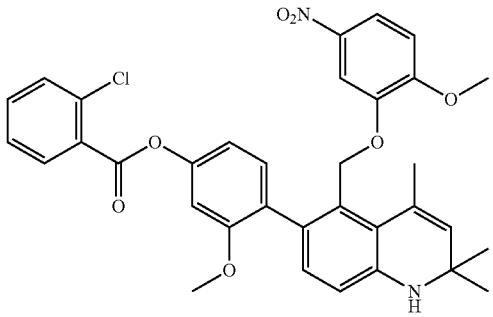 [SMILES: COc1ccc([N+](=O)[O-])cc1OCc1c(-c2ccc(OC(=O)c3ccccc3Cl)cc2OC)ccc2c1C(C)=CC(C)(C)N2]

$^1$H-NMR (400 MHz, DMSO-d$_3$) δ 1.04 (s, 3H), 1.19 (s, 3H), 2.15 (s, 3H), 3.72 (s, 3H), 3.83 (s, 3H), 4.69 (d, J = 12.0 Hz, 1H), 5.28 (d, J = 12.0 Hz, 1H), 5.40 (s, 1H), 6.04 (s, 1H), 6.64 (d, J = 8.2 Hz, 1H), 6.79 (d, J = 8.2 Hz, 1H), 6.84 (dd, J = 8.2, 2.2 Hz, 1H), 7.01 (d, J = 2.2 Hz, 1H), 7.09 (d, J = 9.0 Hz, 1H), 7.22 (d, J = 8.2 Hz, 1H), 7.34 (d, J = 2.7 Hz, 1H), 7.54-7.58 (m, 1H), 7.67-7.69 (m, 2H), 7.82 (dd, J = 9.0, 2.7 Hz, 1H), 8.09 (ddd, J = 7.7, 1.2, 0.7 Hz, 1H)

5-(2-Methoxy-5-nitrophenoxymethyl)-6-[2-methoxy-4-(pyridin-3-ylcarbonyloxy)phenyl]-2,2,4-trimethyl-1,2-dihydroquinoline (Compound No. 1-75)

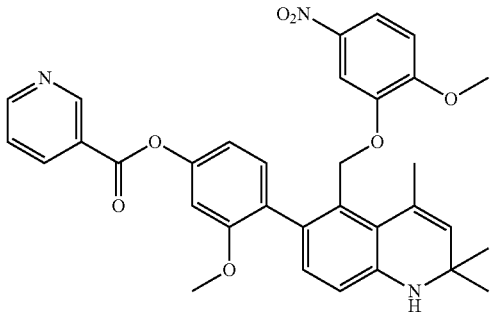 [SMILES: COc1ccc([N+](=O)[O-])cc1OCc1c(-c2ccc(OC(=O)c3cccnc3)cc2OC)ccc2c1C(C)=CC(C)(C)N2]

$^1$H-NMR (400 MHz, DMSO-d$_6$) δ 1.05 (s, 3H), 1.19 (s, 3H), 2.15 (s, 3H), 3.70 (s, 3H), 3.83 (s, 3H), 4.69 (d, J = 11.9 Hz, 1H), 5.28 (d, J = 11.9 Hz, 1H), 5.40 (s, 1H), 6.05 (s, 1H), 6.64 (d, J = 8.2 Hz, 1H), 6.79 (d, J = 8.2 Hz, 1H), 6.85 (dd, J = 8.3, 2.3 Hz, 1H), 7.05 (d, J = 2.3 Hz, 1H), 7.09 (d, J = 9.1 Hz, 1H), 7.21 (d, J = 8.3 Hz, 1H), 7.34 (d, J = 2.7 Hz, 1H), 7.66 (ddd, J = 8.1, 4.9, 1.0 Hz, 1H), 7.82 (dd, J = 9.1, 2.7 Hz, 1H), 8.46 (dt, J = 8.1, 1.9 Hz, 1H), 8.90 (dd, J = 4.9, 1.9 Hz, 1H), 9.25 (dd, J = 1.9, 1.0 Hz, 1H)

5-(2-Methoxy-5-nitrophenoxymethyl)-6-[2-methoxy-4-(pyridin-4-ylcarbonyloxy)phenyl]-2,2,4-trimethyl-1,2-dihydroquinoline (Compound No. 1-76)

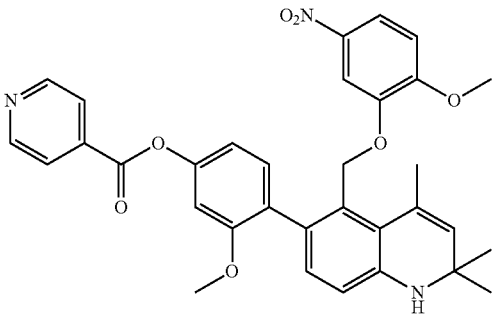 [SMILES: COc1ccc([N+](=O)[O-])cc1OCc1c(-c2ccc(OC(=O)c3ccncc3)cc2OC)ccc2c1C(C)=CC(C)(C)N2]

$^1$H-NMR (500 MHz, DMSO-d$_6$) δ 1.05 (s, 3H), 1.19 (s, 3H), 2.15 (s, 3H), 3.70 (s, 3H), 3.83 (s, 3H), 4.68 (d, J = 11.9 Hz, 1H), 5.27 (d, J = 11.9 Hz, 1H), 5.40 (s, 1H), 6.04 (s, 1H), 6.64 (d, J = 8.1 Hz, 1H), 6.79 (d, J = 8.1 Hz, 1H), 6.85 (dd, J = 8.2, 2.4 Hz, 1H), 7.05 (d, J = 2.4 Hz, 1H), 7.09 (d, J = 9.1 Hz, 1H), 7.22 (d, J = 8.2 Hz, 1H), 7.34 (d, J = 2.7 Hz, 1H), 7.82 (dd, J = 9.1, 2.7 Hz, 1H), 8.00 (d, J = 6.0 Hz, 2H), 8.89 (d, J = 6.0 Hz, 2H)

6-[2-Methoxy-4-(2-methylpyridin-3-ylcarbonyloxy)phenyl]-5-(2-methoxy-5-nitrophenoxymethyl)-2,2,4-trimethyl-1,2-dihydroquinoline (Compound No. 1-77)

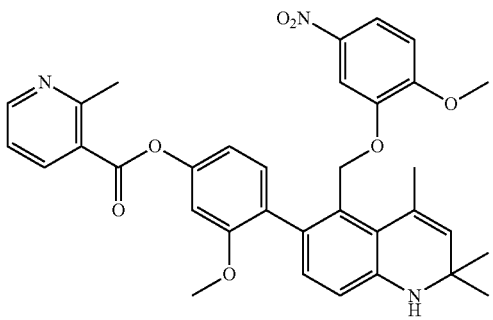 [SMILES: COc1ccc([N+](=O)[O-])cc1OCc1c(-c2ccc(OC(=O)c3cccnc3C)cc2OC)ccc2c1C(C)=CC(C)(C)N2]

$^1$H-NMR (400 MHz, DMSO-d$_6$) δ 1.04 (s, 3H), 1.19 (s, 3H), 2.15 (s, 3H), 2.78 (s, 3H), 3.71 (s, 3H), 3.83 (s, 3H), 4.69 (d, J = 12.3 Hz, 1H), 5.28 (d, J = 12.3 Hz, 1H), 5.40 (s, 1H), 6.04 (s, 1H), 6.64 (d, J = 8.3 Hz, 1H), 6.79 (d, J = 8.3 Hz, 1H), 6.84 (dd, J = 8.3, 2.2 Hz, 1H), 7.04 (d, J = 2.2 Hz, 1H), 7.09 (d, J = 9.0 Hz, 1H), 7.21 (d, J = 8.3 Hz, 1H), 7.33 (d, J = 2.8 Hz, 1H), 7.47 (dd, J = 8.1, 4.9 Hz, 1H), 7.82 (dd, J = 9.0, 2.8 Hz, 1H), 8.42 (dd, J = 8.1, 1.8 Hz, 1H), 8.71 (dd, J = 4.9, 1.8 Hz, 1H)

6-[2-Methoxy-4-(2-methoxybenzoyloxy)phenyl]-5-(2-methoxy-5-nitrophenoxymethyl)-2,2,4-trimethyl-1,2-dihydroquinoline (Compound No. 1-78)

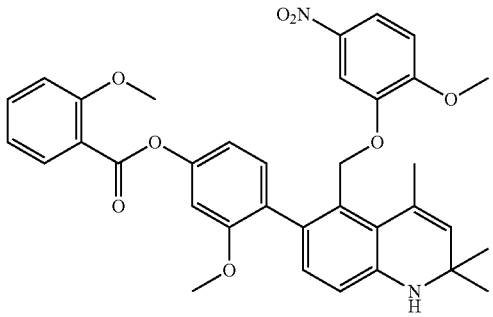 [SMILES: COc1ccc([N+](=O)[O-])cc1OCc1c(-c2ccc(OC(=O)c3ccccc3OC)cc2OC)ccc2c1C(C)=CC(C)(C)N2]

$^1$H-NMR (500 MHz, DMSO-d$_6$) δ 1.04 (s, 3H), 1.19 (s, 3H), 2.15 (s, 3H), 3.71 (s, 3H), 3.83 (s, 3H), 3.87 (s, 3H), 4.69 (d, J = 12.2 Hz, 1H), 5.28 (d, J = 12.2 Hz, 1H), 5.40 (s, 1H), 6.02 (s, 1H), 6.63 (d, J = 8.2 Hz, 1H), 6.77 (dd, J = 7.9, 2.2 Hz, 1H), 6.78 (d, J = 8.2 Hz, 1H), 6.93 (d, J = 2.2 Hz, 1H), 7.09 (d, J = 9.1 Hz, 1H), 7.10 (d, J = 8.1 Hz, 1H), 7.19 (d, J = 7.9 Hz, 1H), 7.23 (d, J = 8.1 Hz, 1H), 7.33 (d, J = 2.6 Hz, 1H), 7.64 (ddd, J = 8.1, 7.3, 1.7 Hz, 1H), 7.82 (dd, J = 9.1, 2.6 Hz, 1H), 7.90 (dd, J = 7.3, 1.7 Hz, 1H)

6-[4-(Furan-2-ylcarbonyloxy)-2-methoxyphenyl]-5-(2-methoxy-5-nitrophenoxymethyl)-2,2,4-trimethyl-1,2-dihydroquinoline (Compound No. 1-79)

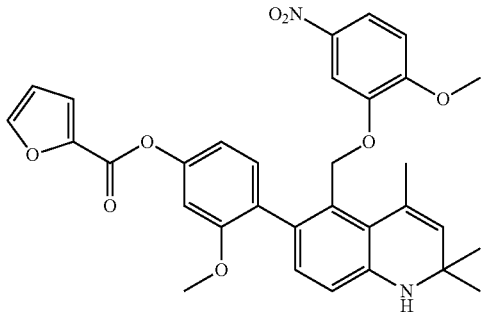 [SMILES: COc1ccc([N+](=O)[O-])cc1OCc1c(-c2ccc(OC(=O)c3ccco3)cc2OC)ccc2c1C(C)=CC(C)(C)N2]

$^1$H-NMR (400 MHz, DMSO-d$_6$) δ 1.05 (s, 3H), 1.19 (s, 3H), 2.15 (s, 3H), 3.69 (s, 3H), 3.82 (s, 3H), 4.67 (d, J = 11.9 Hz, 1H), 5.27 (d, J = 11.9 Hz, 1H), 5.40 (s, 1H), 6.04 (s, 1H), 6.63 (d, J = 8.2 Hz, 1H), 6.78 (d, J = 8.2 Hz, 1H), 6.79 (dd, J = 8.2, 2.2 Hz, 1H), 6.80 (dd, J = 3.5, 1.8 Hz, 1H), 6.97 (d, J = 2.2 Hz, 1H), 7.09 (d, J = 9.2 Hz, 1H), 7.19 (d, J = 8.2 Hz, 1H), 7.33 (d, J = 2.7 Hz, 1H), 7.55 (dd, J = 3.5, 0.9 Hz, 1H), 7.82 (dd, J = 9.2, 2.7 Hz, 1H), 8.10 (dd, J = 1.8, 0.9 Hz, 1H)

6-[4-(2-Chlorobenzoyloxy)-2-methoxyphenyl]-5-(2-methyl-5-nitrophenoxymethyl)-2,2,4-trimethyl-1,2-dihydroquinoline (Compound No. 1-80)

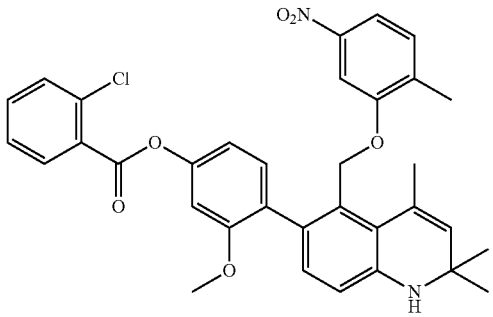 [SMILES: COc1cc(OC(=O)c2ccccc2Cl)ccc1-c1ccc2c(c1COc1cc([N+](=O)[O-])ccc1C)C(C)=CC(C)(C)N2]

$^1$H-NMR (400 MHz, DMSO-d$_6$) δ 0.91 (s, 3H), 1.19 (s, 3H), 2.14 (s, 3H), 2.19 (s, 3H), 3.77 (s, 3H), 4.81 (d, J = 12.9 Hz, 1H), 5.34 (d, J = 12.9 Hz, 1H), 5.41 (s, 1H), 6.06 (s, 1H), 6.64 (d, J = 8.3 Hz, 1H), 6.83 (d, J = 8.3 Hz, 1H), 6.95 (dd, J = 8.2, 2.2 Hz, 1H), 7.08 (d, J = 2.2 Hz, 1H), 7.18 (d, J = 2.2 Hz, 1H), 7.34 (d, J = 8.2 Hz, 1H), 7.35 (d, J = 8.2 Hz, 1H), 7.55-7.59 (m, 1H), 7.64 (dd, J = 8.2, 2.2 Hz, 1H), 7.68-7.69 (m, 2H), 8.11 (d, J = 7.6 Hz, 1H)

5-(2-Methoxy-5-nitrophenoxymethyl)-6-[2-methoxy-4-(thiophen-3-ylcarbonyloxy)phenyl]-2,2,4-trimethyl-1,2-dihydroquinoline (Compound No. 1-81)

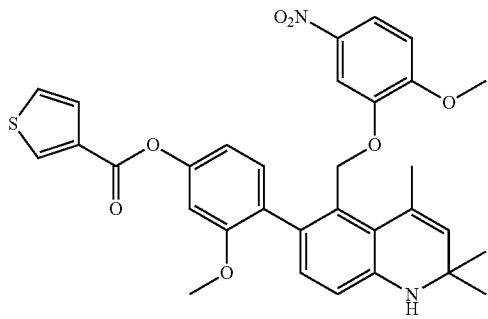 [SMILES: COc1ccc([N+](=O)[O-])cc1OCc1c(-c2ccc(OC(=O)c3ccsc3)cc2OC)ccc2c1C(C)=CC(C)(C)N2]

$^1$H-NMR (500 MHz, DMSO-d$_6$) δ 1.04 (s, 3H), 1.19 (s, 3H), 2.15 (s, 3H), 3.69 (s, 3H), 3.83 (s, 3H), 4.68 (d, J = 11.9 Hz, 1H), 5.27 (d, J = 11.9 Hz, 1H), 5.40 (s, 1H), 6.03 (s, 1H), 6.63 (d, J = 8.2 Hz, 1H), 6.78 (d, J = 8.2 Hz, 2H), 6.96 (d, J = 2.1 Hz, 1H), 7.09 (d, J = 9.1 Hz, 1H), 7.19 (d, J = 8.2 Hz, 1H), 7.33 (d, J = 2.7 Hz, 1H), 7.60 (dd, J = 5.1, 1.2 Hz, 1H), 7.75 (dd, J = 5.1, 3.1 Hz, 1H), 7.82 (dd, J = 9.1, 2.7 Hz, 1H), 8.58 (dd, J = 3.1, 1.2 Hz, 1H)

6-[4-(2-Fluorobenzoyloxy)-2-methoxyphenyl]-5-(2-methoxy-5-nitrophenoxymethyl)-2,2,4-trimethyl-1,2-dihydroquinoline (Compound No. 1-82)

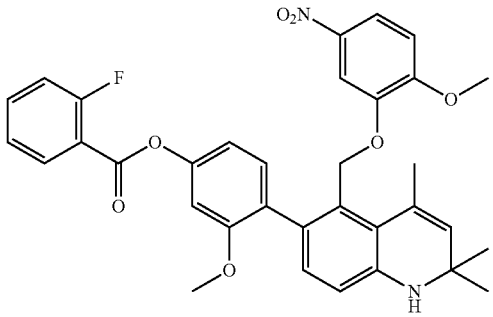 [SMILES: COc1ccc([N+](=O)[O-])cc1OCc1c(-c2ccc(OC(=O)c3ccccc3F)cc2OC)ccc2c1C(C)=CC(C)(C)N2]

$^1$H-NMR (400 MHz, DMSO-d$_6$) δ 1.04 (s, 3H), 1.19 (s, 3H), 2.15 (s, 3H), 3.71 (s, 3H), 3.83 (s, 3H), 4.69 (d, J = 11.9 Hz, 1H), 5.28 (d, J = 11.9 Hz, 1H), 5.40 (s, 1H), 6.04 (s, 1H), 6.63 (d, J = 8.2 Hz, 1H), 6.79 (d, J = 8.2 Hz, 1H), 6.82 (dd, J = 8.2, 2.3 Hz, 1H), 7.01 (d, J = 2.3 Hz, 1H), 7.09 (d, J = 9.0 Hz, 1H), 7.21 (d, J = 8.2 Hz, 1H), 7.34 (d, J = 2.7 Hz, 1H), 7.40-7.46 (m, 2H), 7.75-7.81 (m, 1H), 7.82 (dd, J = 9.0, 2.7 Hz, 1H), 8.09 (t, J = 7.7 Hz, 1H)

6-[4-(4-Fluorobenzoyloxy)-2-methoxyphenyl]-5-(2-methoxy-5-nitrophenoxymethyl)-2,2,4-trimethyl-1,2-dihydroquinoline (Compound No. 1-83)

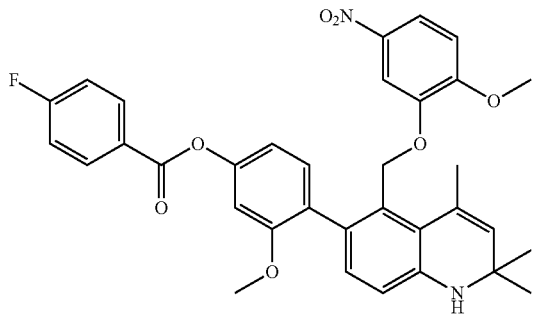 [SMILES: COc1ccc([N+](=O)[O-])cc1OCc1c(-c2ccc(OC(=O)c3ccc(F)cc3)cc2OC)ccc2c1C(C)=CC(C)(C)N2]

$^1$H-NMR (500 MHz, DMSO-d$_6$) δ 1.05 (s, 3H), 1.19 (s, 3H), 2.15 (s, 3H), 3.70 (s, 3H), 3.83 (s, 3H), 4.69 (d, J = 11.9 Hz, 1H), 5.28 (d, J = 11.9 Hz, 1H), 5.40 (s, 1H), 6.03 (s, 1H), 6.63 (d, J = 8.2 Hz, 1H), 6.79 (d, J = 8.2 Hz, 1H), 6.81 (dd, J = 8.1, 2.3 Hz, 1H), 7.00 (d, J = 2.3 Hz, 1H), 7.09 (d, J = 9.1 Hz, 1H), 7.20 (d, J = 8.1 Hz, 1H), 7.33 (d, J = 2.7 Hz, 1H), 7.45 (t, J = 9.1 Hz, 2H), 7.82 (dd, J = 9.1, 2.7 Hz, 1H), 8.19 (dd, J = 9.1, 5.5 Hz, 2H)

6-[2-Methoxy-4-(2-nitrobenzoyloxy)phenyl]-5-(2-methoxy-5-nitrophenoxymethyl)-2,2,4-trimethyl-1,2-dihydroquinoline (Compound No. 1-84)

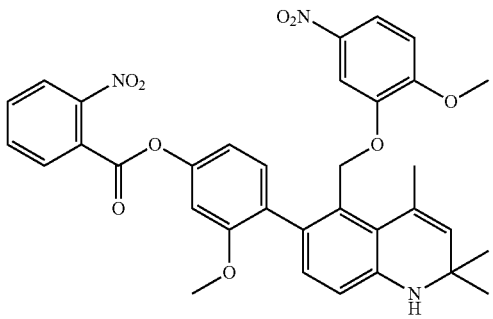 [SMILES: COc1ccc([N+](=O)[O-])cc1OCc1c(-c2ccc(OC(=O)c3ccccc3[N+](=O)[O-])cc2OC)ccc2c1C(C)=CC(C)(C)N2]

$^1$H-NMR (400 MHz, DMSO-d$_6$) δ 1.04 (s, 3H), 1.19 (s, 3H), 2.15 (s, 3H), 3.71 (s, 3H), 3.82 (s, 3H), 4.69 (d, J = 12.1 Hz, 1H), 5.27 (d, J = 12.1 Hz, 1H), 5.40 (s, 1H), 6.05 (s, 1H), 6.63 (d, J = 8.3 Hz, 1H), 6.78 (d, J = 8.3 Hz, 1H), 6.81 (dd, J = 8.2, 2.2 Hz, 1H), 6.97 (d, J = 2.2 Hz, 1H), 7.08 (d, J = 9.0 Hz, 1H), 7.23 (d, J = 8.2 Hz, 1H), 7.33 (d, J = 2.7 Hz, 1H), 7.81 (dd, J = 9.0, 2.7 Hz, 1H), 7.91 (td, J = 7.7, 1.6 Hz, 1H), 7.96 (td, J = 7.7, 1.3 Hz, 1H), 8.10 (dd, J = 7.7, 1.6 Hz, 1H), 8.19 (dd, J = 7.7, 1.3 Hz, 1H)

6-[2-Methoxy-4-(thiophen-3-ylcarbonyloxy)phenyl]-5-(2-methyl-5-nitrophenoxymethyl)-2,2,4-trimethyl-1,2-dihydroquinoline (Compound No. 1-85)

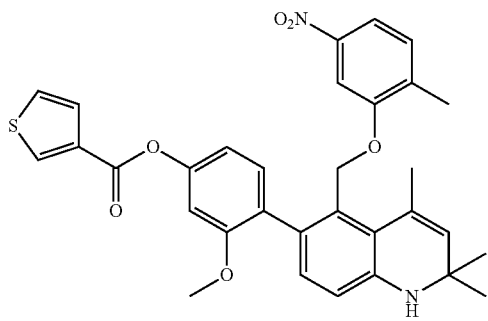 [SMILES: COc1cc(OC(=O)c2ccsc2)ccc1-c1ccc2c(c1COc1cc([N+](=O)[O-])ccc1C)C(C)=CC(C)(C)N2]

$^1$H-NMR (400 MHz, DMSO-d$_6$) δ 0.91 (s, 3H), 1.19 (s, 3H), 2.13 (s, 3H), 2.19 (s, 3H), 3.75 (s, 3H), 4.80 (d, J = 12.7 Hz, 1H), 5.33 (d, J = 12.7 Hz, 1H), 5.41 (s, 1H), 6.05 (s, 1H), 6.63 (d, J = 8.2 Hz, 1H), 6.82 (d, J = 8.2 Hz, 1H), 6.89 (dd, J = 8.3, 2.2 Hz, 1H), 7.02 (d, J = 2.2 Hz, 1H), 7.17 (d, J = 2.1 Hz, 1H), 7.32 (d, J = 8.3 Hz, 1H), 7.34 (d, J = 8.1 Hz, 1H), 7.62 (dd, J = 5.1, 1.3 Hz, 1H), 7.64 (dd, J = 8.1, 2.1 Hz, 1H), 7.75 (dd, J = 5.1, 2.9 Hz, 1H), 8.61 (dd, J = 2.9, 1.3 Hz, 1H)

6-[4-(Furan-3-ylcarbonyloxy)-2-methoxyphenyl]-5-(2-methyl-5-nitrophenoxymethyl)-2,2,4-trimethyl-1,2-dihydroquinoline (Compound No. 1-86)

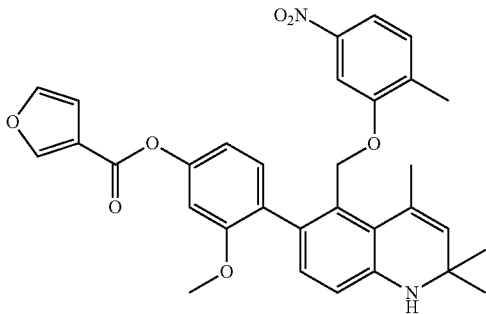 [SMILES: COc1cc(OC(=O)c2ccoc2)ccc1-c1ccc2c(c1COc1cc([N+](=O)[O-])ccc1C)C(C)=CC(C)(C)N2]

$^1$H-NMR (400 MHz, DMSO-$d_6$)
δ 0.91 (s, 3H), 1.18 (s, 3H), 2.13 (s, 3H), 2.19 (s, 3H), 3.74 (s, 3H), 4.79 (d, J = 12.2 Hz, 1H), 5.32 (d, J = 12.2 Hz, 1H), 5.40 (s, 1H), 6.05 (s, 1H), 6.63 (d, J = 8.3 Hz, 1H), 6.82 (d, J = 8.3 Hz, 1H), 6.87 (dd, J = 8.1, 2.4 Hz, 1H), 6.94 (dd, J = 1.7, 0.7 Hz, 1H), 6.99 (d, J = 2.4 Hz, 1H), 7.17 (d, J = 2.3 Hz, 1H), 7.31 (d, J = 8.1 Hz, 1H), 7.33 (d, J = 8.2 Hz, 1H), 7.64 (dd, J = 8.2, 2.3 Hz, 1H), 7.92 (t, J = 1.7 Hz, 1H), 8.64 (dd, J = 1.7, 0.7 Hz, 1H)

6-[2-Methoxy-4-(2-methylpyridin-3-ylcarbonyloxy)phenyl]-5-(2-methyl-5-nitrophenoxymethyl)-2,2,4-trimethyl-1,2-dihydroquinoline (Compound No. 1-87)

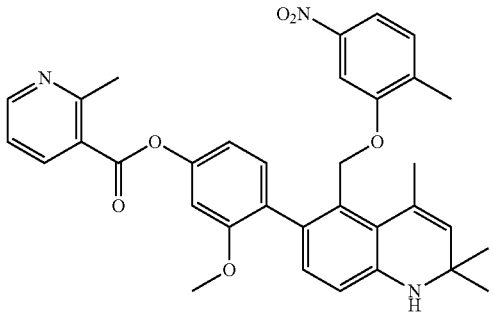 [SMILES: COc1cc(OC(=O)c2cccnc2C)ccc1-c1ccc2c(c1COc1cc([N+](=O)[O-])ccc1C)C(C)=CC(C)(C)N2]

$^1$H-NMR (400 MHz, DMSO-$d_6$)
δ 0.91 (s, 3H), 1.19 (s, 3H), 2.14 (s, 3H), 2.19 (s, 3H), 2.80 (s, 3H), 3.76 (s, 3H), 4.81 (d, J = 12.7 Hz, 1H), 5.34 (d, J = 12.7 Hz, 1H), 5.41 (s, 1H), 6.06 (s, 1H), 6.64 (d, J = 8.3 Hz, 1H), 6.83 (d, J = 8.3 Hz, 1H), 6.95 (dd, J = 8.1, 2.3 Hz, 1H), 7.10 (d, J = 2.3 Hz, 1H), 7.18 (d, J = 2.1 Hz, 1H), 7.34 (d, J = 8.1 Hz, 2H), 7.47 (dd, J = 8.0, 4.9 Hz, 1H), 7.64 (dd, J = 8.1, 2.1 Hz, 1H), 8.45 (dd, J = 8.0, 1.7 Hz, 1H), 8.72 (dd, J = 4.9, 1.7 Hz, 1H)

6-[2-Methoxy-4-(3-methylfuran-2-ylcarbonyloxy)phenyl]-5-(2-methyl-5-nitrophenoxymethyl)-2,2,4-trimethyl-1,2-dihydroquinoline (Compound No. 1-88)

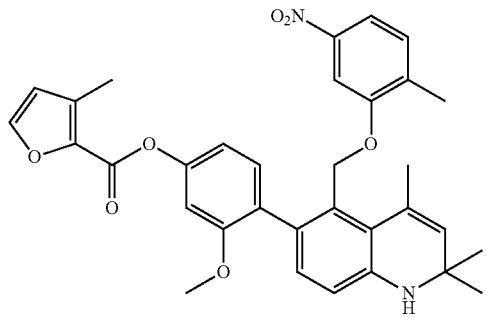 [SMILES: COc1cc(OC(=O)c2occc2C)ccc1-c1ccc2c(c1COc1cc([N+](=O)[O-])ccc1C)C(C)=CC(C)(C)N2]

$^1$H-NMR (500 MHz, DMSO-$d_6$)
δ 0.90 (s, 3H), 1.19 (s, 3H), 2.13 (s, 3H), 2.19 (s, 3H), 2.38 (s, 3H), 3.75 (s, 3H), 4.81 (d, J = 12.5 Hz, 1H), 5.33 (d, J = 12.5 Hz, 1H), 5.40 (s, 1H), 6.04 (s, 1H), 6.63 (d, J = 8.1 Hz, 1H), 6.70 (d, J = 1.7 Hz, 1H), 6.81 (d, J = 8.1 Hz, 1H), 6.89 (dd, J = 8.2, 2.4 Hz, 1H), 7.01 (d, J = 2.4 Hz, 1H), 7.17 (d, J = 2.3 Hz, 1H), 7.31 (d, J = 8.2 Hz, 1H), 7.33 (d, J = 8.2 Hz, 1H), 7.64 (dd, J = 8.2, 2.3 Hz, 1H), 7.95 (d, J = 1.7 Hz, 1H)

6-[2-Methoxy-4-(pyridin-4-ylcarbonyloxy)phenyl]-5-(2-methyl-5-nitrophenoxymethyl)-2,2,4-trimethyl-1,2-dihydroquinoline (Compound No. 1-89)

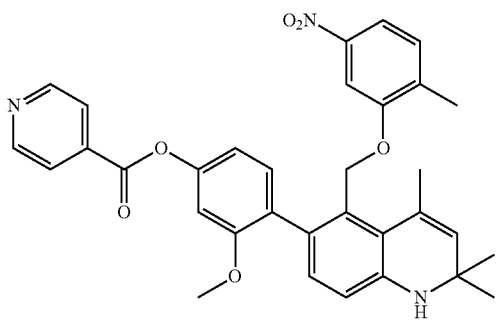 [SMILES: COc1cc(OC(=O)c2ccncc2)ccc1-c1ccc2c(c1COc1cc([N+](=O)[O-])ccc1C)C(C)=CC(C)(C)N2]

$^1$H-NMR (500 MHz, DMSO-$d_6$)
δ 0.91 (s, 3H), 1.19 (s, 3H), 2.13 (s, 3H), 2.19 (s, 3H), 3.75 (s, 3H), 4.81 (d, J = 12.7 Hz, 1H), 5.33 (d, J = 12.7 Hz, 1H), 5.41 (s, 1H), 6.06 (s, 1H), 6.64 (d, J = 8.2 Hz, 1H), 6.83 (d, J = 8.2 Hz, 1H), 6.97 (dd, J = 8.2, 2.1 Hz, 1H), 7.11 (d, J = 2.1 Hz, 1H), 7.18 (d, J = 2.2 Hz, 1H), 7.34 (d, J = 8.2 Hz, 1H), 7.34 (d, J = 8.2 Hz, 1H), 7.65 (dd, J = 8.2, 2.2 Hz, 1H), 8.02 (d, J = 6.1 Hz, 2H), 8.90 (d, J = 6.1 Hz, 2H)

| | |
|---|---|
| 5-(5-Fluoro-2-methylphenoxymethyl)-6-[2-methoxy-4-(2-methoxypyridin-3-ylcarbonyloxy)phenyl]-2,2,4-trimethyl-1,2-dihydroquinoline (Compound No. 1-90)<br>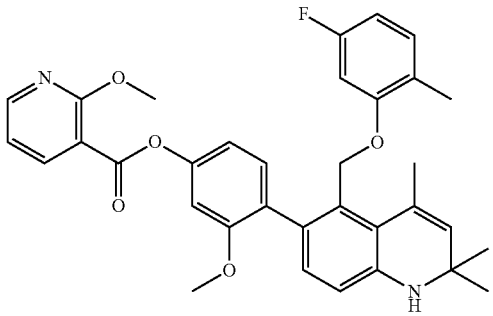 [SMILES: COc1cc(OC(=O)c2cccnc2OC)ccc1-c1ccc2c(c1COc1cc(F)ccc1C)C(C)=CC(C)(C)N2] | $^1$H-NMR (400 MHz, DMSO-d$_6$) δ 1.06 (s, 3H), 1.15 (s, 3H), 2.03 (s, 3H), 2.08 (s, 3H), 3.74 (s, 3H), 3.98 (s, 3H), 4.64 (d, J = 12.1 Hz, 1H), 5.10 (d, J = 12.1 Hz, 1H), 5.40 (s, 1H), 6.04 (s, 1H), 6.37 (dd, J = 11.5, 2.4 Hz, 1H), 6.53 (td, J = 8.4, 2.4 Hz, 1H), 6.65 (d, J = 8.3 Hz, 1H), 6.81 (d, J = 8.3 Hz, 1H), 6.86 (dd, J = 8.1, 2.3 Hz, 1H), 7.01 (d, J = 2.3 Hz, 1H), 7.02-7.06 (m, 1H), 7.20 (dd, J = 7.6, 4.9 Hz, 1H), 7.23 (d, J = 8.1 Hz, 1H), 8.41 (dd, J = 7.6, 2.0 Hz, 1H), 8.48 (dd, J = 4.9, 2.0 Hz, 1H) |
| 6-[2-Methoxy-4-(2-methylpyridin-3-ylcarbonyloxy)phenyl]-5-(2-methoxyphenylaminomethyl)-2,2,4-trimethyl-1,2-dihydroquinoline (Compound No. 1-91)<br>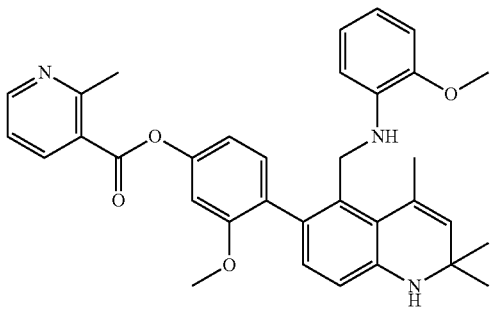 [SMILES: COc1ccccc1NCc1c(-c2ccc(OC(=O)c3cccnc3C)cc2OC)ccc2c1C(C)=CC(C)(C)N2] | $^1$H-NMR (500 MHz, DMSO-d$_6$) δ 1.16 (s, 3H), 1.22 (s, 3H), 2.08 (s, 3H), 2.78 (s, 3H), 3.68 (s, 3H), 3.72 (s, 3H), 3.86 (dd, J = 12.4, 3.3 Hz, 1H), 4.07 (dd, J = 12.4, 6.9 Hz, 1H), 4.26 (dd, J = 6.9, 3.3 Hz, 1H), 5.40 (s, 1H), 6.02 (s, 1H), 6.38 (dd, J = 7.8, 1.2 Hz, 1H), 6.52 (td, J = 7.8, 1.2 Hz, 1H), 6.62 (d, J = 8.2 Hz, 1H), 6.69 (td, J = 7.8, 1.2 Hz, 1H), 6.73 (d, J = 8.2 Hz, 1H), 6.75 (dd, J = 7.8, 1.2 Hz, 1H), 6.88 (dd, J = 8.2, 2.3 Hz, 1H), 7.00 (d, J = 2.3 Hz, 1H), 7.17 (d, J = 8.2 Hz, 1H), 7.45 (dd, J = 7.9, 4.8 Hz, 1H), 8.43 (dd, J = 7.9, 1.8 Hz, 1H), 8.70 (dd, J = 4.8, 1.8 Hz, 1H) |
| 6-(4-Benzoyloxy-2-methoxyphenyl)-5-(2-methoxyphenylaminomethyl)-2,2,4-trimethyl-1,2-dihydroquinoline (Compound No. 1-92)<br>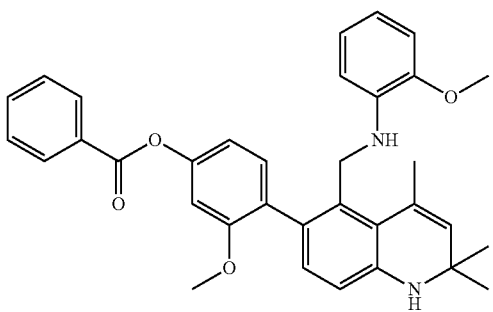 [SMILES: COc1ccccc1NCc1c(-c2ccc(OC(=O)c3ccccc3)cc2OC)ccc2c1C(C)=CC(C)(C)N2] | $^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.86 (dd, J = 12.4, 3.4 Hz, 1H), 4.07 (dd, J = 12.4, 6.4 Hz, 1H), 4.26 (dd, J = 6.4, 3.4 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.3 Hz, 1H), 6.69 (td, J = 7.8, 1.3 Hz, 1H), 6.74 (d, J = 8.3 Hz, 1H), 6.75 (dd, J = 7.8, 1.3 Hz, 1H), 6.85 (dd, J = 8.1, 2.2 Hz, 1H), 6.97 (d, J = 2.2 Hz, 1H), 7.16 (d, J = 8.1 Hz, 1H), 7.61 (t, J = 7.5 Hz, 2H), 7.75 (t, J = 7.5 Hz, 1H), 8.13 (d, J = 7.5 Hz, 2H) |

| Compound | NMR |
|---|---|
| 6-[2-Methoxy-4-(2-methoxybenzoyloxy)phenyl]-5-(2-methoxyphenylaminomethyl)-2,2,4-trimethyl-1,2-dihydroquinoline (Compound No. 1-93) 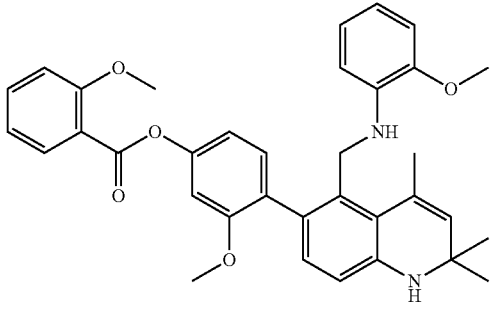 [SMILES: COc1ccccc1NCc1c(-c2ccc(OC(=O)c3ccccc3OC)cc2OC)ccc2c1C(C)=CC(C)(C)N2] | $^1$H-NMR (500 MHz, DMSO-d$_6$) δ 1.16 (s, 3H), 1.22 (s, 3H), 2.06 (s, 3H), 3.67 (s, 3H), 3.72 (s, 3H), 3.85-3.88 (m, 1H), 3.86 (s, 3H), 4.05-4.09 (m, 1H), 4.24-4.26 (m, 1H), 5.40 (s, 1H), 6.01 (s, 1H), 6.38 (dd, J = 7.7, 1.2 Hz, 1H), 6.52 (td, J = 7.7, 1.2 Hz, 1H), 6.62 (d, J = 8.2 Hz, 1H), 6.69 (td, J = 7.7, 1.2 Hz, 1H), 6.73 (d, J = 8.2 Hz, 1H), 6.73-6.75 (m, 1H), 6.80 (dd, J = 8.0, 2.3 Hz, 1H), 6.89 (d, J = 2.3 Hz, 1H), 7.07-7.10 (m, 1H), 7.15 (d, J = 8.0 Hz, 1H), 7.22 (d, J = 7.9 Hz, 1H), 7.63 (td, J = 7.9, 1.7 Hz, 1H), 7.90 (dd, J = 7.9, 1.7 Hz, 1H) |
| 6-[2-Methoxy-4-(2-methylbenzoyloxy)phenyl]-5-(2-methoxyphenylaminomethyl)-2,2,4-trimethyl-1,2-dihydroquinoline (Compound No. 1-94) 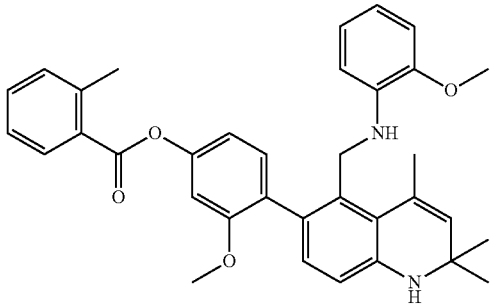 [SMILES: COc1ccccc1NCc1c(-c2ccc(OC(=O)c3ccccc3C)cc2OC)ccc2c1C(C)=CC(C)(C)N2] | $^1$H-NMR (400 MHz, DMSO-d$_6$) δ 1.03 (s, 3H), 1.22 (s, 3H), 2.06 (s, 3H), 2.59 (s, 3H), 3.68 (s, 3H), 3.72 (s, 3H), 3.85-3.88 (m, 1H), 4.05-4.07 (m, 1H), 4.25-4.26 (m, 1H), 5.40 (s, 1H), 6.02 (s, 1H), 6.39 (d, J = 7.8 Hz, 1H), 6.52 (t, J = 7.8 Hz, 1H), 6.63 (d, J = 8.2 Hz, 1H), 6.70 (t, J = 7.8 Hz, 1H), 6.74 (d, J = 8.2 Hz, 1H), 6.75 (d, J = 7.8 Hz, 1H), 6.85 (dd, J = 8.2, 2.2 Hz, 1H), 6.96 (d, J = 2.2 Hz, 1H), 7.15 (d, J = 8.2 Hz, 1H), 7.37-7.42 (m, 2H), 7.56 (t, J = 7.7 Hz, 1H), 8.07 (d, J = 7.7 Hz, 1H) |
| 6-[4-(Furan-3-ylcarbonyloxy)-2-methoxyphenyl]-5-(2-methoxyphenylaminomethyl)-2,2,4-trimethyl-1,2-dihydroquinoline (Compound No. 1-95) 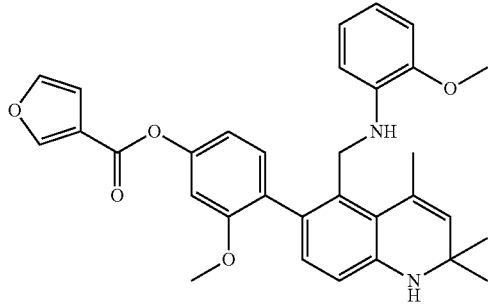 [SMILES: COc1ccccc1NCc1c(-c2ccc(OC(=O)c3ccoc3)cc2OC)ccc2c1C(C)=CC(C)(C)N2] | $^1$H-NMR (500 MHz, DMSO-d$_6$) δ 1.15 (s, 3H), 1.22 (s, 3H), 2.08 (s, 3H), 3.66 (s, 3H), 3.72 (s, 3H), 3.81-3.84 (m, 1H), 4.02-4.05 (m, 1H), 4.24-4.26 (m, 1H), 5.40 (s, 1H), 6.02 (s, 1H), 6.36 (d, J = 7.7 Hz, 1H), 6.52 (t, J = 7.7 Hz, 1H), 6.62 (d, J = 8.3 Hz, 1H), 6.69 (t, J = 7.7 Hz, 1H), 6.73 (d, J = 8.3 Hz, 1H), 6.73-6.75 (m, 1H), 6.80 (dd, J = 8.2, 2.3 Hz, 1H), 6.89 (d, J = 2.3 Hz, 1H), 6.93 (dd, J = 1.7, 0.8 Hz, 1H), 7.14 (d, J = 8.2 Hz, 1H), 7.90 (t, J = 1.7 Hz, 1H), 8.62 (dd, J = 1.7, 0.8 Hz, 1H) |
| 5-(2-Methoxyphenylaminomethyl)-6-[2-methoxy-4-(thiophen-3-ylcarbonyloxy)phenyl]-2,2,4-trimethyl-1,2-dihydroquinoline (Compound No. 1-96) 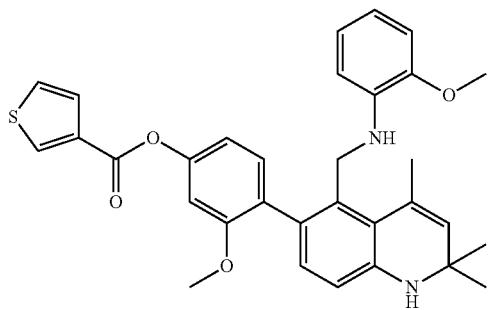 [SMILES: COc1ccccc1NCc1c(-c2ccc(OC(=O)c3ccsc3)cc2OC)ccc2c1C(C)=CC(C)(C)N2] | $^1$H-NMR (500 MHz, DMSO-d$_6$) δ 1.16 (s, 3H), 1.22 (s, 3H), 2.08 (s, 3H), 3.66 (s, 3H), 3.72 (s, 3H), 3.83-3.86 (m, 1H), 4.05-4.08 (m, 1H), 4.24-4.26 (m, 1H), 5.40 (s, 1H), 6.01 (s, 1H), 6.36 (dd, J = 7.7, 1.3 Hz, 1H), 6.52 (td, J = 7.7, 1.3 Hz, 1H), 6.62 (d, J = 8.2 Hz, 1H), 6.69 (td, J = 7.7, 1.3 Hz, 1H), 6.74 (d, J = 8.2 Hz, 1H), 6.74 (dd, J = 7.7, 1.3 Hz, 1H), 6.82 (dd, J = 8.3, 2.1 Hz, 1H), 6.92 (d, J = 2.1 Hz, 1H), 7.15 (d, J = 8.3 Hz, 1H), 7.14 (dd, J = 5.1, 1.4 Hz, 1H), 7.74 (dd, J = 5.1, 2.9 Hz, 1H), 8.59 (dd, J = 2.9, 1.4 Hz, 1H) |

| | |
|---|---|
| 5-(2-Methoxyphenylaminomethyl)-6-[2-methoxy-4-(pyridin-3-ylcarbonyloxy)phenyl]-2,2,4-trimethyl-1,2-dihydroquinoline (Compound No. 1-97)<br>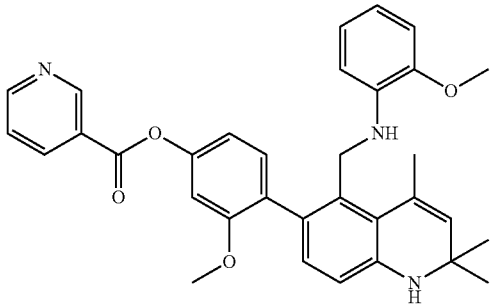 [SMILES: COc1ccccc1NCc1c(-c2ccc(OC(=O)c3cccnc3)cc2OC)ccc2c1C(C)=CC(C)(C)N2] | $^1$H-NMR (500 MHz, DMSO-$d_6$) δ 1.16 (s, 3H), 1.22 (s, 3H), 2.08 (s, 3H), 3.67 (s, 3H), 3.72 (s, 3H), 3.86 (dd, J = 12.2, 3.3 Hz, 1H), 4.06-4.09 (m, 1H), 4.25 (dd, J = 6.8, 3.3 Hz, 1H), 5.40 (s, 1H), 6.02 (s, 1H), 6.38 (dd, J = 7.7, 1.4 Hz, 1H), 6.52 (td, J = 7.7, 1.4 Hz, 1H), 6.62 (d, J = 8.2 Hz, 1H), 6.69 (td, J = 7.7, 1.4 Hz, 1H), 6.74 (d, J = 8.2 Hz, 1H), 6.74-6.76 (m, 1H), 6.90 (dd, J = 8.3, 2.2 Hz, 1H), 7.02 (d, J = 2.2 Hz, 1H), 7.17 (d, J = 8.3 Hz, 1H), 7.65 (ddd, J = 7.9, 4.9, 0.9 Hz, 1H), 8.46 (dt, J = 7.9, 2.0 Hz, 1H), 8.90 (dd, J = 4.9, 2.0 Hz, 1H), 9.26 (dd, J = 2.0, 0.9 Hz, 1H) |
| 6-[4-(2-Chlorobenzoyloxy)-2-methoxyphenyl]-5-(5-fluoro-2-methylphenylaminomethyl)-2,2,4-trimethyl-1,2-dihydroquinoline (Compound No. 1-98)<br>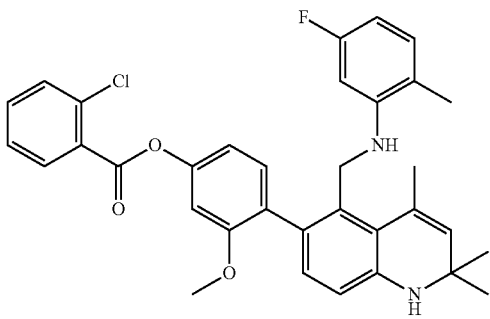 | $^1$H-NMR (400 MHz, DMSO-$d_6$) δ 1.11 (s, 3H), 1.20 (s, 3H), 1.91 (s, 3H), 2.05 (s, 3H), 3.74 (s, 3H), 3.95 (dd, J = 13.1, 5.2 Hz, 1H), 4.10 (dd, J = 13.1, 4.2 Hz, 1H), 4.25 (br s, 1H), 5.41 (s, 1H), 6.04 (s, 1H), 6.07 (dd, J = 12.1, 2.5 Hz, 1H), 6.21 (td, J = 8.4, 2.5 Hz, 1H), 6.63 (d, J = 8.2 Hz, 1H), 6.76 (d, J = 8.2 Hz, 1H), 6.86-6.90 (m, 1H), 6.90 (dd, J = 8.1, 2.4 Hz, 1H), 7.04 (d, J = 2.4 Hz, 1H), 7.27 (d, J = 8.1 Hz, 1H), 7.54-7.58 (m, 1H), 7.67-7.69 (m, 2H), 8.10 (d, J = 7.3 Hz, 1H) |
| 6-[4-(2-Chlorobenzoyloxy)-2-methoxyphenyl]-5-(2-methoxyphenylaminomethyl)-2,2,4-trimethyl-1,2-dihydroquinoline (Compound No. 1-99)<br>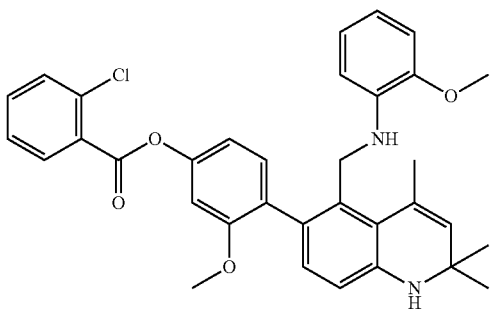 | $^1$H-NMR (400 MHz, DMSO-$d_6$) δ 1.16 (s, 3H), 1.22 (s, 3H), 2.08 (s, 3H), 3.68 (s, 3H), 3.72 (s, 3H), 3.86 (dd, J = 12.1, 2.8 Hz, 1H), 4.03-4.09 (m, 1H), 4.24-4.26 (m, 1H), 5.40 (s, 1H), 6.03 (s, 1H), 6.38 (d, J = 7.5 Hz, 1H), 6.52 (t, J = 7.5 Hz, 1H), 6.62 (d, J = 8.3 Hz, 1H), 6.69 (t, J = 7.5 Hz, 1H), 6.74 (d, J = 8.3 Hz, 1H), 6.74 (d, J = 7.5 Hz, 1H), 6.88 (dd, J = 8.2, 2.3 Hz, 1H), 6.98 (d, J = 2.3 Hz, 1H), 7.18 (d, J = 8.2 Hz, 1H), 7.53-7.57 (m, 1H), 7.66-7.68 (m, 2H), 8.09 (d, J = 7.6 Hz, 1H) |
| 6-(4-Butyryloxy-2-methoxyphenyl)-5-(2-methoxyphenylaminomethyl)-2,2,4-trimethyl-1,2-dihydroquinoline (Compound No. 1-100)<br>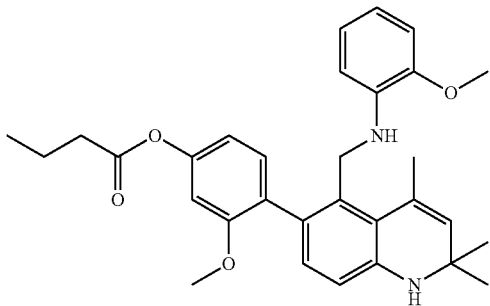 [SMILES: CCCC(=O)Oc1ccc(-c2ccc3c(c2CNc2ccccc2OC)C(C)=CC(C)(C)N3)c(OC)c1] | $^1$H-NMR (400 MHz, CDCl$_3$) δ 1.04 (t, J = 7.3 Hz, 3H), 1.25 (s, 3H), 1.29 (s, 3H), 1.79 (sept, J = 7.3 Hz, 2H), 2.17 (s, 3H), 2.53 (t, J = 7.3 Hz, 2H), 3.66 (s, 3H), 3.75 (s, 3H), 3.87 (br s, 1H), 4.01 (d, J = 12.3 Hz, 1H), 4.14 (d, J = 12.3 Hz, 1H), 4.34 (br s, 1H), 5.46 (s, 1H), 6.38 (dd, J = 7.8, 1.5 Hz, 1H), 6.55-6.59 (m, 1H), 6.56 (d, J = 8.1 Hz, 1H), 6.59 (d, J = 2.2 Hz, 1H), 6.67 (dd, J = 8.1, 2.2 Hz, 1H), 6.69 (dd, J = 7.8, 1.5 Hz, 1H), 6.77 (td, J = 7.8, 1.5 Hz, 1H), 6.85 (d, J = 8.1 Hz, 1H), 7.14 (d, J = 8.1 Hz, 1H) |

6-[4-(2-Fluorobenzoyloxy)-2-methoxyphenyl]-5-(2-methoxyphenylaminomethyl)-2,2,4-trimethyl-1,2-dihydroquinoline (Compound No. 1-101)

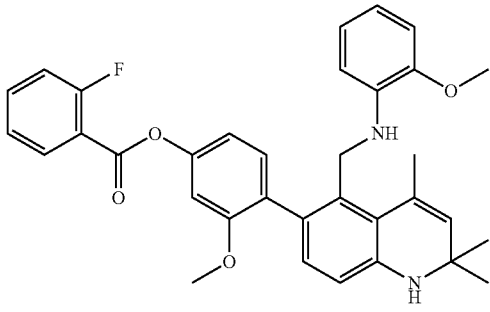

$^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.86 (dd, J = 12.7, 3.3 Hz, 1H), 4.07 (dd, J = 12.7, 6.5 Hz, 1H), 4.25 (dd, J = 6.5, 3.3 Hz, 1H), 5.40 (s, 1H), 6.03 (s, 1H), 6.38 (dd, J = 7.6, 1.2 Hz, 1H), 6.52 (td, J = 7.6, 1.2 Hz, 1H), 6.62 (d, J = 8.2 Hz, 1H), 6.69 (td, J = 7.6, 1.2 Hz, 1H), 6.74 (d, J = 8.2 Hz, 1H), 6.74 (dd, J = 7.6, 1.2 Hz, 1H), 6.86 (dd, J = 8.1, 2.3 Hz, 1H), 6.97 (d, J = 2.3 Hz, 1H), 7.16 (d, J = 8.1 Hz, 1H), 7.39-7.46 (m, 2H), 7.75-7.80 (m, 1H), 8.10 (td, J = 7.7, 1.8 Hz, 1H)

5-(2-Methoxyphenylaminomethyl)-6-[2-methoxy-4-(pyridin-4-ylcarbonyloxy)phenyl]-2,2,4-trimethyl-1,2-dihydroquinoline (Compound No. 1-102)

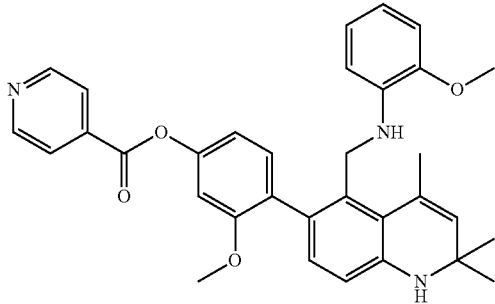 [SMILES: COc1ccccc1NCc1c(-c2ccc(OC(=O)c3ccncc3)cc2OC)ccc2c1C(C)=CC(C)(C)N2]

$^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.3, 3.5 Hz, 1H), 4.07 (dd, J = 12.3, 7.0 Hz, 1H), 4.25 (dd, J = 7.0, 3.5 Hz, 1H), 5.40 (s, 1H), 6.03 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.90 (dd, J = 8.1, 2.2 Hz, 1H), 7.02 (d, J = 2.2 Hz, 1H), 7.18 (d, J = 8.1 Hz, 1H), 8.00 (d, J = 6.1 Hz, 2H), 8.88 (d, J = 6.1 Hz, 2H)

6-(4-Isopropylcarbonyloxy-2-methoxyphenyl)-5-(2-methoxyphenylaminomethyl)-2,2,4-trimethyl-1,2-dihydroquinoline (Compound No. 1-103)

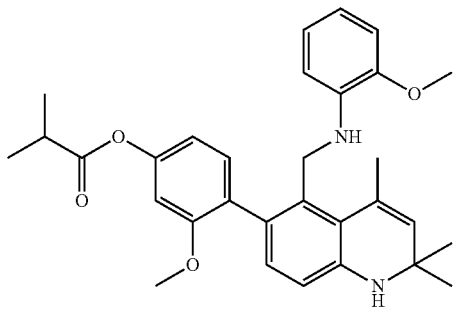

$^1$H-NMR (400 MHz, DMSO-d$_6$) δ 1.15 (s, 3H), 1.21 (s, 3H), 1.22 (d, J = 6.8 Hz, 6H), 2.06 (s, 3H), 2.78 (hept, J = 6.8 Hz, 1H), 3.65 (s, 3H), 3.71 (s, 3H), 3.82 (dd, J = 12.4, 3.2 Hz, 1H), 4.04 (dd, J = 12.4, 6.7 Hz, 1H), 4.23 (dd, J = 6.7, 3.2 Hz, 1H), 5.39 (s, 1H), 6.01 (s, 1H), 6.35 (dd, J = 7.8, 1.6 Hz, 1H), 6.51 (td, J = 7.8, 1.6 Hz, 1H), 6.60 (d, J = 8.3 Hz, 1H), 6.67 (dd, J = 8.1, 2.1 Hz, 1H), 6.68-6.72 (m, 1H), 6.71 (d, J = 8.3 Hz, 1H), 6.74 (dd, J = 7.8, 1.6 Hz, 1H), 6.75 (d, J = 2.1 Hz, 1H), 7.10 (d, J = 8.1 Hz, 1H)

5-(2-Methoxyphenylaminomethyl)-6-[2-methoxy-4-(thiophen-2-ylcarbonyloxy)phenyl]-2,2,4-trimethyl-1,2-dihydroquinoline (Compound No. 1-104)

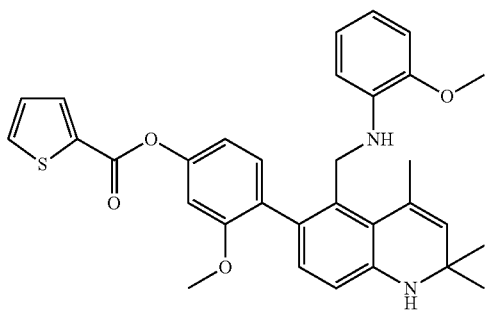

$^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.2, 3.5 Hz, 1H), 4.04-4.08 (m, 1H), 4.24 (dd, J = 6.6, 3.5 Hz, 1H), 5.40 (s, 1H), 6.03 (s, 1H), 6.37 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.73 (d, J = 8.2 Hz, 1H), 6.74 (dd, J = 7.8, 1.3 Hz, 1H), 6.84 (dd, J = 8.1, 2.3 Hz, 1H), 6.94 (d, J = 2.3 Hz, 1H), 7.15 (d, J = 8.1 Hz, 1H), 7.31 (dd, J = 5.0, 3.7 Hz, 1H), 8.01 (dd, J = 3.7, 1.3 Hz, 1H), 8.09 (dd, J = 5.0, 1.3 Hz, 1H)

| | |
|---|---|
| 5-(5-Fluoro-2-methylphenylaminomethyl)-6-[2-methoxy-4-(pyridin-3-ylcarbonyloxy)phenyl]-2,2,4-trimethyl-1,2-dihydroquinoline (Compound No. 1-105)<br />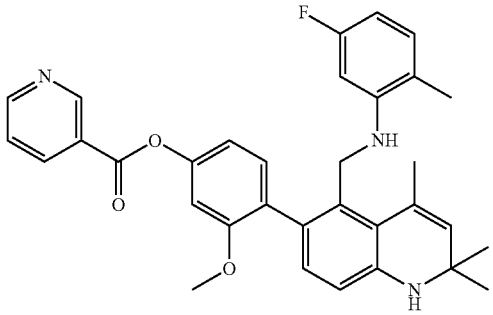 [SMILES: COc1cc(OC(=O)c2cccnc2)ccc1-c1ccc2c(c1CNc1cc(F)ccc1C)C(C)=CC(C)(C)N2] | $^1$H-NMR (500 MHz, DMSO-$d_6$) δ 1.12 (s, 3H), 1.20 (s, 3H), 1.92 (s, 3H), 2.05 (s, 3H), 3.72 (s, 3H), 3.95 (dd, J = 13.1, 4.6 Hz, 1H), 4.10 (dd, J = 13.1, 4.6 Hz, 1H), 4.24 (t, J = 4.6 Hz, 1H), 5.41 (s, 1H), 6.03 (s, 1H), 6.08 (dd, J = 12.4, 2.5 Hz, 1H), 6.21 (td, J = 8.4, 2.5 Hz, 1H), 6.63 (d, J = 8.2 Hz, 1H), 6.77 (d, J = 8.2 Hz, 1H), 6.87-6.90 (m, 1H), 6.92 (dd, J = 8.1, 2.3 Hz, 1H), 7.08 (d, J = 2.3 Hz, 1H), 7.27 (d, J = 8.1 Hz, 1H), 7.66 (ddd, J = 8.0, 4.9, 0.9 Hz, 1H), 8.47 (dt, J = 8.0, 2.0 Hz, 1H), 8.90 (dd, J = 4.9, 2.0 Hz, 1H), 9.27 (dd, J = 2.0, 0.9 Hz, 1H) |
| 5-(5-Fluoro-2-methylphenylaminomethyl)-6-[4-(furan-2-ylcarbonyloxy)-2-methoxyphenyl]-2,2,4-trimethyl-1,2-dihydroquinoline (Compound No. 1-106)<br />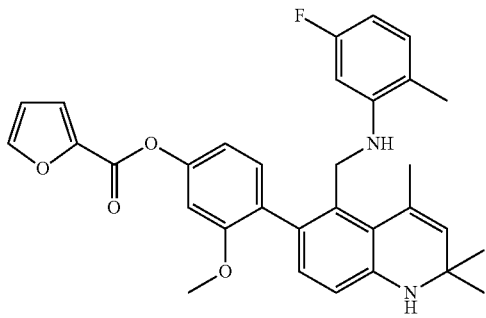 [SMILES: COc1cc(OC(=O)c2ccco2)ccc1-c1ccc2c(c1CNc1cc(F)ccc1C)C(C)=CC(C)(C)N2] | $^1$H-NMR (400 MHz, DMSO-$d_6$) δ 1.11 (s, 3H), 1.20 (s, 3H), 1.90 (s, 3H), 2.05 (s, 3H), 3.71 (s, 3H), 3.93 (dd, J = 13.1, 4.2 Hz, 1H), 4.09 (dd, J = 13.1, 4.2 Hz, 1H), 4.24 (t, J = 4.2 Hz, 1H), 5.41 (s, 1H), 6.04 (s, 1H), 6.06 (dd, J = 12.7, 2.6 Hz, 1H), 6.21 (td, J = 8.5, 2.6 Hz, 1H), 6.62 (d, J = 8.2 Hz, 1H), 6.75 (d, J = 8.2 Hz, 1H), 6.80 (dd, J = 3.6, 1.7 Hz, 1H), 6.84-6.90 (m, 2H), 6.99 (d, J = 2.2 Hz, 1H), 7.24 (d, J = 8.3 Hz, 1H), 7.57 (dd, J = 3.6, 0.8 Hz, 1H), 8.11 (dd, J = 1.7, 0.8 Hz, 1H) |
| 6-[2-Methoxy-4-(3-methoxycarbonylbenzoyloxy)phenyl]-5-(2-methoxyphenylaminomethyl)-2,2,4-trimethyl-1,2-dihydroquinoline (Compound No. 1-107)<br />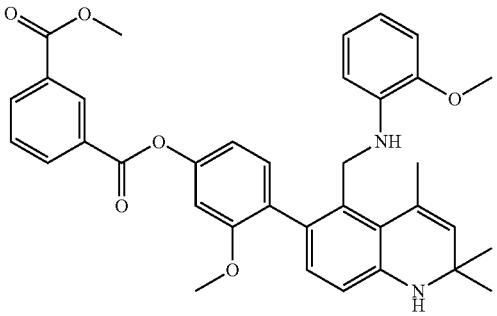 [SMILES: COC(=O)c1cccc(C(=O)Oc2ccc(-c3ccc4c(c3CNc3ccccc3OC)C(C)=CC(C)(C)N4)c(OC)c2)c1] | $^1$H-NMR (500 MHz, DMSO-$d_6$) δ 1.16 (s, 3H), 1.22 (s, 3H), 2.08 (s, 3H), 3.67 (s, 3H), 3.72 (s, 3H), 3.87 (dd, J = 12.4, 3.3 Hz, 1H), 3.91 (s, 3H), 4.07 (dd, J = 12.4, 6.6 Hz, 1H), 4.26 (dd, J = 6.6, 3.3 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.70 (td, J = 7.8, 1.3 Hz, 1H), 6.75 (d, J = 8.2 Hz, 1H), 6.75 (dd, J = 7.8, 1.3 Hz, 1H), 6.89 (dd, J = 8.1, 2.3 Hz, 1H), 7.01 (d, J = 2.3 Hz, 1H), 7.17 (d, J = 8.1 Hz, 1H), 7.78 (t, J = 7.8 Hz, 1H), 8.30 (dt, J = 7.8, 1.5 Hz, 1H), 8.38 (dt, J = 7.8, 1.5 Hz, 1H), 8.64 (t, J = 1.5 Hz, 1H) |

| | |
|---|---|
| 6-[2-Methoxy-4-(4-methylbenzoyloxy)phenyl]-5-(2-methoxyphenylaminomethyl)-2,2,4-trimethyl-1,2-dihydroquinoline (Compound No. 1-108)<br />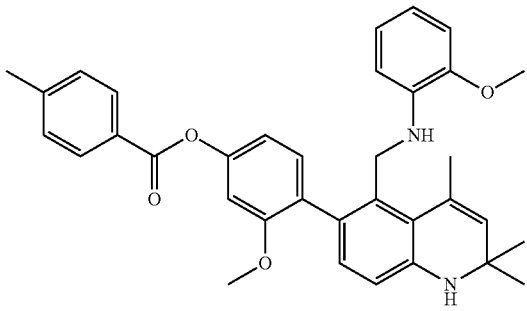 | $^1$H-NMR (500 MHz, DMSO-d$_6$) δ 1.16 (s, 3H), 1.22 (s, 3H), 2.08 (s, 3H), 2.42 (s, 3H), 3.67 (s, 3H), 3.72 (s, 3H), 3.86 (dd, J = 12.2, 3.5 Hz, 1H), 4.07 (dd, J = 12.2, 6.3 Hz, 1H), 4.25 (dd, J = 6.3, 3.5 Hz, 1H), 5.40 (s, 1H), 6.01 (s, 1H), 6.38 (dd, J = 7.7, 1.3 Hz, 1H), 6.52 (td, J = 7.7, 1.3 Hz, 1H), 6.62 (d, J = 8.1 Hz, 1H), 6.69 (td, J = 7.7, 1.3 Hz, 1H), 6.74 (d, J = 8.1 Hz, 1H), 6.74 (dd, J = 7.7, 1.3 Hz, 1H), 6.84 (dd, J = 8.2, 2.2 Hz, 1H), 6.94 (d, J = 2.2 Hz, 1H), 7.15 (d, J = 8.2 Hz, 1H), 7.41 (d, J = 8.4 Hz, 2H), 8.02 (d, J = 8.4 Hz, 2H) |
| 6-[2-Methoxy-4-(4-methoxybenzoyloxy)phenyl]-5-(2-methoxyphenylaminomethyl)-2,2,4-trimethyl-1,2-dihydroquinoline (Compound No. 1-109)<br />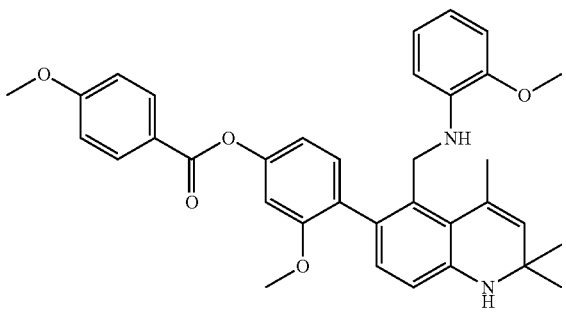 | $^1$H-NMR (500 MHz, DMSO-d$_6$) δ 1.16 (s, 3H), 1.22 (s, 3H), 2.08 (s, 3H), 3.66 (s, 3H), 3.72 (s, 3H), 3.86 (dd, J = 12.5, 3.5 Hz, 1H), 3.87 (s, 3H), 4.07 (dd, J = 12.5, 6.5 Hz, 1H), 4.25 (dd, J = 6.5, 3.5 Hz, 1H), 5.40 (s, 1H), 6.01 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.82 (dd, J = 8.2, 2.4 Hz, 1H), 6.92 (d, J = 2.4 Hz, 1H), 7.12 (d, J = 9.0 Hz, 2H), 7.14 (d, J = 8.2 Hz, 1H), 8.08 (d, J = 9.0 Hz, 2H) |
| 6-[4-(4-Fluorobenzoyloxy)-2-methoxyphenyl]-5-(2-methoxyphenylaminomethyl)-2,2,4-trimethyl-1,2-dihydroquinoline (Compound No. 1-110)<br />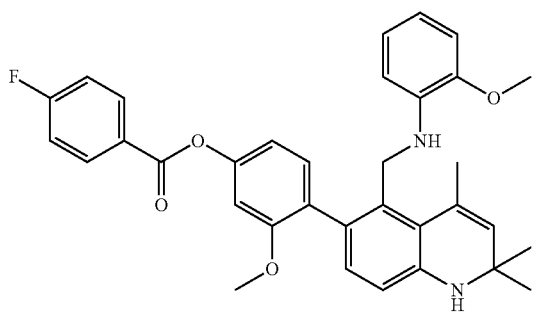 [SMILES: COc1ccccc1NCc1c(-c2ccc(OC(=O)c3ccc(F)cc3)cc2OC)ccc2c1C(C)=CC(C)(C)N2] | $^1$H-NMR (500 MHz, DMSO-d$_6$) δ 1.16 (s, 3H), 1.22 (s, 3H), 2.08 (s, 3H), 3.67 (s, 3H), 3.72 (s, 3H), 3.86 (dd, J = 12.2, 3.1 Hz, 1H), 4.07 (dd, J = 12.2, 6.6 Hz, 1H), 4.25 (dd, J = 6.6, 3.1 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.85 (dd, J = 8.0, 2.4 Hz, 1H), 6.97 (d, J = 2.4 Hz, 1H), 7.16 (d, J = 8.0 Hz, 1H), 7.41-7.47 (m, 2H), 8.18-8.23 (m, 2H) |
| 6-[2-Methoxy-4-(2-methylthiobenzoyloxy)phenyl]-5-(2-methoxyphenylaminomethyl)-2,2,4-trimethyl-1,2-dihydroquinoline (Compound No. 1-111)<br />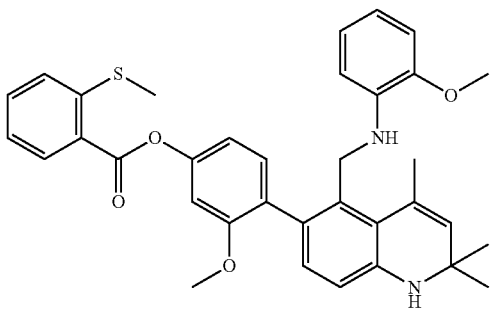 | $^1$H-NMR (400 MHz, DMSO-d$_6$) δ 1.16 (s, 3H), 1.22 (s, 3H), 2.08 (s, 3H), 2.46 (s, 3H), 3.67 (s, 3H), 3.72 (s, 3H), 3.86 (dd, J = 13.0, 3.4 Hz, 1H), 4.07 (dd, J = 13.0, 6.9 Hz, 1H), 4.25 (dd, J = 6.9, 3.4 Hz, 1H), 5.40 (s, 1H), 6.03 (s, 1H), 6.38 (dd, J = 7.8, 1.3 Hz, 1H), 6.52 (td, J = 7.8, 1.3 Hz, 1H), 6.62 (d, J = 8.1 Hz, 1H), 6.69 (td, J = 7.8, 1.3 Hz, 1H), 6.74 (d, J = 8.1 Hz, 1H), 6.74 (dd, J = 7.8, 1.3 Hz, 1H), 6.83 (dd, J = 8.2, 2.2 Hz, 1H), 6.94 (d, J = 2.2 Hz, 1H), 7.16 (d, J = 8.2 Hz, 1H), 7.31 (td, J = 7.8, 1.5 Hz, 1H), 7.46 (dd, J = 7.8, 1.5 Hz, 1H), 7.66 (td, J = 7.8, 1.5 Hz, 1H), 8.17 (dd, J = 7.8, 1.5 Hz, 1H) |

6-[4-(3-Acetylbenzoyloxy)-2-methoxyphenyl]-5-(2-methoxyphenylaminomethyl)-2,2,4-trimethyl-1,2-dihydroquinoline (Compound No. 1-112)

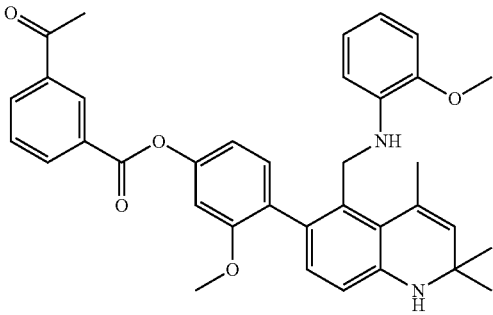 [SMILES: COc1ccccc1NCc1c(-c2ccc(OC(=O)c3cccc(C(C)=O)c3)cc2OC)ccc2c1C(C)=CC(C)(C)N2]

$^1$H-NMR (500 MHz, DMSO-$d_6$) δ 1.16 (s, 3H), 1.22 (s, 3H), 2.08 (s, 3H), 2.67 (s, 3H), 3.67 (s, 3H), 3.72 (s, 3H), 3.86 (dd, J = 12.3, 3.1 Hz, 1H), 4.08 (dd, J = 12.3, 6.7 Hz, 1H), 4.26 (dd, J = 6.7, 3.1 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.1 Hz, 1H), 6.70 (td, J = 7.8, 1.3 Hz, 1H), 6.75 (d, J = 8.1 Hz, 2H), 6.89 (dd, J = 8.2, 2.3 Hz, 1H), 7.00 (d, J = 2.3 Hz, 1H), 7.18 (d, J = 8.2 Hz, 1H), 7.77 (t, J = 7.8 Hz, 1H), 8.31 (dt, J = 7.8, 1.5 Hz, 1H), 8.36 (dt, J = 7.8, 1.5 Hz, 1H), 8.61 (t, J = 1.5 Hz, 1H)

6-[4-(3-Chlorothiophen-2-ylcarbonyloxy)-2-methoxyphenyl]-5-(2-methoxyphenylaminomethyl)-2,2,4-trimethyl-1,2-dihydroquinoline (Compound No. 1-113)

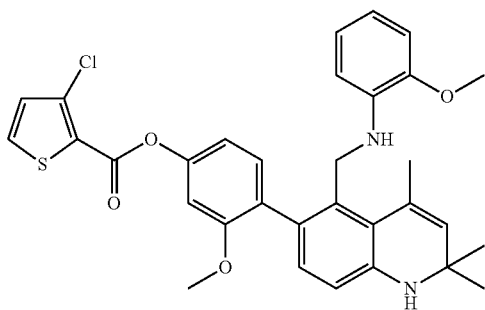 [SMILES: COc1ccccc1NCc1c(-c2ccc(OC(=O)c3sccc3Cl)cc2OC)ccc2c1C(C)=CC(C)(C)N2]

$^1$H-NMR (400 MHz, DMSO-$d_6$) δ 1.16 (s, 3H), 1.22 (s, 3H), 2.08 (s, 3H), 3.67 (s, 3H), 3.72 (s, 3H), 3.86 (dd, J = 12.2, 3.4 Hz, 1H), 4.06 (dd, J = 12.2, 6.6 Hz, 1H), 4.24 (dd, J = 6.6, 3.4 Hz, 1H), 5.40 (s, 1H), 6.03 (s, 1H), 6.37 (dd, J = 7.8, 1.4 Hz, 1H), 6.52 (td, J = 7.8, 1.4 Hz, 1H), 6.62 (d, J = 8.3 Hz, 1H), 6.69 (td, J = 7.8, 1.4 Hz, 1H), 6.73 (d, J = 8.3 Hz, 1H), 6.75 (dd, J = 7.8, 1.4 Hz, 1H), 6.84 (dd, J = 8.3, 2.2 Hz, 1H), 6.96 (d, J = 2.2 Hz, 1H), 7.15 (d, J = 8.3 Hz, 1H), 7.35 (d, J = 5.2 Hz, 1H), 8.14 (d, J = 5.2 Hz, 1H)

6-[2-Methoxy-4-(3-methylfuran-2-ylcarbonyloxy)phenyl]-5-(2-methoxyphenylaminomethyl)-2,2,4-trimethyl-1,2-dihydroquinoline (Compound No. 1-114)

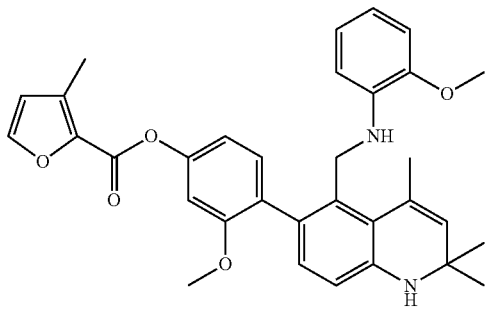 [SMILES: COc1ccccc1NCc1c(-c2ccc(OC(=O)c3occc3C)cc2OC)ccc2c1C(C)=CC(C)(C)N2]

$^1$H-NMR (500 MHz, DMSO-$d_6$) δ 1.15 (s, 3H), 1.22 (s, 3H), 2.07 (s, 3H), 2.36 (s, 3H), 3.66 (s, 3H), 3.72 (s, 3H), 3.87 (dd, J = 12.4, 3.5 Hz, 1H), 4.06 (dd, J = 12.4, 6.9 Hz, 1H), 4.24 (dd, J = 6.9, 3.5 Hz, 1H), 5.39 (s, 1H), 6.01 (s, 1H), 6.37 (dd, J = 7.7, 1.4 Hz, 1H), 6.51 (td, J = 7.7, 1.4 Hz, 1H), 6.61 (d, J = 7.9 Hz, 1H), 6.69 (d, J = 1.4 Hz, 1H), 6.69 (td, J = 7.7, 1.4 Hz, 1H), 6.73 (d, J = 7.9 Hz, 1H), 6.74 (dd, J = 7.7, 1.4 Hz, 1H), 6.81 (dd, J = 8.0, 2.2 Hz, 1H), 6.92 (d, J = 2.2 Hz, 1H), 7.14 (d, J = 8.0 Hz, 1H), 7.94 (d, J = 1.4 Hz, 1H)

5-(2-Methoxyphenylaminomethyl)-6-[2-methoxy-4-(thiazol-4-ylcarbonyloxy)phenyl]-2,2,4-trimethyl-1,2-dihydroquinoline (Compound No. 1-115)

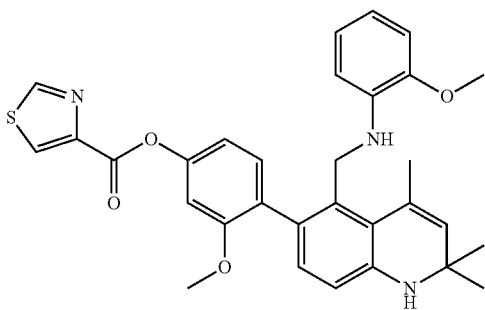 [SMILES: COc1ccccc1NCc1c(-c2ccc(OC(=O)c3cscn3)cc2OC)ccc2c1C(C)=CC(C)(C)N2]

$^1$H-NMR (400 MHz, DMSO-$d_6$) δ 1.16 (s, 3H), 1.22 (s, 3H), 2.08 (s, 3H), 3.67 (s, 3H), 3.72 (s, 3H), 3.86 (dd, J = 11.8, 3.5 Hz, 1H), 4.07 (dd, J = 11.8, 6.8 Hz, 1H), 4.24 (dd, J = 6.8, 3.5 Hz, 1H), 5.40 (s, 1H), 6.02 (s, 1H), 6.37 (dd, J = 7.8, 1.3 Hz, 1H), 6.52 (td, J = 7.8, 1.3 Hz, 1H), 6.62 (d, J = 8.1 Hz, 1H), 6.69 (td, J = 7.8, 1.3 Hz, 1H), 6.74 (d, J = 8.1 Hz, 2H), 6.85 (dd, J = 8.2, 2.2 Hz, 1H), 6.95 (d, J = 2.2 Hz, 1H), 7.16 (d, J = 8.2 Hz, 1H), 8.86 (d, J = 2.0 Hz, 1H), 9.27 (d, J = 2.0 Hz, 1H)

6-[2-Methoxy-4-(6-methylpyridin-3-ylcarbonyloxy)phenyl]-5-(2-methoxyphenylaminomethyl)-2,2,4-trimethyl-1,2-dihydroquinoline (Compound No. 1-116)

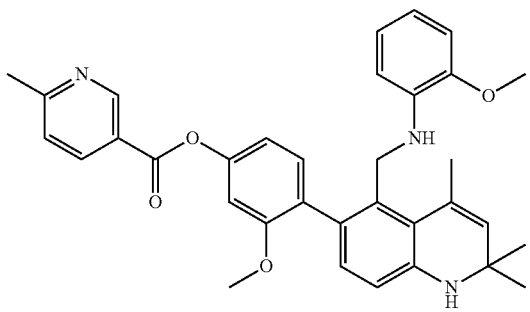

$^1$H-NMR (500 MHz, DMSO-$d_6$) δ 1.16 (s, 3H), 1.22 (s, 3H), 2.08 (s, 3H), 2.60 (s, 3H), 3.67 (s, 3H), 3.72 (s, 3H), 3.85 (dd, J = 12.1, 3.4 Hz, 1H), 4.07 (dd, J = 12.1, 6.4 Hz, 1H), 4.25 (dd, J = 6.4, 3.4 Hz, 1H), 5.40 (s, 1H), 6.02 (s, 1H), 6.37 (dd, J = 7.8, 1.3 Hz, 1H), 6.52 (td, J = 7.8, 1.3 Hz, 1H), 6.62 (d, J = 8.1 Hz, 1H), 6.69 (td, J = 7.8, 1.3 Hz, 1H), 6.74 (d, J = 8.1 Hz, 1H), 6.74 (dd, J = 7.8, 1.3 Hz, 1H), 6.87 (dd, J = 8.1, 2.3 Hz, 1H), 6.99 (d, J = 2.3 Hz, 1H), 7.16 (d, J = 8.1 Hz, 1H), 7.50 (d, J = 8.2 Hz, 1H), 8.33 (dd, J = 8.2, 2.4 Hz, 1H), 9.12 (d, J = 2.4 Hz, 1H)

6-[2-Methoxy-4-(2-methoxypyridin-3-ylcarbonyloxy)phenyl]-5-(2-methoxyphenylaminomethyl)-2,2,4-trimethyl-1,2-dihydroquinoline (Compound No. 1-117)

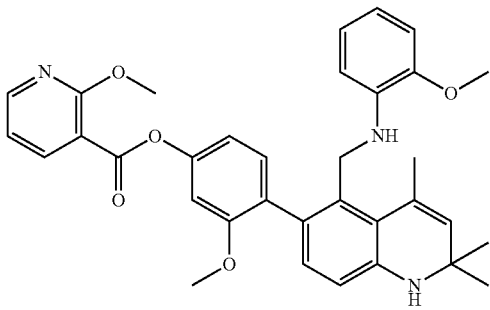 [SMILES: COc1ccccc1NCc1c(-c2ccc(OC(=O)c3cccnc3OC)cc2OC)ccc2c1C(C)=CC(C)(C)N2]

$^1$H-NMR (400 MHz, DMSO-$d_6$) δ 1.16 (s, 3H), 1.22 (s, 3H), 2.08 (s, 3H), 3.67 (s, 3H), 3.72 (s, 3H), 3.85 (dd, J = 12.7, 3.1 Hz, 1H), 3.97 (s, 3H), 4.07 (dd, J = 12.7, 6.8 Hz, 1H), 4.25 (dd, J = 6.8, 3.1 Hz, 1H), 5.40 (s, 1H), 6.02 (s, 1H), 6.37 (dd, J = 7.7, 1.3 Hz, 1H), 6.52 (td, J = 7.7, 1.3 Hz, 1H), 6.62 (d, J = 8.2 Hz, 1H), 6.69 (td, J = 7.7, 1.3 Hz, 1H), 6.73 (d, J = 8.2 Hz, 1H), 6.74 (dd, J = 7.7, 1.3 Hz, 1H), 6.82 (dd, J = 8.1, 2.2 Hz, 1H), 6.93 (d, J = 2.2 Hz, 1H), 7.15 (d, J = 8.1 Hz, 1H), 7.19 (dd, J = 7.5, 4.9 Hz, 1H), 8.39 (dd, J = 7.5, 2.1 Hz, 1H), 8.47 (dd, J = 4.9, 2.1 Hz, 1H)

5-(5-Fluoro-2-methylphenylaminomethyl)-6-[4-(furan-3-ylcarbonyloxy)-2-methoxyphenyl]-2,2,4-trimethyl-1,2-dihydroquinoline (Compound No. 1-118)

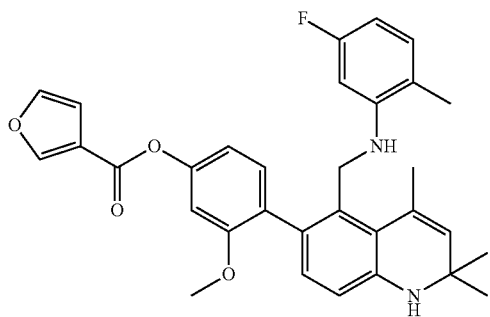 [SMILES: COc1cc(OC(=O)c2ccoc2)ccc1-c1ccc2c(c1CNc1cc(F)ccc1C)C(C)=CC(C)(C)N2]

$^1$H-NMR (400 MHz, DMSO-$d_6$) δ 1.11 (s, 3H), 1.20 (s, 3H), 1.90 (s, 3H), 2.05 (s, 3H), 3.71 (s, 3H), 3.93 (dd, J = 13.2, 4.6 Hz, 1H), 4.08 (dd, J = 13.2, 4.6 Hz, 1H), 4.20-4.25 (m, 1H), 5.41 (s, 1H), 6.03 (s, 1H), 6.06 (dd, J = 12.2, 2.5 Hz, 1H), 6.21 (td, J = 8.4, 2.5 Hz, 1H), 6.62 (d, J = 8.2 Hz, 1H), 6.75 (d, J = 8.2 Hz, 1H), 6.83 (dd, J = 8.1, 2.2 Hz, 1H), 6.86-6.90 (m, 1H), 6.94 (dd, J = 1.7, 0.9 Hz, 1H), 6.96 (d, J = 2.2 Hz, 1H), 7.23 (d, J = 8.1 Hz, 1H), 7.91 (t, J = 1.7 Hz, 1H), 8.63 (dd, J = 1.7, 0.9 Hz, 1H)

| | |
|---|---|
| 5-(5-Fluoro-2-methylphenylaminomethyl)-6-[2-methoxy-4-(pyridin-4-ylcarbonyloxy)phenyl]-2,2,4-trimethyl-1,2-dihydroquinoline (Compound No. 1-119)<br>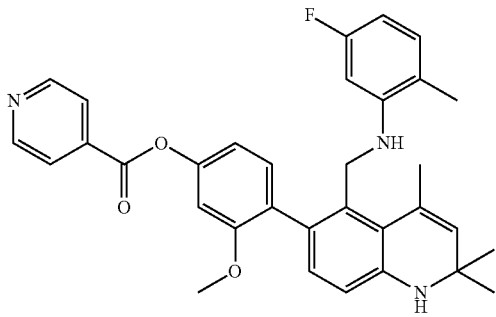 [SMILES: COc1cc(OC(=O)c2ccncc2)ccc1-c1ccc2c(c1CNc1cc(F)ccc1C)C(C)=CC(C)(C)N2] | $^1$H-NMR (400 MHz, DMSO-d$_6$)<br>δ 1.12 (s, 3H), 1.20 (s, 3H), 1.91 (s, 3H), 2.05 (s, 3H), 3.72 (s, 3H), 3.94 (dd, J = 13.1, 4.9 Hz, 1H), 4.10 (dd, J = 13.1, 4.2 Hz, 1H), 4.23-4.26 (m, 1H), 5.41 (s, 1H), 6.04 (s, 1H), 6.07 (dd, J = 12.2, 2.4 Hz, 1H), 6.21 (td, J = 8.4, 2.4 Hz, 1H), 6.63 (d, J = 8.2 Hz, 1H), 6.76 (d, J = 8.2 Hz, 1H), 6.86-6.90 (m, 1H), 6.92 (dd, J = 8.3, 2.2 Hz, 1H), 7.08 (d, J = 2.2 Hz, 1H), 7.27 (d, J = 8.3 Hz, 1H), 8.01 (d, J = 6.1 Hz, 2H), 8.89 (d, J = 6.1 Hz, 2H) |
| 6-[4-(2-Fluorobenzoyloxy)-2-methoxyphenyl]-5-(5-fluoro-2-methylphenylaminomethyl)-2,2,4-trimethyl-1,2-dihydroquinoline (Compound No. 1-120)<br>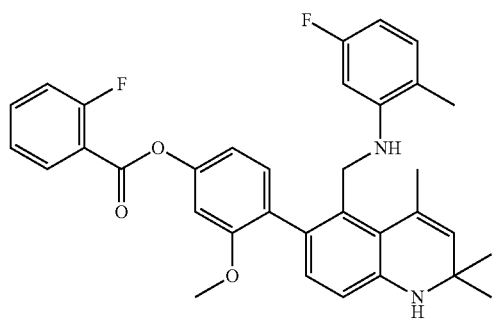 | $^1$H-NMR (400 MHz, DMSO-d$_6$)<br>δ 1.11 (s, 3H), 1.20 (s, 3H), 1.91 (s, 3H), 2.05 (s, 3H), 3.73 (s, 3H), 3.95 (dd, J = 13.4, 4.8 Hz, 1H), 4.10 (dd, J = 13.4, 4.2 Hz, 1H), 4.22-4.27 (m, 1H), 5.41 (s, 1H), 6.03 (s, 1H), 6.07 (dd, J = 12.2, 2.6 Hz, 1H), 6.21 (td, J = 8.5, 2.6 Hz, 1H), 6.62 (d, J = 8.3 Hz, 1H), 6.76 (d, J = 8.3 Hz, 1H), 6.85-6.91 (m, 1H), 6.89 (dd, J = 8.2, 2.2 Hz, 1H), 7.03 (d, J = 2.2 Hz, 1H), 7.26 (d, J = 8.2 Hz, 1H), 7.40-7.47 (m, 2H), 7.75-7.81 (m, 1H), 8.11 (td, J = 7.8, 1.6 Hz, 1H) |
| 5-(5-Fluoro-2-methylphenylaminomethyl)-6-[2-methoxy-4-(thiophen-2-ylcarbonyloxy)phenyl]-2,2,4-trimethyl-1,2-dihydroquinoline (Compound No. 1-121)<br>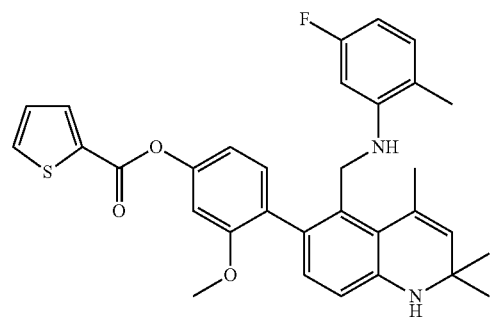 | $^1$H-NMR (400 MHz, DMSO-d$_6$)<br>δ 1.11 (s, 3H), 1.20 (s, 3H), 1.91 (s, 3H), 2.05 (s, 3H), 3.72 (s, 3H), 3.94 (dd, J = 13.0, 5.0 Hz, 1H), 4.09 (dd, J = 13.0, 4.2 Hz, 1H), 4.22-4.26 (m, 1H), 5.41 (s, 1H), 6.03 (s, 1H), 6.07 (dd, J = 12.2, 2.5 Hz, 1H), 6.21 (td, J = 8.4, 2.5 Hz, 1H), 6.62 (d, J = 8.2 Hz, 1H), 6.76 (d, J = 8.2 Hz, 1H), 6.86-6.90 (m, 1H), 6.87 (dd, J = 8.2, 2.3 Hz, 1H), 7.00 (d, J = 2.3 Hz, 1H), 7.24 (d, J = 8.2 Hz, 1H), 7.31 (dd, J = 5.0, 3.7 Hz, 1H), 8.02 (dd, J = 3.7, 1.3 Hz, 1H), 8.10 (dd, J = 5.0, 1.3 Hz, 1H) |
| 5-(5-Fluoro-2-methylphenylaminomethyl)-6-[2-methoxy-4-(2-methylpyridin-3-ylcarbonyloxy)phenyl]-2,2,4-trimethyl-1,2-dihydroquinoline (Compound No. 1-122)<br>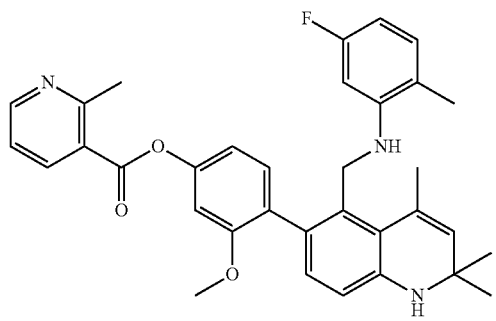 [SMILES: COc1cc(OC(=O)c2cccnc2C)ccc1-c1ccc2c(c1CNc1cc(F)ccc1C)C(C)=CC(C)(C)N2] | $^1$H-NMR (500 MHz, DMSO-d$_6$)<br>δ 1.11 (s, 3H), 1.20 (s, 3H), 1.92 (s, 3H), 2.05 (s, 3H), 2.80 (s, 3H), 3.73 (s, 3H), 3.95 (dd, J = 13.0, 5.0 Hz, 1H), 4.10 (dd, J = 13.0, 4.4 Hz, 1H), 4.24-4.26 (m, 1H), 5.41 (s, 1H), 6.03 (s, 1H), 6.07 (dd, J = 11.9, 2.5 Hz, 1H), 6.21 (td, J = 8.5, 2.5 Hz, 1H), 6.63 (d, J = 8.1 Hz, 1H), 6.76 (d, J = 8.1 Hz, 1H), 6.86-6.90 (m, 1H), 6.91 (dd, J = 8.1, 2.3 Hz, 1H), 7.06 (d, J = 2.3 Hz, 1H), 7.26 (d, J = 8.1 Hz, 1H), 7.46 (dd, J = 7.9, 5.0 Hz, 1H), 8.44 (dd, J = 7.9, 1.8 Hz, 1H), 8.71 (dd, J = 5.0, 1.8 Hz, 1H) |

| Compound | NMR |
|---|---|
| 5-(5-Fluoro-2-methylphenylaminomethyl)-6-[4-(2-methylthiobenzoyloxy)-2-methoxyphenyl]-2,2,4-trimethyl-1,2-dihydroquinoline (Compound No. 1-123) 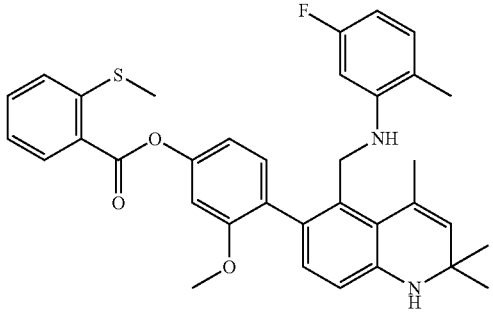 [SMILES: COc1cc(OC(=O)c2ccccc2SC)ccc1-c1ccc2c(c1CNc1cc(F)ccc1C)C(C)=CC(C)(C)N2] | $^1$H-NMR (400 MHz, DMSO-$d_6$) δ 1.11 (s, 3H), 1.20 (s, 3H), 1.91 (s, 3H), 2.05 (s, 3H), 2.47 (s, 3H), 3.72 (s, 3H), 3.95 (dd, J = 13.3, 4.5 Hz, 1H), 4.10 (dd, J = 13.3, 4.3 Hz, 1H), 4.23-4.26 (m, 1H), 5.41 (s, 1H), 6.03 (s, 1H), 6.08 (dd, J = 12.1, 2.5 Hz, 1H), 6.21 (td, J = 8.4, 2.5 Hz, 1H), 6.63 (d, J = 8.2 Hz, 1H), 6.76 (d, J = 8.2 Hz, 1H), 6.86 (dd, J = 8.1, 2.1 Hz, 1H), 6.86-6.90 (m, 1H), 6.99 (d, J = 2.1 Hz, 1H), 7.25 (d, J = 8.1 Hz, 1H), 7.32 (t, J = 8.0 Hz, 1H), 7.47 (d, J = 8.0 Hz, 1H), 7.67 (td, J = 8.0, 1.6 Hz, 1H), 8.18 (dd, J = 8.0, 1.6 Hz, 1H) |
| 5-(5-Fluoro-2-methylphenylaminomethyl)-6-[4-(3-methoxycarbonylbenzoyloxy)-2-methoxyphenyl]-2,2,4-trimethyl-1,2-dihydroquinoline (Compound No. 1-124) 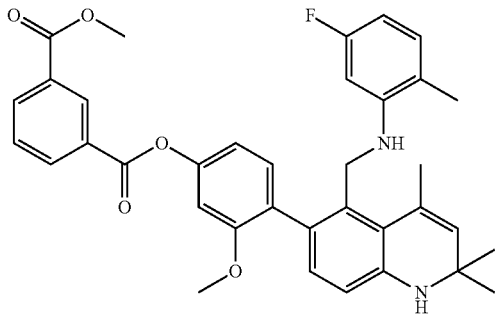 [SMILES: COC(=O)c1cccc(C(=O)Oc2ccc(-c3ccc4c(c3CNc3cc(F)ccc3C)C(C)=CC(C)(C)N4)c(OC)c2)c1] | $^1$H-NMR (500 MHz, DMSO-$d_6$) δ 1.11 (s, 3H), 1.20 (s, 3H), 1.92 (s, 3H), 2.05 (s, 3H), 3.73 (s, 3H), 3.92 (s, 3H), 3.95 (dd, J = 13.1, 4.9 Hz, 1H), 4.10 (dd, J = 13.1, 4.3 Hz, 1H), 4.23-4.25 (m, 1H), 5.41 (s, 1H), 6.03 (s, 1H), 6.08 (dd, J = 12.1, 2.5 Hz, 1H), 6.21 (td, J = 8.4, 2.5 Hz, 1H), 6.63 (d, J = 8.1 Hz, 1H), 6.77 (d, J = 8.1 Hz, 1H), 6.87-6.90 (m, 1H), 6.91 (dd, J = 8.2, 2.1 Hz, 1H), 7.07 (d, J = 2.1 Hz, 1H), 7.27 (d, J = 8.2 Hz, 1H), 7.79 (t, J = 7.8 Hz, 1H), 8.31 (dt, J = 7.8, 1.5 Hz, 1H), 8.39 (dt, J = 7.8, 1.5 Hz, 1H), 8.65 (t, J = 1.5 Hz, 1H) |
| 5-(5-Fluoro-2-methylphenylaminomethyl)-6-[2-methoxy-4-(2-methoxypyridin-3-ylcarbonyloxy)phenyl]-2,2,4-trimethyl-1,2-dihydroquinoline (Compound No. 1-125) 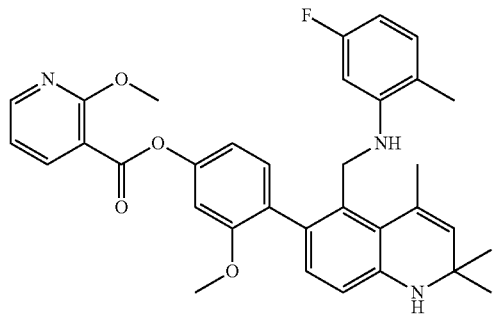 [SMILES: COc1cc(OC(=O)c2cccnc2OC)ccc1-c1ccc2c(c1CNc1cc(F)ccc1C)C(C)=CC(C)(C)N2] | $^1$H-NMR (500 MHz, DMSO-$d_6$) δ 1.11 (s, 3H), 1.20 (s, 3H), 1.91 (s, 3H), 2.05 (s, 3H), 3.72 (s, 3H), 3.95 (dd, J = 13.2, 4.3 Hz, 1H), 3.97 (s, 3H), 4.09 (dd, J = 13.2, 4.3 Hz, 1H), 4.23 (t, J = 4.3 Hz, 1H), 5.41 (s, 1H), 6.02 (s, 1H), 6.07 (dd, J = 12.2, 2.4 Hz, 1H), 6.21 (td, J = 8.4, 2.4 Hz, 1H), 6.62 (d, J = 8.2 Hz, 1H), 6.76 (d, J = 8.2 Hz, 1H), 6.85 (dd, J = 8.0, 2.2 Hz, 1H), 6.87-6.90 (m, 1H), 6.98 (d, J = 2.2 Hz, 1H), 7.19 (dd, J = 7.6, 4.9 Hz, 1H), 7.25 (d, J = 8.0 Hz, 1H), 8.40 (dd, J = 7.6, 2.0 Hz, 1H), 8.47 (dd, J = 4.9, 2.0 Hz, 1H) |
| 5-(5-Fluoro-2-methylphenylaminomethyl)-6-[2-methoxy-4-(3-methylfuran-2-ylcarbonyloxy)phenyl]-2,2,4-trimethyl-1,2-dihydroquinoline (Compound No. 1-126) 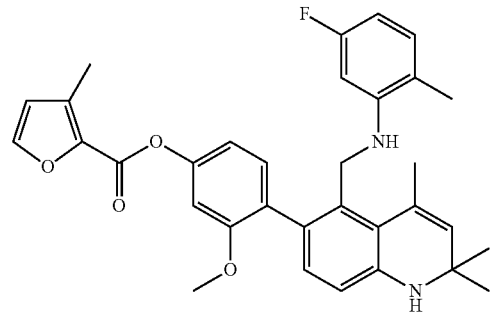 [SMILES: COc1cc(OC(=O)c2occc2C)ccc1-c1ccc2c(c1CNc1cc(F)ccc1C)C(C)=CC(C)(C)N2] | $^1$H-NMR (400 MHz, DMSO-$d_6$) δ 1.11 (s, 3H), 1.19 (s, 3H), 1.91 (s, 3H), 2.04 (s, 3H), 2.38 (s, 3H), 3.72 (s, 3H), 3.94 (dd, J = 12.9, 4.3 Hz, 1H), 4.10 (dd, J = 12.9, 4.3 Hz, 1H), 4.24 (t, J = 4.3 Hz, 1H), 5.41 (s, 1H), 6.03 (s, 1H), 6.06 (dd, J = 12.2, 2.5 Hz, 1H), 6.20 (td, J = 8.5, 2.5 Hz, 1H), 6.62 (d, J = 8.3 Hz, 1H), 6.69 (d, J = 1.7 Hz, 1H), 6.75 (d, J = 8.3 Hz, 1H), 6.84 (dd, J = 8.2, 2.3 Hz, 1H), 6.86-6.90 (m, 1H), 6.98 (d, J = 2.3 Hz, 1H), 7.23 (d, J = 8.2 Hz, 1H), 7.95 (d, J = 1.7 Hz, 1H) |

6-[2-Methoxy-4-(thiophen-2-ylcarbonyloxy)phenyl]-5-(4-methylbenzoyloxymethyl)-2,2,4-trimethyl-1,2-dihydroquinoline (Compound No. 1-127)

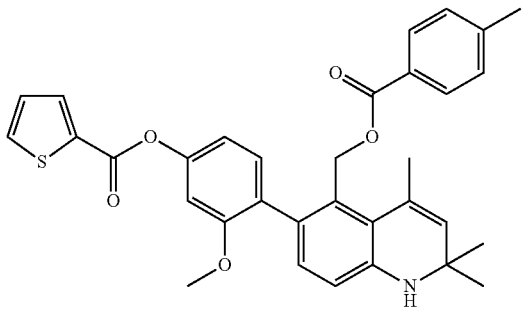 [SMILES: COc1cc(OC(=O)c2cccs2)ccc1-c1ccc2c(c1COC(=O)c1ccc(C)cc1)C(C)=CC(C)(C)N2]

$^1$H-NMR (400 MHz, DMSO-d$_6$) δ 1.15 (s, 3H), 1.23 (s, 3H), 2.09 (s, 3H), 2.35 (s, 3H), 3.67 (s, 3H), 4.99 (d, J = 12.7 Hz, 1H), 5.22 (d, J = 12.7 Hz, 1H), 5.46 (s, 1H), 6.12 (s, 1H), 6.68 (d, J = 8.2 Hz, 1H), 6.80 (d, J = 8.2 Hz, 1H), 6.84 (dd, J = 8.3, 2.2 Hz, 1H), 7.00 (d, J = 2.2 Hz, 1H), 7.20 (d, J = 8.3 Hz, 1H), 7.28 (d, J = 8.3 Hz, 2H), 7.32 (dd, J = 4.9, 3.9 Hz, 1H), 7.73 (d, J = 8.3 Hz, 2H), 8.03 (dd, J = 3.9, 1.3 Hz, 1H), 8.10 (dd, J = 4.9, 1.3 Hz, 1H)

6-[2-Methoxy-4-(6-methylpyridin-3-ylcarbonyloxy)phenyl]-5-(5-methylthiophen-2-ylcarbonyloxymethyl)-2,2,4-trimethyl-1,2-dihydroquinoline (Compound No. 1-128)

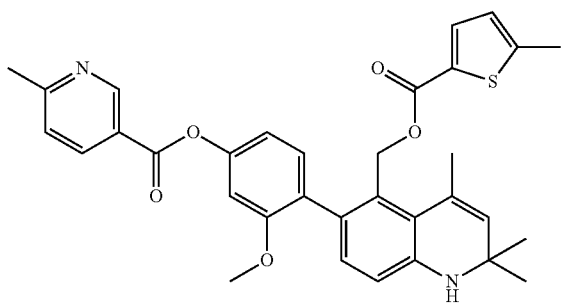

$^1$H-NMR (400 MHz, DMSO-d$_6$) δ 1.15 (s, 3H), 1.22 (s, 3H), 2.10 (s, 3H), 2.47 (s, 3H), 2.61 (s, 3H), 3.68 (s, 3H), 4.92 (d, J = 12.6 Hz, 1H), 5.19 (d, J = 12.6 Hz, 1H), 5.45 (s, 1H), 6.11 (s, 1H), 6.67 (d, J = 8.3 Hz, 1H), 6.80 (d, J = 8.3 Hz, 1H), 6.88 (dd, J = 8.3, 2.2 Hz, 1H), 6.89 (d, J = 3.6 Hz, 1H), 7.05 (d, J = 2.2 Hz, 1H), 7.20 (d, J = 8.3 Hz, 1H), 7.49 (d, J = 3.6 Hz, 1H), 7.52 (d, J = 8.0 Hz, 1H), 8.36 (dd, J = 8.0, 2.6 Hz, 1H), 9.15 (d, J = 2.6 Hz, 1H)

6-[4-(Furan-3-ylcarbonyloxy)-2-methoxyphenyl]-5-(4-methylbenzoyloxymethyl)-2,2,4-trimethyl-1,2-dihydroquinoline (Compound No. 1-129)

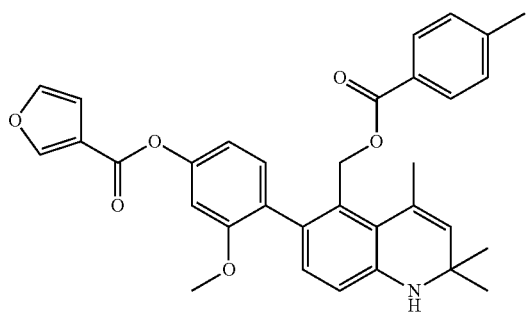 [SMILES: COc1cc(OC(=O)c2ccoc2)ccc1-c1ccc2c(c1COC(=O)c1ccc(C)cc1)C(C)=CC(C)(C)N2]

$^1$H-NMR (400 MHz, DMSO-d$_6$) δ 1.15 (s, 3H), 1.23 (s, 3H), 2.09 (s, 3H), 2.35 (s, 3H), 3.66 (s, 3H), 4.98 (d, J = 12.7 Hz, 1H), 5.21 (d, J = 12.7 Hz, 1H), 5.46 (s, 1H), 6.11 (s, 1H), 6.68 (d, J = 8.2 Hz, 1H), 6.80 (d, J = 8.2 Hz, 1H), 6.80 (dd, J = 8.3, 2.4 Hz, 1H), 6.95 (dd, J = 1.8, 0.7 Hz, 1H), 6.95 (d, J = 2.4 Hz, 1H), 7.19 (d, J = 8.3 Hz, 1H), 7.28 (d, J = 8.1 Hz, 2H), 7.72 (d, J = 8.1 Hz, 2H), 7.92 (t, J = 1.8 Hz, 1H), 8.64 (dd, J = 1.8, 0.7 Hz, 1H)

6-(4-Isobutyryloxy-2-methoxyphenyl)-5-(4-methylbenzoyloxymethyl)-2,2,4-trimethyl-1,2-dihydroquinoline (Compound No. 1-130)

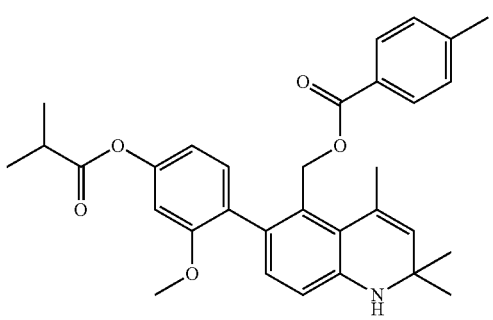 [SMILES: COc1cc(OC(=O)C(C)C)ccc1-c1ccc2c(c1COC(=O)c1ccc(C)cc1)C(C)=CC(C)(C)N2]

$^1$H-NMR (500 MHz, DMSO-d$_6$) δ 1.14 (s, 3H), 1.23 (s, 3H), 1.24 (d, J = 7.0 Hz, 6H), 2.08 (s, 3H), 2.35 (s, 3H), 2.81 (septet, J = 7.0 Hz, 1H), 3.65 (s, 3H), 4.96 (d, J = 12.8 Hz, 1H), 5.20 (d, J = 12.8 Hz, 1H), 5.45 (s, 1H), 6.09 (s, 1H), 6.67 (d, J = 8.1 Hz, 1H), 6.67 (dd, J = 8.2, 2.2 Hz, 1H), 6.77 (d, J = 8.1 Hz, 1H), 6.80 (d, J = 2.2 Hz, 1H), 7.15 (d, J = 8.2 Hz, 1H), 7.27 (d, J = 8.2 Hz, 2H), 7.71 (d, J = 8.2 Hz, 2H)

6-[4-(2-Chlorobenzoyloxy)-2-methoxyphenyl]-5-(4-methylbenzoyloxymethyl)-2,2,4-trimethyl-1,2-dihydroquinoline (Compound No. 1-131)

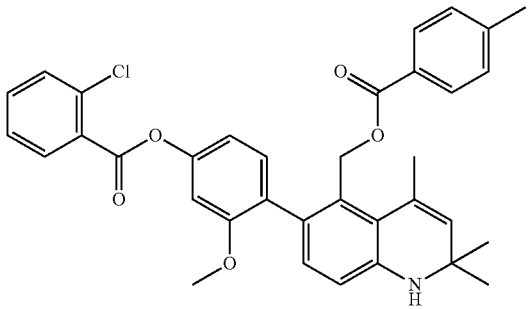

$^1$H-NMR (400 MHz, DMSO-d$_6$) δ 1.15 (s, 3H), 1.23 (s, 3H), 2.09 (s, 3H), 2.35 (s, 3H), 3.69 (s, 3H), 5.00 (d, J = 12.7 Hz, 1H), 5.23 (d, J = 12.7 Hz, 1H), 5.46 (s, 1H), 6.12 (s, 1H), 6.68 (d, J = 8.2 Hz, 1H), 6.81 (d, J = 8.2 Hz, 1H), 6.88 (dd, J = 8.2, 2.3 Hz, 1H), 7.03 (d, J = 2.3 Hz, 1H), 7.23 (d, J = 8.2 Hz, 1H), 7.28 (d, J = 7.9 Hz, 2H), 7.55-7.59 (m, 1H), 7.68-7.69 (m, 2H), 7.73 (d, J = 7.9 Hz, 2H), 8.11 (d, J = 7.3 Hz, 1H)

6-[2-Methoxy-4-(2-methoxybenzoyloxy)phenyl]-5-(4-methylbenzoyloxymethyl)-2,2,4-trimethyl-1,2-dihydroquinoline (Compound No. 1-132)

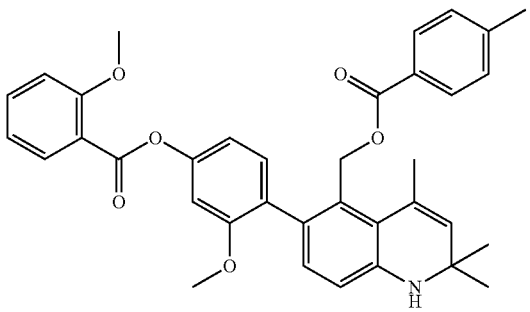 [SMILES: COc1ccccc1C(=O)Oc1ccc(-c2ccc3c(c2COC(=O)c2ccc(C)cc2)C(C)=CC(C)(C)N3)c(OC)c1]

$^1$H-NMR (400 MHz, DMSO-d$_6$) δ 1.15 (s, 3H), 1.23 (s, 3H), 2.09 (s, 3H), 2.35 (s, 3H), 3.68 (s, 3H), 3.88 (s, 3H), 5.00 (d, J = 12.8 Hz, 1H), 5.23 (d, J = 12.8 Hz, 1H), 5.46 (s, 1H), 6.11 (s, 1H), 6.68 (d, J = 8.2 Hz, 1H), 6.80 (d, J = 8.2 Hz, 1H), 6.81 (d, J = 8.1 Hz, 1H), 6.94 (d, J = 2.2 Hz, 1H), 7.08-7.12 (m, 1H), 7.20 (d, J = 8.1 Hz, 1H), 7.24 (d, J = 7.8 Hz, 1H), 7.28 (d, J = 7.9 Hz, 2H), 7.62-7.67 (m, 1H), 7.73 (d, J = 7.9 Hz, 2H), 7.92 (dd, J = 7.8, 1.7 Hz, 1H)

5-(4-Methylbenzoyloxymethyl)-6-[2-methoxy-4-(pyridin-3-ylcarbonyloxy)phenyl]-2,2,4-trimethyl-1,2-dihydroquinoline (Compound No. 1-133)

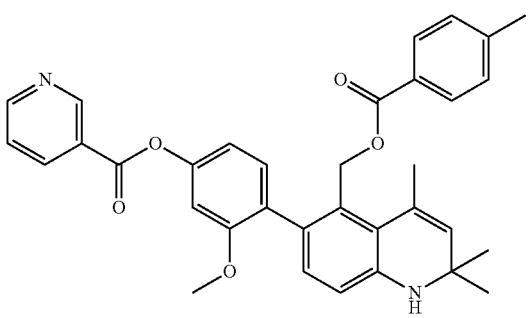 [SMILES: COc1cc(OC(=O)c2cccnc2)ccc1-c1ccc2c(c1COC(=O)c1ccc(C)cc1)C(C)=CC(C)(C)N2]

$^1$H-NMR (500 MHz, DMSO-d$_6$) δ 1.15 (s, 3H), 1.23 (s, 3H), 2.09 (s, 3H), 2.35 (s, 3H), 3.67 (s, 3H), 5.00 (d, J = 12.8 Hz, 1H), 5.23 (d, J = 12.8 Hz, 1H), 5.46 (s, 1H), 6.12 (s, 1H), 6.69 (d, J = 8.2 Hz, 1H), 6.81 (d, J = 8.2 Hz, 1H), 6.90 (dd, J = 8.1, 2.3 Hz, 1H), 7.07 (d, J = 2.3 Hz, 1H), 7.23 (d, J = 8.1 Hz, 1H), 7.28 (d, J = 8.1 Hz, 2H), 7.67 (ddd, J = 7.9, 4.9, 0.8 Hz, 1H), 7.73 (d, J = 8.1 Hz, 2H), 8.47-8.49 (m, 1H), 8.91 (dd, J = 4.9, 1.8 Hz, 1H), 9.28 (dd, J = 2.3, 0.8 Hz, 1H)

6-[4-(Furan-2-ylcarbonyloxy)-2-methoxyphenyl]-5-(4-methylbenzoyloxymethyl)-2,2,4-trimethyl-1,2-dihydroquinoline (Compound No. 1-134)

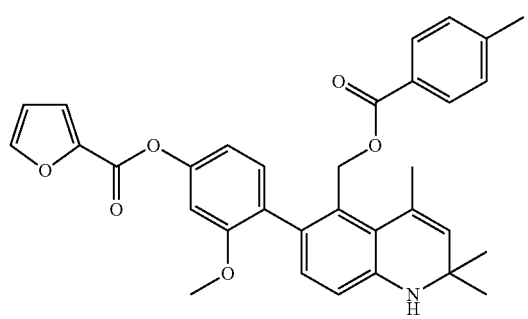 [SMILES: COc1cc(OC(=O)c2ccco2)ccc1-c1ccc2c(c1COC(=O)c1ccc(C)cc1)C(C)=CC(C)(C)N2]

$^1$H-NMR (500 MHz, DMSO-d$_6$) δ 1.15 (s, 3H), 1.23 (s, 3H), 2.09 (s, 3H), 2.35 (s, 3H), 3.66 (s, 3H), 4.99 (d, J = 12.8 Hz, 1H), 5.22 (d, J = 12.8 Hz, 1H), 5.46 (s, 1H), 6.12 (s, 1H), 6.68 (d, J = 7.8 Hz, 1H), 6.80 (d, J = 7.8 Hz, 1H), 6.81 (dd, J = 3.5, 1.7 Hz, 1H), 6.83 (dd, J = 8.2, 2.4 Hz, 1H), 6.99 (d, J = 2.4 Hz, 1H), 7.20 (d, J = 8.2 Hz, 1H), 7.28 (d, J = 7.9 Hz, 2H), 7.57 (dd, J = 3.5, 0.8 Hz, 1H), 7.72 (d, J = 7.9 Hz, 2H), 8.11 (dd, J = 1.7, 0.8 Hz, 1H)

6-(4-Butyryloxy-2-methoxyphenyl)-5-(5-methylthiophen-2-ylcarbonyloxymethyl)-2,2,4-trimethyl-1,2-dihydroquinoline (Compound No. 1-135)

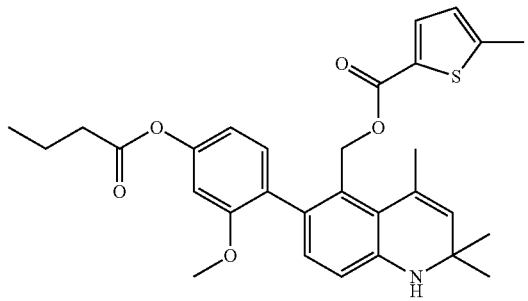 [SMILES: CCCC(=O)Oc1ccc(-c2ccc3c(c2COC(=O)c2ccc(C)s2)C(C)=CC(C)(C)N3)c(OC)c1]

$^1$H-NMR (500 MHz, DMSO-d$_6$)
δ 0.98 (t, J = 7.3 Hz, 3H), 1.14 (s, 3H), 1.21 (s, 3H), 1.67 (sextet, J = 7.3 Hz, 2H), 2.08 (s, 3H), 2.46 (s, 3H), 2.56 (t, J = 7.3 Hz, 2H), 3.65 (s, 3H), 4.89 (d, J = 12.7 Hz, 1H), 5.16 (d, J = 12.7 Hz, 1H), 5.44 (s, 1H), 6.09 (s, 1H), 6.65 (d, J = 8.2 Hz, 1H), 6.68 (dd, J = 8.2, 2.2 Hz, 1H), 6.76 (d, J = 8.2 Hz, 1H), 6.81 (d, J = 2.2 Hz, 1H), 6.88 (dd, J = 3.7, 1.1 Hz, 1H), 7.13 (d, J = 8.2 Hz, 1H), 7.47 (d, J = 3.7 Hz, 1H)

6-[2-Methoxy-4-(2-methoxybenzoyloxy)phenyl]-5-(5-methylthiophen-2-ylcarbonyloxymethyl)-2,2,4-trimethyl-1,2-dihydroquinoline (Compound No. 1-136)

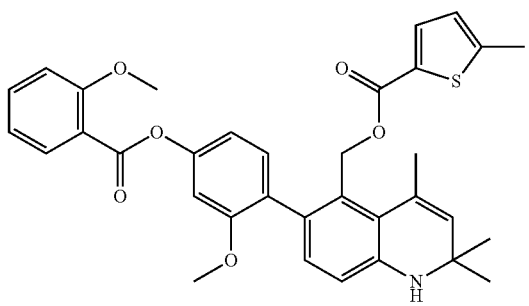

$^1$H-NMR (400 MHz, DMSO-d$_6$)
δ 1.15 (s, 3H), 1.22 (s, 3H), 2.09 (s, 3H), 2.47 (s, 3H), 3.68 (s, 3H), 3.89 (s, 3H), 4.93 (d, J = 12.6 Hz, 1H), 5.19 (d, J = 12.6 Hz, 1H), 5.45 (s, 1H), 6.10 (s, 1H), 6.67 (d, J = 8.1 Hz, 1H), 6.79 (d, J = 8.1 Hz, 1H), 6.81 (dd, J = 8.0, 2.1 Hz, 1H), 6.89 (dd, J = 3.7, 1.0 Hz, 1H), 6.95 (d, J = 2.1 Hz, 1H), 7.09-7.12 (m, 1H), 7.18 (d, J = 8.0 Hz, 1H), 7.24 (d, J = 8.1 Hz, 1H), 7.48 (d, J = 3.7 Hz, 1H), 7.62-7.67 (m, 1H), 7.93 (dd, J = 7.7, 1.8 Hz, 1H)

6-[2-Methoxy-4-(pyridin-3-ylcarbonyloxy)phenyl]-5-(5-methylthiophen-2-ylcarbonyloxymethyl)-2,2,4-trimethyl-1,2-dihydroquinoline (Compound No. 1-137)

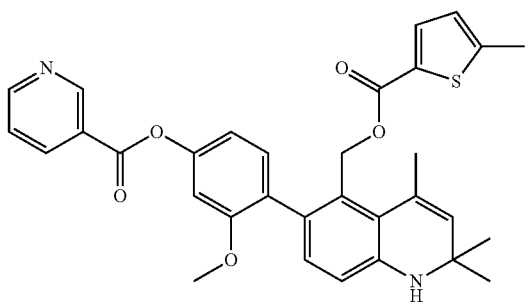 [SMILES: COc1cc(OC(=O)c2cccnc2)ccc1-c1ccc2c(c1COC(=O)c1ccc(C)s1)C(C)=CC(C)(C)N2]

$^1$H-NMR (500 MHz, DMSO-d$_6$)
δ 1.15 (s, 3H), 1.22 (s, 3H), 2.10 (s, 3H), 2.47 (s, 3H), 3.68 (s, 3H), 4.93 (d, J = 12.7 Hz, 1H), 5.19 (d, J = 12.7 Hz, 1H), 5.45 (s, 1H), 6.11 (s, 1H), 6.68 (d, J = 8.2 Hz, 1H), 6.80 (d, J = 8.2 Hz, 1H), 6.89 (dd, J = 3.7, 0.9 Hz, 1H), 6.90 (dd, J = 8.1, 2.1 Hz, 1H), 7.08 (d, J = 2.1 Hz, 1H), 7.21 (d, J = 8.1 Hz, 1H), 7.49 (d, J = 3.7 Hz, 1H), 7.67 (ddd, J = 8.0, 4.9, 0.9 Hz, 1H), 8.49 (dt, J = 8.0, 2.0 Hz, 1H), 8.91 (dd, J = 4.9, 2.0 Hz, 1H), 9.28 (dd, J = 2.0, 0.9 Hz, 1H)

6-[4-(Furan-2-ylcarbonyloxy)-2-methoxyphenyl]-5-(5-methylthiophen-2-ylcarbonyloxymethyl)-2,2,4-trimethyl-1,2-dihydroquinoline (Compound No. 1-138)

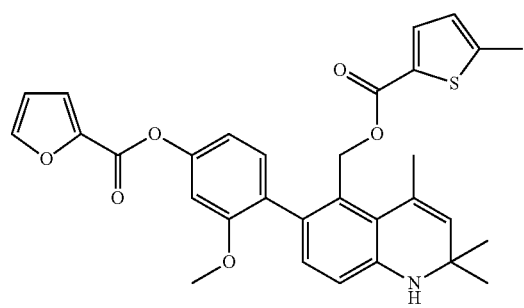 [SMILES: COc1cc(OC(=O)c2ccco2)ccc1-c1ccc2c(c1COC(=O)c1ccc(C)s1)C(C)=CC(C)(C)N2]

$^1$H-NMR (400 MHz, DMSO-d$_6$)
δ 1.15 (s, 3H), 1.22 (s, 3H), 2.09 (s, 3H), 2.47 (s, 3H), 3.67 (s, 3H), 4.92 (d, J = 12.8 Hz, 1H), 5.18 (d, J = 12.8 Hz, 1H), 5.45 (s, 1H), 6.11 (s, 1H), 6.67 (d, J = 8.3 Hz, 1H), 6.78 (d, J = 8.3 Hz, 1H), 6.81 (d, J = 3.7 Hz, 1H), 6.84 (dd, J = 8.2, 2.3 Hz, 1H), 6.88 (dd, J = 3.7, 1.4 Hz, 1H), 6.99 (d, J = 2.3 Hz, 1H), 7.18 (d, J = 8.2 Hz, 1H), 7.48 (d, J = 3.7 Hz, 1H), 7.58 (dd, J = 3.7, 0.8 Hz, 1H), 8.12 (dd, J = 1.4, 0.8 Hz, 1H)

6-[4-(2-Chlorobenzoyloxy)-2-methoxyphenyl]-5-(5-methylthiophen-2-ylcarbonyloxymethyl)-2,2,4-trimethyl-1,2-dihydroquinoline (Compound No. 1-139)

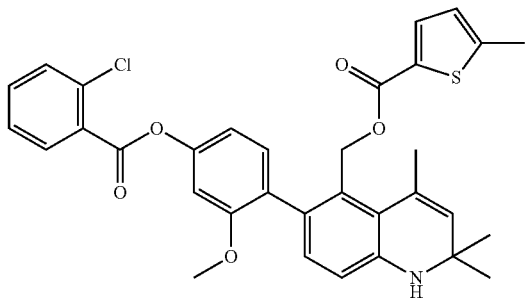 [SMILES: COc1cc(OC(=O)c2ccccc2Cl)ccc1-c1ccc2c(c1COC(=O)c1ccc(C)s1)C(C)=CC(C)(C)N2]

$^1$H-NMR (400 MHz, DMSO-$d_6$) δ 1.15 (s, 3H), 1.22 (s, 3H), 2.10 (s, 3H), 2.47 (s, 3H), 3.69 (s, 3H), 4.93 (d, J = 12.7 Hz, 1H), 5.19 (d, J = 12.7 Hz, 1H), 5.45 (s, 1H), 6.11 (s, 1H), 6.67 (d, J = 8.2 Hz, 1H), 6.79 (d, J = 8.2 Hz, 1H), 6.88 (dd, J = 8.2, 2.3 Hz, 1H), 6.88 (d, J = 3.6 Hz, 1H), 7.04 (d, J = 2.3 Hz, 1H), 7.21 (d, J = 8.2 Hz, 1H), 7.48 (d, J = 3.6 Hz, 1H), 7.55-7.59 (m, 1H), 7.68-7.69 (m, 2H), 8.10-8.13 (m, 1H)

6-[4-(3-Chlorobenzoyloxy)-2-methoxyphenyl]-5-(5-methylthiophen-2-ylcarbonyloxymethyl)-2,2,4-trimethyl-1,2-dihydroquinoline (Compound No. 1-140)

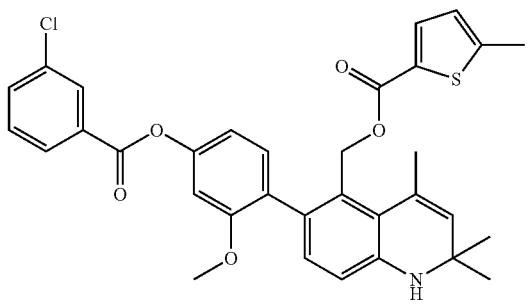 [SMILES: COc1cc(OC(=O)c2cccc(Cl)c2)ccc1-c1ccc2c(c1COC(=O)c1ccc(C)s1)C(C)=CC(C)(C)N2]

$^1$H-NMR (500 MHz, DMSO-$d_6$) δ 1.15 (s, 3H), 1.22 (s, 3H), 2.10 (s, 3H), 2.47 (s, 3H), 3.67 (s, 3H), 4.93 (d, J = 12.5 Hz, 1H), 5.19 (d, J = 12.5 Hz, 1H), 5.45 (s, 1H), 6.10 (s, 1H), 6.67 (d, J = 8.2 Hz, 1H), 6.80 (d, J = 8.2 Hz, 1H), 6.89 (dd, J = 8.2, 2.2 Hz, 1H), 6.89 (d, J = 4.0 Hz, 1H), 7.06 (d, J = 2.2 Hz, 1H), 7.20 (d, J = 8.2 Hz, 1H), 7.49 (d, J = 4.0 Hz, 1H), 7.67 (t, J = 7.8 Hz, 1H), 7.85 (ddd, J = 7.8, 1.9, 1.1 Hz, 1H), 8.10 (ddd, J = 7.8, 1.9, 1.1 Hz, 1H), 8.13 (t, J = 1.9 Hz, 1H)

6-[4-(4-Chlorobenzoyloxy)-2-methoxyphenyl]-5-(5-methylthiophen-2-ylcarbonyloxymethyl)-2,2,4-trimethyl-1,2-dihydroquinoline (Compound No. 1-141)

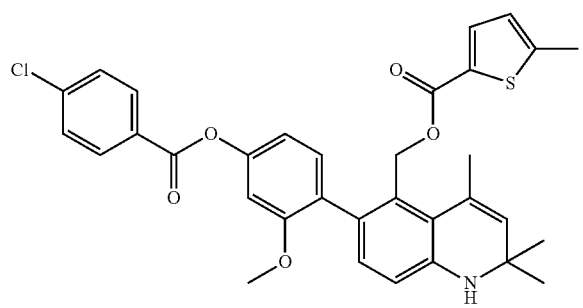 [SMILES: COc1cc(OC(=O)c2ccc(Cl)cc2)ccc1-c1ccc2c(c1COC(=O)c1ccc(C)s1)C(C)=CC(C)(C)N2]

$^1$H-NMR (400 MHz, DMSO-$d_6$) δ 1.15 (s, 3H), 1.22 (s, 3H), 2.09 (s, 3H), 2.47 (s, 3H), 3.67 (s, 3H), 4.92 (d, J = 12.8 Hz, 1H), 5.19 (d, J = 12.8 Hz, 1H), 5.45 (s, 1H), 6.11 (s, 1H), 6.67 (d, J = 8.3 Hz, 1H), 6.79 (d, J = 8.3 Hz, 1H), 6.87 (dd, J = 8.1, 2.2 Hz, 1H), 6.88 (d, J = 3.7 Hz, 1H), 7.03 (d, J = 2.2 Hz, 1H), 7.20 (d, J = 8.1 Hz, 1H), 7.48 (d, J = 3.7 Hz, 1H), 7.70 (d, J = 8.8 Hz, 2H), 8.15 (d, J = 8.8 Hz, 2H)

6-(4-Benzoyloxy-2-methoxyphenyl)-5-(5-methylthiophen-2-ylcarbonyloxymethyl)-2,2,4-trimethyl-1,2-dihydroquinoline (Compound No. 1-142)

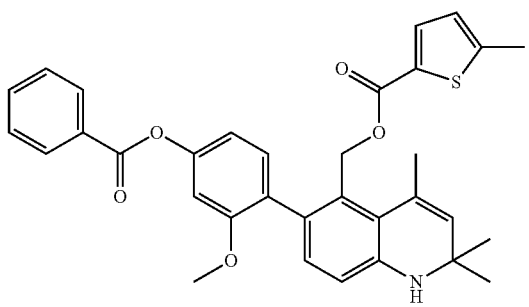

$^1$H-NMR (400 MHz, DMSO-$d_6$) δ 1.15 (s, 3H), 1.22 (s, 3H), 2.10 (s, 3H), 2.47 (s, 3H), 3.68 (s, 3H), 4.93 (d, J = 12.6 Hz, 1H), 5.20 (d, J = 12.6 Hz, 1H), 5.45 (s, 1H), 6.11 (s, 1H), 6.67 (d, J = 8.3 Hz, 1H), 6.80 (d, J = 8.3 Hz, 1H), 6.86 (dd, J = 8.2, 2.2 Hz, 1H), 6.89 (d, J = 3.8 Hz, 1H), 7.02 (d, J = 2.2 Hz, 1H), 7.20 (d, J = 8.2 Hz, 1H), 7.49 (d, J = 3.8 Hz, 1H), 7.63 (dd, J = 8.2, 7.5 Hz, 2H), 7.76 (tt, J = 7.5, 1.4 Hz, 1H), 8.15 (dd, J = 8.2, 1.4 Hz, 2H)

6-[2-Methoxy-4-(2-methylbenzoyloxy)phenyl]-5-(5-methylthiophen-2-ylcarbonyloxymethyl)-2,2,4-trimethyl-1,2-dihydroquinoline (Compound No. 1-143)

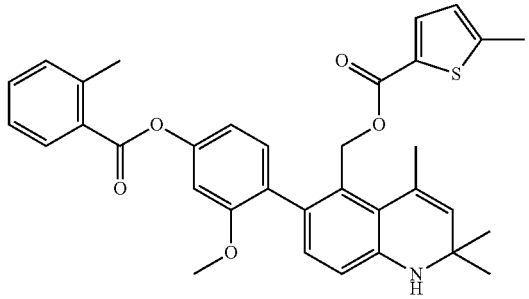 [SMILES: COc1cc(OC(=O)c2ccccc2C)ccc1-c1ccc2c(c1COC(=O)c1ccc(C)s1)C(C)=CC(C)(C)N2]

¹H-NMR (400 MHz, DMSO-d₆) δ 1.15 (s, 3H), 1.22 (s, 3H), 2.10 (s, 3H), 2.47 (s, 3H), 2.61 (s, 3H), 3.68 (s, 3H), 4.94 (d, J = 12.7 Hz, 1H), 5.20 (d, J = 12.7 Hz, 1H), 5.45 (s, 1H), 6.11 (s, 1H), 6.68 (d, J = 8.1 Hz, 1H), 6.79 (d, J = 8.1 Hz, 1H), 6.86 (dd, J = 8.1, 2.2 Hz, 1H), 6.89 (d, J = 3.8 Hz, 1H), 7.02 (d, J = 2.2 Hz, 1H), 7.20 (d, J = 8.1 Hz, 1H), 7.40-7.43 (m, 1H), 7.42 (d, J = 7.7 Hz, 1H), 7.49 (d, J = 3.8 Hz, 1H), 7.58 (td, J = 7.7, 1.2 Hz, 1H), 8.10 (dd, J = 7.7, 1.2 Hz, 1H)

6-[4-(2-Fluorobenzoyloxy)-2-methoxyphenyl]-5-(5-methylthiophen-2-ylcarbonyloxymethyl)-2,2,4-trimethyl-1,2-dihydroquinoline (Compound No. 1-144)

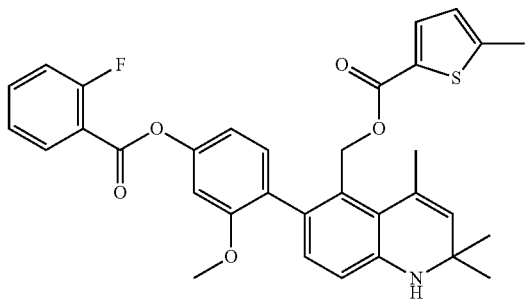 [SMILES: COc1cc(OC(=O)c2ccccc2F)ccc1-c1ccc2c(c1COC(=O)c1ccc(C)s1)C(C)=CC(C)(C)N2]

¹H-NMR (400 MHz, DMSO-d₆) δ 1.15 (s, 3H), 1.22 (s, 3H), 2.10 (s, 3H), 2.47 (s, 3H), 3.68 (s, 3H), 4.93 (d, J = 12.7 Hz, 1H), 5.20 (d, J = 12.7 Hz, 1H), 5.45 (s, 1H), 6.11 (s, 1H), 6.68 (d, J = 8.2 Hz, 1H), 6.80 (d, J = 8.2 Hz, 1H), 6.87 (dd, J = 8.2, 2.3 Hz, 1H), 6.89 (d, J = 3.8 Hz, 1H), 7.03 (d, J = 2.3 Hz, 1H), 7.20 (d, J = 8.2 Hz, 1H), 7.41-7.46 (m, 2H), 7.49 (d, J = 3.8 Hz, 1H), 7.77-7.82 (m, 1H), 8.12 (td, J = 7.7, 1.7 Hz, 1H)

6-[2-Methoxy-4-(4-methoxybenzoyloxy)phenyl]-5-(5-methylthiophen-2-ylcarbonyloxymethyl)-2,2,4-trimethyl-1,2-dihydroquinoline (Compound No. 1-145)

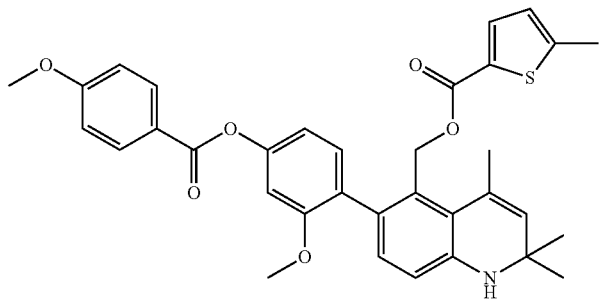

¹H-NMR (400 MHz, DMSO-d₆) δ 1.15 (s, 3H), 1.22 (s, 3H), 2.09 (s, 3H), 2.47 (s, 3H), 3.67 (s, 3H), 3.88 (s, 3H), 4.93 (d, J = 12.7 Hz, 1H), 5.19 (d, J = 12.7 Hz, 1H), 5.45 (s, 1H), 6.10 (s, 1H), 6.67 (d, J = 8.2 Hz, 1H), 6.79 (d, J = 8.2 Hz, 1H), 6.83 (dd, J = 8.1, 2.2 Hz, 1H), 6.89 (dd, J = 3.7, 1.2 Hz, 1H), 6.98 (d, J = 2.2 Hz, 1H), 7.14 (d, J = 8.9 Hz, 2H), 7.18 (d, J = 8.1 Hz, 1H), 7.49 (d, J = 3.7 Hz, 1H), 8.10 (d, J = 8.9 Hz, 2H)

6-[2-Methoxy-4-(pyrimidin-5-ylcarbonyloxy)phenyl]-5-(5-methylthiophen-2-ylcarbonyloxymethyl)-2,2,4-trimethyl-1,2-dihydroquinoline (Compound No. 1-146)

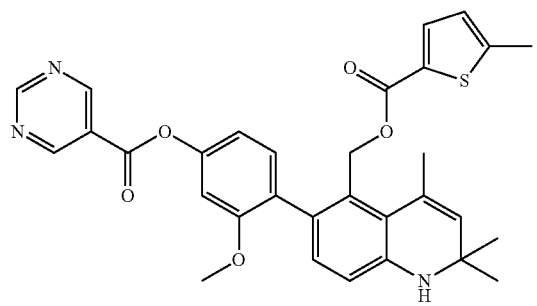 [SMILES: COc1cc(OC(=O)c2cncnc2)ccc1-c1ccc2c(c1COC(=O)c1ccc(C)s1)C(C)=CC(C)(C)N2]

¹H-NMR (400 MHz, DMSO-d₆) δ 1.15 (s, 3H), 1.22 (s, 3H), 2.10 (s, 3H), 2.47 (s, 3H), 3.68 (s, 3H), 4.92 (d, J = 12.6 Hz, 1H), 5.19 (d, J = 12.6 Hz, 1H), 5.45 (s, 1H), 6.11 (s, 1H), 6.68 (d, J = 8.2 Hz, 1H), 6.80 (d, J = 8.2 Hz, 1H), 6.89 (d, J = 3.6 Hz, 1H), 6.93 (dd, J = 8.2, 2.3 Hz, 1H), 7.10 (d, J = 2.3 Hz, 1H), 7.22 (d, J = 8.2 Hz, 1H), 7.49 (d, J = 3.6 Hz, 1H), 9.44 (s, 2H), 9.51 (s, 1H)

6-[2-Methoxy-4-(thiophen-3-ylcarbonyloxy)phenyl]-5-(5-methylthiophen-2-ylcarbonyloxymethyl)-2,2,4-trimethyl-1,2-dihydroquinoline (Compound No. 1-147)

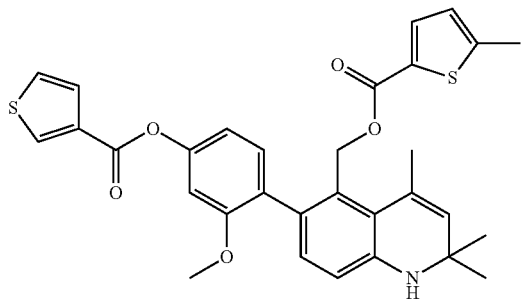 [SMILES: COc1cc(OC(=O)c2ccsc2)ccc1-c1ccc2c(c1COC(=O)c1ccc(C)s1)C(C)=CC(C)(C)N2]

¹H-NMR (400 MHz, DMSO-d₆) δ 1.15 (s, 3H), 1.22 (s, 3H), 2.10 (s, 3H), 2.47 (s, 3H), 3.67 (s, 3H), 4.92 (d, J = 13.2 Hz, 1H), 5.19 (d, J = 13.2 Hz, 1H), 5.45 (s, 1H), 6.11 (s, 1H), 6.67 (d, J = 8.2 Hz, 1H), 6.79 (d, J = 8.2 Hz, 1H), 6.83 (dd, J = 8.2, 2.2 Hz, 1H), 6.89 (d, J = 3.8 Hz, 1H), 6.99 (d, J = 2.2 Hz, 1H), 7.19 (d, J = 8.2 Hz, 1H), 7.49 (d, J = 3.8 Hz, 1H), 7.63 (dd, J = 5.1, 1.3 Hz, 1H), 7.76 (dd, J = 5.1, 2.9 Hz, 1H), 8.62 (dd, J = 2.9, 1.3 Hz, 1H)

6-[4-(Furan-3-ylcarbonyloxy)-2-methoxyphenyl]-5-(5-methylthiophen-2-ylcarbonyloxymethyl)-2,2,4-trimethyl-1,2-dihydroquinoline (Compound No. 1-148)

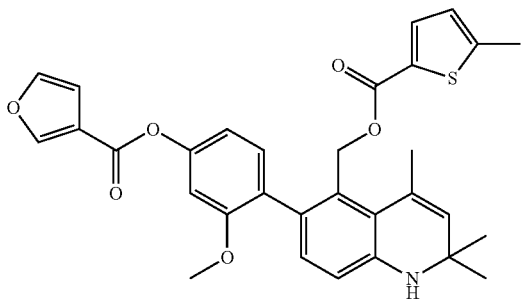 [SMILES: COc1cc(OC(=O)c2ccoc2)ccc1-c1ccc2c(c1COC(=O)c1ccc(C)s1)C(C)=CC(C)(C)N2]

¹H-NMR (400 MHz, DMSO-d₆) δ 1.15 (s, 3H), 1.22 (s, 3H), 2.10 (s, 3H), 2.47 (s, 3H), 3.67 (s, 3H), 4.91 (d, J = 12.5 Hz, 1H), 5.18 (d, J = 12.5 Hz, 1H), 5.45 (s, 1H), 6.11 (s, 1H), 6.67 (d, J = 8.1 Hz, 1H), 6.79 (d, J = 8.1 Hz, 1H), 6.81 (dd, J = 8.2, 2.3 Hz, 1H), 6.89 (d, J = 3.7 Hz, 1H), 6.95 (dd, J = 1.7, 0.7 Hz, 1H), 6.96 (d, J = 2.3 Hz, 1H), 7.18 (d, J = 8.2 Hz, 1H), 7.48 (d, J = 3.7 Hz, 1H), 7.93 (t, J = 1.7 Hz, 1H), 8.65 (dd, J = 1.7, 0.7 Hz, 1H)

6-[2-Methoxy-4-(3-methoxycarbonylbenzoyloxy)phenyl]-5-(5-methylthiophen-2-ylcarbonyloxymethyl)-2,2,4-trimethyl-1,2-dihydroquinoline (Compound No. 1-149)

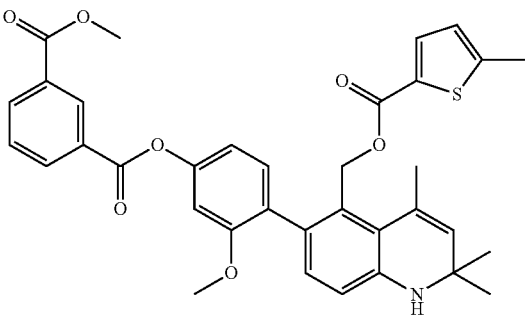 [SMILES: COC(=O)c1cccc(C(=O)Oc2ccc(-c3ccc4c(c3COC(=O)c3ccc(C)s3)C(C)=CC(C)(C)N4)c(OC)c2)c1]

¹H-NMR (400 MHz, DMSO-d₆) δ 1.15 (s, 3H), 1.22 (s, 3H), 2.10 (s, 3H), 2.47 (s, 3H), 3.68 (s, 3H), 3.93 (s, 3H), 4.93 (d, J = 12.6 Hz, 1H), 5.20 (d, J = 12.6 Hz, 1H), 5.45 (s, 1H), 6.12 (s, 1H), 6.68 (d, J = 8.3 Hz, 1H), 6.80 (d, J = 8.3 Hz, 1H), 6.89 (dd, J = 8.2, 2.3 Hz, 1H), 6.89 (d, J = 3.6 Hz, 1H), 7.07 (d, J = 2.3 Hz, 1H), 7.21 (d, J = 8.2 Hz, 1H), 7.49 (d, J = 3.6 Hz, 1H), 7.80 (td, J = 7.8, 0.5 Hz, 1H), 8.31 (ddd, J = 7.8, 1.7, 1.2 Hz, 1H), 8.40 (ddd, J = 7.8, 1.7, 1.2 Hz, 1H), 8.66 (td, J = 1.7, 0.5 Hz, 1H)

6-[4-(3-Acetylbenzoyloxy)-2-methoxyphenyl]-5-(5-methylthiophen-2-ylcarbonyloxymethyl)-2,2,4-trimethyl-1,2-dihydroquinoline (Compound No. 1-150)

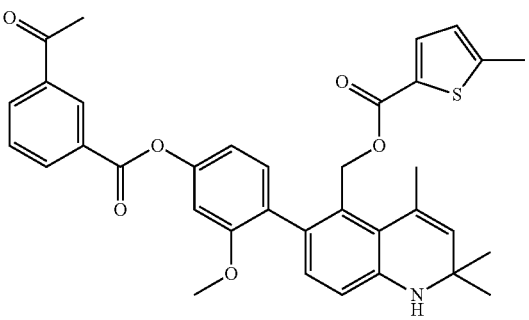 [SMILES: COc1cc(OC(=O)c2cccc(C(C)=O)c2)ccc1-c1ccc2c(c1COC(=O)c1ccc(C)s1)C(C)=CC(C)(C)N2]

¹H-NMR (400 MHz, DMSO-d₆) δ 1.15 (s, 3H), 1.22 (s, 3H), 2.10 (s, 3H), 2.47 (s, 3H), 2.69 (s, 3H), 3.68 (s, 3H), 4.93 (d, J = 12.7 Hz, 1H), 5.20 (d, J = 12.7 Hz, 1H), 5.45 (s, 1H), 6.12 (s, 1H), 6.68 (d, J = 8.3 Hz, 1H), 6.80 (d, J = 8.3 Hz, 1H), 6.89 (dd, J = 8.2, 2.2 Hz, 1H), 6.89 (d, J = 3.8 Hz, 1H), 7.06 (d, J = 2.2 Hz, 1H), 7.21 (d, J = 8.2 Hz, 1H), 7.49 (d, J = 3.8 Hz, 1H), 7.79 (t, J = 7.8 Hz, 1H), 8.33 (dt, J = 7.8, 1.5 Hz, 1H), 8.39 (dt, J = 7.8, 1.5 Hz, 1H), 8.63 (t, J = 1.5 Hz, 1H)

6-[2-Methoxy-4-(2-methylthiobenzoyloxy)phenyl]-5-(5-methylthiophen-2-ylcarbonyloxymethyl)-2,2,4-trimethyl-1,2-dihydroquinoline (Compound No. 1-151)

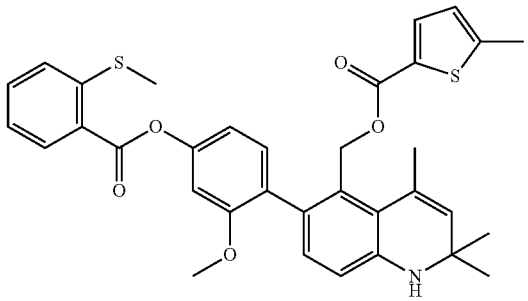

$^1$H-NMR (400 MHz, DMSO-d$_6$) δ 1.15 (s, 3H), 1.22 (s, 3H), 2.10 (s, 3H), 2.46 (s, 3H), 2.47 (s, 3H), 3.68 (s, 3H), 4.94 (d, J = 12.6 Hz, 1H), 5.20 (d, J = 12.6 Hz, 1H), 5.45 (s, 1H), 6.12 (s, 1H), 6.68 (d, J = 8.2 Hz, 1H), 6.79 (d, J = 8.2 Hz, 1H), 6.84 (dd, J = 8.3, 2.3 Hz, 1H), 6.89 (d, J = 3.5 Hz, 1H), 6.99 (d, J = 2.3 Hz, 1H), 7.20 (d, J = 8.3 Hz, 1H), 7.34 (t, J = 7.6 Hz, 1H), 7.48 (d, J = 8.4 Hz, 1H), 7.49 (d, J = 3.5 Hz, 1H), 7.68 (ddd, J = 8.4, 7.6, 1.5 Hz, 1H), 8.20 (dd, J = 7.6, 1.5 Hz, 1H)

6-[2-Methoxy-4-(thiophen-2-ylcarbonyloxy)phenyl]-5-(5-methylthiophen-2-ylcarbonyloxymethyl)-2,2,4-trimethyl-1,2-dihydroquinoline (Compound No. 1-152)

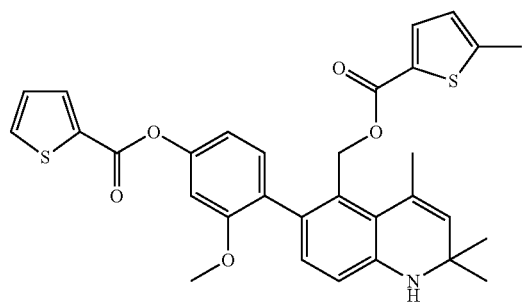

$^1$H-NMR (500 MHz, DMSO-d$_6$) δ 1.15 (s, 3H), 1.22 (s, 3H), 2.09 (s, 3H), 2.47 (s, 3H), 3.67 (s, 3H), 4.92 (d, J = 12.8 Hz, 1H), 5.19 (d, J = 12.8 Hz, 1H), 5.45 (s, 1H), 6.11 (s, 1H), 6.67 (d, J = 8.2 Hz, 1H), 6.79 (d, J = 8.2 Hz, 1H), 6.84 (dd, J = 8.2, 2.2 Hz, 1H), 6.89 (d, J = 3.7 Hz, 1H), 7.00 (d, J = 2.2 Hz, 1H), 7.19 (d, J = 8.2 Hz, 1H), 7.32 (dd, J = 4.9, 3.8 Hz, 1H), 7.48 (d, J = 3.7 Hz, 1H), 8.04 (dd, J = 3.8, 1.3 Hz, 1H), 8.10 (dd, J = 4.9, 1.3 Hz, 1H)

6-[2-Methoxy-4-(2-methylpyridin-3-ylcarbonyloxy)phenyl]-5-(5-methylthiophen-2-ylcarbonyloxymethyl)-2,2,4-trimethyl-1,2-dihydroquinoline (Compound No. 1-153)

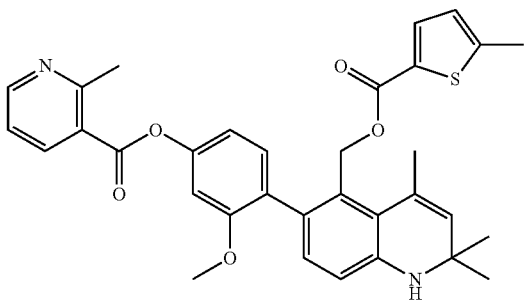 [SMILES: COc1cc(OC(=O)c2cccnc2C)ccc1-c1ccc2c(c1COC(=O)c1ccc(C)s1)C(C)=CC(C)(C)N2]

$^1$H-NMR (400 MHz, DMSO-d$_6$) δ 1.15 (s, 3H), 1.22 (s, 3H), 2.10 (s, 3H), 2.47 (s, 3H), 2.81 (s, 3H), 3.69 (s, 3H), 4.93 (d, J = 12.7 Hz, 1H), 5.20 (d, J = 12.7 Hz, 1H), 5.46 (s, 1H), 6.12 (s, 1H), 6.68 (d, J = 8.3 Hz, 1H), 6.80 (d, J = 8.3 Hz, 1H), 6.89 (dd, J = 8.2, 2.2 Hz, 1H), 6.89 (d, J = 3.8 Hz, 1H), 7.07 (d, J = 2.2 Hz, 1H), 7.21 (d, J = 8.2 Hz, 1H), 7.47-7.49 (m, 2H), 8.46 (dd, J = 7.9, 1.8 Hz, 1H), 8.72 (dd, J = 4.9, 1.8 Hz, 1H)

6-[4-(3-Chlorothiophen-2-ylcarbonyloxy)-2-methoxyphenyl]-5-(5-methylthiophen-2-ylcarbonyloxymethyl)-2,2,4-trimethyl-1,2-dihydroquinoline (Compound No. 1-154)

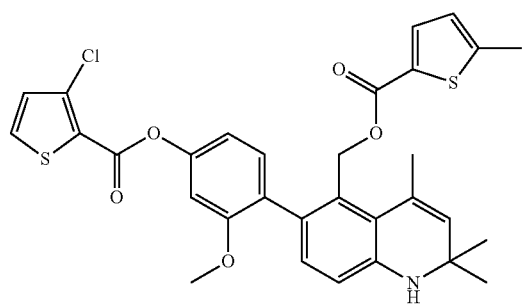 [SMILES: COc1cc(OC(=O)c2sccc2Cl)ccc1-c1ccc2c(c1COC(=O)c1ccc(C)s1)C(C)=CC(C)(C)N2]

$^1$H-NMR (400 MHz, DMSO-d$_6$) δ 1.15 (s, 3H), 1.22 (s, 3H), 2.10 (s, 3H), 2.47 (s, 3H), 3.68 (s, 3H), 4.92 (d, J = 12.7 Hz, 1H), 5.19 (d, J = 12.7 Hz, 1H), 5.45 (s, 1H), 6.12 (s, 1H), 6.67 (d, J = 8.3 Hz, 1H), 6.79 (d, J = 8.3 Hz, 1H), 6.85 (dd, J = 8.2, 2.2 Hz, 1H), 6.89 (d, J = 3.6 Hz, 1H), 7.02 (d, J = 2.2 Hz, 1H), 7.19 (d, J = 8.2 Hz, 1H), 7.37 (d, J = 5.4 Hz, 1H), 7.49 (d, J = 3.6 Hz, 1H), 8.16 (d, J = 5.4 Hz, 1H)

| | |
|---|---|
| 6-[2-Methoxy-4-(thiazol-4-ylcarbonyloxy)phenyl]-5-(5-methylthiophen-2-ylcarbonyloxymethyl)-2,2,4-trimethyl-1,2-dihydroquinoline (Compound No. 1-155)<br>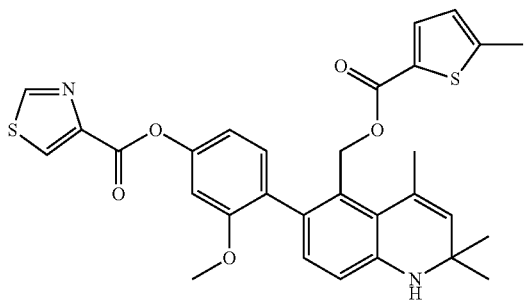 [SMILES: COc1cc(OC(=O)c2cscn2)ccc1-c1ccc2c(c1COC(=O)c1ccc(C)s1)C(C)=CC(C)(C)N2] | $^1$H-NMR (500 MHz, DMSO-$d_6$) δ 1.15 (s, 3H), 1.22 (s, 3H), 2.10 (s, 3H), 2.47 (s, 3H), 3.67 (s, 3H), 4.93 (d, J = 12.5 Hz, 1H), 5.19 (d, J = 12.5 Hz, 1H), 5.45 (s, 1H), 6.10 (s, 1H), 6.67 (d, J = 8.2 Hz, 1H), 6.80 (d, J = 8.2 Hz, 1H), 6.86 (dd, J = 8.2, 2.2 Hz, 1H), 6.89 (d, J = 3.8 Hz, 1H), 7.01 (d, J = 2.2 Hz, 1H), 7.20 (d, J = 8.2 Hz, 1H), 7.48 (d, J = 3.8 Hz, 1H), 8.88 (d, J = 2.0 Hz, 1H), 9.28 (d, J = 2.0 Hz, 1H) |
| 6-[2-Methoxy-4-(pyridin-4-ylcarbonyloxy)phenyl]-5-(5-methylthiophen-2-ylcarbonyloxymethyl)-2,2,4-trimethyl-1,2-dihydroquinoline (Compound No. 1-156)<br>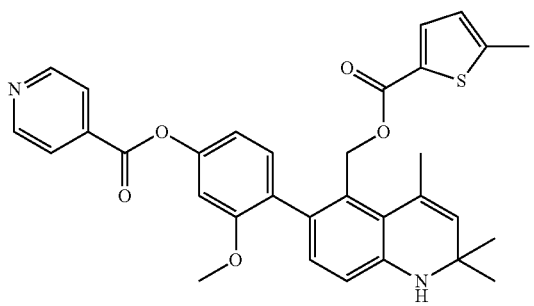 [SMILES: COc1cc(OC(=O)c2ccncc2)ccc1-c1ccc2c(c1COC(=O)c1ccc(C)s1)C(C)=CC(C)(C)N2] | $^1$H-NMR (400 MHz, DMSO-$d_6$) δ 1.15 (s, 3H), 1.22 (s, 3H), 2.10 (s, 3H), 2.47 (s, 3H), 3.68 (s, 3H), 4.92 (d, J = 12.7 Hz, 1H), 5.19 (d, J = 12.7 Hz, 1H), 5.45 (s, 1H), 6.12 (s, 1H), 6.67 (d, J = 8.1 Hz, 1H), 6.80 (d, J = 8.1 Hz, 1H), 6.89 (d, J = 3.6 Hz, 1H), 6.90 (dd, J = 8.2, 2.2 Hz, 1H), 7.08 (d, J = 2.2 Hz, 1H), 7.22 (d, J = 8.2 Hz, 1H), 7.49 (d, J = 3.6 Hz, 1H), 8.03 (d, J = 5.9 Hz, 2H), 8.90 (d, J = 5.9 Hz, 2H) |
| 5-(4-Methoxybenzoyloxymethyl)-6-[2-methoxy-4-(pyridin-3-ylcarbonyloxy)phenyl]-2,2,4-trimethyl-1,2-dihydroquinoline (Compound No. 1-157)<br>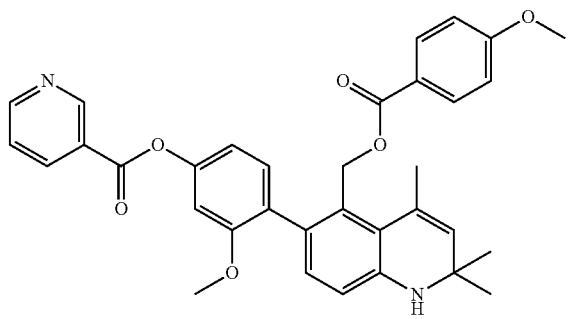 [SMILES: COc1ccc(C(=O)OCc2c(-c3ccc(OC(=O)c4cccnc4)cc3OC)ccc3c2C(C)=CC(C)(C)N3)cc1] | $^1$H-NMR (400 MHz, DMSO-$d_6$) δ 1.16 (s, 3H), 1.24 (s, 3H), 2.10 (s, 3H), 3.67 (s, 3H), 3.81 (s, 3H), 4.98 (d, J = 12.9 Hz, 1H), 5.21 (d, J = 12.9 Hz, 1H), 5.46 (s, 1H), 6.12 (s, 1H), 6.68 (d, J = 8.2 Hz, 1H), 6.81 (d, J = 8.2 Hz, 1H), 6.90 (dd, J = 8.2, 2.2 Hz, 1H), 7.00 (dt, J = 8.9, 2.2 Hz, 2H), 7.07 (d, J = 2.2 Hz, 1H), 7.22 (d, J = 8.2 Hz, 1H), 7.67 (ddd, J = 8.0, 4.9, 0.8 Hz, 1H), 7.79 (dt, J = 8.9, 2.2 Hz, 2H), 8.48 (dt, J = 8.0, 2.0 Hz, 1H), 8.91 (dd, J = 4.9, 2.0 Hz, 1H), 9.28 (dd, J = 2.0, 0.8 Hz, 1H) |
| 6-[4-(2-Chlorobenzoyloxy)-2-methoxyphenyl]-5-(4-methoxybenzoyloxymethyl)-2,2,4-trimethyl-1,2-dihydroquinoline (Compound No. 1-158)<br>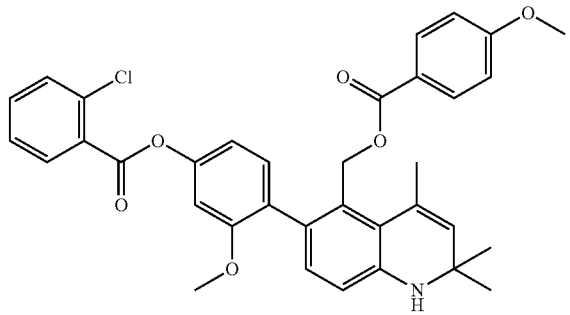 [SMILES: COc1ccc(C(=O)OCc2c(-c3ccc(OC(=O)c4ccccc4Cl)cc3OC)ccc3c2C(C)=CC(C)(C)N3)cc1] | $^1$H-NMR (400 MHz, DMSO-$d_6$) δ 1.15 (s, 3H), 1.24 (s, 3H), 2.10 (s, 3H), 3.69 (s, 3H), 3.81 (s, 3H), 4.98 (d, J = 12.9 Hz, 1H), 5.21 (d, J = 12.9 Hz, 1H), 5.46 (s, 1H), 6.12 (s, 1H), 6.68 (d, J = 8.2 Hz, 1H), 6.80 (d, J = 8.2 Hz, 1H), 6.88 (dd, J = 8.3, 2.2 Hz, 1H), 6.99 (dt, J = 8.9, 2.1 Hz, 2H), 7.03 (d, J = 2.2 Hz, 1H), 7.23 (d, J = 8.3 Hz, 1H), 7.55-7.59 (m, 1H), 7.68-7.69 (m, 2H), 7.78 (dt, J = 8.9, 2.1 Hz, 2H), 8.10-8.12 (m, 1H) |

6-[4-(Furan-2-ylcarbonyloxy)-2-methoxyphenyl]-5-(4-methoxybenzoyloxymethyl)-2,2,4-trimethyl-1,2-dihydroquinoline (Compound No. 1-159)

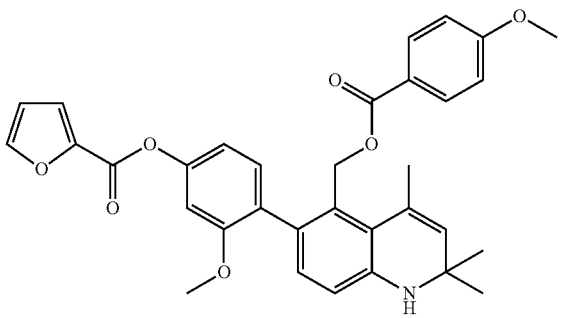 [SMILES: COc1ccc(C(=O)OCc2c(-c3ccc(OC(=O)c4ccco4)cc3OC)ccc3c2C(C)=CC(C)(C)N3)cc1]

$^1$H-NMR (400 MHz, DMSO-d$_6$) δ 1.15 (s, 3H), 1.23 (s, 3H), 2.09 (s, 3H), 3.66 (s, 3H), 3.81 (s, 3H), 4.97 (d, J = 12.9 Hz, 1H), 5.20 (d, J = 12.9 Hz, 1H), 5.46 (s, 1H), 6.11 (s, 1H), 6.67 (d, J = 8.3 Hz, 1H), 6.80 (d, J = 8.3 Hz, 1H), 6.81 (dd, J = 3.6, 1.7 Hz, 1H), 6.83 (dd, J = 8.1, 2.3 Hz, 1H), 6.99 (d, J = 2.3 Hz, 1H), 6.99 (dt, J = 9.1, 2.1 Hz, 2H), 7.20 (d, J = 8.1 Hz, 1H), 7.57 (dd, J = 3.6, 0.9 Hz, 1H), 7.78 (dt, J = 9.1, 2.1 Hz, 2H), 8.12 (dd, J = 1.7, 0.9 Hz, 1H)

5-(5-Bromothiophen-2-ylcarbonyloxymethyl)-6-[2-methoxy-4-(pyridin-3-ylcarbonyloxy)phenyl]-2,2,4-trimethyl-1,2-dihydroquinoline (Compound No. 1-160)

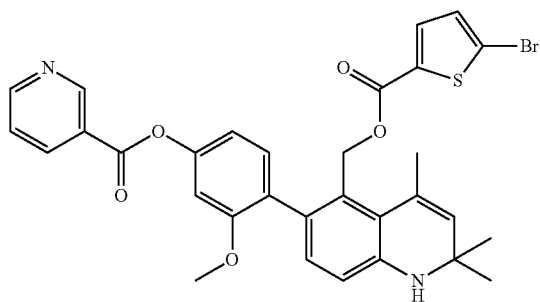 [SMILES: COc1cc(OC(=O)c2cccnc2)ccc1-c1ccc2c(c1COC(=O)c1ccc(Br)s1)C(C)=CC(C)(C)N2]

$^1$H-NMR (500 MHz, DMSO-d$_6$) δ 1.14 (s, 3H), 1.22 (s, 3H), 2.10 (s, 3H), 3.68 (s, 3H), 4.99 (d, J = 12.8 Hz, 1H), 5.23 (d, J = 12.8 Hz, 1H), 5.47 (s, 1H), 6.13 (s, 1H), 6.68 (d, J = 8.2 Hz, 1H), 6.80 (d, J = 8.2 Hz, 1H), 6.91 (dd, J = 8.2, 2.3 Hz, 1H), 7.08 (d, J = 2.3 Hz, 1H), 7.21 (d, J = 8.2 Hz, 1H), 7.34 (d, J = 4.1 Hz, 1H), 7.50 (d, J = 4.1 Hz, 1H), 7.67 (dd, J = 7.9, 4.7 Hz, 1H), 8.49 (dt, J = 7.9, 2.0 Hz, 1H), 8.91 (dd, J = 4.7, 2.0 Hz, 1H), 9.28 (d, J = 2.0 Hz, 1H)

5-(5-Bromothiophen-2-ylcarbonyloxymethyl)-6-[4-(2-chlorobenzoyloxy)-2-methoxyphenyl]-2,2,4-trimethyl-1,2-dihydroquinoline (Compound No. 1-161)

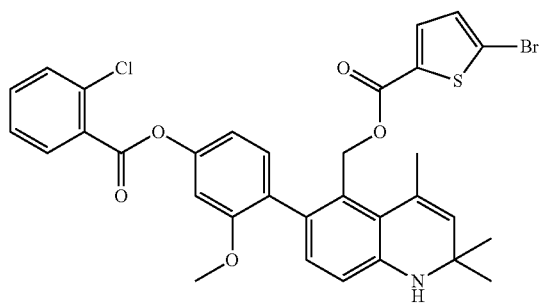 [SMILES: COc1cc(OC(=O)c2ccccc2Cl)ccc1-c1ccc2c(c1COC(=O)c1ccc(Br)s1)C(C)=CC(C)(C)N2]

$^1$H-NMR (400 MHz, DMSO-d$_6$) δ 1.13 (s, 3H), 1.23 (s, 3H), 2.10 (s, 3H), 3.69 (s, 3H), 4.99 (d, J = 12.7 Hz, 1H), 5.23 (d, J = 12.9 Hz, 1H), 5.47 (s, 1H), 6.14 (s, 1H), 6.68 (d, J = 8.2 Hz, 1H), 6.80 (d, J = 8.2 Hz, 1H), 6.89 (dd, J = 8.2, 2.2 Hz, 1H), 7.04 (d, J = 2.2 Hz, 1H), 7.22 (d, J = 8.2 Hz, 1H), 7.34 (d, J = 4.2 Hz, 1H), 7.50 (d, J = 4.2 Hz, 1H), 7.55-7.59 (m, 1H), 7.68-7.70 (m, 2H), 8.11-13 (m, 1H)

5-(5-Bromothiophen-2-ylcarbonyloxymethyl)-6-[4-(furan-2-ylcarbonyloxy)-2-methoxyphenyl]-2,2,4-trimethyl-1,2-dihydroquinoline (Compound No. 1-162)

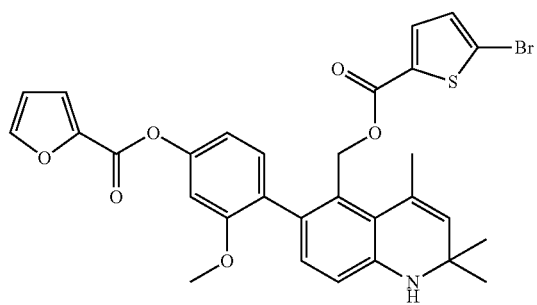 [SMILES: COc1cc(OC(=O)c2ccco2)ccc1-c1ccc2c(c1COC(=O)c1ccc(Br)s1)C(C)=CC(C)(C)N2]

$^1$H-NMR (400 MHz, DMSO-d$_6$) δ 1.13 (s, 3H), 1.22 (s, 3H), 2.10 (s, 3H), 3.67 (s, 3H), 4.98 (d, J = 12.6 Hz, 1H), 5.22 (d, J = 12.6 Hz, 1H), 5.46 (s, 1H), 6.13 (s, 1H), 6.67 (d, J = 8.3 Hz, 1H), 6.79 (d, J = 8.3 Hz, 1H), 6.82 (dd, J = 3.5, 1.7 Hz, 1H), 6.85 (dd, J = 8.3, 2.2 Hz, 1H), 7.00 (d, J = 2.2 Hz, 1H), 7.19 (d, J = 8.3 Hz, 1H), 7.33 (d, J = 4.0 Hz, 1H), 7.50 (d, J = 4.0 Hz, 1H), 7.58 (dd, J = 3.5, 0.8 Hz, 1H), 8.12 (dd, J = 1.7, 0.8 Hz, 1H)

6-[4-(2-Chlorobenzoyloxy)-2-methoxyphenyl]-5-(3-fluorobenzoyloxymethyl)-2,2,4-trimethyl-1,2-dihydroquinoline (Compound No. 1-163)

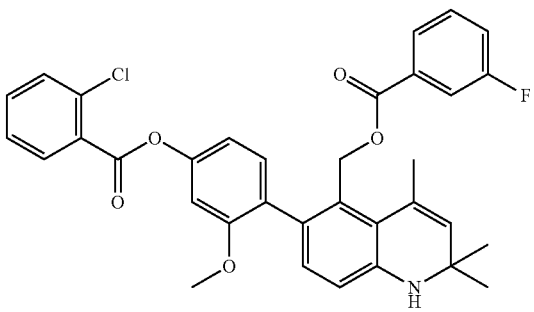 [SMILES: COc1cc(OC(=O)c2ccccc2Cl)ccc1-c1ccc2c(c1COC(=O)c1cccc(F)c1)C(C)=CC(C)(C)N2]

$^1$H-NMR (400 MHz, DMSO-d$_6$)
δ 1.14 (s, 3H), 1.24 (s, 3H), 2.11 (s, 3H), 3.69 (s, 3H), 5.08 (d, J = 12.9 Hz, 1H), 5.29 (d, J = 12.9 Hz, 1H), 5.49 (s, 1H), 6.15 (s, 1H), 6.69 (d, J = 8.2 Hz, 1H), 6.82 (d, J = 8.2 Hz, 1H), 6.89 (dd, J = 8.2, 2.4 Hz, 1H), 7.04 (d, J = 2.4 Hz, 1H), 7.24 (d, J = 8.2 Hz, 1H), 7.48-7.59 (m, 4H), 7.65-7.70 (m, 3H), 8.10-8.13 (m, 1H)

6-(4-Isopropylcarbonyloxy-2-methoxyphenyl)-5-(5-methylthiophen-2-ylcarbonyloxymethyl)-2,2,4-trimethyl-1,2-dihydroquinoline (Compound No. 1-164)

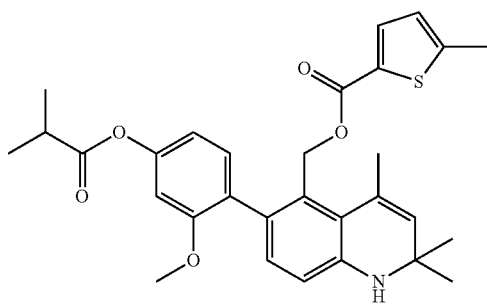 [SMILES: COc1cc(OC(=O)C(C)C)ccc1-c1ccc2c(c1COC(=O)c1ccc(C)s1)C(C)=CC(C)(C)N2]

$^1$H-NMR (400 MHz, DMSO-d$_6$)
δ 1.14 (s, 3H), 1.21 (s, 3H), 1.25 (d, J = 6.9 Hz, 6H), 2.08 (s, 3H), 2.47 (s, 3H), 2.81 (heptet, J = 6.9 Hz, 1H), 3.66 (s, 3H), 4.89 (d, J = 12.7 Hz, 1H), 5.17 (d, J = 12.7 Hz, 1H), 5.44 (s, 1H), 6.10 (s, 1H), 6.66 (d, J = 8.3 Hz, 1H), 6.68 (dd, J = 8.2, 2.2 Hz, 1H), 6.76 (d, J = 8.3 Hz, 1H), 6.81 (d, J = 2.2 Hz, 1H), 6.88 (d, J = 3.6 Hz, 1H), 7.14 (d, J = 8.2 Hz, 1H), 7.47 (d, J = 3.6 Hz, 1H)

6-[4-(2-Acetoxybenzoyloxy)-2-methoxyphenyl]-5-(5-methylthiophen-2-ylcarbonyloxymethyl)-2,2,4-trimethyl-1,2-dihydroquinoline (Compound No. 1-165)

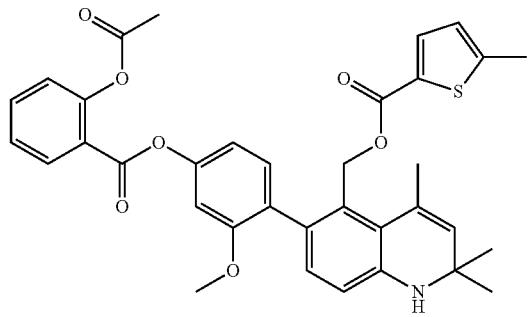 [SMILES: COc1cc(OC(=O)c2ccccc2OC(C)=O)ccc1-c1ccc2c(c1COC(=O)c1ccc(C)s1)C(C)=CC(C)(C)N2]

$^1$H-NMR (500 MHz, DMSO-d$_6$)
δ 1.15 (s, 3H), 1.22 (s, 3H), 2.10 (s, 3H), 2.27 (s, 3H), 2.47 (s, 3H), 3.67 (s, 3H), 4.93 (d, J = 12.7 Hz, 1H), 5.19 (d, J = 12.7 Hz, 1H), 5.45 (s, 1H), 6.11 (s, 1H), 6.67 (d, J = 8.2 Hz, 1H), 6.79 (d, J = 8.2 Hz, 1H), 6.79 (dd, J = 8.2, 1.8 Hz, 1H), 6.88 (d, J = 3.7 Hz, 1H), 6.95 (d, J = 1.8 Hz, 1H), 7.20 (d, J = 8.2 Hz, 1H), 7.34 (dd, J = 7.8, 1.3 Hz, 1H), 7.48 (d, J = 3.7 Hz, 1H), 7.51 (td, J = 7.8, 1.3 Hz, 1H), 7.79 (td, J = 7.8, 1.3 Hz, 1H), 8.18 (dd, J = 7.8, 1.3 Hz, 1H)

6-[2-Methoxy-4-(2-methoxypyridin-3-ylcarbonyloxy)phenyl]-5-(5-methylthiophen-2-ylcarbonyloxymethyl)-2,2,4-trimethyl-1,2-dihydroquinoline (Compound No. 1-166)

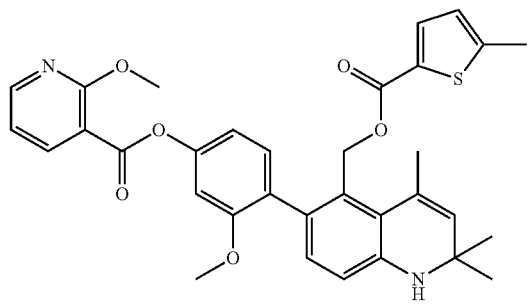 [SMILES: COc1cc(OC(=O)c2cccnc2OC)ccc1-c1ccc2c(c1COC(=O)c1ccc(C)s1)C(C)=CC(C)(C)N2]

$^1$H-NMR (400 MHz, DMSO-d$_6$)
δ 1.15 (s, 3H), 1.22 (s, 3H), 2.10 (s, 3H), 2.47 (s, 3H), 3.68 (s, 3H), 3.99 (s, 3H), 4.92 (d, J = 12.6 Hz, 1H), 5.19 (d, J = 12.6 Hz, 1H), 5.45 (s, 1H), 6.11 (s, 1H), 6.67 (d, J = 8.2 Hz, 1H), 6.79 (d, J = 8.2 Hz, 1H), 6.83 (dd, J = 8.3, 2.2 Hz, 1H), 6.89 (d, J = 3.8 Hz, 1H), 6.98 (d, J = 2.2 Hz, 1H), 7.19 (d, J = 8.3 Hz, 1H), 7.21 (dd, J = 7.6, 4.9 Hz, 1H), 7.49 (d, J = 3.8 Hz, 1H), 8.41 (dd, J = 7.6, 2.0 Hz, 1H), 8.48 (dd, J = 4.9, 2.0 Hz, 1H)

| Compound | NMR |
|---|---|
| 6-[2-Methoxy-4-(3-methylbenzoyloxy)phenyl]-5-(5-methylthiophen-2-ylcarbonyloxymethyl)-2,2,4-trimethyl-1,2-dihydroquinoline (Compound No. 1-167)<br />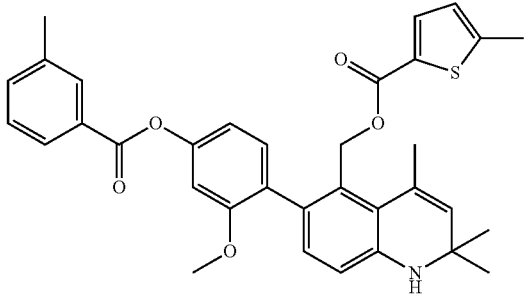 [SMILES: COc1cc(OC(=O)c2cccc(C)c2)ccc1-c1ccc2c(c1COC(=O)c1ccc(C)s1)C(C)=CC(C)(C)N2] | $^1$H-NMR (500 MHz, DMSO-d$_6$) δ 1.15 (s, 3H), 1.22 (s, 3H), 2.10 (s, 3H), 2.43 (s, 3H), 2.47 (s, 3H), 3.67 (s, 3H), 4.93 (d, J = 12.7 Hz, 1H), 5.19 (d, J = 12.7 Hz, 1H), 5.45 (s, 1H), 6.10 (s, 1H), 6.67 (d, J = 8.1 Hz, 1H), 6.80 (d, J = 8.1 Hz, 1H), 6.85 (dd, J = 8.2, 2.1 Hz, 1H), 6.89 (d, J = 3.8 Hz, 1H), 7.01 (d, J = 2.1 Hz, 1H), 7.20 (d, J = 8.2 Hz, 1H), 7.49 (d, J = 3.8 Hz, 1H), 7.51 (t, J = 7.6 Hz, 1H), 7.57 (d, J = 7.6 Hz, 1H), 7.95 (d, J = 7.6 Hz, 1H), 7.97 (s, 1H) |
| 6-[2-Methoxy-4-(4-methylbenzoyloxy)phenyl]-5-(5-methylthiophen-2-ylcarbonyloxymethyl)-2,2,4-trimethyl-1,2-dihydroquinoline (Compound No. 1-168)<br />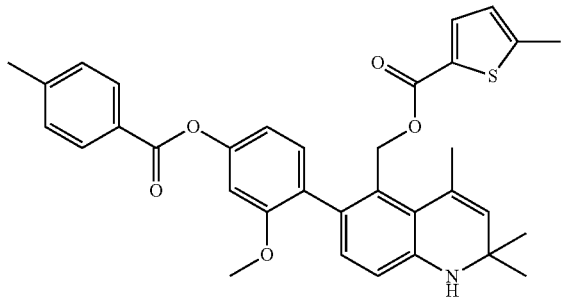 | $^1$H-NMR (500 MHz, DMSO-d$_6$) δ 1.15 (s, 3H), 1.22 (s, 3H), 2.10 (s, 3H), 2.43 (s, 3H), 2.47 (s, 3H), 3.67 (s, 3H), 4.93 (d, J = 12.5 Hz, 1H), 5.19 (d, J = 12.5 Hz, 1H), 5.45 (s, 1H), 6.10 (s, 1H), 6.67 (d, J = 8.2 Hz, 1H), 6.80 (d, J = 8.2 Hz, 1H), 6.84 (dd, J = 8.2, 2.4 Hz, 1H), 6.89 (d, J = 3.7 Hz, 1H), 7.00 (d, J = 2.4 Hz, 1H), 7.19 (d, J = 8.2 Hz, 1H), 7.43 (d, J = 8.1 Hz, 2H), 7.49 (d, J = 3.7 Hz, 1H), 8.04 (d, J = 8.1 Hz, 2H) |
| 6-[4-(4-Fluorobenzoyloxy)-2-methoxyphenyl]-5-(5-methylthiophen-2-ylcarbonyloxymethyl)-2,2,4-trimethyl-1,2-dihydroquinoline (Compound No. 1-169)<br />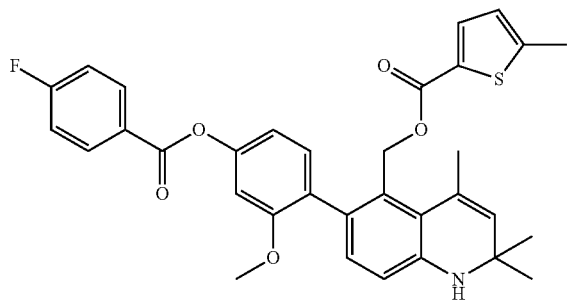 [SMILES: COc1cc(OC(=O)c2ccc(F)cc2)ccc1-c1ccc2c(c1COC(=O)c1ccc(C)s1)C(C)=CC(C)(C)N2] | $^1$H-NMR (400 MHz, DMSO-d$_6$) δ 1.15 (s, 3H), 1.22 (s, 3H), 2.10 (s, 3H), 2.47 (s, 3H), 3.67 (s, 3H), 4.93 (d, J = 12.7 Hz, 1H), 5.19 (d, J = 12.7 Hz, 1H), 5.45 (s, 1H), 6.11 (s, 1H), 6.67 (d, J = 8.1 Hz, 1H), 6.79 (d, J = 8.1 Hz, 1H), 6.86 (dd, J = 8.2, 2.3 Hz, 1H), 6.89 (d, J = 3.8 Hz, 1H), 7.03 (d, J = 2.3 Hz, 1H), 7.20 (d, J = 8.2 Hz, 1H), 7.44-7.49 (m, 2H), 7.49 (d, J = 3.8 Hz, 1H), 8.20-8.24 (m, 2H) |
| 6-[2-Methoxy-4-(2-nitrobenzoyloxy)phenyl]-5-(5-methylthiophen-2-ylcarbonyloxymethyl)-2,2,4-trimethyl-1,2-dihydroquinoline (Compound No. 1-170)<br />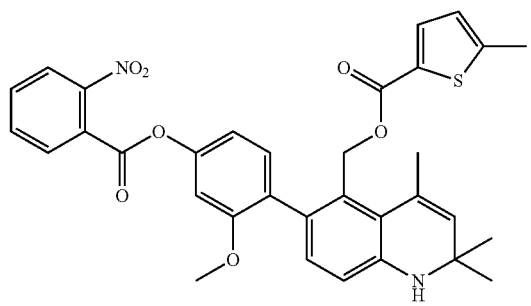 [SMILES: COc1cc(OC(=O)c2ccccc2[N+](=O)[O-])ccc1-c1ccc2c(c1COC(=O)c1ccc(C)s1)C(C)=CC(C)(C)N2] | $^1$H-NMR (400 MHz, DMSO-d$_6$) δ 1.14 (s, 3H), 1.22 (s, 3H), 2.10 (s, 3H), 2.47 (s, 3H), 3.69 (s, 3H), 4.92 (d, J = 12.7 Hz, 1H), 5.19 (d, J = 12.7 Hz, 1H), 5.45 (s, 1H), 6.12 (s, 1H), 6.67 (d, J = 8.2 Hz, 1H), 6.79 (d, J = 8.2 Hz, 1H), 6.86 (dd, J = 8.2, 2.2 Hz, 1H), 6.88 (d, J = 3.6 Hz, 1H), 6.99 (d, J = 2.2 Hz, 1H), 7.24 (d, J = 8.2 Hz, 1H), 7.48 (d, J = 3.6 Hz, 1H), 7.92 (td, J = 7.6, 1.4 Hz, 1H), 7.97 (td, J = 7.6, 1.4 Hz, 1H), 8.13 (dd, J = 7.6, 1.4 Hz, 1H), 8.20 (dd, J = 7.6, 1.4 Hz, 1H) |

| | |
|---|---|
| 6-[2-Methoxy-4-(3-methylfuran-2-ylcarbonyloxy)phenyl]-5-(5-methylthiophen-2-ylcarbonyloxymethyl)-2,2,4-trimethyl-1,2-dihydroquinoline (Compound No. 1-171)<br />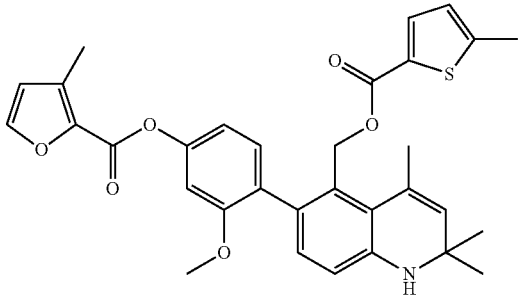 [SMILES: COc1cc(OC(=O)c2occc2C)ccc1-c1ccc2c(c1COC(=O)c1ccc(C)s1)C(C)=CC(C)(C)N2] | $^1$H-NMR (400 MHz, DMSO-d$_6$) δ 1.14 (s, 3H), 1.22 (s, 3H), 2.09 (s, 3H), 2.39 (s, 3H), 2.47 (s, 3H), 3.67 (s, 3H), 4.93 (d, J = 12.7 Hz, 1H), 5.19 (d, J = 12.7 Hz, 1H), 5.45 (s, 1H), 6.11 (s, 1H), 6.67 (d, J = 8.2 Hz, 1H), 6.70 (d, J = 1.7 Hz, 1H), 6.78 (d, J = 8.2 Hz, 1H), 6.82 (dd, J = 8.3, 2.3 Hz, 1H), 6.88 (d, J = 3.8 Hz, 1H), 6.98 (d, J = 2.3 Hz, 1H), 7.18 (d, J = 8.3 Hz, 1H), 7.48 (d, J = 3.8 Hz, 1H), 7.96 (d, J = 1.7 Hz, 1H) |
| 6-(4-Benzoyloxy-2-methoxyphenyl)-5-(4-methylbenzoyloxymethyl)-2,2,4-trimethyl-1,2-dihydroquinoline (Compound No. 1-172)<br />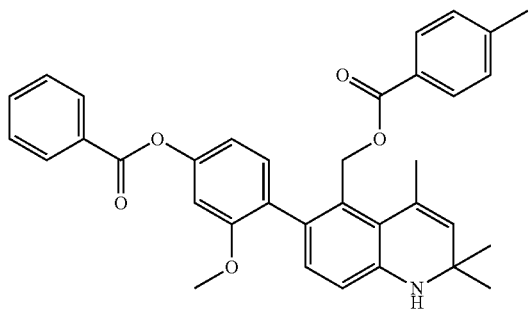 [SMILES: COc1cc(OC(=O)c2ccccc2)ccc1-c1ccc2c(c1COC(=O)c1ccc(C)cc1)C(C)=CC(C)(C)N2] | $^1$H-NMR (500 MHz, DMSO-d$_6$) δ 1.15 (s, 3H), 1.24 (s, 3H), 2.09 (s, 3H), 2.35 (s, 3H), 3.67 (s, 3H), 5.00 (d, J = 12.8 Hz, 1H), 5.23 (d, J = 12.8 Hz, 1H), 5.46 (s, 1H), 6.11 (s, 1H), 6.69 (d, J = 8.2 Hz, 1H), 6.81 (d, J = 8.2 Hz, 1H), 6.86 (dd, J = 8.2, 2.2 Hz, 1H), 7.02 (d, J = 2.2 Hz, 1H), 7.21 (d, J = 8.2 Hz, 1H), 7.28 (d, J = 8.1 Hz, 2H), 7.62 (t, J = 7.8 Hz, 2H), 7.73 (d, J = 8.1 Hz, 2H), 7.75-7.78 (m, 1H), 8.14-8.16 (m, 2H) |
| 6-[2-Methoxy-4-(2-methylbenzoyloxy)phenyl]-5-(4-methylbenzoyloxymethyl)-2,2,4-trimethyl-1,2-dihydroquinoline (Compound No. 1-173)<br />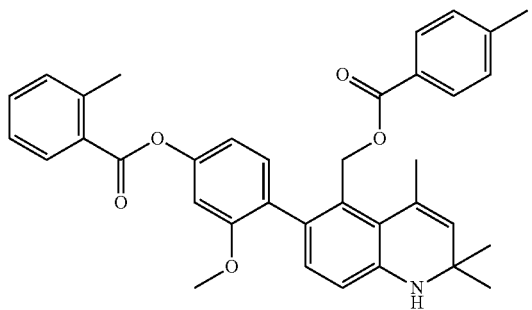 | $^1$H-NMR (400 MHz, DMSO-d$_6$) δ 1.15 (s, 3H), 1.24 (s, 3H), 2.09 (s, 3H), 2.35 (s, 3H), 2.61 (s, 3H), 3.68 (s, 3H), 5.01 (d, J = 12.9 Hz, 1H), 5.24 (d, J = 12.9 Hz, 1H), 5.46 (s, 1H), 6.12 (s, 1H), 6.69 (d, J = 8.1 Hz, 1H), 6.81 (d, J = 8.1 Hz, 1H), 6.86 (dd, J = 8.1, 2.2 Hz, 1H), 7.02 (d, J = 2.2 Hz, 1H), 7.21 (d, J = 8.1 Hz, 1H), 7.28 (d, J = 8.2 Hz, 2H), 7.41 (t, J = 7.4 Hz, 1H), 7.42 (d, J = 7.4 Hz, 1H), 7.56-7.60 (m, 1H), 7.73 (d, J = 8.2 Hz, 2H), 8.09 (d, J = 7.4 Hz, 1H) |

| | |
|---|---|
| 6-(4-Cyclohexylcarbonyloxy-2-methoxyphenyl)-5-(5-fluoro-2-methylphenoxymethyl)-2,2,4-trimethyl-1,2-dihydroquinoline (Compound No. 1-174)<br>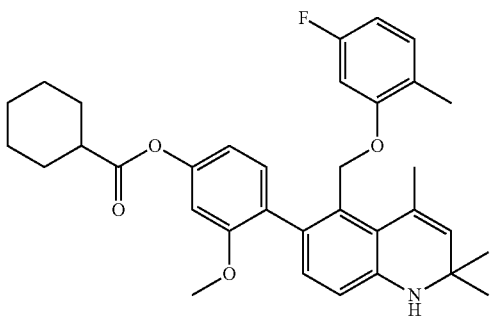 [SMILES: COc1cc(OC(=O)C2CCCCC2)ccc1-c1ccc2c(c1COc1cc(F)ccc1C)C(C)=CC(C)(C)N2] | $^1$H-NMR (400 MHz, DMSO-d$_6$) δ 1.05 (s, 3H), 1.15 (s, 3H), 1.17-1.72 (m, 10H), 1.99-2.01 (m, 1H), 2.01 (s, 3H), 2.07 (s, 3H), 3.71 (s, 3H), 4.61 (d, J = 12.1 Hz, 1H), 5.07 (d, J = 12.1 Hz, 1H), 5.39 (s, 1H), 6.03 (s, 1H), 6.34 (dd, J = 11.5, 2.4 Hz, 1H), 6.52 (td, J = 8.4, 2.4 Hz, 1H), 6.63 (d, J = 8.3 Hz, 1H), 6.70 (dd, J = 8.3, 2.3 Hz, 1H), 6.78 (d, J = 8.3 Hz, 1H), 6.82 (d, J = 2.3 Hz, 1H), 7.01-7.05 (m, 1H), 7.17 (d, J = 8.3 Hz, 1H) |
| 6-(4-Acryloyloxy-2-methoxyphenyl)-5-(5-fluoro-2-methylphenoxymethyl)-2,2,4-trimethyl-1,2-dihydroquinoline (Compound No. 1-175)<br>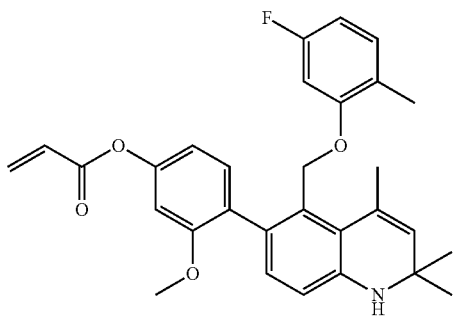 [SMILES: C=CC(=O)Oc1ccc(-c2ccc3c(c2COc2cc(F)ccc2C)C(C)=CC(C)(C)N3)c(OC)c1] | $^1$H-NMR (500 MHz, CDCl$_3$) δ 1.12 (s, 3H), 1.23 (s, 3H), 2.07 (s, 3H), 2.16 (s, 3H), 3.75 (s, 3H), 4.75 (d, J = 11.9 Hz, 1H), 5.11 (d, J = 11.9 Hz, 1H), 5.45 (s, 1H), 6.03 (d, J = 10.4 Hz, 1H), 6.19 (dd, J = 11.0, 2.4 Hz, 1H), 6.34 (dd, J = 17.7, 10.4 Hz, 1H), 6.42 (td, J = 8.3, 2.4 Hz, 1H), 6.58 (d, J = 8.4 Hz, 1H), 6.62 (d, J = 17.7 Hz, 1H), 6.75 (d, J = 2.1 Hz, 1H), 6.78 (dd, J = 8.2, 2.1 Hz, 1H), 6.91 (d, J = 8.4 Hz, 1H), 6.92-6.95 (m, 1H), 7.26 (d, J = 8.2 Hz, 1H) |

Example 2

6-(5-Acetoxy-2-methoxyphenyl)-5-(5-fluoro-2-methylphenoxymethyl)-2,2,4-trimethyl-1,2-dihydroquinoline (Compound No. 2)

5-(5-Fluoro-2-methylphenoxymethyl)-6-(5-hydroxy-2-methoxyphenyl)-2,2,4-trimethyl-1,2-dihydroquinoline (Reference Compound No. 5-2, 62.5 mg, 0.14 mmol) and triethylamine (154 μL, 1.11 mmol) were dissolved in anhydrous methylene dichloride (1 mL), acetic anhydride (52 μL, 0.55 mmol) was added thereto, and then the mixture was stirred at room temperature for 1.5 hours. Chloroform (10 mL) was added to the reaction mixture, the mixture was washed with water (10 mL) and saturated brine (300 mL) successively, dried over anhydrous magnesium sulfate, and then the solvent was removed under reduced pressure. The residue was purified by silica gel column chromatography (hexane-ethyl acetate) to give the titled compound (56.6 mg) as a colorless amorphous product. (Yield 83%)

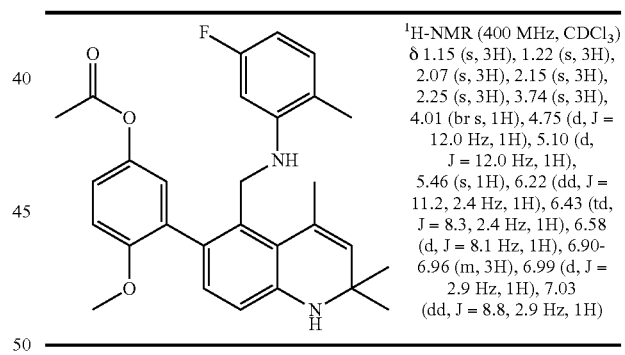

$^1$H-NMR (400 MHz, CDCl$_3$) δ 1.15 (s, 3H), 1.22 (s, 3H), 2.07 (s, 3H), 2.15 (s, 3H), 2.25 (s, 3H), 3.74 (s, 3H), 4.01 (br s, 1H), 4.75 (d, J = 12.0 Hz, 1H), 5.10 (d, J = 12.0 Hz, 1H), 5.46 (s, 1H), 6.22 (dd, J = 11.2, 2.4 Hz, 1H), 6.43 (td, J = 8.3, 2.4 Hz, 1H), 6.58 (d, J = 8.1 Hz, 1H), 6.90-6.96 (m, 3H), 6.99 (d, J = 2.9 Hz, 1H), 7.03 (dd, J = 8.8, 2.9 Hz, 1H)

Example 3

6-(4-Aminoacetoxy-2-methoxyphenyl)-5-(5-fluoro-2-methylphen oxymethyl)-2,2,4-trimethyl-1,2-dihydroquinoline monohydrochloride (Compound No. 3-1)

6-(4-t-Butoxycarbonylaminoacetoxy-2-methoxyphenyl)-5-(5-fluoro-2-methylphenoxymethyl)-2,2,4-trimethyl-1,2-dihydroquinoline (Reference Compound No. 1-2, 20.1 mg, 0.034 mmol) was dissolved in 1,4-dioxane (0.5 mL), 4N HCl/1,4-dioxane solution (34 μL) was added thereto, and then the mixture was stirred at room temperature overnight. The reaction mixture was concentrated under reduced pressure to give the titled compound (17.5 mg) as a colorless solid. (Yield 98%)

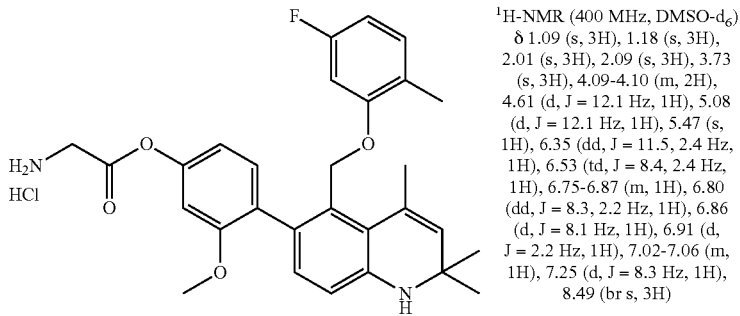

¹H-NMR (400 MHz, DMSO-d₆) δ 1.09 (s, 3H), 1.18 (s, 3H), 2.01 (s, 3H), 2.09 (s, 3H), 3.73 (s, 3H), 4.09-4.10 (m, 2H), 4.61 (d, J = 12.1 Hz, 1H), 5.08 (d, J = 12.1 Hz, 1H), 5.47 (s, 1H), 6.35 (dd, J = 11.5, 2.4 Hz, 1H), 6.53 (td, J = 8.4, 2.4 Hz, 1H), 6.75-6.87 (m, 1H), 6.80 (dd, J = 8.3, 2.2 Hz, 1H), 6.86 (d, J = 8.1 Hz, 1H), 6.91 (d, J = 2.2 Hz, 1H), 7.02-7.06 (m, 1H), 7.25 (d, J = 8.3 Hz, 1H), 8.49 (br s, 3H)

Using Compound No. 1-37, the following Compound No. 3-2 was obtained by a method similar to that of Compound No. 3-1.

5-(5-Fluoro-2-methylphenoxymethyl)-6-[2-methoxy-4-(piperidin-4-ylcarbonyloxy)phenyl]-2,2,4-trimethyl-1,2-dihydroquinoline monohydrochloride (Compound No. 3-2)

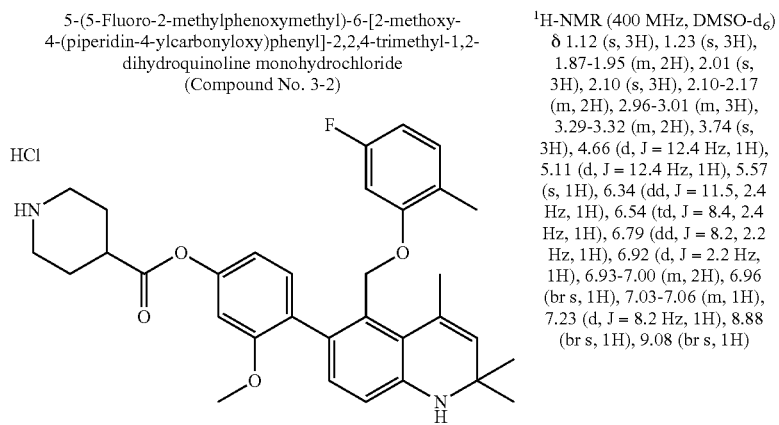

¹H-NMR (400 MHz, DMSO-d₆) δ 1.12 (s, 3H), 1.23 (s, 3H), 1.87-1.95 (m, 2H), 2.01 (s, 3H), 2.10 (s, 3H), 2.10-2.17 (m, 2H), 2.96-3.01 (m, 3H), 3.29-3.32 (m, 2H), 3.74 (s, 3H), 4.66 (d, J = 12.4 Hz, 1H), 5.11 (d, J = 12.4 Hz, 1H), 5.57 (s, 1H), 6.34 (dd, J = 11.5, 2.4 Hz, 1H), 6.54 (td, J = 8.4, 2.4 Hz, 1H), 6.79 (dd, J = 8.2, 2.2 Hz, 1H), 6.92 (d, J = 2.2 Hz, 1H), 6.93-7.00 (m, 2H), 6.96 (br s, 1H), 7.03-7.06 (m, 1H), 7.23 (d, J = 8.2 Hz, 1H), 8.88 (br s, 1H), 9.08 (br s, 1H)

Example 4

5-(5-Fluoro-2-methylphenoxymethyl)-6-(2-methoxy-4-methylsulfonyloxyphenyl)-2,2,4-trimethyl-1,2-dihydroquinoline (Compound No. 4-1)

5-(5-Fluoro-2-methylphenoxymethyl)-6-(4-hydroxy-2-methoxyphenyl)-2,2,4-trimethyl-1,2-dihydroquinoline (Reference Compound No. 5-1, 61.0 mg, 0.141 mmol) was dissolved in methylene dichloride (2 mL), methanesulfonyl chloride (26 µL, 0.34 mmol) and triethylamine (92 µL, 0.66 mmol) were added thereto, and then the mixture was stirred at room temperature overnight. The reaction mixture was purified by silica gel column chromatography (hexane-ethyl acetate) to give the titled compound (58.0 mg) as a pale pink solid. (Yield 82%)

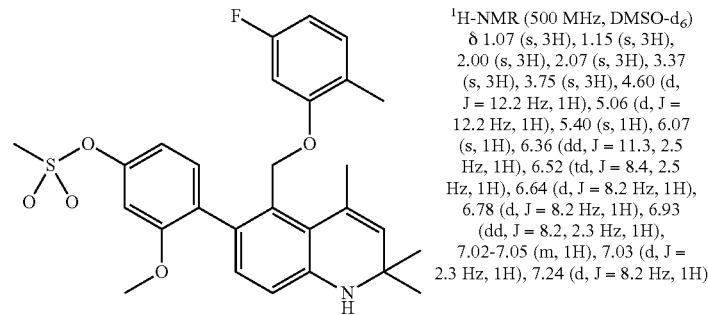

¹H-NMR (500 MHz, DMSO-d₆) δ 1.07 (s, 3H), 1.15 (s, 3H), 2.00 (s, 3H), 2.07 (s, 3H), 3.37 (s, 3H), 3.75 (s, 3H), 4.60 (d, J = 12.2 Hz, 1H), 5.06 (d, J = 12.2 Hz, 1H), 5.40 (s, 1H), 6.07 (s, 1H), 6.36 (dd, J = 11.3, 2.5 Hz, 1H), 6.52 (td, J = 8.4, 2.5 Hz, 1H), 6.64 (d, J = 8.2 Hz, 1H), 6.78 (d, J = 8.2 Hz, 1H), 6.93 (dd, J = 8.2, 2.3 Hz, 1H), 7.02-7.05 (m, 1H), 7.03 (d, J = 2.3 Hz, 1H), 7.24 (d, J = 8.2 Hz, 1H)

Using any compounds among Reference Compounds No. 5-1, 5-3~5-6 and 5-10~5-11, the following Compounds (No. 4-2~4-36) were obtained by a method similar to that of Compound No. 4-1.

6-(4-Benzylsulfonyloxy-2-methoxyphenyl)-5-(5-fluoro-2-methylphenoxymethyl)-2,2,4-trimethyl-1,2-dihydroquinoline (Compound No. 4-2)

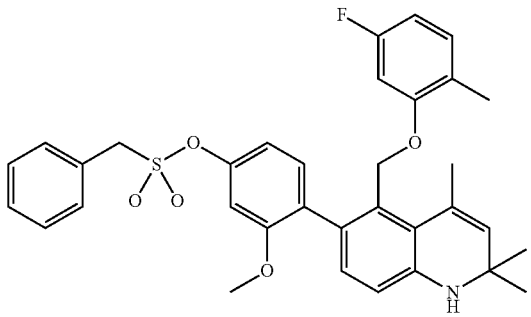 [SMILES: COc1cc(OS(O)(O)Cc2ccccc2)ccc1-c1ccc2c(c1COc1cc(F)ccc1C)C(C)=CC(C)(C)N2]

$^1$H-NMR (500 MHz, DMSO-d$_6$) δ 1.06 (s, 3H), 1.15 (s, 3H), 2.01 (s, 3H), 2.06 (s, 3H), 3.70 (s, 3H), 4.58 (d, J = 12.1 Hz, 1H), 4.97 (s, 2H), 5.05 (d, J = 12.1 Hz, 1H), 5.40 (s, 1H), 6.07 (s, 1H), 6.37 (dd, J = 11.3, 2.4 Hz, 1H), 6.52 (td, J = 8.4, 2.4 Hz, 1H), 6.63 (d, J = 8.2 Hz, 1H), 6.76 (d, J = 8.2 Hz, 1H), 6.81 (d, J = 2.3 Hz, 1H), 6.83 (dd, J = 8.2, 2.3 Hz, 1H), 7.02-7.05 (m, 1H), 7.21 (d, J = 8.2 Hz, 1H), 7.41-7.44 (m, 3H), 7.47-7.49 (m, 2H)

5-(5-Fluoro-2-methylphenoxymethyl)-6-(2-methoxy-4-propylsulfonyloxyphenyl)-2,2,4-trimethyl-1,2-dihydroquinoline (Compound No. 4-3)

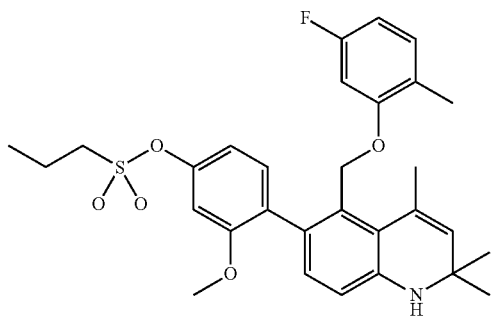 [SMILES: CCCS(O)(O)Oc1ccc(-c2ccc3c(c2COc2cc(F)ccc2C)C(C)=CC(C)(C)N3)c(OC)c1]

$^1$H-NMR (400 MHz, DMSO-d$_6$) δ 1.01 (t, J = 7.5 Hz, 3H), 1.07 (s, 3H), 1.15 (s, 3H), 1.83 (sextet, J = 7.5 Hz, 2H), 2.00 (s, 3H), 2.06 (s, 3H), 3.48 (t, J = 7.5 Hz, 2H), 3.75 (s, 3H), 4.58 (d, J = 12.0 Hz, 1H), 5.05 (d, J = 12.0 Hz, 1H), 5.40 (s, 1H), 6.07 (s, 1H), 6.36 (dd, J = 11.5, 2.4 Hz, 1H), 6.53 (td, J = 8.4, 2.4 Hz, 1H), 6.64 (d, J = 8.1 Hz, 1H), 6.77 (d, J = 8.1 Hz, 1H), 6.91 (dd, J = 8.3, 2.4 Hz, 1H), 6.98 (d, J = 2.4 Hz, 1H), 7.01-7.05 (m, 1H), 7.23 (d, J = 8.3 Hz, 1H)

6-(4-Ethylsulfonyloxy-2-methoxyphenyl)-5-(5-fluoro-2-methylphenoxymethyl)-2,2,4-trimethyl-1,2-dihydroquinoline (Compound No. 4-4)

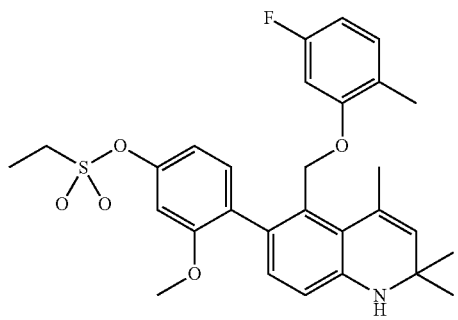 [SMILES: CCS(O)(O)Oc1ccc(-c2ccc3c(c2COc2cc(F)ccc2C)C(C)=CC(C)(C)N3)c(OC)c1]

$^1$H-NMR (400 MHz, DMSO-d$_6$) δ 1.07 (s, 3H), 1.15 (s, 3H), 1.35 (t, J = 7.3 Hz, 3H), 2.00 (s, 3H), 2.06 (s, 3H), 3.50 (q, J = 7.3 Hz, 2H), 3.75 (s, 3H), 4.58 (d, J = 12.0 Hz, 1H), 5.05 (d, J = 12.0 Hz, 1H), 5.40 (s, 1H), 6.07 (s, 1H), 6.36 (dd, J = 11.5, 2.5 Hz, 1H), 6.53 (td, J = 8.4, 2.5 Hz, 1H), 6.64 (d, J = 8.2 Hz, 1H), 6.77 (d, J = 8.2 Hz, 1H), 6.91 (dd, J = 8.3, 2.4 Hz, 1H), 6.98 (d, J = 2.4 Hz, 1H), 7.01-7.05 (m, 1H), 7.23 (d, J = 8.3 Hz, 1H)

| Compound | NMR |
|---|---|
| 5-(5-Fluoro-2-methylphenoxymethyl)-6-(4-isopropylsulfonyloxy-2-methoxyphenyl)-2,2,4-trimethyl-1,2-dihydroquinoline (Compound No. 4-5)<br />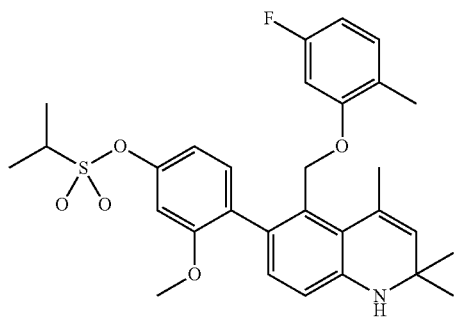 [SMILES: COc1cc(OS(O)(O)C(C)C)ccc1-c1ccc2c(c1COc1cc(F)ccc1C)C(C)=CC(C)(C)N2] | ¹H-NMR (500 MHz, DMSO-d₆) δ 1.07 (s, 3H), 1.15 (s, 3H), 1.42 (d, J = 6.7 Hz, 6H), 2.01 (s, 3H), 2.06 (s, 3H), 3.70 (septet, J = 6.7 Hz, 1H), 3.75 (s, 3H), 4.58 (d, J = 12.2 Hz, 1H), 5.05 (d, J = 12.2 Hz, 1H), 5.40 (s, 1H), 6.07 (s, 1H), 6.37 (dd, J = 11.3, 2.5 Hz, 1H), 6.53 (td, J = 8.5, 2.5 Hz, 1H), 6.64 (d, J = 8.2 Hz, 1H), 6.77 (d, J = 8.2 Hz, 1H), 6.90 (dd, J = 8.2, 2.4 Hz, 1H), 6.95 (d, J = 2.4 Hz, 1H), 7.02-7.05 (m, 1H), 7.23 (d, J = 8.2 Hz, 1H) |
| 6-(4-Butylsulfonyloxy-2-methoxyphenyl)-5-(5-fluoro-2-methylphenoxymethyl)-2,2,4-trimethyl-1,2-dihydroquinoline (Compound No. 4-6)<br />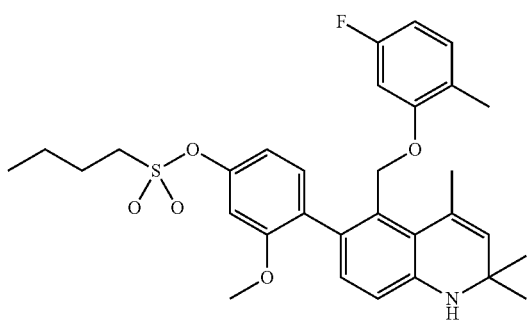 [SMILES: CCCCS(O)(O)Oc1ccc(-c2ccc3c(c2COc2cc(F)ccc2C)C(C)=CC(C)(C)N3)c(OC)c1] | ¹H-NMR (400 MHz, DMSO-d₆) δ 0.89 (t, J = 7.6 Hz, 3H), 1.07 (s, 3H), 1.15 (s, 3H), 1.42 (sextet, J = 7.6 Hz, 2H), 1.78 (quintet, J = 7.6 Hz, 2H), 2.00 (s, 3H), 2.06 (s, 3H), 3.49 (t, J = 7.6 Hz, 2H), 3.75 (s, 3H), 4.58 (d, J = 12.1 Hz, 1H), 5.05 (d, J = 12.1 Hz, 1H), 5.40 (s, 1H), 6.07 (s, 1H), 6.36 (dd, J = 11.5, 2.4 Hz, 1H), 6.53 (td, J = 8.4, 2.4 Hz, 1H), 6.64 (d, J = 8.2 Hz, 1H), 6.77 (d, J = 8.2 Hz, 1H), 6.92 (dd, J = 8.3, 2.3 Hz, 1H), 6.98 (d, J = 2.3 Hz, 1H), 7.01-7.05 (m, 1H), 7.23 (d, J = 8.3 Hz, 1H) |
| 5-(2-Methoxy-5-nitrophenoxymethyl)-6-(2-methoxy-4-propylsulfonyloxyphenyl)-2,2,4-trimethyl-1,2-dihydroquinoline (Compound No. 4-7)<br />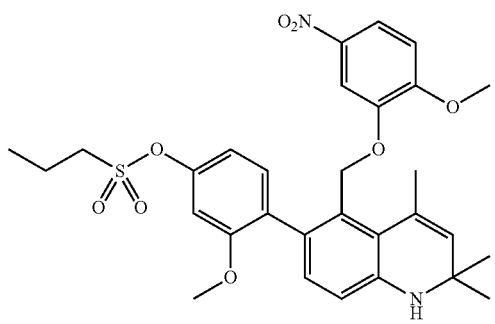 [SMILES: CCCS(=O)(=O)Oc1ccc(-c2ccc3c(c2COc2cc([N+](=O)[O-])ccc2OC)C(C)=CC(C)(C)N3)c(OC)c1] | ¹H-NMR (500 MHz, DMSO-d₆) δ 0.99 (t, J = 7.3 Hz, 3H), 1.06 (s, 3H), 1.18 (s, 3H), 1.81 (tq, J = 7.6, 7.3 Hz, 2H), 2.14 (s, 3H), 3.44 (t, J = 7.6 Hz, 2H), 3.71 (s, 3H), 3.82 (s, 3H), 4.63 (d, J = 11.9 Hz, 1H), 5.23 (d, J = 11.9 Hz, 1H), 5.41 (s, 1H), 6.05 (s, 1H), 6.62 (d, J = 8.2 Hz, 1H), 6.75 (d, J = 8.2 Hz, 1H), 6.83 (dd, J = 8.2, 2.4 Hz, 1H), 6.92 (d, J = 2.4 Hz, 1H), 7.08 (d, J = 9.1 Hz, 1H), 7.19 (d, J = 8.2 Hz, 1H), 7.32 (d, J = 2.7 Hz, 1H), 7.81 (dd, J = 9.1, 2.7 Hz, 1H) |
| 6-(4-Cyclopropylsulfonyloxy-2-methoxyphenyl)-5-(2-methoxy-5-nitrophenoxymethyl)-2,2,4-trimethyl-1,2-dihydroquinoline (Compound No. 4-8)<br />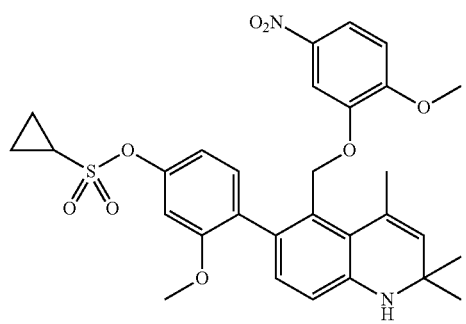 [SMILES: COc1ccc([N+](=O)[O-])cc1OCc1c(-c2ccc(OS(=O)(=O)C3CC3)cc2OC)ccc2c1C(C)=CC(C)(C)N2] | ¹H-NMR (400 MHz, CDCl₃) δ 1.04 (s, 3H), 1.08-1.12 (m, 2H), 1.23-1.26 (m, 2H), 1.27 (s, 3H), 2.27 (s, 3H), 2.55-2.61 (m, 1H), 3.77 (s, 3H), 3.84 (s, 3H), 4.77 (d, J = 12.4 Hz, 1H), 5.35 (d, J = 12.4 Hz, 1H), 5.47 (s, 1H), 6.07 (s, 1H), 6.56 (d, J = 8.2 Hz, 1H), 6.78 (d, J = 9.0 Hz, 1H), 6.85 (d, J = 8.2 Hz, 1H), 6.86 (d, J = 2.2 Hz, 1H), 6.90 (dd, J = 8.3, 2.2 Hz, 1H), 7.27 (d, J = 2.7 Hz, 1H), 7.30 (d, J = 8.3 Hz, 1H), 7.78 (dd, J = 9.0, 2.7 Hz, 1H) |

6-(4-Isopropylsulfonyloxy-2-methoxyphenyl)-5-(2-methoxy-5-nitrophenoxymethyl)-2,2,4-trimethyl-1,2-dihydroquinoline (Compound No. 4-9)

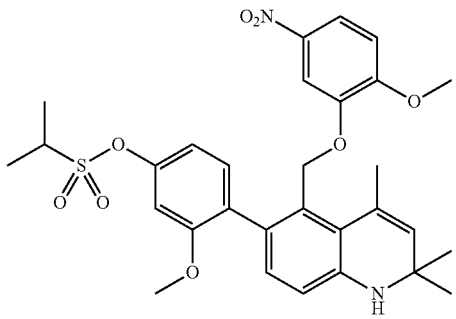 [SMILES: COc1ccc([N+](=O)[O-])cc1OCc1c(-c2ccc(OS(=O)(=O)C(C)C)cc2OC)ccc2c1C(C)=CC(C)(C)N2]

$^1$H-NMR (500 MHz, DMSO-$d_6$) δ 1.06 (s, 3H), 1.18 (s, 3H), 1.39 (d, J = 6.7 Hz, 6H), 2.14 (s, 3H), 3.62-3.67 (m, 1H), 3.71 (s, 3H), 3.82 (s, 3H), 4.61 (d, J = 11.9 Hz, 1H), 5.23 (d, J = 11.9 Hz, 1H), 5.41 (s, 1H), 6.05 (s, 1H), 6.62 (d, J = 8.1 Hz, 1H), 6.74 (d, J = 8.1 Hz, 1H), 6.82 (dd, J = 8.2, 2.4 Hz, 1H), 6.89 (d, J = 2.4 Hz, 1H), 7.08 (d, J = 9.1 Hz, 1H), 7.18 (d, J = 8.2 Hz, 1H), 7.32 (d, J = 2.7 Hz, 1H), 7.81 (dd, J = 9.1, 2.7 Hz, 1H)

5-(2-Methoxy-5-nitrophenoxymethyl)-6-[2-methoxy-4-(3,3,3-trifluoropropylsulfonyloxy)phenyl]-2,2,4-trimethyl-1,2-dihydroquinoline (Compound No. 4-10)

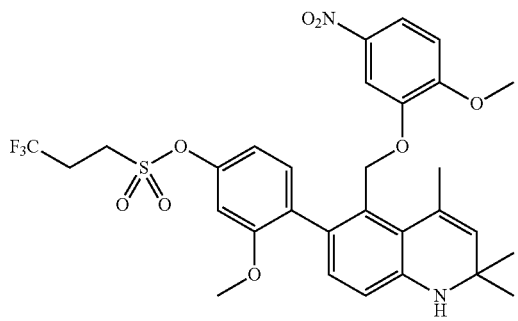 [SMILES: COc1ccc([N+](=O)[O-])cc1OCc1c(-c2ccc(OS(=O)(=O)CCC(F)(F)F)cc2OC)ccc2c1C(C)=CC(C)(C)N2]

$^1$H-NMR (500 MHz, DMSO-$d_6$) δ 1.06 (s, 3H), 1.18 (s, 3H), 2.14 (s, 3H), 2.92-2.95 (m, 2H), 3.71 (s, 3H), 3.78-3.82 (m, 2H), 3.82 (s, 3H), 4.62 (d, J = 11.9 Hz, 1H), 5.23 (d, J = 11.9 Hz, 1H), 5.41 (s, 1H), 6.06 (s, 1H), 6.62 (d, J = 8.2 Hz, 1H), 6.75 (d, J = 8.2 Hz, 1H), 6.89 (dd, J = 8.3, 2.4 Hz, 1H), 7.01 (d, J = 2.4 Hz, 1H), 7.07 (d, J = 9.1 Hz, 1H), 7.21 (d, J = 8.3 Hz, 1H), 7.32 (d, J = 2.6 Hz, 1H), 7.81 (dd, J = 9.1, 2.6 Hz, 1H)

6-(4-Ethylsulfonyloxy-2-methoxyphenyl)-5-(2-methyl-5-nitrophenoxymethyl)-2,2,4-trimethyl-1,2-dihydroquinoline (Compound No. 4-11)

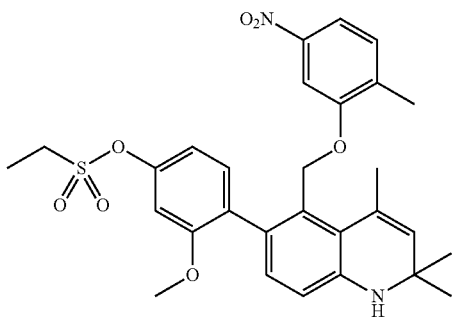 [SMILES: CCS(=O)(=O)Oc1ccc(-c2ccc3c(c2COc2cc([N+](=O)[O-])ccc2C)C(C)=CC(C)(C)N3)c(OC)c1]

1H-NMR (400 MHz, DMSO-$d_6$) δ 0.93 (s, 3H), 1.18 (s, 3H), 1.35 (t, J = 7.3 Hz, 3H), 2.13 (s, 3H), 2.17 (s, 3H), 3.51 (q, J = 7.3 Hz, 2H), 3.76 (s, 3H), 4.76 (d, J = 12.6 Hz, 1H), 5.29 (d, J = 12.6 Hz, 1H), 5.41 (s, 1H), 6.07 (s, 1H), 6.62 (d, J = 8.3 Hz, 1H), 6.78 (d, J = 8.3 Hz, 1H), 6.95 (dd, J = 8.2, 2.3 Hz, 1H), 6.99 (d, J = 2.3 Hz, 1H), 7.15 (d, J = 2.1 Hz, 1H), 7.31 (d, J = 8.2 Hz, 1H), 7.33 (d, J = 8.2 Hz, 1H), 7.64 (dd, J = 8.2, 2.1 Hz, 1H)

6-(2-Methoxy-4-propylsulfonyloxyphenyl)-5-(2-methyl-5-nitrophenoxymethyl)-2,2,4-trimethyl-1,2-dihydroquinoline (Compound No. 4-12)

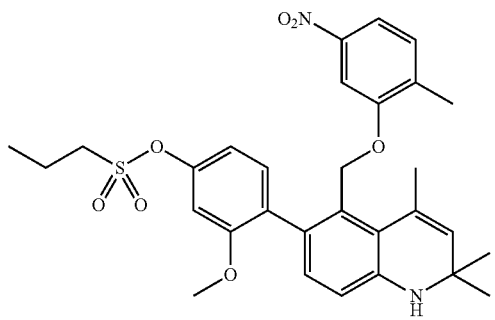 [SMILES: CCCS(=O)(=O)Oc1ccc(-c2ccc3c(c2COc2cc([N+](=O)[O-])ccc2C)C(C)=CC(C)(C)N3)c(OC)c1]

$^1$H-NMR (500 MHz, DMSO-$d_6$) δ 0.93 (s, 3H), 1.01 (t, J = 7.5 Hz, 3H), 1.18 (s, 3H), 1.80-1.87 (m, 2H), 2.13 (s, 3H), 2.17 (s, 3H), 3.49 (t, J = 7.6 Hz, 2H), 3.76 (s, 3H), 4.76 (d, J = 12.5 Hz, 1H), 5.29 (d, J = 12.5 Hz, 1H), 5.41 (s, 1H), 6.07 (s, 1H), 6.62 (d, J = 8.2 Hz, 1H), 6.79 (d, J = 8.2 Hz, 1H), 6.94 (dd, J = 8.2, 2.4 Hz, 1H), 6.98 (d, J = 2.4 Hz, 1H), 7.15 (d, J = 2.2 Hz, 1H), 7.31 (d, J = 8.2 Hz, 1H), 7.33 (d, J = 8.0 Hz, 1H), 7.64 (dd, J = 8.0, 2.2 Hz, 1H)

| | |
|---|---|
| 6-(4-Isopropylsulfonyloxy-2-methoxyphenyl)-5-(2-methyl-5-nitrophenoxymethyl)-2,2,4-trimethyl-1,2-dihydroquinoline (Compound No. 4-13) 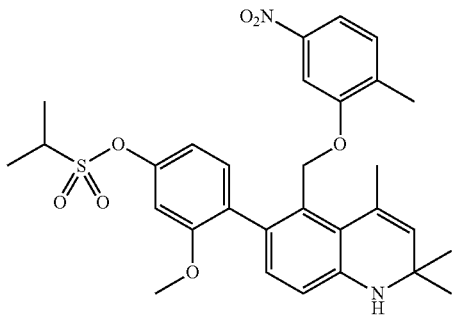 [SMILES: COc1cc(OS(=O)(=O)C(C)C)ccc1-c1ccc2c(c1COc1cc([N+](=O)[O-])ccc1C)C(C)=CC(C)(C)N2] | ¹H-NMR (500 MHz, DMSO-d₆) δ 0.93 (s, 3H), 1.18 (s, 3H), 1.42 (d, J = 6.7 Hz, 6H), 2.13 (s, 3H), 2.17 (s, 3H), 3.68-3.74 (m, 1H), 3.76 (s, 3H), 4.75 (d, J = 12.5 Hz, 1H), 5.28 (d, J = 12.5 Hz, 1H), 5.41 (s, 1H), 6.07 (s, 1H), 6.62 (d, J = 8.2 Hz, 1H), 6.79 (d, J = 8.2 Hz, 1H), 6.93 (dd, J = 8.2, 2.2 Hz, 1H), 6.95 (d, J = 2.2 Hz, 1H), 7.16 (d, J = 2.1 Hz, 1H), 7.31 (d, J = 8.2 Hz, 1H), 7.33 (d, J = 8.2 Hz, 1H), 7.64 (dd, J = 8.2, 2.1 Hz, 1H) |
| 6-(4-Cyclopropylsulfonyloxy-2-methoxyphenyl)-5-(5-fluoro-2-methylphenoxymethyl)-2,2,4-trimethyl-1,2-dihydroquinoline (Compound No. 4-14) 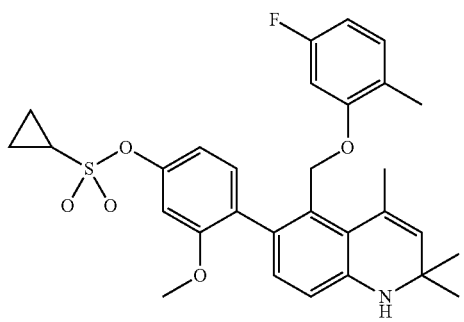 [SMILES: COc1cc(OS(O)(O)C2CC2)ccc1-c1ccc2c(c1COc1cc(F)ccc1C)C(C)=CC(C)(C)N2] | ¹H-NMR (500 MHz, DMSO-d₆) δ 0.89-0.94 (m, 2H), 1.04-1.08 (m, 2H), 1.08 (s, 3H), 1.15 (s, 3H), 2.01 (s, 3H), 2.07 (s, 3H), 3.01 (tt, J = 7.9, 4.9 Hz, 1H), 3.75 (s, 3H), 4.56 (d, J = 12.1 Hz, 1H), 5.04 (d, J = 12.1 Hz, 1H), 5.41 (s, 1H), 6.07 (s, 1H), 6.38 (dd, J = 11.3, 2.4 Hz, 1H), 6.53 (td, J = 8.6, 2.4 Hz, 1H), 6.64 (d, J = 8.2 Hz, 1H), 6.78 (d, J = 8.2 Hz, 1H), 6.93 (dd, J = 8.2, 2.4 Hz, 1H), 7.01-7.05 (m, 1H), 7.03 (d, J = 2.4 Hz, 1H), 7.22 (d, J = 8.2 Hz, 1H) |
| 5-(5-Fluoro-2-methylphenoxymethyl)-6-(4-isobutylsulfonyloxy-2-methoxyphenyl)-2,2,4-trimethyl-1,2-dihydroquinoline (Compound No. 4-15) 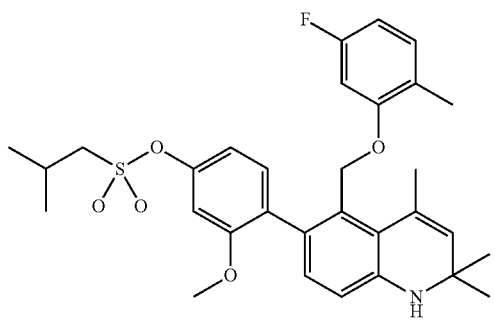 | ¹H-NMR (500 MHz, DMSO-d₆) δ 1.06 (d, J = 7.0 Hz, 6H), 1.07 (s, 3H), 1.15 (s, 3H), 2.00 (s, 3H), 2.06 (s, 3H), 2.21-2.26 (m, 1H), 3.43 (d, J = 6.4 Hz, 2H), 3.75 (s, 3H), 4.59 (d, J = 12.1 Hz, 1H), 5.05 (d, J = 12.1 Hz, 1H), 5.40 (s, 1H), 6.06 (s, 1H), 6.36 (dd, J = 11.5, 2.6 Hz, 1H), 6.53 (td, J = 8.5, 2.6 Hz, 1H), 6.64 (d, J = 8.2 Hz, 1H), 6.77 (d, J = 8.2 Hz, 1H), 6.92 (dd, J = 8.3, 2.2 Hz, 1H), 6.98 (d, J = 2.2 Hz, 1H), 7.01-7.05 (m, 1H), 7.23 (d, J = 8.3 Hz, 1H) |
| 6-(4-Cyclopentylsulfonyloxy-2-methoxyphenyl)-5-(5-fluoro-2-methylphenoxymethyl)-2,2,4-trimethyl-1,2-dihydroquinoline (Compound No. 4-16) 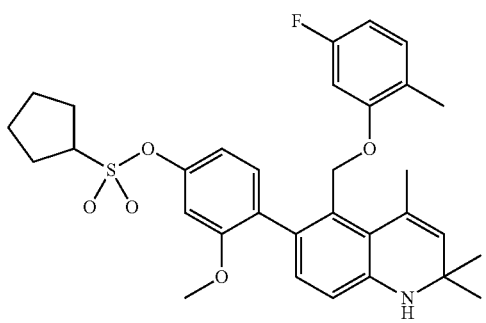 [SMILES: COc1cc(OS(O)(O)C2CCCC2)ccc1-c1ccc2c(c1COc1cc(F)ccc1C)C(C)=CC(C)(C)N2] | ¹H-NMR (500 MHz, DMSO-d₆) δ 1.07 (s, 3H), 1.15 (s, 3H), 1.57-1.65 (m, 2H), 1.68-1.75 (m, 2H), 1.95-2.02 (m, 2H), 2.01 (s, 3H), 2.04-2.11 (m, 2H), 2.06 (s, 3H), 3.75 (s, 3H), 3.94 (tt, J = 8.9, 6.7 Hz, 1H), 4.57 (d, J = 11.9 Hz, 1H), 5.05 (d, J = 11.9 Hz, 1H), 5.40 (s, 1H), 6.06 (s, 1H), 6.37 (dd, J = 11.3, 2.4 Hz, 1H), 6.53 (td, J = 8.4, 2.4 Hz, 1H), 6.64 (d, J = 8.2 Hz, 1H), 6.77 (d, J = 8.2 Hz, 1H), 6.90 (dd, J = 8.2, 2.1 Hz, 1H), 6.95 (d, J = 2.1 Hz, 1H), 7.02-7.05 (m, 1H), 7.23 (d, J = 8.2 Hz, 1H) |

| | |
|---|---|
| 5-(5-Fluoro-2-methylphenoxymethyl)-6-[2-methoxy-4-(3,3,3-trifluoropropylsulfonyloxy)phenyl]-2,2,4-trimethyl-1,2-dihydroquinoline (Compound No. 4-17)<br>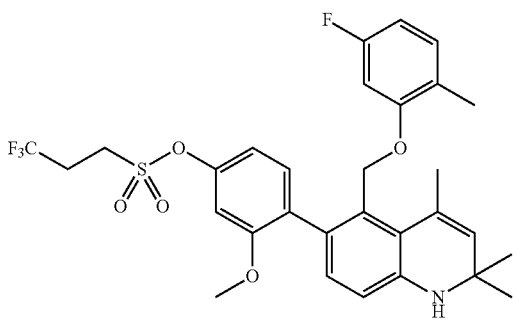 [SMILES: COc1cc(OS(=O)(=O)CCC(F)(F)F)ccc1-c1ccc2c(c1COc1cc(F)ccc1C)C(C)=CC(C)(C)N2] | $^1$H-NMR (500 MHz, DMSO-d$_6$) δ 1.07 (s, 3H), 1.15 (s, 3H), 2.00 (s, 3H), 2.06 (s, 3H), 2.90-3.00 (m, 2H), 3.75 (s, 3H), 3.83-3.87 (m, 2H), 4.59 (d, J = 12.1 Hz, 1H), 5.05 (d, J = 12.1 Hz, 1H), 5.40 (s, 1H), 6.07 (s, 1H), 6.35 (dd, J = 11.5, 2.4 Hz, 1H), 6.52 (td, J = 8.4, 2.4 Hz, 1H), 6.64 (d, J = 8.2 Hz, 1H), 6.78 (d, J = 8.2 Hz, 1H), 6.97 (dd, J = 8.2, 2.3 Hz, 1H), 7.01-7.05 (m, 1H), 7.06 (d, J = 2.3 Hz, 1H), 7.25 (d, J = 8.2 Hz, 1H) |
| 5-(2-Methoxyphenylaminomethyl)-6-(2-methoxy-4-propylsulfonyloxyphenyl)-2,2,4-trimethyl-1,2-dihydroquinoline (Compound No. 4-18)<br>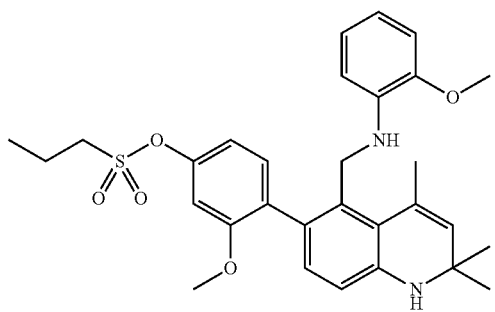 [SMILES: CCCS(=O)(=O)Oc1ccc(-c2ccc3c(c2CNc2ccccc2OC)C(C)=CC(C)(C)N3)c(OC)c1] | $^1$H-NMR (400 MHz, DMSO-d$_6$) δ 0.99 (t, J = 7.5 Hz, 3H), 1.15 (s, 3H), 1.21 (s, 3H), 1.76-1.85 (m, 2H), 2.07 (s, 3H), 3.42-3.46 (m, 2H), 3.68 (s, 3H), 3.71 (s, 3H), 3.83 (dd, J = 12.3, 3.5 Hz, 1H), 4.00 (dd, J = 12.3, 6.7 Hz, 1H), 4.18 (dd, J = 6.7, 3.5 Hz, 1H), 5.40 (s, 1H), 6.05 (s, 1H), 6.33 (dd, J = 7.7, 1.3 Hz, 1H), 6.50 (td, J = 7.7, 1.3 Hz, 1H), 6.60 (d, J = 8.2 Hz, 1H), 6.66 (td, J = 7.7, 1.3 Hz, 1H), 6.70 (d, J = 8.2 Hz, 1H), 6.73 (dd, J = 7.7, 1.3 Hz, 1H), 6.88 (dd, J = 8.1, 2.1 Hz, 1H), 6.90 (d, J = 2.1 Hz, 1H), 7.17 (d, J = 8.1 Hz, 1H) |
| 6-(4-Isopropylsulfonyloxy-2-methoxyphenyl)-5-(2-methoxyphenylaminomethyl)-2,2,4-trimethyl-1,2-dihydroquinoline (Compound No. 4-19)<br>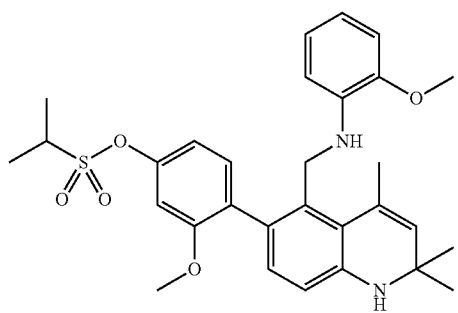 [SMILES: COc1ccccc1NCc1c(-c2ccc(OS(=O)(=O)C(C)C)cc2OC)ccc2c1C(C)=CC(C)(C)N2] | $^1$H-NMR (400 MHz, DMSO-d$_6$) δ 1.15 (s, 3H), 1.21 (s, 3H), 1.39 (d, J = 6.8 Hz, 6H), 2.07 (s, 3H), 3.60-3.67 (m, 1H), 3.69 (s, 3H), 3.71 (s, 3H), 3.83 (dd, J = 12.6, 3.5 Hz, 1H), 4.00 (dd, J = 12.6, 6.6 Hz, 1H), 4.18 (dd, J = 6.6, 3.5 Hz, 1H), 5.40 (s, 1H), 6.04 (s, 1H), 6.33 (dd, J = 7.7, 1.3 Hz, 1H), 6.51 (td, J = 7.7, 1.3 Hz, 1H), 6.60 (d, J = 8.2 Hz, 1H), 6.67 (td, J = 7.7, 1.3 Hz, 1H), 6.70 (d, J = 8.2 Hz, 1H), 6.73 (dd, J = 7.7, 1.3 Hz, 1H), 6.87 (d, J = 2.3 Hz, 1H), 6.87 (dd, J = 8.8, 2.3 Hz, 1H), 7.17 (d, J = 8.8 Hz, 1H) |
| 6-(2-Methoxy-4-methylsulfonyloxyphenyl)-5-(2-methoxyphenylaminomethyl)-2,2,4-trimethyl-1,2-dihydroquinoline (Compound No. 4-20)<br>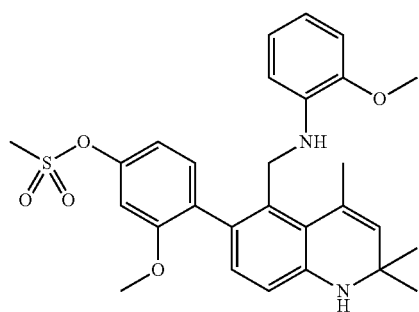 | $^1$H-NMR (500 MHz, CDCl$_3$) δ 1.26 (s, 3H), 1.30 (s, 3H), 2.19 (s, 3H), 3.01 (s, 3H), 3.70 (s, 3H), 3.75 (s, 3H), 3.89 (brs, 1H), 4.00 (d, J = 12.4 Hz, 1H), 4.06 (d, J = 12.4 Hz, 1H), 4.28 (s, 1H), 5.47 (s, 1H), 6.34 (dd, J = 7.8, 1.3 Hz, 1H), 6.56 (td, J = 7.8, 1.3 Hz, 1H), 6.56 (d, J = 7.9 Hz, 1H), 6.68 (dd, J = 7.8, 1.3 Hz, 1H), 6.75 (td, J = 7.8, 1.3 Hz, 1H), 6.78 (d, J = 2.2 Hz, 1H), 6.81 (d, J = 7.9 Hz, 1H), 6.82 (dd, J = 8.1, 2.2 Hz, 1H), 7.18 (d, J = 8.1 Hz, 1H) |

5-(5-Fluoro-2-methylphenylaminomethyl)-6-(2-methoxy-4-propylsulfonyloxyphenyl)-2,2,4-trimethyl-1,2-dihydroquinoline (Compound No. 4-21)

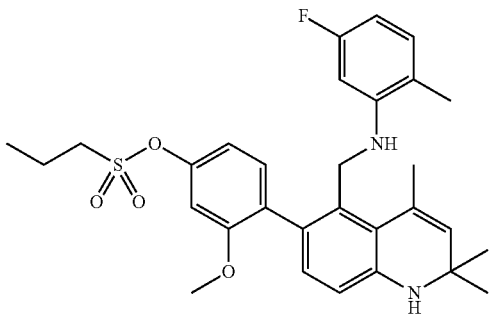 [SMILES: CCCS(=O)(=O)Oc1ccc(-c2ccc3c(c2CNc2cc(F)ccc2C)C(C)=CC(C)(C)N3)c(OC)c1]

$^1$H-NMR (500 MHz, DMSO-d$_6$) δ 1.00 (t, J = 7.5 Hz, 3H), 1.11 (s, 3H), 1.19 (s, 3H), 1.78-1.86 (m, 2H), 1.88 (s, 3H), 2.05 (s, 3H), 3.43-3.48 (m, 2H), 3.73 (s, 3H), 3.89 (dd, J = 13.1, 4.9 Hz, 1H), 4.07 (dd, J = 13.1, 4.3 Hz, 1H), 4.20-4.23 (m, 1H), 5.41 (s, 1H), 6.03 (dd, J = 12.2, 2.5 Hz, 1H), 6.04 (s, 1H), 6.19 (td, J = 8.5, 2.5 Hz, 1H), 6.61 (d, J = 8.1 Hz, 1H), 6.72 (d, J = 8.1 Hz, 1H), 6.84-6.88 (m, 1H), 6.91 (dd, J = 8.2, 2.4 Hz, 1H), 6.95 (d, J = 2.4 Hz, 1H), 7.25 (d, J = 8.2 Hz, 1H)

6-(4-Cyclopropylsulfonyloxy-2-methoxyphenyl)-5-(2-methoxyphenylaminomethyl)-2,2,4-trimethyl-1,2-dihydroquinoline (Compound No. 4-22)

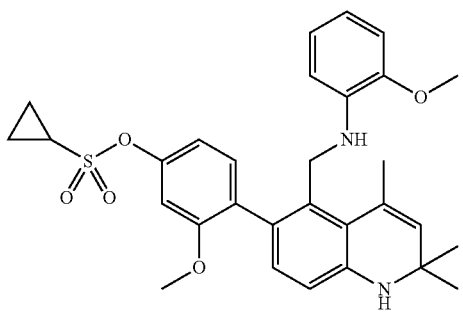 [SMILES: COc1ccccc1NCc1c(-c2ccc(OS(=O)(=O)C3CC3)cc2OC)ccc2c1C(C)=CC(C)(C)N2]

$^1$H-NMR (500 MHz, DMSO-d$_6$) δ 0.80-1.05 (m, 4H), 1.15 (s, 3H), 1.22 (s, 3H), 2.09 (s, 3H), 2.91 (tt, J = 7.9, 4.9 Hz, 1H), 3.68 (s, 3H), 3.71 (s, 3H), 3.81 (dd, J = 12.4, 3.4 Hz, 1H), 3.99 (dd, J = 12.4, 6.2 Hz, 1H), 4.18 (dd, J = 6.2, 3.4 Hz, 1H), 5.40 (s, 1H), 6.03 (s, 1H), 6.32 (dd, J = 7.8, 1.2 Hz, 1H), 6.50 (td, J = 7.8, 1.2 Hz, 1H), 6.61 (d, J = 8.4 Hz, 1H), 6.66 (td, J = 7.8, 1.2 Hz, 1H), 6.71 (d, J = 8.4 Hz, 1H), 6.72 (dd, J = 7.8, 1.2 Hz, 1H), 6.89 (dd, J = 8.2, 2.2 Hz, 1H), 6.96 (d, J = 2.2 Hz, 1H), 7.17 (d, J = 8.2 Hz, 1H)

6-(4-Ethylsulfonyloxy-2-methoxyphenyl)-5-(2-methoxyphenylaminomethyl)-2,2,4-trimethyl-1,2-dihydroquinoline (Compound No. 4-23)

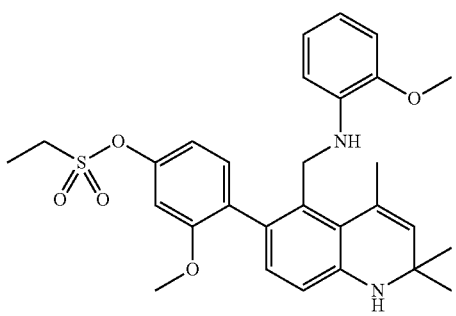 [SMILES: CCS(=O)(=O)Oc1ccc(-c2ccc3c(c2CNc2ccccc2OC)C(C)=CC(C)(C)N3)c(OC)c1]

$^1$H-NMR (500 MHz, DMSO-d$_6$) δ 1.15 (s, 3H), 1.21 (s, 3H), 1.32 (t, J = 7.3 Hz, 3H), 2.08 (s, 3H), 3.44 (q, J = 7.3 Hz, 2H), 3.69 (s, 3H), 3.71 (s, 3H), 3.84 (dd, J = 12.4, 3.7 Hz, 1H), 3.99 (dd, J = 12.4, 6.3 Hz, 1H), 4.18 (dd, J = 6.3, 3.7 Hz, 1H), 5.40 (s, 1H), 6.03 (s, 1H), 6.33 (dd, J = 7.8, 1.3 Hz, 1H), 6.50 (td, J = 7.8, 1.3 Hz, 1H), 6.60 (d, J = 8.1 Hz, 1H), 6.66 (td, J = 7.8, 1.3 Hz, 1H), 6.70 (d, J = 8.1 Hz, 1H), 6.73 (dd, J = 7.8, 1.3 Hz, 1H), 6.88 (dd, J = 8.2, 2.4 Hz, 1H), 6.90 (d, J = 2.4 Hz, 1H), 7.17 (d, J = 8.2 Hz, 1H)

6-(4-Cyclopentylsulfonyloxy-2-methoxyphenyl)-5-(2-methoxyphenylaminomethyl)-2,2,4-trimethyl-1,2-dihydroquinoline (Compound No. 4-24)

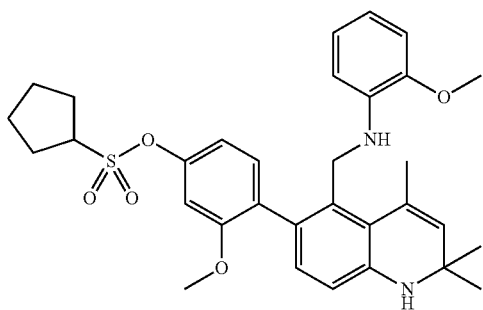 [SMILES: COc1ccccc1NCc1c(-c2ccc(OS(=O)(=O)C3CCCC3)cc2OC)ccc2c1C(C)=CC(C)(C)N2]

$^1$H-NMR (500 MHz, DMSO-d$_6$) δ 1.15 (s, 3H), 1.21 (s, 3H), 1.55-1.63 (m, 2H), 1.65-1.73 (m, 2H), 1.92-1.99 (m, 2H), 2.00-2.07 (m, 2H), 2.07 (s, 3H), 3.69 (s, 3H), 3.71 (s, 3H), 3.83 (dd, J = 12.7, 3.9 Hz, 1H), 3.85-3.91 (m, 1H), 3.99 (dd, J = 12.7, 6.2 Hz, 1H), 4.18 (dd, J = 6.2, 3.9 Hz, 1H), 5.40 (s, 1H), 6.03 (s, 1H), 6.33 (dd, J = 7.8, 1.2 Hz, 1H), 6.50 (td, J = 7.8, 1.2 Hz, 1H), 6.60 (d, J = 8.2 Hz, 1H), 6.66 (td, J = 7.8, 1.2 Hz, 1H), 6.70 (d, J = 8.2 Hz, 1H), 6.73 (dd, J = 7.8, 1.2 Hz, 1H), 6.87 (d, J = 2.3 Hz, 1H), 6.87 (dd, J = 8.9, 2.3 Hz, 1H), 7.17 (d, J = 8.9 Hz, 1H)

| Compound | NMR |
|---|---|
| 5-(5-Fluoro-2-methylphenylaminomethyl)-6-(2-methoxy-4-methylsulfonyloxyphenyl)-2,2,4-trimethyl-1,2-dihydroquinoline (Compound No. 4-25) 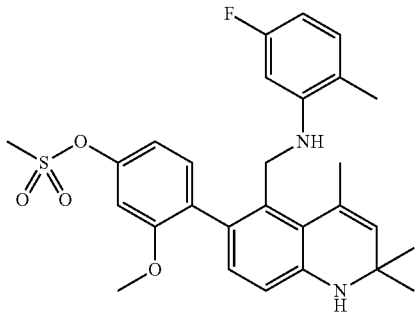 | $^1$H-NMR (500 MHz, DMSO-$d_6$) δ 1.11 (s, 3H), 1.19 (s, 3H), 1.88 (s, 3H), 2.05 (s, 3H), 3.34 (s, 3H), 3.74 (s, 3H), 3.90 (dd, J = 13.1, 4.4 Hz, 1H), 4.08 (dd, J = 13.1, 4.4 Hz, 1H), 4.23 (t, J = 4.4 Hz, 1H), 5.41 (s, 1H), 6.02 (dd, J = 12.2, 2.4 Hz, 1H), 6.04 (s, 1H), 6.19 (td, J = 8.5, 2.4 Hz, 1H), 6.61 (d, J = 8.2 Hz, 1H), 6.72 (d, J = 8.2 Hz, 1H), 6.85-6.88 (m, 1H), 6.92 (dd, J = 8.2, 2.3 Hz, 1H), 7.00 (d, J = 2.3 Hz, 1H), 7.26 (d, J = 8.2 Hz, 1H) |
| 6-[2-Methoxy-4-(3,3,3-trifluoropropylsulfonyloxy)phenyl]-5-(5-methylthiophen-2-ylcarbonyloxymethyl)-2,2,4-trimethyl-1,2-dihydroquinoline (Compound No. 4-26) 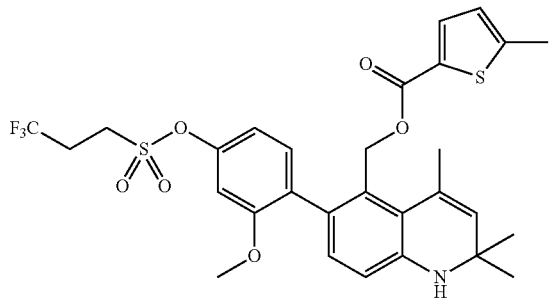 [SMILES: COc1cc(OS(=O)(=O)CCC(F)(F)F)ccc1-c1ccc2c(c1COC(=O)c1ccc(C)s1)C(C)=CC(C)(C)N2] | $^1$H-NMR (400 MHz, DMSO-$d_6$) δ 1.14 (s, 3H), 1.21 (s, 3H), 2.10 (s, 3H), 2.46 (s, 3H), 2.94-3.01 (m, 2H), 3.69 (s, 3H), 3.88 (t, J = 7.9 Hz, 2H), 4.90 (d, J = 12.6 Hz, 1H), 5.16 (d, J = 12.6 Hz, 1H), 5.45 (s, 1H), 6.14 (s, 1H), 6.66 (d, J = 8.2 Hz, 1H), 6.76 (d, J = 8.2 Hz, 1H), 6.88 (d, J = 3.9 Hz, 1H), 6.94 (dd, J = 8.3, 2.2 Hz, 1H), 7.04 (d, J = 2.2 Hz, 1H), 7.22 (d, J = 8.3 Hz, 1H), 7.46 (d, J = 3.9 Hz, 1H) |
| 6-(2-Methoxy-4-propylsulfonyloxyphenyl)-5-(5-methylthiophen-2-ylcarbonyloxymethyl)-2,2,4-trimethyl-1,2-dihydroquinoline (Compound No. 4-27) 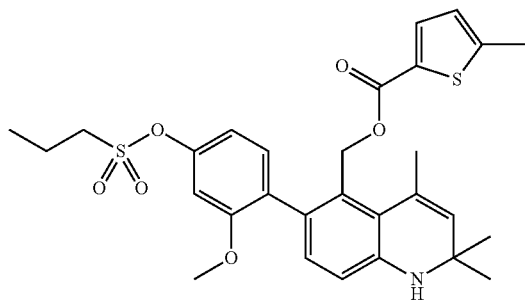 [SMILES: CCCS(=O)(=O)Oc1ccc(-c2ccc3c(c2COC(=O)c2ccc(C)s2)C(C)=CC(C)(C)N3)c(OC)c1] | $^1$H-NMR (400 MHz, DMSO-$d_6$) δ 1.02 (t, J = 7.5 Hz, 3H), 1.12 (s, 3H), 1.19 (s, 3H), 1.84 (sextet, J = 7.5 Hz, 2H), 2.08 (s, 3H), 2.44 (s, 3H), 3.47 (t, J = 7.5 Hz, 2H), 3.73 (s, 3H), 4.88 (d, J = 12.6 Hz, 1H), 5.14 (d, J = 12.6 Hz, 1H), 5.45 (s, 1H), 6.07 (s, 1H), 6.65 (d, J = 8.3 Hz, 1H), 6.74 (d, J = 8.3 Hz, 1H), 6.87 (d, J = 3.7 Hz, 1H), 6.87 (dd, J = 8.3, 2.3 Hz, 1H), 6.92 (d, J = 2.3 Hz, 1H), 7.18 (d, J = 8.3 Hz, 1H), 7.44 (d, J = 3.7 Hz, 1H) |
| 6-(4-Isobutylsulfonyloxy-2-methoxyphenyl)-5-(5-methylthiophen-2-ylcarbonyloxymethyl)-2,2,4-trimethyl-1,2-dihydroquinoline (Compound No. 4-28) 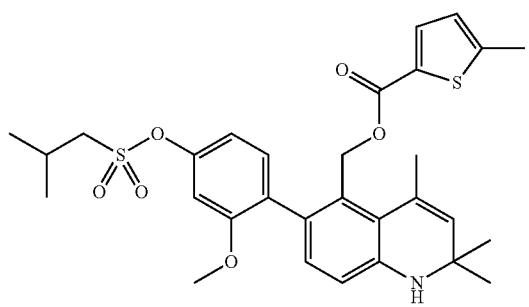 [SMILES: COc1cc(OS(=O)(=O)CC(C)C)ccc1-c1ccc2c(c1COC(=O)c1ccc(C)s1)C(C)=CC(C)(C)N2] | $^1$H-NMR (500 MHz, DMSO-$d_6$) δ 1.08 (d, J = 6.7 Hz, 6H), 1.14 (s, 3H), 1.21 (s, 3H), 2.10 (s, 3H), 2.22-2.30 (m, 1H), 2.47 (s, 3H), 3.45 (d, J = 6.7 Hz, 2H), 3.68 (s, 3H), 4.89 (d, J = 12.5 Hz, 1H), 5.15 (d, J = 12.5 Hz, 1H), 5.45 (s, 1H), 6.12 (s, 1H), 6.66 (d, J = 8.2 Hz, 1H), 6.75 (d, J = 8.2 Hz, 1H), 6.88 (d, J = 3.6 Hz, 1H), 6.89 (dd, J = 8.2, 2.4 Hz, 1H), 6.95 (d, J = 2.4 Hz, 1H), 7.20 (d, J = 8.2 Hz, 1H), 7.46 (d, J = 3.6 Hz, 1H) |

6-(4-Isopropylsulfonyloxy-2-methoxyphenyl)-5-(5-methylthiophen-2-ylcarbonyloxymethyl)-2,2,4-trimethyl-1,2-dihydroquinoline (Compound No. 4-29)

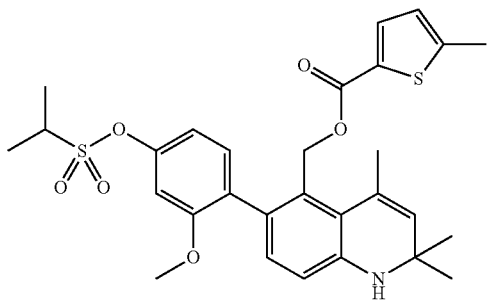 [SMILES: COc1cc(OS(=O)(=O)C(C)C)ccc1-c1ccc2c(c1COC(=O)c1ccc(C)s1)C(C)=CC(C)(C)N2]

$^1$H-NMR (400 MHz, DMSO-d$_6$) δ 1.14 (s, 3H), 1.21 (s, 3H), 1.44 (d, J = 6.8 Hz, 6H), 2.10 (s, 3H), 2.47 (s, 3H), 3.69 (s, 3H), 3.73 (heptet, J = 6.6 Hz, 1H), 4.89 (d, J = 12.7 Hz, 1H), 5.16 (d, J = 12.7 Hz, 1H), 5.45 (s, 1H), 6.13 (s, 1H), 6.66 (d, J = 8.3 Hz, 1H), 6.75 (d, J = 8.3 Hz, 1H), 6.88 (d, J = 3.7 Hz, 1H), 6.89 (dd, J = 8.3, 2.3 Hz, 1H), 6.93 (d, J = 2.3 Hz, 1H), 7.20 (d, J = 8.3 Hz, 1H), 7.46 (d, J = 3.7 Hz, 1H)

6-(4-Cyclopentylsulfonyloxy-2-methoxyphenyl)-5-(5-methylthiophen-2-ylcarbonyloxymethyl)-2,2,4-trimethyl-1,2-dihydroquinoline (Compound No. 4-30)

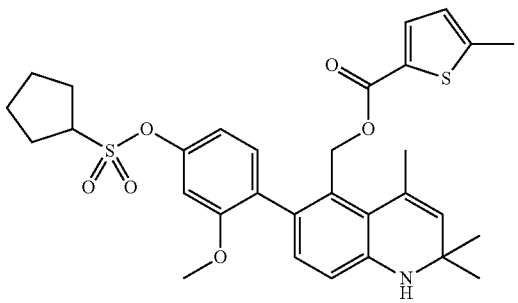 [SMILES: COc1cc(OS(=O)(=O)C2CCCC2)ccc1-c1ccc2c(c1COC(=O)c1ccc(C)s1)C(C)=CC(C)(C)N2]

$^1$H-NMR (500 MHz, DMSO-d$_6$) δ 1.14 (s, 3H), 1.21 (s, 3H), 1.60-1.67 (m, 2H), 1.70-1.77 (m, 2H), 1.97-2.04 (m, 2H), 2.05-2.14 (m, 2H), 2.09 (s, 3H), 2.47 (s, 3H), 3.69 (s, 3H), 3.97 (tt, J = 8.9, 6.9 Hz, 1H), 4.89 (d, J = 12.7 Hz, 1H), 5.15 (d, J = 12.7 Hz, 1H), 5.45 (s, 1H), 6.12 (s, 1H), 6.66 (d, J = 8.2 Hz, 1H), 6.75 (d, J = 8.2 Hz, 1H), 6.88 (d, J = 3.8 Hz, 1H), 6.88 (dd, J = 8.1, 2.6 Hz, 1H), 6.92 (d, J = 2.6 Hz, 1H), 7.19 (d, J = 8.1 Hz, 1H), 7.46 (d, J = 3.8 Hz, 1H)

6-(2-Methoxy-4-methylsulfonyloxyphenyl)-5-(5-methylthiophen-2-ylcarbonyloxymethyl)-2,2,4-trimethyl-1,2-dihydroquinoline (Compound No. 4-31)

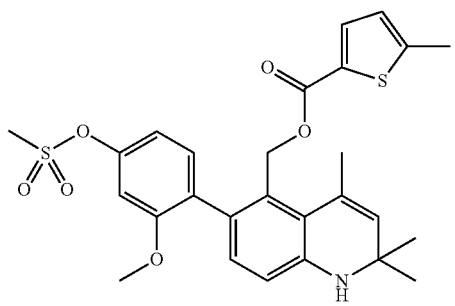

$^1$H-NMR (400 MHz, DMSO-d$_6$) δ 1.14 (s, 3H), 1.21 (s, 3H), 2.10 (s, 3H), 2.47 (s, 3H), 3.39 (s, 3H), 3.68 (s, 3H), 4.91 (d, J = 12.7 Hz, 1H), 5.16 (d, J = 12.7 Hz, 1H), 5.45 (s, 1H), 6.13 (s, 1H), 6.66 (d, J = 8.3 Hz, 1H), 6.76 (d, J = 8.3 Hz, 1H), 6.88 (d, J = 3.8 Hz, 1H), 6.91 (dd, J = 8.3, 2.3 Hz, 1H), 7.01 (d, J = 2.3 Hz, 1H), 7.20 (d, J = 8.3 Hz, 1H), 7.46 (d, J = 3.8 Hz, 1H)

6-(4-Ethylsulfonyloxy-2-methoxyphenyl)-5-(5-methylthiophen-2-ylcarbonyloxymethyl)-2,2,4-trimethyl-1,2-dihydroquinoline (Compound No. 4-32)

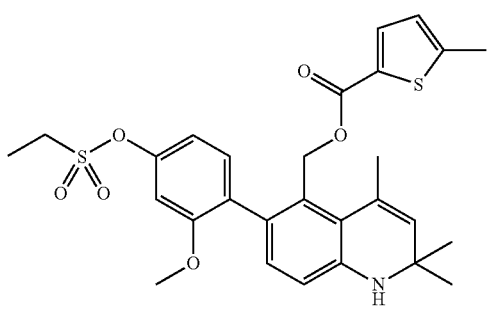 [SMILES: CCS(=O)(=O)Oc1ccc(-c2ccc3c(c2COC(=O)c2ccc(C)s2)C(C)=CC(C)(C)N3)c(OC)c1]

$^1$H-NMR (500 MHz, DMSO-d$_6$) δ 1.14 (s, 3H), 1.21 (s, 3H), 1.38 (t, J = 7.3 Hz, 3H), 2.09 (s, 3H), 2.47 (s, 3H), 3.58 (q, J = 7.3 Hz, 2H), 3.69 (s, 3H), 4.90 (d, J = 12.7 Hz, 1H), 5.15 (d, J = 12.7 Hz, 1H), 5.45 (s, 1H), 6.12 (s, 1H), 6.66 (d, J = 8.2 Hz, 1H), 6.75 (d, J = 8.2 Hz, 1H), 6.88 (d, J = 3.6 Hz, 1H), 6.89 (dd, J = 8.3, 2.3 Hz, 1H), 6.96 (d, J = 2.3 Hz, 1H), 7.20 (d, J = 8.3 Hz, 1H), 7.46 (d, J = 3.6 Hz, 1H)

| Compound | NMR |
|---|---|
| 6-(4-Butylsulfonyloxy-2-methoxyphenyl)-5-(5-methylthiophen-2-ylcarbonyloxymethyl)-2,2,4-trimethyl-1,2-dihydroquinoline (Compound No. 4-33) 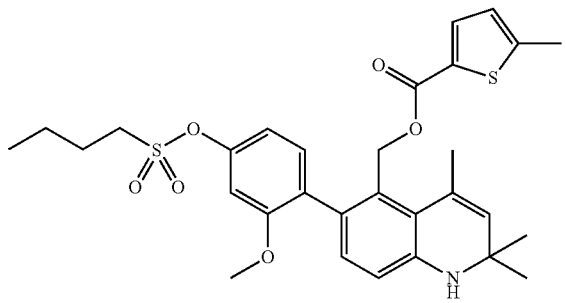 [SMILES: CCCCS(=O)(=O)Oc1ccc(-c2ccc3c(c2COC(=O)c2ccc(C)s2)C(C)=CC(C)(C)N3)c(OC)c1] | $^1$H-NMR (500 MHz, DMSO-$d_6$) δ 0.91 (t, J = 7.3 Hz, 3H), 1.14 (s, 3H), 1.21 (s, 3H), 1.40-1.49 (m, 2H), 1.77-1.84 (m, 2H), 2.10 (s, 3H), 2.47 (s, 3H), 3.50-3.57 (m, 2H), 3.68 (s, 3H), 4.90 (d, J = 12.7 Hz, 1H), 5.15 (d, J = 12.7 Hz, 1H), 5.45 (s, 1H), 6.11 (s, 1H), 6.66 (d, J = 8.2 Hz, 1H), 6.75 (d, J = 8.2 Hz, 1H), 6.88 (d, J = 3.8 Hz, 1H), 6.89 (dd, J = 8.2, 2.1 Hz, 1H), 6.96 (d, J = 2.1 Hz, 1H), 7.20 (d, J = 8.2 Hz, 1H), 7.46 (d, J = 3.8 Hz, 1H) |
| 6-(4-Cyclopropylsulfonyloxy-2-methoxyphenyl)-5-(5-methylthiophen-2-ylcarbonyloxymethyl)-2,2,4-trimethyl-1,2-dihydroquinoline (Compound No. 4-34) 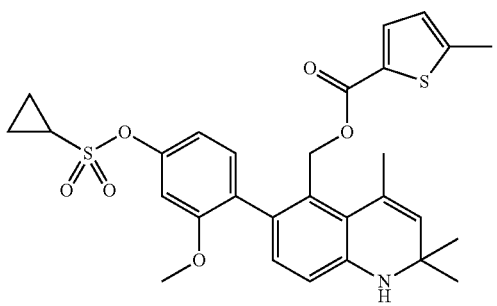 [SMILES: COc1cc(OS(=O)(=O)C2CC2)ccc1-c1ccc2c(c1COC(=O)c1ccc(C)s1)C(C)=CC(C)(C)N2] | $^1$H-NMR (500 MHz, DMSO-$d_6$) δ 0.98-1.04 (m, 2H), 1.12-1.19 (m, 2H), 1.15 (s, 3H), 1.21 (s, 3H), 2.10 (s, 3H), 2.46 (s, 3H), 3.02-3.12 (m, 1H), 3.68 (s, 3H), 4.90 (d, J = 12.5 Hz, 1H), 5.14 (d, J = 12.5 Hz, 1H), 5.45 (s, 1H), 6.11 (s, 1H), 6.66 (d, J = 8.1 Hz, 1H), 6.76 (d, J = 8.1 Hz, 1H), 6.88 (d, J = 3.6 Hz, 1H), 6.91 (dd, J = 8.2, 2.1 Hz, 1H), 7.00 (d, J = 2.1 Hz, 1H), 7.19 (d, J = 8.2 Hz, 1H), 7.46 (d, J = 3.6 Hz, 1H) |
| 6-(2-Methoxy-4-propylsulfonyloxyphenyl)-5-(4-methylbenzoyloxymethyl)-2,2,4-trimethyl-1,2-dihydroquinoline (Compound No. 4-35) 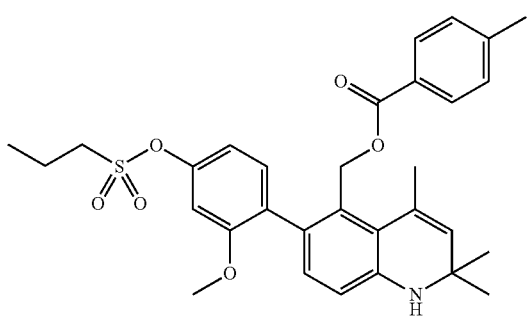 [SMILES: CCCS(=O)(=O)Oc1ccc(-c2ccc3c(c2COC(=O)c2ccc(C)cc2)C(C)=CC(C)(C)N3)c(OC)c1] | $^1$H-NMR (500 MHz, DMSO-$d_6$) δ 1.03 (t, J = 7.3 Hz, 3H), 1.14 (s, 3H), 1.22 (s, 3H), 1.81-1.88 (m, 2H), 2.09 (s, 3H), 2.35 (s, 3H), 3.48-3.51 (m, 2H), 3.68 (s, 3H), 4.96 (d, J = 12.7 Hz, 1H), 5.19 (d, J = 12.7 Hz, 1H), 5.46 (s, 1H), 6.13 (s, 1H), 6.67 (d, J = 8.1 Hz, 1H), 6.76 (d, J = 8.1 Hz, 1H), 6.88 (dd, J = 8.2, 2.3 Hz, 1H), 6.94 (d, J = 2.3 Hz, 1H), 7.21 (d, J = 8.2 Hz, 1H), 7.27 (d, J = 8.2 Hz, 2H), 7.70 (d, J = 8.2 Hz, 2H) |
| 6-(4-Isopropylsulfonyloxy-2-methoxyphenyl)-5-(4-methylbenzoyloxymethyl)-2,2,4-trimethyl-1,2-dihydroquinoline (Compound No. 4-36) 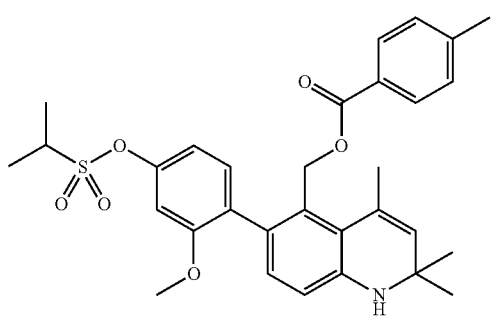 [SMILES: COc1cc(OS(=O)(=O)C(C)C)ccc1-c1ccc2c(c1COC(=O)c1ccc(C)cc1)C(C)=CC(C)(C)N2] | $^1$H-NMR (400 MHz, DMSO-$d_6$) δ 1.14 (s, 3H), 1.23 (s, 3H), 1.43 (d, J = 6.8 Hz, 6H), 2.09 (s, 3H), 2.35 (s, 3H), 3.68 (s, 3H), 3.68-3.75 (m, 1H), 4.96 (d, J = 12.8 Hz, 1H), 5.19 (d, J = 12.8 Hz, 1H), 5.46 (s, 1H), 6.13 (s, 1H), 6.67 (d, J = 8.3 Hz, 1H), 6.77 (d, J = 8.3 Hz, 1H), 6.87 (dd, J = 8.2, 2.3 Hz, 1H), 6.92 (d, J = 2.3 Hz, 1H), 7.21 (d, J = 8.2 Hz, 1H), 7.27 (d, J = 8.2 Hz, 2H), 7.70 (d, J = 8.2 Hz, 2H) |

Example 5

5-(5-Fluoro-2-methylphenoxymethyl)-6-(2-methoxy-4-methoxycarbonyloxyphenyl)-2,2,4-trimethyl-1,2-dihydroquinoline (Compound No. 5-1)

5-(5-Fluoro-2-methylphenoxymethyl)-6-(4-hydroxy-2-methoxyphenyl)-2,2,4-trimethyl-1,2-dihydroquinoline (Reference Compound No. 5-1, 25.0 mg, 0.058 mmol) was dissolved in tetrahydrofuran (0.5 mL), triethylamine (23 μL, 0.17 mmol) and methyl chlorocarbonate (6.8 μL, 0.088 mmol) were added thereto, and then the mixture was stirred at room temperature for 20 minutes. The reaction mixture was purified by silica gel column chromatography (hexane-ethyl acetate) to give the titled compound (28.0 mg) as a colorless amorphous product. (Yield 99%)

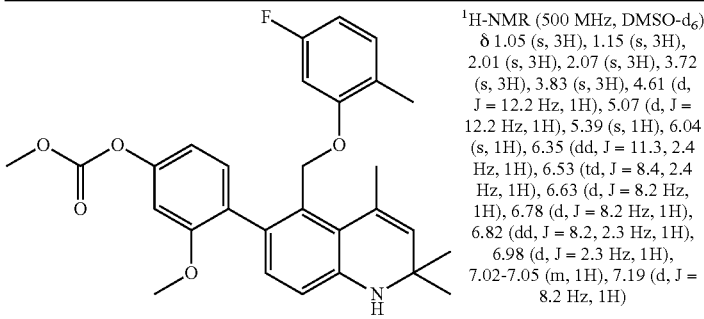

$^{1}$H-NMR (500 MHz, DMSO-$d_6$) δ 1.05 (s, 3H), 1.15 (s, 3H), 2.01 (s, 3H), 2.07 (s, 3H), 3.72 (s, 3H), 3.83 (s, 3H), 4.61 (d, J = 12.2 Hz, 1H), 5.07 (d, J = 12.2 Hz, 1H), 5.39 (s, 1H), 6.04 (s, 1H), 6.35 (dd, J = 11.3, 2.4 Hz, 1H), 6.53 (td, J = 8.4, 2.4 Hz, 1H), 6.63 (d, J = 8.2 Hz, 1H), 6.78 (d, J = 8.2 Hz, 1H), 6.82 (dd, J = 8.2, 2.3 Hz, 1H), 6.98 (d, J = 2.3 Hz, 1H), 7.02-7.05 (m, 1H), 7.19 (d, J = 8.2 Hz, 1H)

Using any compounds among Reference Compounds No. 5-1, 5-4, 5-6 and 5-10, the following Compounds (No. 5-2~5-11) were obtained by a method similar to that of Compound No. 5-1.

5-(5-Fluoro-2-methylphenoxymethyl)-6-(2-methoxy-4-phenoxycarbonyloxyphenyl)-2,2,4-trimethyl-1,2-dihydroquinoline (Compound No. 5-2)

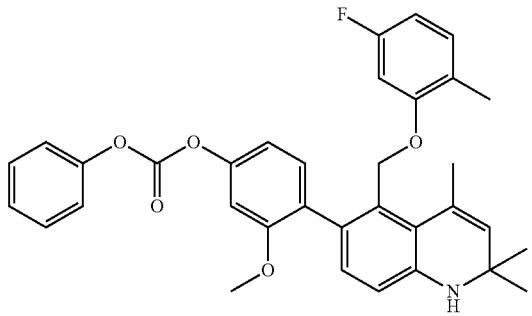 [SMILES: COc1cc(OC(=O)Oc2ccccc2)ccc1-c1ccc2c(c1COc1cc(F)ccc1C)C(C)=CC(C)(C)N2]

$^{1}$H-NMR (500 MHz, DMSO-$d_6$) δ 1.06 (s, 3H), 1.15 (s, 3H), 2.02 (s, 3H), 2.07 (s, 3H), 3.75 (s, 3H), 4.62 (d, J = 12.2 Hz, 1H), 5.08 (d, J = 12.2 Hz, 1H), 5.40 (s, 1H), 6.05 (s, 1H), 6.36 (dd, J = 11.3, 2.4 Hz, 1H), 6.52 (td, J = 8.4, 2.4 Hz, 1H), 6.64 (d, J = 8.2 Hz, 1H), 6.79 (d, J = 8.2 Hz, 1H), 6.97 (dd, J = 8.2, 2.4 Hz, 1H), 7.02-7.05 (m, 1H), 7.14 (d, J = 2.4 Hz, 1H), 7.23 (d, J = 8.2 Hz, 1H), 7.34 (t, J = 7.6 Hz, 1H), 7.39 (d, J = 7.6 Hz, 2H), 7.49 (t, J = 7.6 Hz, 2H)

6-[4-(2-Chlorophenoxycarbonyloxy)-2-methoxyphenyl]-5-(5-fluoro-2-methylphenoxymethyl)-2,2,4-trimethyl-1,2-dihydroquinoline (Compound No. 5-3)

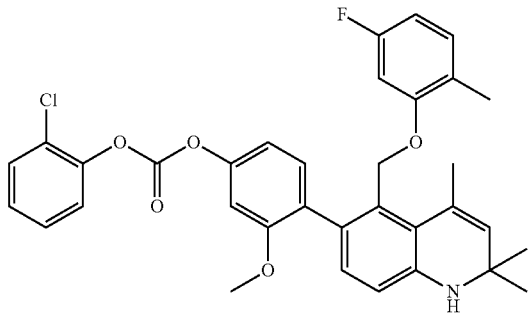 [SMILES: COc1cc(OC(=O)Oc2ccccc2Cl)ccc1-c1ccc2c(c1COc1cc(F)ccc1C)C(C)=CC(C)(C)N2]

1H-NMR (400 MHz, DMSO-$d_6$) δ 1.06 (s, 3H), 1.15 (s, 3H), 2.01 (s, 3H), 2.07 (s, 3H), 3.76 (s, 3H), 4.61 (d, J = 11.9 Hz, 1H), 5.07 (d, J = 11.9 Hz, 1H), 5.40 (s, 1H), 6.06 (s, 1H), 6.37 (dd, J = 11.5, 2.4 Hz, 1H), 6.52 (td, J = 8.4, 2.5 Hz, 1H), 6.64 (d, J = 8.2 Hz, 1H), 6.79 (d, J = 8.2 Hz, 1H), 6.96 (dd, J = 8.3, 2.3 Hz, 1H), 7.01-7.05 (m, 1H), 7.10 (d, J = 2.3 Hz, 1H), 7.25 (d, J = 8.3 Hz, 1H), 7.39 (td, J = 7.9, 1.6 Hz, 1H), 7.48 (td, J = 7.9, 1.7 Hz, 1H), 7.61 (dd, J = 7.9, 1.6 Hz, 1H), 7.66 (dd, J = 7.9, 1.7 Hz, 1H)

5-(5-Fluoro-2-methylphenoxymethyl)-6-[2-methoxy-4-(2-methoxyphenoxycarbonyloxy)phenyl]-2,2,4-trimethyl-1,2-dihydroquinoline (Compound No. 5-4)

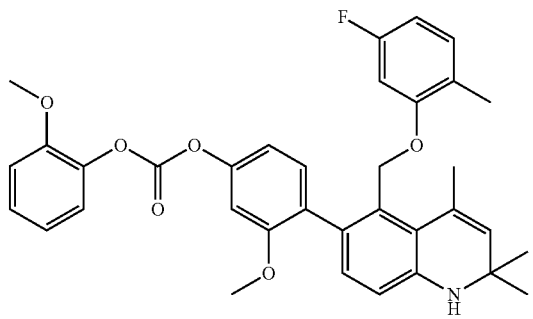

$^1$H-NMR (500 MHz, DMSO-d$_6$) δ 1.06 (s, 3H), 1.15 (s, 3H), 2.01 (s, 3H), 2.07 (s, 3H), 3.76 (s, 3H), 3.86 (s, 3H), 4.62 (d, J = 12.1 Hz, 1H), 5.07 (d, J = 12.1 Hz, 1H), 5.40 (s, 1H), 6.05 (s, 1H), 6.36 (dd, J = 11.3, 2.4 Hz, 1H), 6.52 (td, J = 8.4, 2.4 Hz, 1H), 6.64 (d, J = 8.2 Hz, 1H), 6.78 (d, J = 8.2 Hz, 1H), 6.91 (dd, J = 8.2, 2.3 Hz, 1H), 7.01 (td, J = 8.0, 1.4 Hz, 1H), 7.02-7.05 (m, 1H), 7.05 (d, J = 2.3 Hz, 1H), 7.20 (dd, J = 8.0, 1.4 Hz, 1H), 7.23 (d, J = 8.2 Hz, 1H), 7.31 (td, J = 8.0, 1.6 Hz, 1H), 7.35 (dd, J = 8.0, 1.6 Hz, 1H)

6-(4-Benzyloxycarbonyloxy-2-methoxyphenyl)-5-(5-fluoro-2-methylphenoxymethyl)-2,2,4-trimethyl-1,2-dihydroquinoline (Compound No. 5-5)

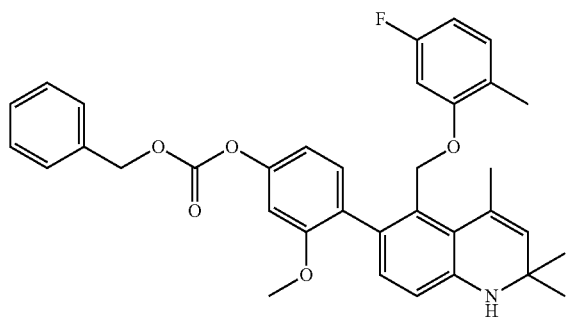 [SMILES: COc1cc(OC(=O)OCc2ccccc2)ccc1-c1ccc2c(c1COc1cc(F)ccc1C)C(C)=CC(C)(C)N2]

$^1$H-NMR (500 MHz, DMSO-d$_6$) δ 1.05 (s, 3H), 1.15 (s, 3H), 2.01 (s, 3H), 2.06 (s, 3H), 3.72 (s, 3H), 4.61 (d, J = 12.1 Hz, 1H), 5.07 (d, J = 12.1 Hz, 1H), 5.27 (s, 2H), 5.39 (s, 1H), 6.04 (s, 1H), 6.35 (dd, J = 11.3, 2.4 Hz, 1H), 6.52 (td, J = 8.4, 2.4 Hz, 1H), 6.63 (d, J = 8.2 Hz, 1H), 6.77 (d, J = 8.2 Hz, 1H), 6.84 (dd, J = 8.2, 2.3 Hz, 1H), 7.00 (d, J = 2.3 Hz, 1H), 7.02-7.05 (m, 1H), 7.19 (d, J = 8.2 Hz, 1H), 7.37-7.47 (m, 5H)

5-(5-Fluoro-2-methylphenoxymethyl)-6-[2-methoxy-4-(2,2,2-trichloroethoxycarbonyloxy)phenyl]-2,2,4-trimethyl-1,2-dihydroquinoline (Compound No. 5-6)

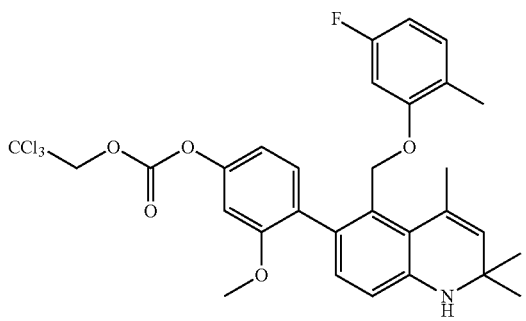

$^1$H-NMR (400 MHz, DMSO-d$_6$) δ 1.06 (s, 3H), 1.15 (s, 3H), 2.01 (s, 3H), 2.06 (s, 3H), 3.74 (s, 3H), 4.61 (d, J = 11.1 Hz, 1H), 5.06 (s, 2H), 5.07 (d, J = 11.1 Hz, 1H), 5.40 (s, 1H), 6.06 (s, 1H), 6.36 (dd, J = 11.5, 2.4 Hz, 1H), 6.53 (td, J = 8.4, 2.4 Hz, 1H), 6.64 (d, J = 8.2 Hz, 1H), 6.78 (d, J = 8.2 Hz, 1H), 6.90 (dd, J = 8.3, 2.2 Hz, 1H), 7.02-7.06 (m, 1H), 7.05 (d, J = 2.2 Hz, 1H), 7.23 (d, J = 8.3 Hz, 1H)

6-[4-(4-Chlorophenoxycarbonyloxy)-2-methoxyphenyl]-5-(2-methoxy-5-nitrophenoxymethyl)-2,2,4-trimethyl-1,2-dihydroquinoline (Compound No. 5-7)

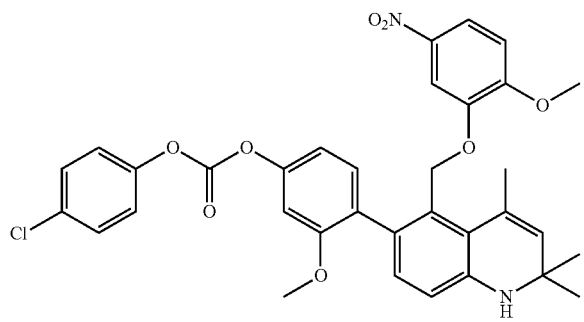 [SMILES: COc1ccc([N+](=O)[O-])cc1OCc1c(-c2ccc(OC(=O)Oc3ccc(Cl)cc3)cc2OC)ccc2c1C(C)=CC(C)(C)N2]

$^1$H-NMR (500 MHz, DMSO-d$_6$) δ 1.05 (s, 3H), 1.18 (s, 3H), 2.14 (s, 3H), 3.71 (s, 3H), 3.81 (s, 3H), 4.65 (d, J = 11.9 Hz, 1H), 5.25 (d, J = 11.9 Hz, 1H), 5.40 (s, 1H), 6.03 (s, 1H), 6.62 (d, J = 8.2 Hz, 1H), 6.76 (d, J = 8.2 Hz, 1H), 6.90 (dd, J = 8.2, 2.3 Hz, 1H), 7.08 (d, J = 9.1 Hz, 1H), 7.10 (d, J = 2.3 Hz, 1H), 7.19 (d, J = 8.2 Hz, 1H), 7.31 (d, J = 2.7 Hz, 1H), 7.43 (d, J = 8.9 Hz, 2H), 7.55 (d, J = 8.9 Hz, 2H), 7.81 (dd, J = 9.1, 2.7 Hz, 1H)

| Compound | NMR |
|---|---|
| 6-(2-Methoxy-4-methoxycarbonyloxyphenyl)-5-(2-methoxyphenylaminomethyl)-2,2,4-trimethyl-1,2-dihydroquinoline (Compound No. 5-8) 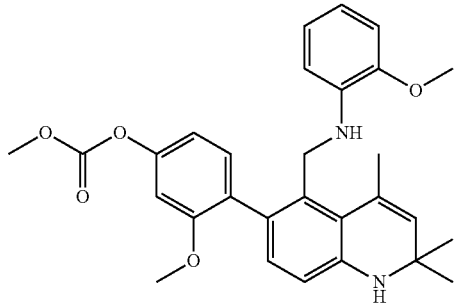 | $^1$H-NMR (500 MHz, DMSO-$d_6$) δ 1.15 (s, 3H), 1.21 (s, 3H), 2.06 (s, 3H), 3.65 (s, 3H), 3.71 (s, 3H), 3.82 (s, 3H), 3.84 (dd, J = 12.8, 3.5 Hz, 1H), 4.01-4.05 (m, 1H), 4.21 (dd, J = 6.6, 3.5 Hz, 1H), 5.39 (s, 1H), 6.00 (s, 1H), 6.34 (dd, J = 7.8, 1.3 Hz, 1H), 6.51 (td, J = 7.8, 1.3 Hz, 1H), 6.60 (d, J = 8.2 Hz, 1H), 6.67 (td, J = 7.8, 1.3 Hz, 1H), 6.70 (d, J = 8.2 Hz, 1H), 6.73 (dd, J = 7.8, 1.3 Hz, 1H), 6.79 (dd, J = 8.2, 2.2 Hz, 1H), 6.89 (d, J = 2.2 Hz, 1H), 7.11 (d, J = 8.2 Hz, 1H) |
| 6-(4-Chlorophenyloxycarbonyloxy-2-methoxyphenyl)-5-(2-methoxyphenylaminomethyl)-2,2,4-trimethyl-1,2-dihydroquinoline (Compound No. 5-9) 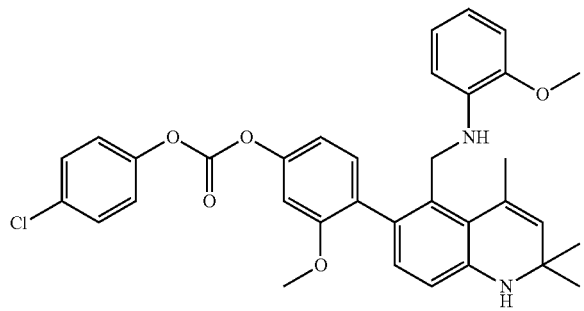 [SMILES: COc1ccccc1NCc1c(-c2ccc(OC(=O)Oc3ccc(Cl)cc3)cc2OC)ccc2c1C(C)=CC(C)(C)N2] | $^1$H-NMR (400 MHz, DMSO-$d_6$) δ 1.15 (s, 3H), 1.21 (s, 3H), 2.07 (s, 3H), 3.68 (s, 3H), 3.71 (s, 3H), 3.84 (dd, J = 12.6, 3.4 Hz, 1H), 4.04 (dd, J = 12.6, 6.5 Hz, 1H), 4.22 (dd, J = 6.5, 3.4 Hz, 1H), 5.39 (s, 1H), 6.02 (s, 1H), 6.35 (dd, J = 7.9, 1.3 Hz, 1H), 6.50 (td, J = 7.9, 1.3 Hz, 1H), 6.61 (d, J = 8.3 Hz, 1H), 6.67 (td, J = 7.9, 1.3 Hz, 1H), 6.71 (d, J = 8.3 Hz, 1H), 6.73 (dd, J = 7.9, 1.3 Hz, 1H), 6.93 (dd, J = 8.1, 2.4 Hz, 1H), 7.06 (d, J = 2.4 Hz, 1H), 7.16 (d, J = 8.1 Hz, 1H), 7.43 (d, J = 9.0 Hz, 2H), 7.54 (d, J = 9.0 Hz, 2H) |
| 6-(2-Methoxy-4-methoxycarbonyloxyphenyl)-5-(5-methylthiophen-2-ylcarbonyloxymethyl)-2,2,4-trimethyl-1,2-dihydroquinoline (Compound No. 5-10) 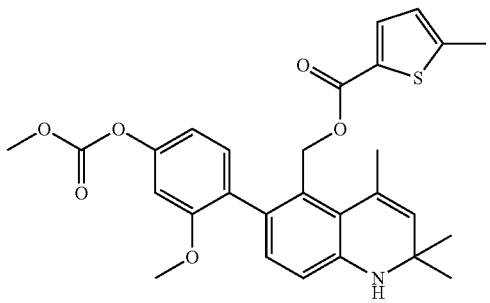 | $^1$H-NMR (400 MHz, DMSO-$d_6$) δ 1.14 (s, 3H), 1.21 (s, 3H), 2.08 (s, 3H), 2.47 (s, 3H), 3.66 (s, 3H), 3.84 (s, 3H), 4.89 (d, J = 12.7 Hz, 1H), 5.16 (d, J = 12.7 Hz, 1H), 5.44 (s, 1H), 6.10 (s, 1H), 6.66 (d, J = 8.3 Hz, 1H), 6.76 (d, J = 8.3 Hz, 1H), 6.80 (dd, J = 8.2, 2.2 Hz, 1H), 6.88 (d, J = 3.7 Hz, 1H), 6.95 (d, J = 2.2 Hz, 1H), 7.15 (d, J = 8.2 Hz, 1H), 7.47 (d, J = 3.7 Hz, 1H) |
| 6-[4-(4-Chlorophenoxycarbonyloxy)-2-methoxyphenyl]-5-(5-fluoro-2-methylphenoxymethyl)-2,2,4-trimethyl-1,2-dihydroquinoline (Compound No. 5-11) 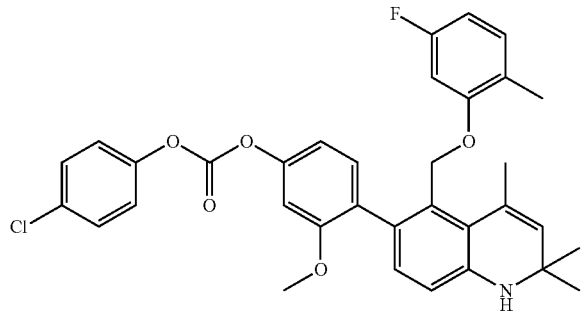 [SMILES: COc1cc(OC(=O)Oc2ccc(Cl)cc2)ccc1-c1ccc2c(c1COc1cc(F)ccc1C)C(C)=CC(C)(C)N2] | $^1$H-NMR (500 MHz, DMSO-$d_6$) δ 1.06 (s, 3H), 1.15 (s, 3H), 2.01 (s, 3H), 2.07 (s, 3H), 3.75 (s, 3H), 4.61 (d, J = 12.1 Hz, 1H), 5.07 (d, J = 12.1 Hz, 1H), 5.40 (s, 1H), 6.05 (s, 1H), 6.36 (dd, J = 11.3, 2.4 Hz, 1H), 6.52 (td, J = 8.4, 2.4 Hz, 1H), 6.64 (d, J = 8.1 Hz, 1H), 6.79 (d, J = 8.1 Hz, 1H), 6.97 (dd, J = 8.2, 2.4 Hz, 1H), 7.02-7.05 (m, 1H), 7.15 (d, J = 2.4 Hz, 1H), 7.23 (d, J = 8.2 Hz, 1H), 7.45 (d, J = 9.1 Hz, 2H), 7.55 (d, J = 9.1 Hz, 2H) |

Example 6

5-(5-Fluoro-2-methylphenoxymethyl)-6-(2-methoxy-4-phenylaminocarbonyloxyphenyl)-2,2,4-trimethyl-1,2-dihydroquinoline (Compound No. 6-1)

5-(5-Fluoro-2-methylphenoxymethyl)-6-(4-hydroxy-2-methoxyphenyl)-2,2,4-trimethyl-1,2-dihydroquinoline (Reference Compound No. 5-1, 25.0 mg, 0.058 mmol) was dissolved in tetrahydrofuran (0.5 mL), triethylamine (19.3 μL, 0.138 mmol) and phenyl isocyanate (9.5 μL, 0.087 mmol) were added thereto, and then the mixture was stirred at room temperature for 2 hours. The reaction mixture was purified by silica gel column chromatography (hexane-ethyl acetate) to give the titled compound (27.3 mg) as a colorless amorphous product. (Yield 86%)

Compound No. 6, 25.0 mg, 0.0383 mmol), 1,1'-carbonyldiimidazole (62.0 mg, 0.382 mmol) and 4-dimethylaminopyridine (0.5 mg, 0.004 mmol) was dissolved in anhydrous tetrahydrofuran (1 mL), and then the mixture was stirred at room temperature for 4.5 hours. N,N,N'-Trimethylethylenediamine (39.2 mg, 0.383 mmol) was added thereto, the mixture was stirred at 60° C. for 2 hours. The reaction mixture was purified by silica gel column chromatography (hexane-ethyl acetate). The obtained colorless amorphous product was dissolved in N, N-dimethylformamide (1 mL) and piperidine (50 μL) was added thereto. After the reaction mixture was stirred

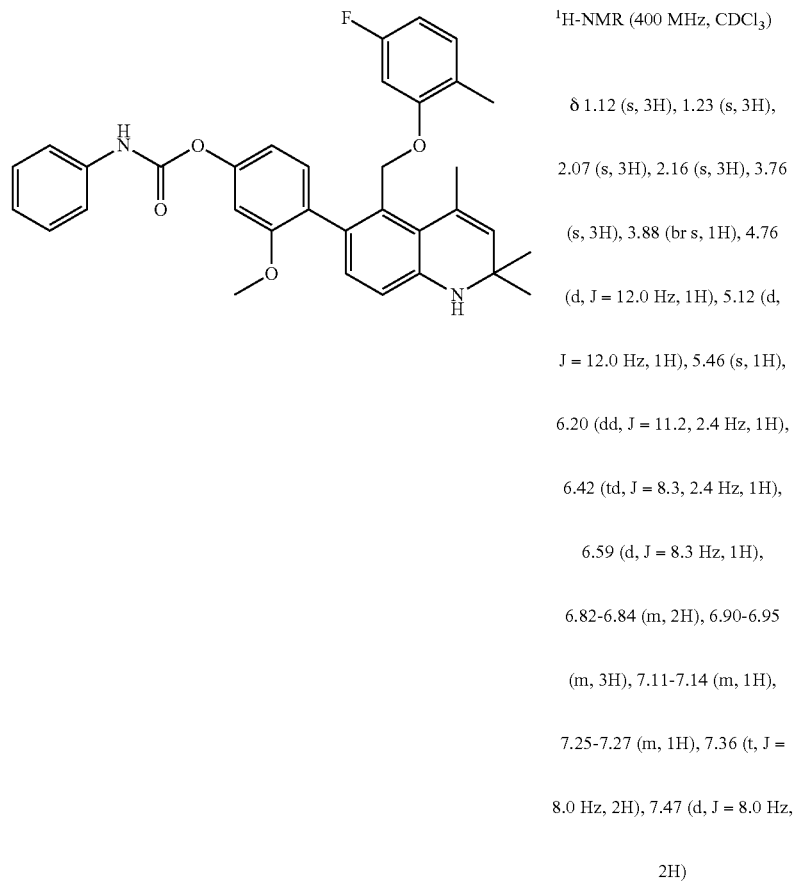

$^1$H-NMR (400 MHz, CDCl$_3$)

δ 1.12 (s, 3H), 1.23 (s, 3H), 2.07 (s, 3H), 2.16 (s, 3H), 3.76 (s, 3H), 3.88 (br s, 1H), 4.76 (d, J = 12.0 Hz, 1H), 5.12 (d, J = 12.0 Hz, 1H), 5.46 (s, 1H), 6.20 (dd, J = 11.2, 2.4 Hz, 1H), 6.42 (td, J = 8.3, 2.4 Hz, 1H), 6.59 (d, J = 8.3 Hz, 1H), 6.82-6.84 (m, 2H), 6.90-6.95 (m, 3H), 7.11-7.14 (m, 1H), 7.25-7.27 (m, 1H), 7.36 (t, J = 8.0 Hz, 2H), 7.47 (d, J = 8.0 Hz, 2H)

6-[4-[N-(2-Dimethylaminoethyl)-N-methylaminocarbonyloxy]-2-methoxyphenyl]-5-(2-methoxylphenylaminomethyl)-2,2,4-trimethyl-1,2-dihydroquinoline (Compound No. 6-2)

A mixture of 6-(4-hydroxy-2-methoxyphenyl)-5-[N-(2-methoxyphenyl)-N-(9-fluorenylmethoxycarbonyl)aminomethyl]-2,2,4-trimethyl-1,2-dihydroquinoline (Reference Compound No. 6, 25.0 mg, 0.0383 mmol), 1,1'-carbonyldiimidazole at room temperature for 15 minutes, the mixture was diluted with ethyl acetate (20 mL). The mixture was washed with water (15 mL) and saturated brine (15 mL) successively, dried over anhydrous magnesium sulfate, and then the solvent was removed under reduced pressure. The obtained residue was purified by silica gel column chromatography (hexane-ethyl acetate) to give the titled compound (9.9 mg) as a colorless amorphous product. (Yield 47%)

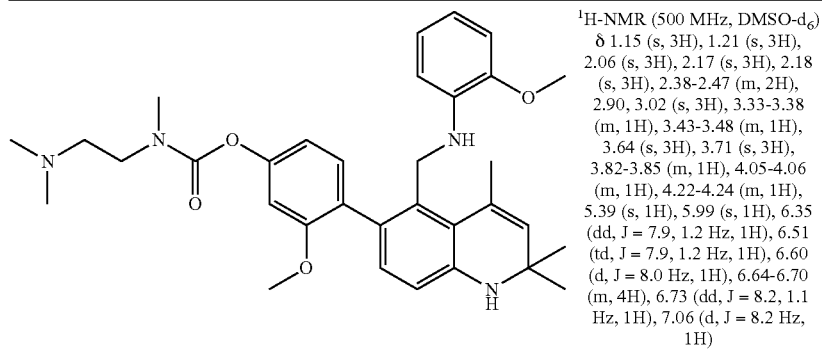

¹H-NMR (500 MHz, DMSO-d₆)
δ 1.15 (s, 3H), 1.21 (s, 3H), 2.06 (s, 3H), 2.17 (s, 3H), 2.18 (s, 3H), 2.38-2.47 (m, 2H), 2.90, 3.02 (s, 3H), 3.33-3.38 (m, 1H), 3.43-3.48 (m, 1H), 3.64 (s, 3H), 3.71 (s, 3H), 3.82-3.85 (m, 1H), 4.05-4.06 (m, 1H), 4.22-4.24 (m, 1H), 5.39 (s, 1H), 5.99 (s, 1H), 6.35 (dd, J = 7.9, 1.2 Hz, 1H), 6.51 (td, J = 7.9, 1.2 Hz, 1H), 6.60 (d, J = 8.0 Hz, 1H), 6.64-6.70 (m, 4H), 6.73 (dd, J = 8.2, 1.1 Hz, 1H), 7.06 (d, J = 8.2 Hz, 1H)

6-(4-Dimethylaminocarbonyloxy-2-methoxyphenyl)-5-(5-fluoro-2-methylphenoxymethyl)-2,2,4-trimethyl-1,2-dihydroquinoline (Compound No. 6-3)

5-(5-Fluoro-2-methylphenoxymethyl)-6-(4-hydroxy-2-methoxyphenyl)-2,2,4-trimethyl-1,2-dihydroquinoline (Reference Compound No. 5-1, 25 mg, 0.058 mmol) was dissolved in pyridine (1 mL), N,N-dimethylcarbamoyl chloride (6.9 μL, 0.075 mmol) was added thereto, and then the mixture was stirred at 100° C. for 3 hours. N,N-Dimethylcarbamoyl chloride (3.0 μL, 0.033 mmol) was added to the reaction mixture and the mixture was stirred at 100° C. for 1 hour. The reaction mixture was diluted with ethyl acetate (20 mL). The mixture was washed with 0.2 N aqueous HCl solution (75 mL), water (50 mL), and saturated brine (50 mL) successively, dried over anhydrous magnesium sulfate, and then the solvent was removed under reduced pressure. The obtained residue was purified by silica gel column chromatography (1ˢᵗ time: hexane-ethyl acetate, 2ⁿᵈ time: toluene-ethyl acetate) to give the titled compound (8.5 mg) as a colorless amorphous product. (Yield 29%)

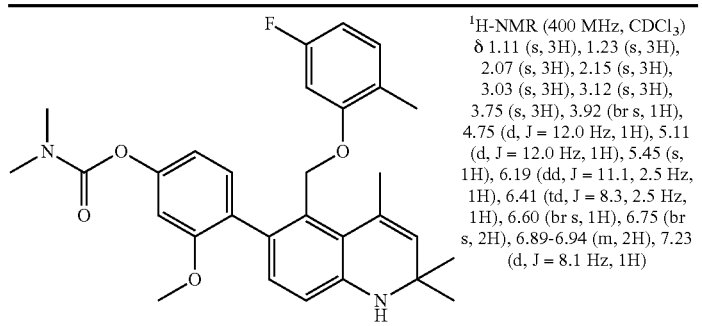

¹H-NMR (400 MHz, CDCl₃)
δ 1.11 (s, 3H), 1.23 (s, 3H), 2.07 (s, 3H), 2.15 (s, 3H), 3.03 (s, 3H), 3.12 (s, 3H), 3.75 (s, 3H), 3.92 (br s, 1H), 4.75 (d, J = 12.0 Hz, 1H), 5.11 (d, J = 12.0 Hz, 1H), 5.45 (s, 1H), 6.19 (dd, J = 11.1, 2.5 Hz, 1H), 6.41 (td, J = 8.3, 2.5 Hz, 1H), 6.60 (br s, 1H), 6.75 (br s, 2H), 6.89-6.94 (m, 2H), 7.23 (d, J = 8.1 Hz, 1H)

Using any compounds among Reference Compounds No. 5-1, 5-3~5-6 and 5-10~5-11, the following Compounds (No. 6-4~6-39) were obtained by a method similar to those of Compounds No. 6-1~6-3.

6-[4-(2-Chlorophenylaminocarbonyloxy)-2-methoxyphenyl]-5-(5-fluoro-2-methylphenoxymethyl)-2,2,4-trimethyl-1,2-dihydroquinoline (Compound No. 6-4)

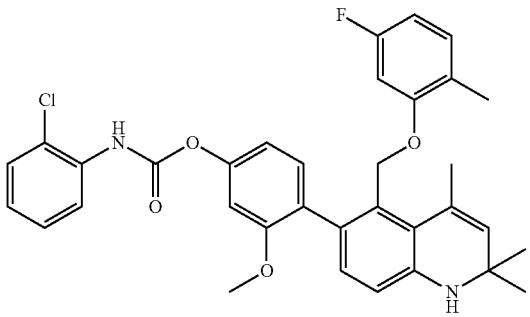 [SMILES: COc1cc(OC(=O)Nc2ccccc2Cl)ccc1-c1ccc2c(c1COc1cc(F)ccc1C)C(C)=CC(C)(C)N2]

¹H-NMR (400 MHz, CDCl₃)
δ 1.13 (s, 3H), 1.23 (s, 3H), 2.08 (s, 3H), 2.16 (s, 3H), 3.77 (s, 3H), 3.88 (br s, 1H), 4.76 (d, J = 12.1 Hz, 1H), 5.12 (d, J = 12.1 Hz, 1H), 5.46 (s, 1H), 6.20 (dd, J = 11.2, 2.5 Hz, 1H), 6.43 (td, J = 8.4, 2.5 Hz, 1H), 6.59 (d, J = 8.2 Hz, 1H), 6.84 (d, J = 2.4 Hz, 1H), 6.85 (dd, J = 8.2, 2.4 Hz, 1H), 6.91 (d, J = 8.2 Hz, 1H), 6.92-6.96 (m, 1H), 7.03-7.08 (m, 1H), 7.28 (d, J = 8.2 Hz, 1H), 7.29-7.33 (m, 1H), 7.40 (dd, J = 8.1, 1.5 Hz, 1H), 7.50 (br s, 1H), 8.21 (d, J = 7.1 Hz, 1H)

6-[4-(3-Chlorophenylaminocarbonyloxy)-2-methoxyphenyl]-5-(5-fluoro-2-methylphenoxymethyl)-2,2,4-trimethyl-1,2-dihydroquinoline (Compound No. 6-5)

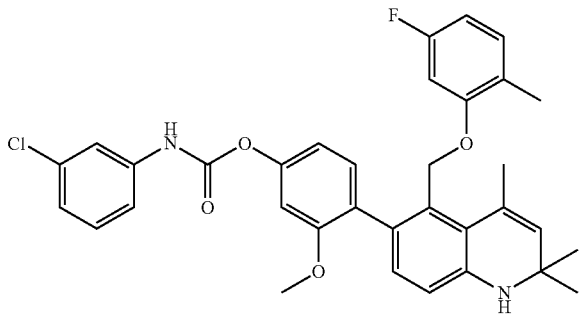 [SMILES: COc1cc(OC(=O)Nc2cccc(Cl)c2)ccc1-c1ccc2c(c1COc1cc(F)ccc1C)C(C)=CC(C)(C)N2]

$^1$H-NMR (400 MHz, CDCl$_3$) δ 1.12 (s, 3H), 1.23 (s, 3H), 2.07 (s, 3H), 2.16 (s, 3H), 3.76 (s, 3H), 3.88 (br s, 1H), 4.75 (d, J = 12.0 Hz, 1H), 5.12 (d, J = 12.0 Hz, 1H), 5.46 (s, 1H), 6.20 (dd, J = 11.2, 2.4 Hz, 1H), 6.42 (td, J = 8.3, 2.4 Hz, 1H), 6.59 (d, J = 8.1 Hz, 1H), 6.81-6.83 (m, 2H), 6.91 (d, J = 8.1 Hz, 1H), 6.92-6.95 (m, 1H), 7.09-7.11 (m, 1H), 7.25-7.32 (m, 4H), 7.58 (br s, 1H)

6-[4-(4-Chlorophenylaminocarbonyloxy)-2-methoxyphenyl]-5-(5-fluoro-2-methylphenoxymethyl)-2,2,4-trimethyl-1,2-dihydroquinoline (Compound No. 6-6)

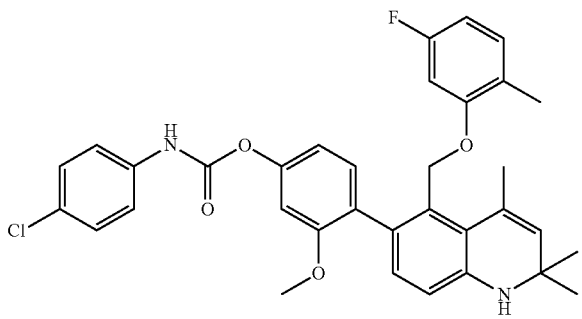 [SMILES: COc1cc(OC(=O)Nc2ccc(Cl)cc2)ccc1-c1ccc2c(c1COc1cc(F)ccc1C)C(C)=CC(C)(C)N2]

$^1$H-NMR (500 MHz, CDCl$_3$) δ 1.12 (s, 3H), 1.23 (s, 3H), 2.07 (s, 3H), 2.16 (s, 3H), 3.76 (s, 3H), 3.87 (br s, 1H), 4.75 (d, J = 12.2 Hz, 1H), 5.11 (d, J = 12.2 Hz, 1H), 5.46 (s, 1H), 6.20 (dd, J = 11.3, 2.4 Hz, 1H), 6.42 (td, J = 8.2, 2.4 Hz, 1H), 6.59 (d, J = 8.1 Hz, 1H), 6.81 (d, J = 1.9 Hz, 1H), 6.82 (dd, J = 6.9, 1.9 Hz, 1H), 6.90 (d, J = 8.1 Hz, 1H), 6.92-6.95 (m, 1H), 7.25-7.27 (m, 2H), 7.32 (d, J = 8.7 Hz, 2H), 7.42 (d, J = 8.7 Hz, 2H)

5-(5-Fluoro-2-methylphenoxymethyl)-6-[2-methoxy-4-(pyridin-3-ylaminocarbonyloxy)phenyl]-2,2,4-trimethyl-1,2-dihydroquinoline (Compound No. 6-7)

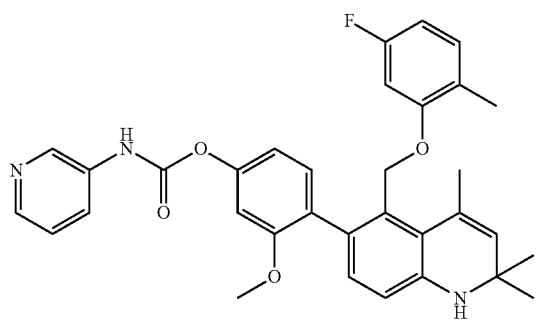 [SMILES: COc1cc(OC(=O)Nc2cccnc2)ccc1-c1ccc2c(c1COc1cc(F)ccc1C)C(C)=CC(C)(C)N2]

$^1$H-NMR (500 MHz, CDCl$_3$) δ 1.13 (s, 3H), 1.23 (s, 3H), 2.07 (s, 3H), 2.16 (s, 3H), 3.76 (s, 3H), 3.91 (br s, 1H), 4.75 (d, J = 12.1 Hz, 1H), 5.12 (d, J = 12.1 Hz, 1H), 5.46 (s, 1H), 6.20 (dd, J = 11.0, 2.5 Hz, 1H), 6.43 (td, J = 8.3, 2.5 Hz, 1H), 6.59 (d, J = 8.2 Hz, 1H), 6.82 (d, J = 2.3 Hz, 1H), 6.83 (dd, J = 8.1, 2.3 Hz, 1H), 6.90 (d, J = 8.2 Hz, 1H), 6.92-6.95 (m, 1H), 7.07 (br s, 1H), 7.27 (d, J = 8.1 Hz, 1H), 7.31 (dd, J = 7.5, 4.9 Hz, 1H), 8.07 (d, J = 7.5 Hz, 1H), 8.38 (dd, J = 4.9, 1.8 Hz, 1H), 8.59 (d, J = 1.8 Hz, 1H)

5-(5-Fluoro-2-methylphenoxymethyl)-6-[2-methoxy-4-(2-methoxyphenylaminocarbonyloxy)phenyl]-2,2,4-trimethyl-1,2-dihydroquinoline (Compound No. 6-8)

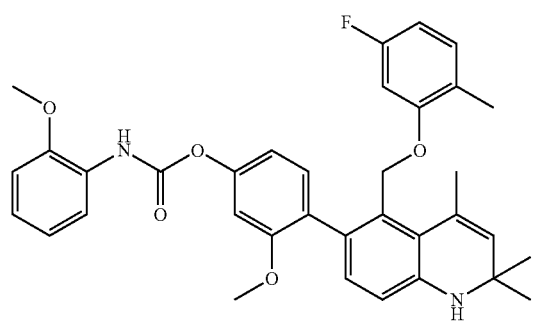

$^1$H-NMR (500 MHz, CDCl$_3$) δ 1.12 (s, 3H), 1.23 (s, 3H), 2.07 (s, 3H), 2.16 (s, 3H), 3.76 (s, 3H), 3.85 (br s, 1H), 3.92 (s, 3H), 4.76 (d, J = 12.2 Hz, 1H), 5.12 (d, J = 12.2 Hz, 1H), 5.45 (s, 1H), 6.20 (dd, J = 11.3, 2.4 Hz, 1H), 6.42 (td, J = 8.2, 2.4 Hz, 1H), 6.59 (d, J = 7.9 Hz, 1H), 6.83-6.85 (m, 2H), 6.90-6.95 (m, 2H), 6.91 (d, J = 7.9 Hz, 1H), 6.99 (td, J = 7.8, 1.3 Hz, 1H), 7.05 (td, J = 7.8, 1.6 Hz, 1H), 7.25-7.27 (m, 1H), 7.60 (br s, 1H), 8.12 (br s, 1H)

5-(5-Fluoro-2-methylphenoxymethyl)-6-[2-methoxy-4-(3-methoxyphenylaminocarbonyloxy)phenyl]-2,2,4-trimethyl-1,2-dihydroquinoline (Compound No. 6-9)

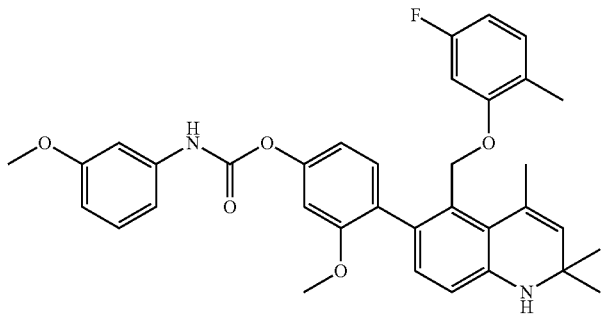

$^1$H-NMR (400 MHz, CDCl$_3$)
δ 1.12 (s, 3H), 1.23 (s, 3H), 2.07 (s, 3H), 2.16 (s, 3H), 3.76 (s, 3H), 3.81 (s, 3H), 3.86 (br s, 1H), 4.75 (d, J = 12.0 Hz, 1H), 5.12 (d, J = 12.0 Hz, 1H), 5.45 (s, 1H), 6.20 (dd, J = 11.1, 2.5 Hz, 1H), 6.42 (td, J = 8.3, 2.5 Hz, 1H), 6.59 (d, J = 8.1 Hz, 1H), 6.68 (dd, J = 7.9, 2.1 Hz, 1H), 6.81-6.84 (m, 2H), 6.90 (d, J = 8.3 Hz, 1H), 6.91-6.95 (m, 3H), 7.22-7.28 (m, 3H)

5-(5-Fluoro-2-methylphenoxymethyl)-6-[2-methoxy-4-(4-methoxyphenylaminocarbonyloxy)phenyl]-2,2,4-trimethyl-1,2-dihydroquinoline (Compound No. 6-10)

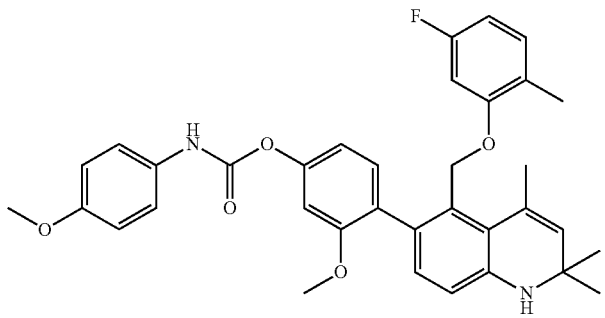

$^1$H-NMR (400 MHz, CDCl$_3$)
δ 1.12 (s, 3H), 1.23 (s, 3H), 2.07 (s, 3H), 2.16 (s, 3H), 3.76 (s, 3H), 3.81 (s, 3H), 3.86 (br s, 1H), 4.75 (d, J = 12.0 Hz, 1H), 5.12 (d, J = 12.0 Hz, 1H), 5.45 (s, 1H), 6.20 (dd, J = 11.2, 2.4 Hz, 1H), 6.42 (td, J = 8.3, 2.4 Hz, 1H), 6.59 (d, J = 8.1 Hz, 1H), 6.81-6.83 (m, 3H), 6.88-6.95 (m, 3H), 6.91 (d, J = 8.1 Hz, 1H), 7.24-7.27 (m, 1H), 7.38 (d, J = 8.3 Hz, 2H)

5-(5-Fluoro-2-methylphenoxymethyl)-6-[2-methoxy-4-(4-methoxycarbonylphenylaminocarbonyloxy)phenyl]-2,2,4-trimethyl-1,2-dihydroquinoline (Compound No. 6-11)

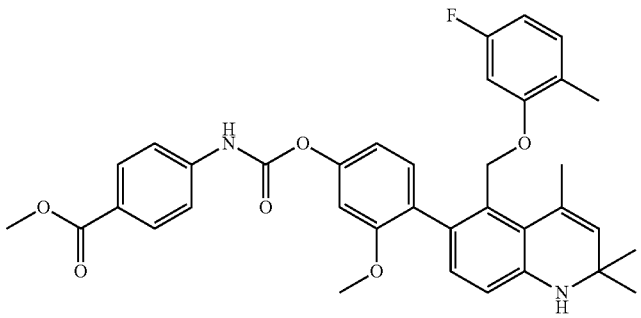

$^1$H-NMR (400 MHz, CDCl$_3$)
δ 1.12 (s, 3H), 1.23 (s, 3H), 2.08 (s, 3H), 2.16 (s, 3H), 3.77 (s, 3H), 3.87 (br s, 1H), 3.91 (s, 3H), 4.75 (d, J = 12.1 Hz, 1H), 5.12 (d, J = 12.1 Hz, 1H), 5.46 (s, 1H), 6.20 (dd, J = 11.2, 2.4 Hz, 1H), 6.43 (td, J = 8.3, 2.4 Hz, 1H), 6.59 (d, J = 8.1 Hz, 1H), 6.82 (d, J = 1.9 Hz, 1H), 6.83 (dd, J = 7.1, 1.9 Hz, 1H), 6.91 (d, J = 8.1 Hz, 1H), 6.92-6.96 (m, 1H), 7.12 (br s, 1H), 7.28 (d, J = 7.1 Hz, 1H), 7.54 (d, J = 8.8 Hz, 2H), 8.05 (d, J = 8.8 Hz, 2H)

5-(5-Fluoro-2-methylphenoxymethyl)-6-[2-methoxy-4-(4-methylphenylaminocarbonyloxy)phenyl]-2,2,4-trimethyl-1,2-dihydroquinoline (Compound No. 6-12)

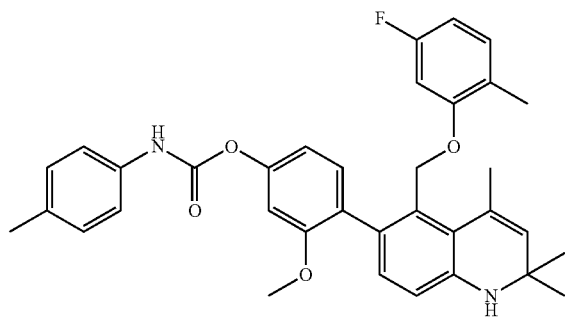

$^1$H-NMR (500 MHz, CDCl$_3$)
δ 1.12 (s, 3H), 1.23 (s, 3H), 2.07 (s, 3H), 2.16 (s, 3H), 2.33 (s, 3H), 3.76 (s, 3H), 3.89 (br s, 1H), 4.76 (d, J = 12.1 Hz, 1H), 5.12 (d, J = 12.1 Hz, 1H), 5.45 (s, 1H), 6.20 (dd, J = 11.0, 2.4 Hz, 1H), 6.42 (td, J = 8.4, 2.4 Hz, 1H), 6.59 (d, J = 7.9 Hz, 1H), 6.82-6.83 (m, 2H), 6.87 (br s, 1H), 6.90-6.95 (m, 2H), 7.15 (d, J = 7.9 Hz, 2H), 7.25 (d, J = 7.0 Hz, 1H), 7.35 (d, J = 7.9 Hz, 2H)

6-[4-(4-Cyanophenylaminocarbonyloxy)-2-methoxyphenyl]-5-(5-fluoro-2-methylphenoxymethyl)-2,2,4-trimethyl-1,2-dihydroquinoline (Compound No. 6-13)

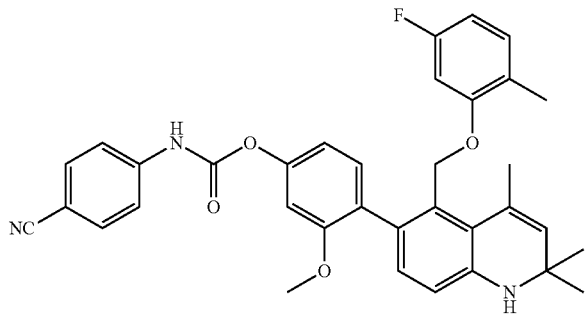 [SMILES: COc1cc(OC(=O)Nc2ccc(C#N)cc2)ccc1-c1ccc2c(c1COc1cc(F)ccc1C)C(C)=CC(C)(C)N2]

$^1$H-NMR (500 MHz, CDCl$_3$) δ 1.13 (s, 3H), 1.23 (s, 3H), 2.07 (s, 3H), 2.16 (s, 3H), 3.76 (s, 3H), 3.91 (br s, 1H), 4.74 (d, J = 11.9 Hz, 1H), 5.11 (d, J = 11.9 Hz, 1H), 5.46 (s, 1H), 6.19 (dd, J = 11.2, 2.5 Hz, 1H), 6.43 (td, J = 8.2, 2.5 Hz, 1H), 6.59 (d, J = 8.2 Hz, 1H), 6.81-6.83 (m, 2H), 6.90 (d, J = 8.2 Hz, 1H), 6.92-6.95 (m, 1H), 7.16 (br s, 1H), 7.28 (d, J = 8.2 Hz, 1H), 7.60 (d, J = 8.9 Hz, 2H), 7.65 (d, J = 8.9 Hz, 2H)

5-(5-Fluoro-2-methylphenoxymethyl)-6-[2-methoxy-4-(piperidin-1-ylcarbonyloxy)phenyl]-2,2,4-trimethyl-1,2-dihydroquinoline (Compound No. 6-14)

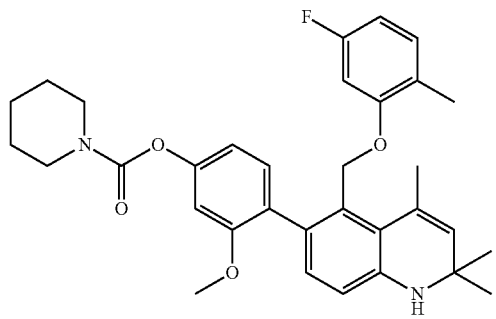 [SMILES: COc1cc(OC(=O)N2CCCCC2)ccc1-c1ccc2c(c1COc1cc(F)ccc1C)C(C)=CC(C)(C)N2]

$^1$H-NMR (400 MHz, DMSO-d$_6$) δ 1.04 (s, 3H), 1.14 (s, 3H), 1.55 (br s, 6H), 2.02 (s, 3H), 2.07 (s, 3H), 3.41 (br s, 2H), 3.55 (br s, 2H), 3.71 (s, 3H), 4.61 (d, J = 12.2 Hz, 1H), 5.08 (d, J = 12.2 Hz, 1H), 5.39 (s, 1H), 6.02 (s, 1H), 6.34 (dd, J = 11.2, 2.4 Hz, 1H), 6.52 (td, J = 8.4, 2.4 Hz, 1H), 6.63 (d, J = 8.3 Hz, 1H), 6.71 (dd, J = 8.2, 2.2 Hz, 1H), 6.77 (d, J = 8.3 Hz, 1H), 6.83 (d, J = 2.2 Hz, 1H), 7.01-7.05 (m, 1H), 7.14 (d, J = 8.2 Hz, 1H)

6-(4-Isopropylaminocarbonyloxy-2-methoxyphenyl)-5-(5-fluoro-2-methylphenoxymethyl)-2,2,4-trimethyl-1,2-dihydroquinoline (Compound No. 6-15)

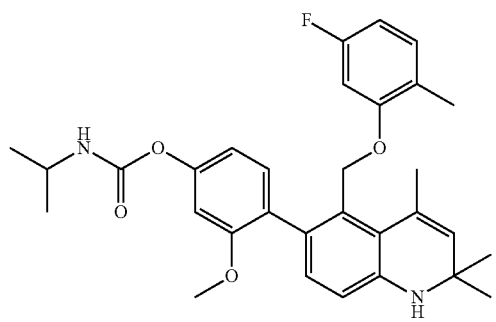 [SMILES: COc1cc(OC(=O)NC(C)C)ccc1-c1ccc2c(c1COc1cc(F)ccc1C)C(C)=CC(C)(C)N2]

$^1$H-NMR (400 MHz, DMSO-d$_6$) δ 1.03 (s, 3H), 1.13 (d, J = 6.6 Hz, 6H), 1.14 (s, 3H), 2.01 (s, 3H), 2.07 (s, 3H), 3.64-3.68 (m, 1H), 3.71 (s, 3H), 4.63 (d, J = 12.3 Hz, 1H), 5.08 (d, J = 12.3 Hz, 1H), 5.39 (s, 1H), 6.02 (s, 1H), 6.32 (dd, J = 11.6, 2.4 Hz, 1H), 6.52 (td, J = 8.4, 2.4 Hz, 1H), 6.62 (d, J = 8.2 Hz, 1H), 6.69 (dd, J = 8.1, 2.2 Hz, 1H), 6.77 (d, J = 8.2 Hz, 1H), 6.80 (d, J = 2.2 Hz, 1H), 7.01-7.05 (m, 1H), 7.13 (d, J = 8.1 Hz, 1H), 7.67 (d, J = 7.8 Hz, 1H)

6-[2-Methoxy-4-(morpholin-4-ylcarbonyloxy)phenyl]-5-(2-methoxy-5-nitrophenoxymethyl)-2,2,4-trimethyl-1,2-dihydroquinoline (Compound No. 6-16)

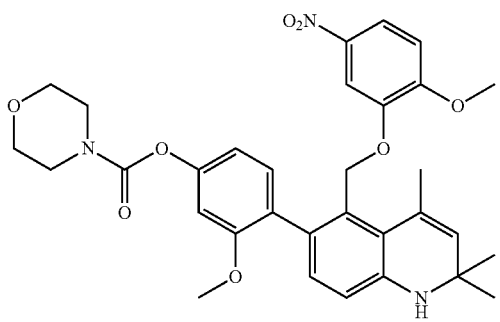 [SMILES: COc1ccc([N+](=O)[O-])cc1OCc1c(-c2ccc(OC(=O)N3CCOCC3)cc2OC)ccc2c1C(C)=CC(C)(C)N2]

$^1$H-NMR (500 MHz, DMSO-d$_6$) δ 1.03 (s, 3H), 1.18 (s, 3H), 2.14 (s, 3H), 3.41-3.64 (m, 8H), 3.68 (s, 3H), 3.82 (s, 3H), 4.66 (d, J = 11.9 Hz, 1H), 5.25 (d, J = 11.9 Hz, 1H), 5.39 (s, 1H), 6.01 (s, 1H), 6.61 (d, J = 8.2 Hz, 1H), 6.66 (dd, J = 8.2, 2.3 Hz, 1H), 6.75 (d, J = 8.2 Hz, 1H), 6.81 (d, J = 2.3 Hz, 1H), 7.08 (d, J = 9.0 Hz, 1H), 7.12 (d, J = 8.2 Hz, 1H), 7.30 (d, J = 2.7 Hz, 1H), 7.81 (dd, J = 9.0, 2.7 Hz, 1H)

| Compound | NMR |
|---|---|
| 6-[4-[N-(2-Diethylaminoethyl)-N-methylaminocarbonyloxy]-2-methoxyphenyl]-5-(5-fluoro-2-methylphenoxymethyl)-2,2,4-trimethyl-1,2-dihydroquinoline (Compound No. 6-17)<br>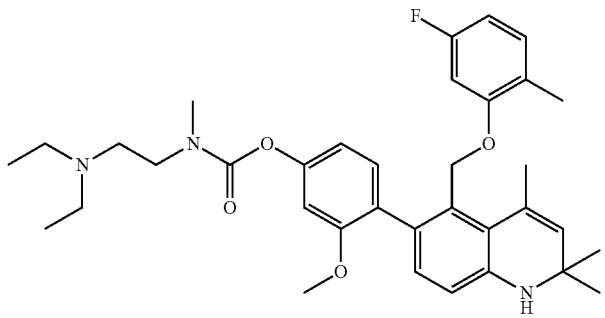 [SMILES: CCN(CC)CCN(C)C(=O)Oc1ccc(-c2ccc3c(c2COc2cc(F)ccc2C)C(C)=CC(C)(C)N3)c(OC)c1] | $^1$H-NMR (400 MHz, CDCl$_3$) δ 1.06 (t, J = 7.2 Hz, 6H), 1.11 (s, 3H), 1.22 (s, 3H), 2.07 (s, 3H), 2.15 (s, 3H), 2.59 (q, J = 7.2 Hz, 4H), 2.66-2.73 (m, 2H), 3.05, 3.14 (s, 3H), 3.42-3.52 (m, 2H), 3.75 (s, 3H), 4.76 (d, J = 11.5 Hz, 1H), 5.11 (d, J = 11.5 Hz, 1H), 5.44 (s, 1H), 6.19 (dd, J = 11.2, 2.3 Hz, 1H), 6.41 (td, J = 8.3, 2.3 Hz, 1H), 6.57 (d, J = 8.1 Hz, 1H), 6.73-6.77 (m, 2H), 6.88-6.94 (m, 2H), 7.22 (d, J = 8.3 Hz, 1H) |
| 6-[4-[N-Benzyl-N-(2-dimethylaminoethyl)aminocarbonyloxy]-2-methoxyphenyl]-5-(5-fluoro-2-methylphenoxymethyl)-2,2,4-trimethyl-1,2-dihydroquinoline (Compound No. 6-18)<br>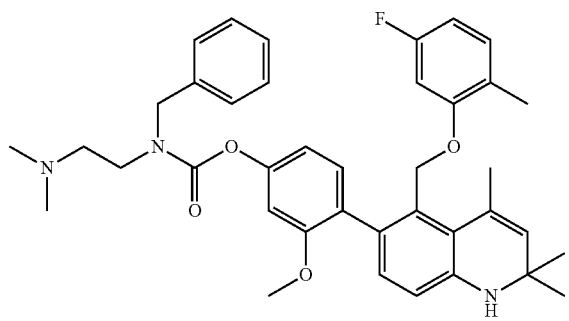 | $^1$H-NMR (400 MHz, CDCl$_3$) δ 1.13 (s, 3H), 1.25 (s, 3H), 2.07 (s, 3H), 2.16 (s, 3H), 2.85 (s, 6H), 3.13-3.23 (m, 2H), 3.77 (s, 3H), 3.81-3.96 (m, 2H), 4.66-4.85 (m, 3H), 5.11 (d, J = 12.2 Hz, 1H), 5.47 (s, 1H), 6.18 (dd, J = 11.1, 2.4 Hz, 1H), 6.42 (td, J = 8.3, 2.4 Hz, 1H), 6.65 (d, J = 7.8 Hz, 1H), 6.79 (dd, J = 8.1, 1.7 Hz, 1H), 6.88-6.96 (m, 3H), 7.25 (d, J = 8.1 Hz, 1H), 7.32-7.52 (m, 5H) |
| 6-[4-[N-Benzyl-N-(2-dimethylaminoethyl)aminocarbonyloxy]-2-methoxyphenyl]-5-(2-methoxy-5-nitrophenoxymethyl)-2,2,4-trimethyl-1,2-dihydroquinoline (Compound No. 6-19)<br>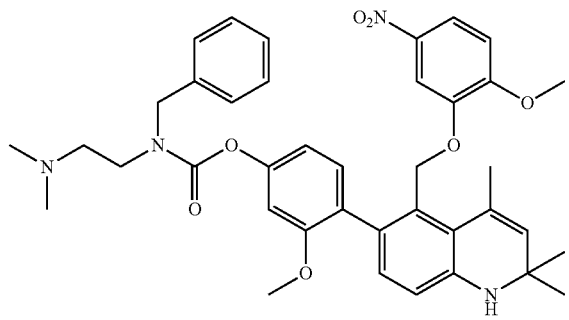 | $^1$H-NMR (500 MHz, CDCl$_3$) δ 0.99 (s, 3H), 1.26 (s, 3H), 2.24 (s, 3H), 2.26 (s, 6H), 2.50-2.51 (m, 2H), 3.46 (t, J = 7.0 Hz, 2H), 3.74, 3.77 (s, 3H), 3.82, 3.83 (s, 3H), 4.61, 4.70 (s, 2H), 4.84-4.89 (m, 1H), 5.36-5.41 (m, 1H), 5.44 (s, 1H), 6.55 (d, J = 7.6 Hz, 1H), 6.67-6.88 (m, 4H), 7.27-7.38 (m, 7H), 7.76 (d, J = 8.9 Hz, 1H) |
| 6-[4-[N-(2-Dimethylaminoethyl)-N-ethylaminocarbonyloxy]-2-methoxyphenyl]-5-(5-fluoro-2-methylphenoxymethyl)-2,2,4-trimethyl-1,2-dihydroquinoline (Compound No. 6-20)<br>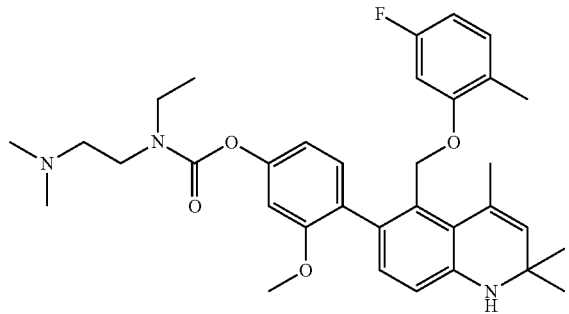 | $^1$H-NMR (500 MHz, CDCl$_3$) δ 1.10 (s, 3H), 1.22 (s, 3H), 1.26 (t, J = 7.4 Hz, 3H), 2.07 (s, 3H), 2.15 (s, 3H), 2.30 (s, 6H), 2.52-2.59 (m, 2H), 3.40-3.52 (m, 4H), 3.75 (s, 3H), 4.76 (d, J = 11.9 Hz, 1H), 5.11 (d, J = 11.9 Hz, 1H), 5.44 (s, 1H), 6.19 (dd, J = 11.3, 2.4 Hz, 1H), 6.41 (td, J = 8.4, 2.4 Hz, 1H), 6.57 (d, J = 8.2 Hz, 1H), 6.74-6.77 (m, 2H), 6.87-6.94 (m, 2H), 7.22 (d, J = 8.6 Hz, 1H) |

5-(2-Methoxyphenylaminomethyl)-6-[2-methoxy-4-(pyridin-3-ylaminocarbonyloxy)phenyl]-2,2,4-trimethyl-1,2-dihydroquinoline (Compound No. 6-21)

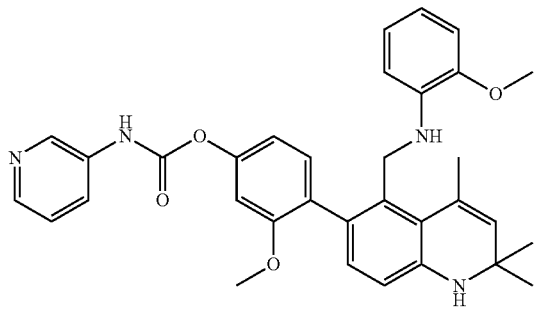 [SMILES: COc1ccccc1NCc1c(-c2ccc(OC(=O)Nc3cccnc3)cc2OC)ccc2c1C(C)=CC(C)(C)N2]

¹H-NMR (400 MHz, CDCl₃) δ 1.26 (s, 3H), 1.30 (s, 3H), 2.17 (s, 3H), 3.68 (s, 3H), 3.75 (s, 3H), 3.86 (brs, 1H), 4.03 (d, J = 12.1 Hz, 1H), 4.15 (d, J = 12.1 Hz, 1H), 4.34 (s, 1H), 5.46 (s, 1H), 6.39 (dd, J = 7.7, 1.4 Hz, 1H), 6.57 (d, J = 8.1 Hz, 1H), 6.57 (td, J = 7.7, 1.4 Hz, 1H), 6.70 (dd, J = 7.7, 1.4 Hz, 1H), 6.71 (d, J = 2.3 Hz, 1H), 6.77 (dd, J = 8.2, 2.3 Hz, 1H), 6.78 (td, J = 7.7, 1.4 Hz, 1H), 6.86 (d, J = 8.1 Hz, 1H), 7.02 (s, 1H), 7.18 (d, J = 8.2 Hz, 1H), 7.30 (dd, J = 8.4, 4.8 Hz, 1H), 8.02-8.07 (m, 1H), 8.37 (dd, J = 4.8, 1.5 Hz, 1H), 8.57 (d, J = 2.2 Hz, 1H)

6-[4-[N-(2-Dimethylaminoethyl)-N-methylaminocarbonyloxy]-2-methoxyphenyl]-5-(5-fluoro-2-methylphenylaminomethyl)-2,2,4-trimethyl-1,2-dihydroquinoline (Compound No. 6-22)

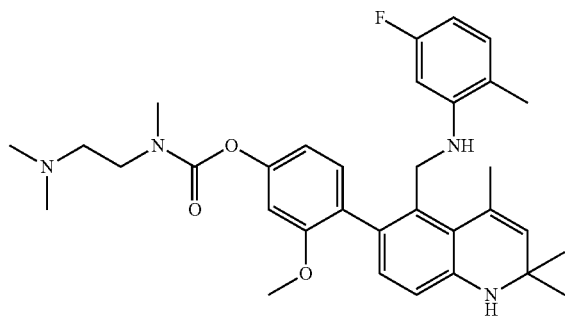

¹H-NMR (400 MHz, CDCl₃) δ 1.24 (s, 3H), 1.29 (s, 3H), 1.93 (s, 3H), 2.10 (s, 3H), 2.30 (s, 6H), 2.53-2.58 (m, 2H), 3.04, 3.12 (s, 3H), 3.47-3.55 (m, 2H), 3.69 (s, 4H), 4.09 (s, 3H), 5.48 (s, 1H), 6.08 (dd, J = 11.7, 2.4 Hz, 1H), 6.23 (td, J = 8.4, 2.4 Hz, 1H), 6.58 (d, J = 8.1 Hz, 1H), 6.70-6.75 (m, 2H), 6.85-6.88 (m, 2H), 7.14 (d, J = 8.1 Hz, 1H)

6-[4-[N-(2-Dimethylaminoethyl)-N-ethylaminocarbonyloxy]-2-methoxyphenyl]-5-(5-fluoro-2-methylphenylaminomethyl)-2,2,4-trimethyl-1,2-dihydroquinoline (Compound No. 6-23)

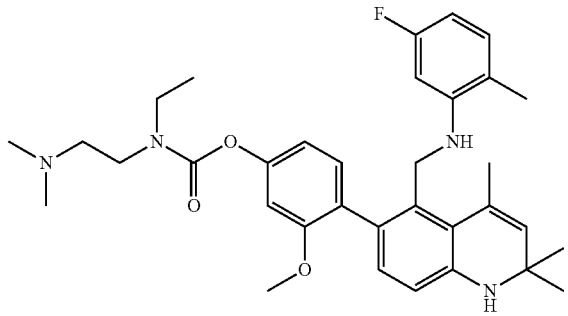

¹H-NMR (400 MHz, CDCl₃) δ 1.21-1.27 (m, 3H), 1.24 (s, 3H), 1.29 (s, 3H), 1.93 (s, 3H), 2.10 (s, 3H), 2.30 (s, 6H), 2.53-2.58 (m, 2H), 3.40-3.52 (m, 4H), 3.70 (s, 4H), 4.10 (s, 2H), 5.48 (br s, 1H), 6.08 (dd, J = 11.8, 2.4 Hz, 1H), 6.23 (td, J = 8.4, 2.4 Hz, 1H), 6.58 (d, J = 8.1 Hz, 1H), 6.69-6.72 (m, 1H), 6.74 (dd, J = 8.1, 2.2 Hz, 1H), 6.84-6.89 (m, 2H), 7.14 (d, J = 8.1 Hz, 1H)

6-[2-Methoxy-4-(pyridin-3-ylaminocarbonyloxy)phenyl]-5-(5-methylthiophen-2-ylcarbonyloxymethyl)-2,2,4-trimethyl-1,2-dihydroquinoline (Compound No. 6-24)

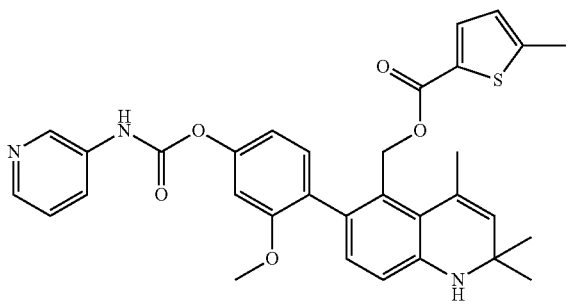 [SMILES: COc1cc(OC(=O)Nc2cccnc2)ccc1-c1ccc2c(c1COC(=O)c1ccc(C)s1)C(C)=CC(C)(C)N2]

¹H-NMR (400 MHz, CDCl₃) δ 1.26 (s, 3H), 1.30 (s, 3H), 2.19 (s, 3H), 2.48 (s, 3H), 3.71 (s, 3H), 3.89 (s, 1H), 5.02 (d, J = 12.7 Hz, 1H), 5.33 (d, J = 12.7 Hz, 1H), 5.51 (s, 1H), 6.61 (d, J = 8.1 Hz, 1H), 6.71 (d, J = 3.7 Hz, 1H), 6.76 (s, 1H), 6.77 (dd, J = 8.4, 2.2 Hz, 1H), 6.90 (d, J = 8.1 Hz, 1H), 7.06 (s, 1H), 7.23 (d, J = 8.4 Hz, 1H), 7.31 (dd, J = 8.3, 4.8 Hz, 1H), 7.50 (d, J = 3.7 Hz, 1H), 8.07 (d, J = 8.3 Hz, 1H), 8.37 (d, J = 4.8 Hz, 1H), 8.59 (d, J = 2.2 Hz, 1H)

| | |
|---|---|
| 6-[4-[N-(2-Dimethylaminoethyl)-N-methylaminocarbonyloxy]-2-methoxyphenyl]-5-(5-methylthiophen-2-ylcarbonyloxymethyl)-2,2,4-trimethyl-1,2-dihydroquinoline (Compound No. 6-25)<br />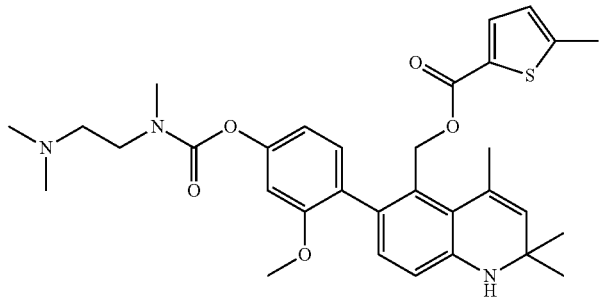 | $^1$H-NMR (400 MHz, DMSO-d$_6$) δ 1.14 (s, 3H), 1.21 (s, 3H), 2.08 (s, 3H), 2.18 (s, 3H), 2.20 (s, 3H), 2.39-2.48 (m, 2H), 2.47 (s, 3H), 2.92, 3.05 (s, 3H), 3.34-3.39 (m, 1H), 3.48-3.50 (m, 1H), 3.65 (s, 3H), 4.89 (d, J = 12.7 Hz, 1H), 5.17 (d, J = 12.7 Hz, 1H), 5.44 (s, 1H), 6.08 (s, 1H), 6.64-6.70 (m, 1H), 6.65 (d, J = 8.3 Hz, 1H), 6.75 (d, J = 8.3 Hz, 1H), 6.77-6.80 (m, 1H), 6.88 (d, J = 3.8 Hz, 1H), 7.10 (d, J = 8.3 Hz, 1H), 7.47 (d, J = 3.8 Hz, 1H) |
| 6-[2-Methoxy-4-(morpholin-4-ylcarbonyloxy)phenyl]-5-(5-methylthiophen-2-ylcarbonyloxymethyl)-2,2,4-trimethyl-1,2-dihydroquinoline (Compound No. 6-26)<br />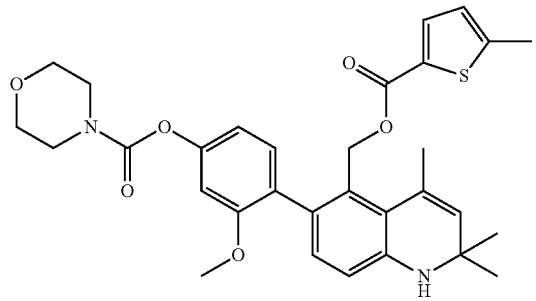 [SMILES: COc1cc(OC(=O)N2CCOCC2)ccc1-c1ccc2c(c1COC(=O)c1ccc(C)s1)C(C)=CC(C)(C)N2] | $^1$H-NMR (400 MHz, DMSO-d$_6$) δ 1.14 (s, 3H), 1.21 (s, 3H), 2.08 (s, 3H), 2.47 (s, 3H), 3.39-3.47 (m, 2H), 3.56-3.62 (m, 2H), 3.64-3.67 (m, 4H), 3.65 (s, 3H), 4.88 (d, J = 12.6 Hz, 1H), 5.17 (d, J = 12.6 Hz, 1H), 5.44 (s, 1H), 6.09 (s, 1H), 6.65 (d, J = 8.2 Hz, 1H), 6.71 (dd, J = 8.2, 2.2 Hz, 1H), 6.76 (d, J = 8.2 Hz, 1H), 6.83 (d, J = 2.2 Hz, 1H), 6.88 (d, J = 3.6 Hz, 1H), 7.11 (d, J = 8.2 Hz, 1H), 7.47 (d, J = 3.6 Hz, 1H) |
| 6-[4-(4-Chlorophenylaminocarbonyloxy)-2-methoxyphenyl]-5-(5-methylthiophen-2-ylcarbonyloxymethyl)-2,2,4-trimethyl-1,2-dihydroquinoline (Compound No. 6-27)<br />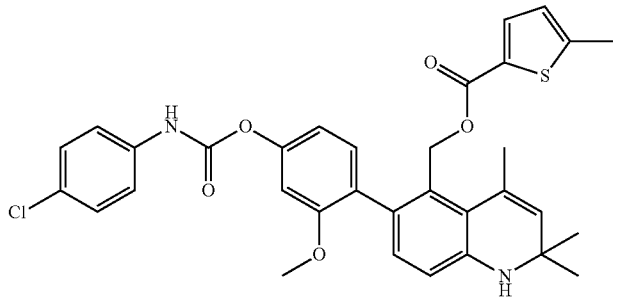 [SMILES: COc1cc(OC(=O)Nc2ccc(Cl)cc2)ccc1-c1ccc2c(c1COC(=O)c1ccc(C)s1)C(C)=CC(C)(C)N2] | $^1$H-NMR (500 MHz, CDCl$_3$) δ 1.25 (s, 3H), 1.30 (s, 3H), 2.18 (s, 3H), 2.48 (s, 3H), 3.70 (s, 3H), 3.89 (br s, 1H), 5.02 (d, J = 12.5 Hz, 1H), 5.32 (d, J = 12.5 Hz, 1H), 5.50 (s, 1H), 6.61 (d, J = 8.2 Hz, 1H), 6.71 (d, J = 3.9 Hz, 1H), 6.75 (d, J = 2.4 Hz, 1H), 6.76 (dd, J = 8.8, 2.4 Hz, 1H), 6.89 (d, J = 8.2 Hz, 1H), 6.97 (br s, 1H), 7.21 (d, J = 8.8 Hz, 1H), 7.31 (d, J = 8.9 Hz, 2H), 7.43 (d, J = 8.9 Hz, 2H), 7.49 (d, J = 3.9 Hz, 1H) |
| 6-[4-[N-(2-Dimethylaminoethyl)-N-ethylaminocarbonyloxy]-2-methoxyphenyl]-5-(5-methylthiophen-2-ylcarbonyloxymethyl)-2,2,4-trimethyl-1,2-dihydroquinoline (Compound No. 6-28)<br />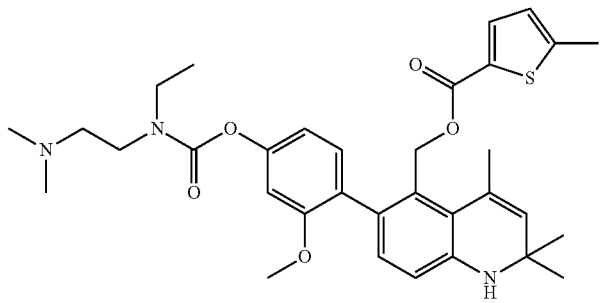 | $^1$H-NMR (400 MHz, DMSO-d$_6$) δ 1.14 (s, 3H), 1.22 (s, 3H), 1.23 (t, J = 6.6 Hz, 3H), 2.08 (s, 3H), 2.18 (s, 3H), 2.20 (s, 3H), 2.37-2.41 (m, 2H), 2.47 (s, 3H), 3.32-3.45 (m, 4H), 3.66 (s, 3H), 4.90 (d, J = 12.6 Hz, 1H), 5.17 (d, J = 12.6 Hz, 1H), 5.44 (s, 1H), 6.08 (s, 1H), 6.65-6.68 (m, 1H), 6.66 (d, J = 8.1 Hz, 1H), 6.76 (d, J = 8.1 Hz, 1H), 6.79 (br s, 1H), 6.88 (d, J = 3.7 Hz, 1H), 7.11 (d, J = 8.3 Hz, 1H), 7.47 (d, J = 3.7 Hz, 1H) |

6-[4-[N-Benzyl-N-(2-dimethylaminoethyl)aminocarbonyloxy]-2-methoxyphenyl]-5-(5-methylthiophen-2-ylcarbonyloxymethyl)-2,2,4-trimethyl-1,2-dihydroquinoline (Compound No. 6-29)

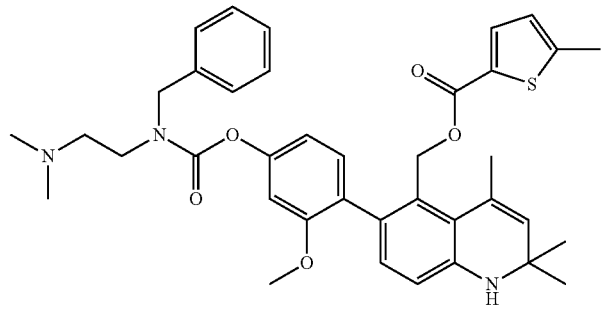

$^1$H-NMR (500 MHz, DMSO-$d_6$) δ 1.14 (s, 3H), 1.21 (s, 3H), 2.09 (s, 3H), 2.15 (s, 6H), 2.40-2.45 (m, 2H), 2.47 (s, 3H), 3.35-3.43 (m, 2H), 3.63-3.68 (m, 3H), 4.55 (s, 1H), 4.67 (s, 1H), 4.88-4.92 (m, 1H), 5.13-5.19 (m, 1H), 5.44 (s, 1H), 6.08 (s, 1H), 6.61-6.77 (m, 2H), 6.87-6.88 (m, 1H), 7.09-7.14 (m, 1H), 7.19-7.32 (m, 3H), 7.34-7.39 (m, 4H), 7.46-7.48 (m, 1H)

6-[4-[N-(2-Dimethylaminoethyl)-N-methylaminocarbonyloxy]-2-methoxyphenyl]-5-(4-methylbenzoyloxymethyl)-2,2,4-trimethyl-1,2-dihydroquinoline (Compound No. 6-30)

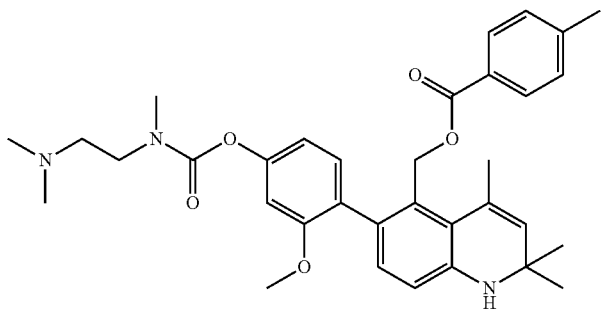

$^1$H-NMR (500 MHz, CDCl$_3$) δ 1.25 (s, 3H), 1.30 (s, 3H), 2.16 (s, 3H), 2.30 (s, 6H), 2.38 (s, 3H), 2.53-2.57 (m, 2H), 3.03, 3.11 (s, 3H), 3.47-3.54 (m, 2H), 3.68 (s, 3H), 5.06 (d, J = 12.5 Hz, 1H), 5.36 (d, J = 12.5 Hz, 1H), 5.49 (s, 1H), 6.61 (d, J = 8.2 Hz, 1H), 6.67-6.70 (m, 2H), 6.88-6.91 (m, 1H), 7.17 (d, J = 8.2 Hz, 1H), 7.17 (d, J = 8.2 Hz, 2H), 7.84 (d, J = 8.2 Hz, 2H)

5-(5-Fluoro-2-methylphenoxymethyl)-6-[2-methoxy-4-(morpholin-4-ylcarbonyloxy)phenyl]-2,2,4-trimethyl-1,2-dihydroquinoline (Compound No. 6-31)

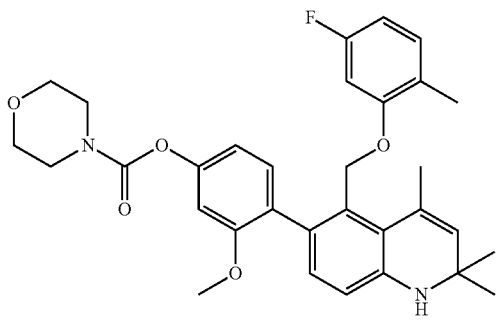 [SMILES: COc1cc(OC(=O)N2CCOCC2)ccc1-c1ccc2c(c1COc1cc(F)ccc1C)C(C)=CC(C)(C)N2]

$^1$H-NMR (400 MHz, DMSO-$d_6$) δ 1.04 (s, 3H), 1.14 (s, 3H), 2.02 (s, 3H), 2.07 (s, 3H), 3.42 (br s, 2H), 3.58 (br s, 2H), 3.65 (t, J = 4.8 Hz, 4H), 3.71 (s, 3H), 4.61 (d, J = 12.2 Hz, 1H), 5.07 (d, J = 12.2 Hz, 1H), 5.39 (s, 1H), 6.02 (s, 1H), 6.34 (dd, J = 11.5, 2.4 Hz, 1H), 6.52 (td, J = 8.4, 2.4 Hz, 1H), 6.63 (d, J = 8.3 Hz, 1H), 6.74 (dd, J = 8.1, 2.3 Hz, 1H), 6.78 (d, J = 8.3 Hz, 1H), 6.86 (d, J = 2.3 Hz, 1H), 7.01-7.05 (m, 1H), 7.15 (d, J = 8.1 Hz, 1H)

6-[2-Methoxy-4-(morpholin-4-ylcarbonyloxy)phenyl]-5-(2-methyl-5-nitrophenoxymethyl)-2,2,4-trimethyl-1,2-dihydroquinoline (Compound No. 6-32)

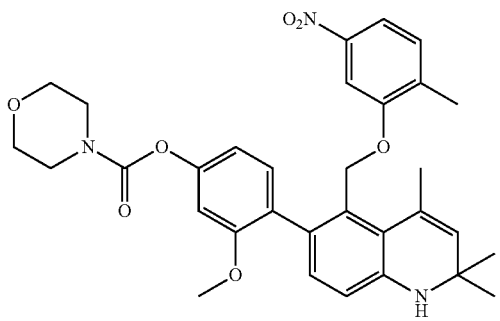 [SMILES: COc1cc(OC(=O)N2CCOCC2)ccc1-c1ccc2c(c1COc1cc([N+](=O)[O-])ccc1C)C(C)=CC(C)(C)N2]

$^1$H-NMR (500 MHz, DMSO-$d_6$) δ 0.89 (s, 3H), 1.18 (s, 3H), 2.12 (s, 3H), 2.18 (s, 3H), 3.38-3.48 (m, 2H), 3.51-3.63 (m, 2H), 3.63-3.67 (m, 4H), 3.73 (s, 3H), 4.77 (d, J = 12.5 Hz, 1H), 5.31 (d, J = 12.5 Hz, 1H), 5.40 (s, 1H), 6.02 (s, 1H), 6.62 (d, J = 8.2 Hz, 1H), 6.77 (dd, J = 8.2, 2.0 Hz, 1H), 6.79 (d, J = 8.2 Hz, 1H), 6.87 (d, J = 2.0 Hz, 1H), 7.14 (d, J = 2.1 Hz, 1H), 7.25 (d, J = 8.2 Hz, 1H), 7.33 (d, J = 8.2 Hz, 1H), 7.63 (dd, J = 8.2, 2.1 Hz, 1H)

| Compound | NMR |
|---|---|
| 6-(4-Dimethylaminocarbonyloxy-2-methoxyphenyl)-5-(2-methyl-5-nitrophenoxymethyl)-2,2,4-trimethyl-1,2-dihydroquinoline (Compound No. 6-33)<br>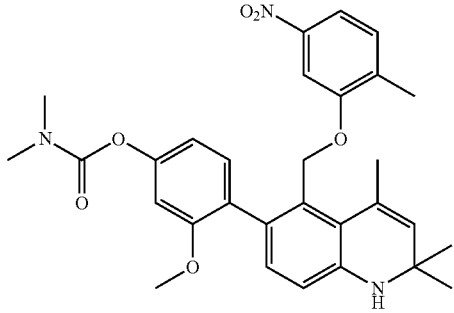 | $^1$H-NMR (500 MHz, DMSO-d$_6$) δ 0.89 (s, 3H), 1.18 (s, 3H), 2.12 (s, 3H), 2.18 (s, 3H), 2.92 (s, 3H), 3.05 (s, 3H), 3.73 (s, 3H), 4.78 (d, J = 12.5 Hz, 1H), 5.31 (d, J = 12.5 Hz, 1H), 5.39 (s, 1H), 6.02 (s, 1H), 6.62 (d, J = 8.2 Hz, 1H), 6.74 (dd, J = 8.2, 2.3 Hz, 1H), 6.79 (d, J = 8.2 Hz, 1H), 6.84 (d, J = 2.3 Hz, 1H), 7.14 (d, J = 2.1 Hz, 1H), 7.24 (d, J = 8.2 Hz, 1H), 7.33 (d, J = 8.2 Hz, 1H), 7.63 (dd, J = 8.2, 2.1 Hz, 1H) |
| 6-(4-Dimethylaminocarbonyloxy-2-methoxyphenyl)-5-(2-methoxyphenylaminomethyl)-2,2,4-trimethyl-1,2-dihydroquinoline (Compound No. 6-34)<br>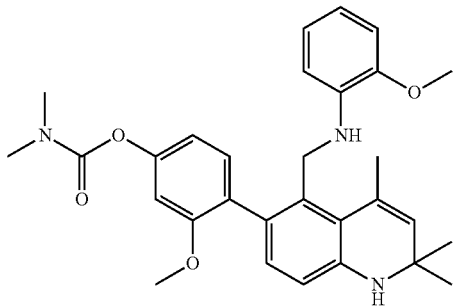 | $^1$H-NMR (400 MHz, DMSO-d$_6$) δ 1.15 (s, 3H), 1.21 (s, 3H), 2.06 (s, 3H), 2.90 (s, 3H), 3.02 (s, 3H), 3.64 (s, 3H), 3.71 (s, 3H), 3.82 (dd, J = 12.1, 3.3 Hz, 1H), 4.04 (dd, J = 12.1, 6.8 Hz, 1H), 4.23 (dd, J = 6.8, 3.3 Hz, 1H), 5.39 (s, 1H), 5.99 (s, 1H), 6.35 (dd, J = 7.8, 1.3 Hz, 1H), 6.51 (td, J = 7.8, 1.3 Hz, 1H), 6.60 (d, J = 8.3 Hz, 1H), 6.67 (dd, J = 7.8, 1.3 Hz, 1H), 6.68 (td, J = 7.8, 1.3 Hz, 1H), 6.70 (d, J = 8.3 Hz, 1H), 6.74 (dd, J = 8.1, 1.8 Hz, 1H), 6.75 (d, J = 1.8 Hz, 1H), 7.06 (d, J = 8.1 Hz, 1H) |
| 6-[2-Methoxy-4-(morpholin-4-ylcarbonyloxy)phenyl]-5-(2-methoxyphenylaminomethyl)-2,2,4-trimethyl-1,2-dihydroquinoline (Compound No. 6-35)<br>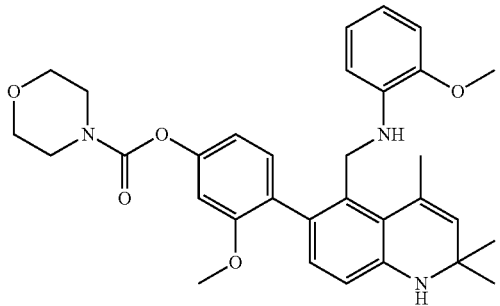 [SMILES: COc1ccccc1NCc1c(-c2ccc(OC(=O)N3CCOCC3)cc2OC)ccc2c1C(C)=CC(C)(C)N2] | $^1$H-NMR (400 MHz, DMSO-d$_6$) δ 1.15 (s, 3H), 1.21 (s, 3H), 2.07 (s, 3H), 3.38-3.43 (m, 2H), 3.54-3.59 (m, 2H), 3.61-3.64 (m, 4H), 3.64 (s, 3H), 3.71 (s, 3H), 3.82 (dd, J = 13.1, 3.7 Hz, 1H), 4.04 (dd, J = 13.1, 6.6 Hz, 1H), 4.23 (dd, J = 6.6, 3.7 Hz, 1H), 5.39 (s, 1H), 5.99 (s, 1H), 6.35 (dd, J = 7.7, 1.3 Hz, 1H), 6.51 (td, J = 7.7, 1.3 Hz, 1H), 6.60 (d, J = 8.3 Hz, 1H), 6.65-6.75 (m, 4H), 6.78 (d, J = 2.2 Hz, 1H), 7.07 (d, J = 8.3 Hz, 1H) |
| 5-(5-Fluoro-2-methylphenylaminomethyl)-6-[2-methoxy-4-(morpholin-4-ylcarbonyloxy)phenyl]-2,2,4-trimethyl-1,2-dihydroquinoline (Compound No. 6-36)<br>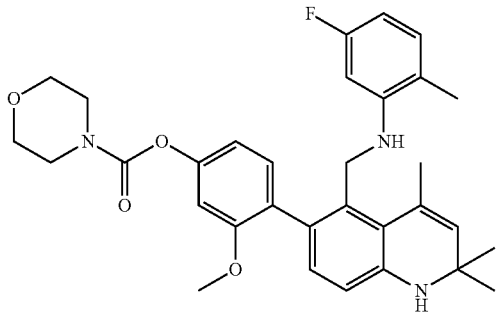 [SMILES: COc1cc(OC(=O)N2CCOCC2)ccc1-c1ccc2c(c1CNc1cc(F)ccc1C)C(C)=CC(C)(C)N2] | $^1$H-NMR (400 MHz, DMSO-d$_6$) δ 1.10 (s, 3H), 1.19 (s, 3H), 1.90 (s, 3H), 2.04 (s, 3H), 3.38-3.44 (m, 2H), 3.54-3.60 (m, 2H), 3.63-3.66 (m, 4H), 3.70 (s, 3H), 3.91 (dd, J = 13.2, 4.8 Hz, 1H), 4.06 (dd, J = 13.2, 4.8 Hz, 1H), 4.19-4.23 (m, 1H), 5.40 (s, 1H), 6.01 (s, 1H), 6.04 (dd, J = 12.1, 2.5 Hz, 1H), 6.20 (td, J = 8.4, 2.5 Hz, 1H), 6.60 (d, J = 8.2 Hz, 1H), 6.73 (d, J = 8.2 Hz, 1H), 6.73 (dd, J = 8.2, 2.1 Hz, 1H), 6.84 (d, J = 2.1 Hz, 1H), 6.85-6.90 (m, 1H), 7.16 (d, J = 8.2 Hz, 1H) |

| | |
|---|---|
| 6-(4-Dimethylaminocarbonyloxy-2-methoxyphenyl)-5-(5-methylthiophen-2-ylcarbonyloxymethyl)-2,2,4-trimethyl-1,2-dihydroquinoline (Compound No. 6-37)<br>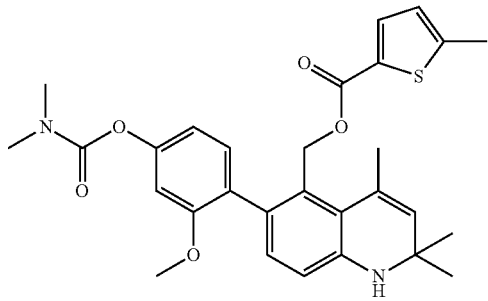 | $^1$H-NMR (500 MHz, CDCl$_3$) δ 1.25 (s, 3H), 1.29 (s, 3H), 2.17 (s, 3H), 2.48 (s, 3H), 3.02 (s, 3H), 3.10 (s, 3H), 3.69 (s, 3H), 3.95 (br s, 1H), 5.00 (d, J = 12.5 Hz, 1H), 5.32 (d, J = 12.5 Hz, 1H), 5.49 (s, 1H), 6.60 (d, J = 7.9 Hz, 1H), 6.68-6.71 (m, 3H), 6.90 (d, J = 8.2 Hz, 1H), 7.18 (d, J = 8.6 Hz, 1H), 7.50 (d, J = 3.7 Hz, 1H) |
| 6-(4-[N-(2-Dimethylaminoethyl)-N-methylaminocarbonyloxy]-2-methoxyphenyl)-5-(5-fluoro-2-methylphenoxymethyl)-2,2,4-trimethyl-1,2-dihydroquinoline (Compound No. 6-38)<br>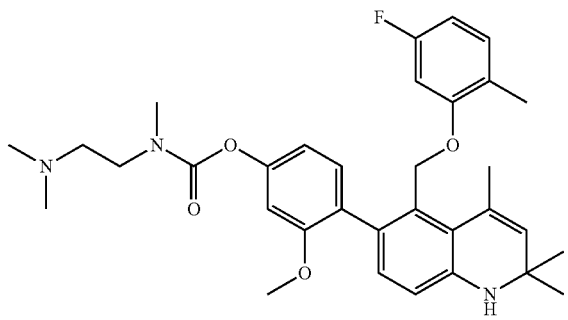 | $^1$H-NMR (500 MHz, DMSO-d$_6$) δ 1.04 (s, 3H), 1.14 (s, 3H), 2.02 (s, 3H), 2.07 (s, 3H), 2.18 (s, 3H), 2.20 (m, 3H), 2.41-2.54 (m, 2H), 2.92-3.04 {m, 3H), 3.30-3.37 (m, 2H), 3.71 (s, 3H), 4.62 (d, J = 12.1 Hz, 1H), 5.08 (d, J = 12.1 Hz, 1H), 5.39 (s, 1H), 6.01 (s, 1H), 6.34 (dd, J = 11.8, 2.2 Hz, 1H), 6.52 (td, J = 8.2, 2.2 Hz, 1H), 6.63 (d, J = 7.9 Hz, 1H), 6.68-6.72 (m, 1H), 6.77 (d, J = 7.9 Hz, 1H), 6.81-6.83 (m, 1H), 7.02-7.05 (m, 1H), 7.15 (d, J = 8.2 Hz, 1H) |
| 6-[4-[N-(2-Dimethylaminoethyl)-N-(pyridin-3-ylmethyl)aminocarbonyloxy]-2-methoxyphenyl]-5-(5-fluoro-2-methylphenoxymethyl)-2,2,4-trimethyl-1,2-dihydroquinoline (Compound No. 6-39)<br>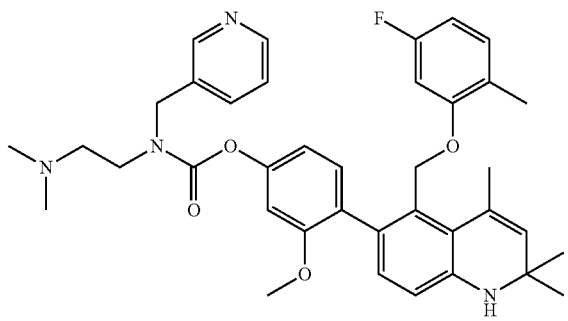 | $^1$H-NMR (500 MHz, CDCl$_3$) δ 1.11 (s, 3H), 1.23 (s, 3H), 2.07 (s, 3H), 2.15 (s, 3H), 2.28 (s, 3H), 2.30-2.34 (m, 3H), 2.54-2.62 (m, 2H), 3.50-3.54 (m, 2H), 3.73-3.77 (m, 3H), 4.64 (s, 1H), 4.72-4.77 (m, 2H), 5.08-5.13 (m, 1H), 5.44 (s, 1H), 6.17-6.21 (m, 1H), 6.41 (td, J = 8.2, 2.4 Hz, 1H), 6.58 (d, J = 7.9 Hz, 1H), 6.71-6.78 (m, 2H), 6.86-6.95 (m, 2H), 7.22-7.35 (m, 2H), 7.72-7.76 (m, 1H), 8.56-8.65 (m, 2H) |

PREPARATION EXAMPLES

Hereinafter, typical preparation examples of the present compound are shown.

1) Tablet (in 150 mg)

| | |
|---|---|
| The present compound | 1 mg |
| Lactose | 100 mg |
| Cornstarch | 40 mg |
| Carboxymethyl cellulose calcium | 4.5 mg |
| Hydroxypropyl cellulose | 4 mg |
| Magnesium stearate | 0.5 mg |

A tablet of the above-mentioned formulation is coated with 3 mg of a coating agent (for example, a coating agent which is used conventionally such as hydroxypropylmethyl cellulose, macrogol or a silicone resin), whereby an objective tablet can be obtained. In addition, a desired tablet can be obtained by appropriately changing the kind and/or amount of the present compound and additives.

2) Capsule (in 150 mg)

| | |
|---|---|
| The present compound | 5 mg |
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the kind and/or amount of the present compound and additives.

3) Eye Drop (in 100 mL)

| | |
|---|---|
| The present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kind and/or amount of the present compound and additives.

[Pharmacological Test]

1. Evaluation Test for Binding Activity to GR

In order to evaluate a binding activity of the present compound to GR, a receptor competitor assay was carried out by a fluorescence polarization method. In the assay, a GR competitor assay kit (manufactured by Invitrogen, cat No. P2816) was used, and a procedure was carried out according to the protocol attached to the kit. Hereinafter, the specific method will be described.

(Preparation of Reagents)

GR screening buffer: A buffer containing 10 mM potassium phosphate (pH 7.4), 20 mM sodium molybdate ($Na_2MoO_4$), 0.1 mM ethylene diamine tetraacetic acid (EDTA), 5 mM dithiothreitol (DTT), 0.1 mM stabilizing peptide and 2% dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.

(Preparation of Test Compound Solution)

After a test compound was dissolved in dimethylsulfoxide, the resulting solution was diluted with GR screening buffer, whereby a 20 µM test compound solution was prepared.

(Test Method and Measurement Method)

1) The test compound solution was added in an amount of 10 µL into each well of a 384-well plate, and then, 4×GS1 solution and 4×GR solution were added in an amount of 5 µL into each well, respectively.

2) The plate was incubated in a dark place at room temperature for 2 to 4 hours.

3) By using a multimode plate reader, Analyst™ HT (manufactured by LJL Biosystems), fluorescence polarization of each well was measured. As the blank, a well containing GR screening buffer in place of the test compound and 4×GS1 solution was used.

4) The same procedure as that in the above 1) to 3) was carried out except that GR screening buffer was used in place of the test compound solution, and the obtained result was taken as the negative control.

5) The same procedure as that in the above 1) to 3) was carried out except that 2 mM dexamethasone was used in place of the test compound solution, and the obtained result was taken as the positive control.

(Calculation Equation of GR Binding Ratio)

A GR binding ratio (%) was calculated according to the following equation.

$$GR \text{ binding ratio}(\%) = 100 \times [1 - (\text{fluorescence polarization of test compound solution} - \text{fluorescence polarization of positive control solution})/(\text{fluorescence polarization of negative control solution} - \text{fluorescence polarization of positive control solution})]$$

(Test Results and Discussion)

As an example of the test results, the GR binding ratios (%) of the test compounds (Compound 1-3, Compound 1-6, Compound 1-7, Compound 1-8, Compound 1-9, Compound 1-12, Compound 1-13, Compound 1-14, Compound 1-15, Compound 1-17, Compound 1-18, Compound 1-19, Compound 1-25, Compound 1-33, Compound 1-36, Compound 1-38, Compound 1-40, Compound 1-45, Compound 1-48, Compound 1-49, Compound 1-54, Compound 1-55, Compound 1-57, Compound 1-58, Compound 1-68, Compound 1-69, Compound 1-72, Compound 1-81, Compound 1-91, Compound 1-92, Compound 1-95, Compound 1-97, Compound 1-98, Compound 1-99, Compound 1-101, Compound 1-102, Compound 1-104, Compound 1-105, Compound 1-106, Compound 1-107, Compound 1-110, Compound 1-111, Compound 1-114, Compound 1-117, Compound 1-119, Compound 1-122, Compound 1-125, Compound 1-126, Compound 1-128, Compound 1-133, Compound 1-136, Compound 1-137, Compound 1-138, Compound 1-139, Compound 1-141, Compound 1-142, Compound 1-143, Compound 1-144, Compound 1-147, Compound 1-148, Compound 1-151, Compound 1-153, Compound 1-155, Compound 1-156, Compound 1-157, Compound 1-160, Compound 1-162, Compound 1-164, Compound 1-165, Compound 1-166, Compound 1-169, Compound 1-170, Compound 1-171, Compound 4-3, Compound 4-4, Compound 4-5, Compound 4-6, Compound 4-8, Compound 4-11, Compound 4-12, Compound 4-14, Compound 4-18, Compound 4-20, Compound 4-21, Compound 4-26, Compound 4-27, Compound 4-29, Compound 4-30, Compound 4-32, Compound 4-34, Compound 6-3, Compound 6-20, Compound 6-26, Compound 6-27, Compound 6-31, Compound 6-33, Compound 6-35, Compound 6-37) are shown in below.

All of these compounds showed the GR binding rate of 64% or more.

2. Evaluation Test for GR Agonist Activity

In order to evaluate a GR agonist activity of the present compound, the inhibitory effects on the IL-6 production induced by lipopolysaccharide (LPS) in human corneal epithelial cells. IL-6 levels in the conditioned medium were measured using the HTRF human IL-6 Kit (boehringer-Ingelheim, Cat No. 62IL6PEB), and the procedure was carried out according to the protocol attached to the kit. Hereinafter, the specific method will be described.

(Preparation of Reagents)

LPS solution: After LPS was dissolved in phosphate buffer solution (hereinafter referred to as PBS(−)), the resulting solution was diluted with 10% FBS-DMEM/F12 medium, whereby a 1 µg/mL LPS solution was prepared.

(Preparation of Test Compound Solution and Dexamethasone (hereinafter referred to as DEX) Solution)

After a test compound was dissolved in dimethylsulfoxide (hereinafter referred to as DMSO), the resulting solution was diluted with 10% FBS-DMEM/F12 medium, whereby a 100 µM test compound solution was prepared. A 100 µM DEX solution was prepared by the same method, and the inhibitory ratio of IL-6 production of DEX was evaluated to use for calculating efficacy (% DEX).

(Used Cell and Method of Cell Culture)

Used cell: SV40-immortalized human corneal epithelial cells (HCE-T) (RIKEN)

Passaging Method:

1) Subconfluent HCE-T cells were rinsed with PBS (−), and treated with trypsin-EDTA solution to detach cells.

2) Trypsin was inactivated by adding SHEM medium (supplemented hormone epithelial medium: DMEM/Ham's F12 containing 15% FBS, 5 µg/mL insulin, 0.1 µg/mL choleratoxin, 10 ng/mL human EGF, 40 µg/mL gentamicin) to the flasks.

3) The above cell suspension was collected, and centrifuged at 1000 rpm for 5 minutes to obtain precipitate cells.

4) The cells were resuspended in SHEM medium and dispensed into new culture flasks, and the flasks were incubated in a $CO_2$ incubator (temperature:37° C., $CO_2$ concentration: 5%).

(Test Method and Measurement Method)

1) HCE-T cells were harvested, and seeded at $2.0 \times 10^4$ cells/0.1 mL/well in a 96-well plate.

2) After incubation overnight, the medium was removed and a 80 µL of new 10% FBS-DMEM/Ham's F12 medium was added into each well.

3) A 10 µL of test compounds solution was added into each well.

4) A 10 µL of LPS solution was added into each well.

5) As a negative control, a 10 µL of 10% FBS-DMEM/Ham's F12 medium was added into each well instead of a test compound solution and a LPS solution.

6) As a positive control, a 10 µL of 10% FBS-DMEM/Ham's F12 medium containing 1% DMSO was added into each well instead of a test compound solution.

7) After 4 hours incubation, supernatants were collected and IL-6 levels in the supernatants were quantitated using the HTRF human IL-6 Kit.

8) The inhibition ratio of IL-6 production (%) was calculated according to the following equation.

(Calculation Equation of the Inhibition Ratio of IL-6 Production)

The inhibition ratio of IL-6 production (%) was calculated according to the following equation.

The inhibition ratio of IL-6 production(%)=100×[1−(IL-6 level in each group−mean value of IL-6 level in negative control)/(mean value of IL-6 level in positive control−mean value of IL-6 level in negative control)](%)

Furthermore, the inhibition ratio of IL-6 production (efficacy (% DEX)) was also calculated according to the following equation.

Efficacy(% $DEX$)=100×{(mean value of IL-6 inhibition in compound-treated group)/(mean value of IL-6 inhibition in DEX-treated group)}(%)

(Result and Discussion)

As an example of the test results, the IL-6 production inhibitory effect (% DEX) of the test compounds (Compound 1-3, Compound 1-6, Compound 1-7, Compound 1-8, Compound 1-9, Compound 1-12, Compound 1-13, Compound 1-14, Compound 1-15, Compound 1-17, Compound 1-18, Compound 1-19, Compound 1-25, Compound 1-33, Compound 1-36, Compound 1-38, Compound 1-40, Compound 1-45, Compound 1-48, Compound 1-49, Compound 1-54, Compound 1-55, Compound 1-57, Compound 1-58, Compound 1-68, Compound 1-69, Compound 1-72, Compound 1-81, Compound 1-91, Compound 1-92, Compound 1-95, Compound 1-97, Compound 1-98, Compound 1-99, Compound 1-101, Compound 1-102, Compound 1-104, Compound 1-105, Compound 1-106, Compound 1-107, Compound 1-110, Compound 1-111, Compound 1-114, Compound 1-117, Compound 1-119, Compound 1-122, Compound 1-125, Compound 1-126, Compound 1-128, Compound 1-133, Compound 1-136, Compound 1-137, Compound 1-138, Compound 1-139, Compound 1-141, Compound 1-142, Compound 1-143, Compound 1-144, Compound 1-147, Compound 1-148, Compound 1-151, Compound 1-153, Compound 1-155, Compound 1-156, Compound 1-157, Compound 1-160, Compound 1-162, Compound 1-164, Compound 1-165, Compound 1-166, Compound 1-169, Compound 1-170, Compound 1-171, Compound 4-3, Compound 4-4, Compound 4-5, Compound 4-6, Compound 4-8, Compound 4-11, Compound 4-12, Compound 4-14, Compound 4-18, Compound 4-20, Compound 4-21, Compound 4-26, Compound 4-27, Compound 4-29, Compound 4-30, Compound 4-32, Compound 4-34, Compound 6-3, Compound 6-20, Compound 6-26, Compound 6-27, Compound 6-31, Compound 6-33, Compound 6-35, Compound 6-37) are shown in Table I.

TABLE I

| Compound | IL-6 inhibition (% DEX) |
| --- | --- |
| Compound 1-3 | 76 |
| Compound 1-6 | 93 |
| Compound 1-7 | 78 |
| Compound 1-8 | 94 |
| Compound 1-9 | 79 |
| Compound 1-12 | 85 |
| Compound 1-13 | 94 |
| Compound 1-14 | 79 |
| Compound 1-15 | 77 |
| Compound 1-17 | 84 |
| Compound 1-18 | 77 |
| Compound 1-19 | 78 |
| Compound 1-25 | 83 |
| Compound 1-33 | 82 |
| Compound 1-36 | 75 |
| Compound 1-38 | 75 |
| Compound 1-40 | 75 |
| Compound 1-45 | 77 |
| Compound 1-48 | 73 |
| Compound 1-49 | 96 |
| Compound 1-54 | 75 |
| Compound 1-55 | 76 |
| Compound 1-57 | 86 |
| Compound 1-58 | 76 |
| Compound 1-68 | 72 |
| Compound 1-69 | 72 |
| Compound 1-72 | 82 |
| Compound 1-81 | 76 |
| Compound 1-91 | 92 |
| Compound 1-92 | 79 |
| Compound 1-95 | 87 |
| Compound 1-97 | 81 |
| Compound 1-98 | 78 |
| Compound 1-99 | 89 |
| Compound 1-101 | 81 |
| Compound 1-102 | 99 |
| Compound 1-104 | 84 |
| Compound 1-105 | 97 |
| Compound 1-106 | 82 |
| Compound 1-107 | 85 |
| Compound 1-110 | 83 |
| Compound 1-111 | 81 |
| Compound 1-114 | 87 |
| Compound 1-117 | 95 |
| Compound 1-119 | 75 |
| Compound 1-122 | 89 |
| Compound 1-125 | 81 |
| Compound 1-126 | 81 |
| Compound 1-128 | 79 |
| Compound 1-133 | 74 |
| Compound 1-136 | 89 |
| Compound 1-137 | 83 |
| Compound 1-138 | 79 |
| Compound 1-139 | 104 |
| Compound 1-141 | 78 |
| Compound 1-142 | 97 |
| Compound 1-143 | 96 |

TABLE I-continued

| Compound | IL-6 inhibition (% DEX) |
|---|---|
| Compound 1-144 | 94 |
| Compound 1-147 | 80 |
| Compound 1-148 | 86 |
| Compound 1-151 | 90 |
| Compound 1-153 | 89 |
| Compound 1-155 | 83 |
| Compound 1-156 | 90 |
| Compound 1-157 | 76 |
| Compound 1-160 | 88 |
| Compound 1-162 | 81 |
| Compound 1-164 | 85 |
| Compound 1-165 | 93 |
| Compound 1-166 | 91 |
| Compound 1-169 | 78 |
| Compound 1-170 | 77 |
| Compound 1-171 | 87 |
| Compound 4-3 | 81 |
| Compound 4-4 | 89 |
| Compound 4-5 | 90 |
| Compound 4-6 | 82 |
| Compound 4-8 | 78 |
| Compound 4-11 | 75 |
| Compound 4-12 | 77 |
| Compound 4-14 | 80 |
| Compound 4-18 | 89 |
| Compound 4-20 | 75 |
| Compound 4-21 | 82 |
| Compound 4-26 | 77 |
| Compound 4-27 | 101 |
| Compound 4-29 | 92 |
| Compound 4-30 | 93 |
| Compound 4-32 | 77 |
| Compound 4-34 | 86 |
| Compound 6-3 | 83 |
| Compound 6-20 | 79 |
| Compound 6-26 | 84 |
| Compound 6-27 | 94 |
| Compound 6-31 | 86 |
| Compound 6-33 | 78 |
| Compound 6-35 | 87 |
| Compound 6-37 | 85 |

As shown in Table I, the present compound showed an excellent IL-6 production inhibitory effect. Therefore, the present compound can be used as a GR agonist, and is useful as a preventive or therapeutic agent for inflammatory diseases, particularly the inflammatory diseases of anterior or posterior segment of eyeball and inflammatory bone/joint diseases.

3. Inhibitory Effect on the Vascular Hyper-Permeability in Allergic Conjunctivitis Model In order to evaluate anti-allergic effect, inhibitory effect on the vascular hyper-permeability in allergic conjunctivitis model in mice was examined. This effect was calculated based on dye leakages of vehicle-treated group (control group) and test compound-treated group.

(Preparation of Test Compound Suspension)

By adding 0.5% polysorbate 80/saline to the test compound, a 1% (W/V) test compound suspension was prepared.

(Procedure of Allergic Conjunctivitis Model and Evaluating Method)

1) Ovalbumin absorbed on aluminum hydroxide gel was dissolved in saline (20 μg ovalbumin/mL), and male BALE/c mice, 6 weeks old, were actively sensitized to the antigen by intraperitoneal injections of 500 μL of it.

2) On the 6th day from sensitization, sensitized mice were boosted by additional intraperitoneal injections of 500 μL ovalbumin absorbed on aluminum hydroxide gel (20 μg ovalbumin/mL).

3) On the 11th day, 12th day, 13th day, 14th day and 15th day from the first sensitization, allergic conjunctivitis were induced by installations to the right eyes of the mice of 2 μg of 50% glycerol solution containing 15% (W/V) ovalbumin.

4) 2 μg of test compound suspension per eye was instilled to the right eye of the above mice 15 min, 1 hr and 3 hrs before ovalbumin instillation (three times) on the 15th day from sensitization. In vehicle-treated group (control group), the mice were instilled with 0.5% polysorbate 80/saline in substitution for test compound suspension.

5) Just before ovalbumin instillation on the 15th day from sensitization, all animals received a tail intravenous injection of 0.1% Evans blue dye. The right periocular tissues of the mice, which were the leaked parts of dye, were collected 30 min after ovalbumin instillation. The dye was extracted from the tissues with the dye extraction liquid. Then the absorbance of the dye extract was measured. The dye leakage was calculated from the absorbance value, and the inhibition ratio of the vascular hyper-permeability of test compound-treated group was calculated according to calculation equation 1.

The inhibition ratio of the vascular hyper-permeability of test compound-treated group(%)=(1−$A_x/A_o$)×100    (Calculation Equation 1)

Ao: Dye leakage in vehicle-treated group (control group)

Ax: Dye leakage in test compound-treated group (Test Results and Discussion)

As an example of the test results, the inhibition ratio of the vascular hyper-permeability of test compounds (compound 1-7, compound 1-12, compound 1-13, compound 1-18, compound 1-72, compound 1-97, compound 1-102, compound 1-105, compound 1-136, compound 1-137, compound 1-138, compound 1-139 or compound 4-18) are shown in table II.

TABLE II

[Inhibitory effect on the vascular hyper-permeability in allergic conjunctivitis model]

| Compound | The inhibition ratio of the vascular hyper-permeability (%) |
|---|---|
| Compound 1-7 | 28 |
| Compound 1-12 | 17 |
| Compound 1-13 | 24 |
| Compound 1-18 | 30 |
| Compound 1-72 | 21 |
| Compound 1-97 | 21 |
| Compound 1-102 | 16 |
| Compound 1-105 | 18 |
| Compound 1-136 | 15 |
| Compound 1-137 | 26 |
| Compound 1-138 | 16 |
| Compound 1-139 | 15 |
| Compound 4-18 | 21 |

(The values were the mean value of 5-6 eyes, 5-6 animals.)

As shown in Table II, the present compound has inhibitory effect on the vascular hyper-permeability. Therefore, the present compound is useful as a preventive or therapeutic agent for anterior ocular inflammatory diseases.

4. Evaluation Test for Inhibitory Effect of Choroidal Neovascularization

The choroidal neovascularization (CNV) model in rats is known as one of the popular methods for evaluating the CNV inhibitory effect of drugs. This method is reported in Graefe's Arch. Cli. Exp. Ophthalmol., 235, 313-319 (1997). According to this method, the CNV examinations were performed to evaluate the CNV inhibitory effect of test compounds by comparing the incidence rates of CNV in vehicle group (control group) with test compound-treated groups.

(Preparation of Test Compound Suspension)

For eye drop administration, a 1% (w/v) test compound suspension was prepared by adding 0.5% polysorbate 80/saline to the test compound. For subconjunctival injection, a 20 mg/mL test compound suspension was prepared by adding 0.5% hydrogenated castor oil/saline to the test compound.

(Procedure of Laser Induced Choroidal Neovascularization Model in Rats)

1) Brown Norway male rats (7-8 weeks, 140-240 g) were anesthetized with intramuscular injection (1 mL/kg) of the mixed solution (5% ketamine HCl: 2% xylazine HCl=7:1).

2) After mydriasis using tropicamide phenylephrine hydrochloride eye drops (trade name Mydrin P), laser photocoagulation of bruch's membrane in rats was performed with krypton laser photocoagulation machine. Laser irradiation was performed at 8-9 points per eye avoiding thick retinal blood vessels in ocular fundus and focusing on the depth of retina. The conditions were 100 μm spot size, 100 mW power, 0.1 second duration.

3) After laser photocoagulation, photographs of ocular fundus were taken and the laser photocoagulation (laser irradiation) points were confirmed.

(Test Method and Measurement Method)

1) In case of eye drops administration, a test compound suspension was administrated four times a day from laser irradiation day (the 1st day) to the 8th day. In case of subconjunctival injection, a 50 μL test compound suspension was injected into conjunctivae just after laser irradiation.

2) In vehicle group (control group), 0.5% polysorbate 80/saline or 0.5% hydrogenated castor oil/saline was used instead of a test compound suspension. And the test was performed according to the method 1). These results were adopted as a control.

(Evaluation Method)

1) 7 days after laser irradiation, 0.1 mL of 10% fluorescein was injected into rat tail vein and fluorescein angiography was performed.

2) When the fluorescent leakage was not detected in the fluorescent angiography, the spot was judged to be a negative spot. When the fluorescent leakage was detected, the spot was judged to be a positive spot. When the fluorescent leakage was detected as a little leakage, two spots were counted as one positive spot.

3) The neovascular incidence rate was calculated according to the equation 1. According to the equation 2, the ratio of neovascular incidence rate in test compound group to vehicle group was calculated.

$$\text{Neovascular incidence rate}(\%) = (\text{Positive spots/all spots}) \times 100 \quad \text{(Equation 1)}$$

$$\text{Angiogenic inhibition ratio in test compound group }(\%) = (1 - A_x/A_o) \times 100 \quad \text{(Equation 2)}$$

$A_o$: Neovascular incidence rate in vehicle group (control group)

$A_x$: Neovascular incidence rate in test compound group (Test Result and Discussion)

As an example of the test results, angiogenic inhibition ratios (%) of the test compounds (compound 1-9, compound 1-12, compound 1-13, compound 1-14, compound 1-17, compound 1-19, compound 1-25, compound 1-33, compound 1-49, compound 1-72, compound 4-5, compound 4-8, compound 4-18, compound 6-3, compound 6-31, compound 6-35) are shown in Table III

TABLE III

[Inhibitory effect on choroidal neovascularization]

| Compound | Angiogenic inhibition ratio (%) |
| --- | --- |
| Compound 1-9 | 31 |
| Compound 1-12 | 37 |
| Compound 1-13 | 38 |
| Compound 1-14 | 46 |
| Compound 1-17 | 35 |
| Compound 1-19 | 30 |
| Compound 1-25 | 50 |
| Compound 1-33 | 29 |
| Compound 1-49 | 23 |
| Compound 1-72 | 28 |
| Compound 4-5 | 38 |
| Compound 4-8 | 26 |
| Compound 4-18 | 35 |
| Compound 6-3 | 38 |
| Compound 6-31 | 45 |
| Compound 6-35 | 26 |

(Each value was the mean value of 7-8 eyes in 4 rats)

As shown in Table III, the present compound inhibits the neovascularization compared with vehicle and has the inhibitory effect of choroidal neovascularization. Therefore, the present compound is useful for a preventive and therapeutic agent for posterior eye inflammatory disease.

5. Test for Therapeutic Effects on Corneal Disorder

In order to evaluate the improvement effect of corneal disorder with dry eye of the present compounds, using male SD rats, corneal disorder models were produced according to the method of Fujihara et al. (Invest. Ophthalmol. Vis. Sci. 42 (1): 96-100 (2001)). After the production of the corneal disorder models, the improvement ratio of the corneal disorder was assessed according to the method of Murakami et al. (Journal of the eye 21 (1): 87-90 (2004)).

(Preparation of Test Compound Ophthalmic Suspensions)

A 0.03% (W/V) test compound ophthalmic suspension was prepared by adding vehicle containing polysorbate 80 and the general additives to test compound.

(Procedure of Corneal Disorder Model Associated with Dry Eye and Estimation Method of Corneal Disorder)

1) Male SD rats were systemically anesthetized by an administration of Somnopentyl. Subsequently the exorbital lacrimal gland of each rat was removed and a corneal damage was induced over a period of 2 months.

2) The test compound ophthalmic suspension was instilled into both eyes 6 times a day for 14 days. In a control group, vehicle was instilled in the same way.

3) Fourteen days after the start of instillation, the damaged parts of the cornea were stained with fluorescein. For each of the upper, middle and lower parts of the cornea, the degree of fluorescein staining was evaluated by scoring according to the criteria shown below and the mean value of the total scores for each of the above-mentioned parts was calculated. The score range in each divided section is 0 to 3 and the minimum score unit is 0.5. 0.5 was provided as an intermediate value between each score 0, 1, 2, 3.
(Evaluation Criteria)
0: No punctate staining
1: Scattered staining (each punctate staining being separated)
2: Moderate staining (a part of punctate staining being adjacent)
3: Heavy staining (each punctate staining being adjacent)

Improvement ratio of test compound instillation group
(%)=(Ao−Ax)/(Ao−An)×100    (Calculation Equation)

Ao: the mean value of corneal disorder score in vehicle instilled (control) group
Ax: the mean value of corneal disorder score in test compound instilled group
An: the mean value of corneal disorder score in normal rat group.
(Test Result and Discussion)
As an example of the test results, the improvement ratios of corneal disorder (%) of the test compounds (Compound 1-12, Compound 1-13, Compound 1-72 and Compound 4-18) are shown in Table IV.

TABLE IV

[Improvement Effect of Corneal Disorder]

| Compounds | Improvement ratio of corneal disorder (%) |
|---|---|
| Compound 1-12 | 69 |
| Compound 1-13 | 61 |
| Compound 1-72 | 67 |
| Compound 4-18 | 56 |

(Each value was calculated from the mean value of 8 eyes in 4 animals)

As shown in Table IV, the present compound improves a corneal disorder compared to vehicle. Therefore the present compound is useful as a preventive or therapeutic agent for corneal disorder with dry eye and the like.

6. Inhibitory Effect Test on the Vascular Hyper-Permeability in the Atopic Dermatitis Model.

In order to evaluate the effects in atopic dermatitis of the present compound, the inhibitory effects of test compound on the vascular hyper-permeability in the atopic dermatitis model in mice were investigated. Procedure of atopic dermatitis model and estimation method was used according to the method of Nagai et al. (J. Pharmacol. Exp. Ther., 283: 321-327 (1997)) with modification. The inhibitory effects were calculated based on dye leakage in vehicle-treated group (control) and test compound-treated group.
(Preparation of Test Compound Ointment)
The test compound was mixed with white petrolatum, whereby a 1% (W/W) test compound ointment was prepared.
(Procedure of Atopic Dermatitis Model and Estimation Method)
1) Mice were challenged by topical instillation of 25 μL of 0.15% DNFB solution on both sides of both ears once a week for 5 weeks.
2) Test compounds were administered by topical instillation of 25 μL ointments on each side of both ears five times a week from the previous day of the 1st DNFB painting to the previous day of 5th DNFB painting, 21 times in total. Mice were painted with the test compound ointment onto the ear, 25 μL to the inner and 25 μL to outer side. In vehicle-treated group (control group), white petrolatum was administered by topical instillation in the same way.

3) Dyes, a solution of 0.2% Evans blue, were administered to mice intravenously just after the 5th DNFB painting. Ear tissues were removed 2 hours after the intravenous injection of dyes. Then each removed tissue was put into dye extract and dye was extracted. The absorbance of each extract was determined with a spectrophotometer. The amount of dye leakage was calculated from obtained absorbance. The inhibition ratio of the vascular hyper-permeability associated with atopic dermatitis of test compound-treatment group was calculated according to the following equation 1.

The inhibition ratio of the vascular hyper-permeability of test compound-treatment group(%)=(1−Ax/Ao)×100    (Calculation Equation 1)

Ao: the amount of dye leakage in vehicle-treated group (Control)
Ax: the amount of dye leakage in test compound-treated group
(Result and Discussion)
As an example of the test results, the inhibition ratio of the vascular hyper-permeability (%) of the test compounds (Compound 1-12, Compound 1-13, Compound 1-72 and Compound 4-18) are shown in Table V.

TABLE V

Inhibitory Effect of the vascular hyper-permeability in atopic dermatitis model

| Compounds | Inhibition ratio of the the vascular hyper-permeability (%) |
|---|---|
| Compound 1-12 | 22 |
| Compound 1-13 | 13 |
| Compound 1-72 | 15 |
| Compound 4-18 | 30 |

(Each value was calculated from the mean value of 12 ears in 6 animals)

As shown in Table V, the present compounds inhibited the vascular hyper-permeability associated with atopic dermatitis compared to vehicle. Therefore the present compound is useful as a preventive or therapeutic agent for dermatitis disorder associated with atopic dermatitis and the like.

INDUSTRIAL APPLICABILITY

The present inventions are useful as glucocorticoid receptor agonists, a pharmaceutical composition comprising the glucocorticoid receptor agonists as an active ingredient, a preventive and the therapeutic agent for inflammatory disease comprising the glucocorticoid receptor agonists as an active ingredient, and a preventive and the therapeutic agent for ocular inflammatory diseases or dermatitis comprising the glucocorticoid receptor agonists as an active ingredient.

Especially, the present inventions are useful as preventive or therapeutic agents for inflammatory disease on anterior ocular segment such as keratitis, keratoconjunctivitis, conjunctivitis, blepharitis, dry eye syndrome (it is also called "dry eye"), allergic conjunctivitis, anterior uveitis, inflammation on anterior ocular segment after operation and inflammation by rejection of eye organization transplant; the inflammatory disease on posterior ocular segment such as age-related macular degeneration (early age-related macular degeneration, dry type age-related macular degeneration and/or wet type age-related macular degeneration), diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury, retinitis, uvetis, scleritis, optic neuritis.

The invention claimed is:

1. A method of treating an inflammatory disease or immune disease, which comprises administering to a patient in need thereof a therapeutically effective amount of a compound represented by formula (1) or a salt thereof:

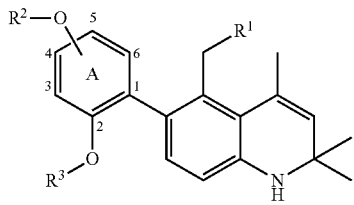

(1)

wherein $R^1$ represents formula (2a), (3a), (4a) or (5a);

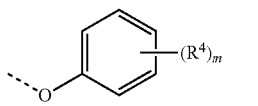

(2a)

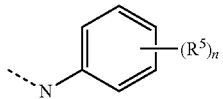

(3a)

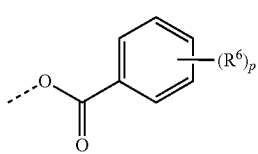

(4a)

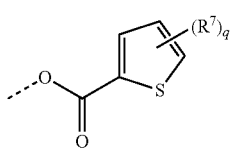

(5a)

$R^2$ represents —(CO)—$R^8$, —(CO)O—$R^9$, —(SO)—$R^{10}$, —(SO$_2$)—$R^{11}$ or —(CO)N$R^{12}R^{13}$;

$R^2$—O— is substituted at the 4- or -5-position of benzene ring A;

$R^3$ represents a lower alkyl group;

$R^4$, $R^5$, $R^6$ or $R^7$ represents a halogen atom, a lower alkyl group which may have a substituent, a lower alkenyl group, a lower alkynyl group, a lower alkoxy group, a nitro group or a formyl group;

m, n, p or q represents 0, 1 or 2;

in the case where m, n, p or q is 2, each $R^4$, $R^5$, $R^6$ or $R^7$ may be the same or different;

$R^8$, $R^9$, $R^{10}$ or $R^{11}$ represents a lower alkyl group which may have a substituent, a lower alkenyl group, a lower cycloalkyl group, an aryl group which may have a substituent or a heterocyclic group which may have a substituent;

$R^{12}$ and $R^{13}$ may be the same or different and represent a hydrogen atom, a lower alkyl group which may have a substituent, an aryl group which may have a substituent or a heterocyclic group.

2. The method according to claim 1, wherein in formula (1), $R^1$ represents formula (2a), (3a), (4a) or (5a)

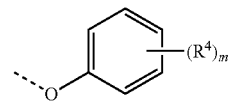

(2a)

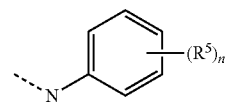

(3a)

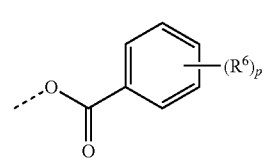

(4a)

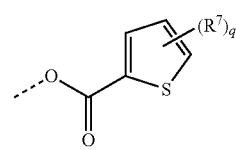

(5a)

$R^2$ represents —(CO)—$R^8$, —(CO)O—$R^9$, —(SO)—$R^{10}$, —(SO$_2$)—$R^{11}$ or —(CO)N$R^{12}R^{13}$;

$R^2$—O— is substituted at the 4- or -5-position of benzene ring A;

$R^3$ represents a lower alkyl group;

$R^4$ represents a halogen atom, a lower alkyl group, a lower alkoxy group or a nitro group;

$R^5$ represents a halogen atom, a lower alkyl group or a lower alkoxy group;

$R^6$ represents a halogen atom, a lower alkyl group or a lower alkoxy group;

$R^7$ represents a halogen atom or a lower alkyl group;

m, n or p represents 1 or 2;

in the case where m, n or p is 2, each $R^4$, $R^5$ or $R^6$ may be the same or different;

q represents 1;

$R^8$ represents a lower alkyl group which may have a substituent, a lower alkenyl group, a lower cycloalkyl group, an aryl group which may have a substituent or a heterocyclic group which may have a substituent;

$R^9$ represents a lower alkyl group which may have a substituent or an aryl group which may have a substituent;

$R^{19}$ or $R^{11}$ represents a lower alkyl group which may have a substituent or a lower cycloalkyl group;

$R^{12}$ and $R^{13}$ may be the same or different and represent a hydrogen atom, a lower alkyl group which may have a substituent, an aryl group which may have a substituent or a heterocyclic group.

3. The method according to claim 1, wherein in formula (1),
R¹ represents formula (2a-1), (2a-2), (2a-3), (3a-1), (3a-2), (4a-1), (4a-2), (4a-3), (5a-1) or (5a-2)

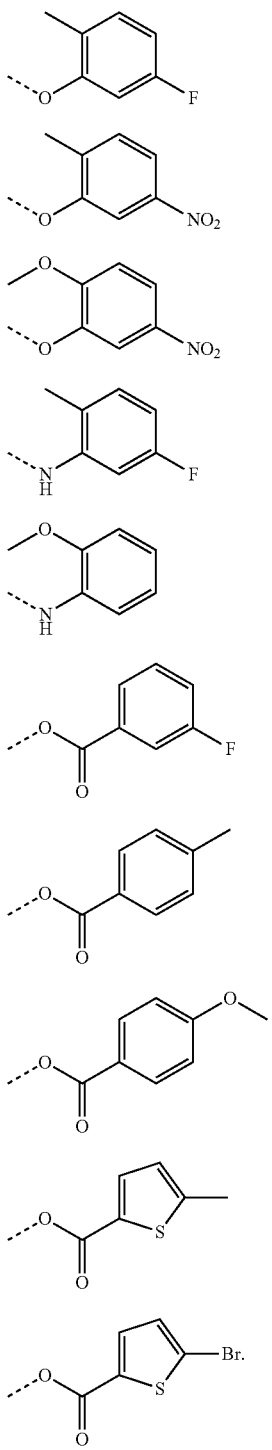

4. The method according to claim 3, wherein in formula (1),
R¹ represents formula (2a-1), (2a-2), (2a-3), (3a-1), (3a-2), (4a-2) or (5a-1).

5. The method according to claim 1, wherein in formula (1),
R² represents —(CO)—R⁸, —(CO)O—R⁹, —(SO₂)—R¹¹ or —(CO)NR¹²R¹³.

6. The method according to claim 5, wherein in formula (1),
R² represents —(CO)—R⁸ or —(SO₂)—R¹¹.

7. The method according to claim 6, wherein in formula (1),
R² represents —(CO)—R⁸.

8. The method according to claim 1, wherein in formula (1),
R³ represents a methyl group.

9. The method according to claim 1, wherein in formula (1),
R²—O— is substituted at the 4-position of benzene ring A.

10. A method of treating an inflammatory disease or immune disease, which comprises administering to a patient in need thereof a therapeutically effective amount of a compound or a salt thereof selected from the group consisting of:
6-[4-(Furan-2-ylcarbonyloxy)-2-methoxyphenyl]-5-(2-methoxyphenylaminomethyl)-2,2,4-trimethyl-1,2-dihydroquinoline,
5-(5-Fluoro-2-methylphenoxymethyl)-6-[2-methoxy-4-(2-methoxybenzoyloxy)phenyl]-2,2,4-trimethyl-1,2-dihydroquinoline,
6-[4-(2-Chlorobenzoyloxy)-2-methoxyphenyl]-5-(5-fluoro-2-methylphenoxymethyl)-2,2,4-trimethyl-1,2-dihydroquinoline,
5-(5-Fluoro-2-methylphenoxymethyl)-6-[2-methoxy-4-(pyridin-3-ylcarbonyloxy)phenyl]-2,2,4-trimethyl-1,2-dihydroquinoline,
6-(4-Butyryloxy-2-methoxyphenyl)-5-(5-fluoro-2-methylphenoxymethyl)-2,2,4-trimethyl-1,2-dihydroquinoline,
5-(5-Fluoro-2-methylphenoxymethyl)-6-[2-methoxy-4-(thiophen-3-ylcarbonyloxy)phenyl]-2,2,4-trimethyl-1,2-dihydroquinoline,
5-(5-Fluoro-2-methylphenoxymethyl)-6-[4-(furan-2-ylcarbonyloxy)-2-methoxyphenyl]-2,2,4-trimethyl-1,2-dihydroquinoline,
5-(5-Fluoro-2-methylphenoxymethyl)-6-(4-isobutyryloxy-2-methoxyphenyl)-2,2,4-trimethyl-1,2-dihydroquinoline,
5-(5-Fluoro-2-methylphenoxymethyl)-6-(2-methoxy-4-phenylacetoxyphenyl)-2,2,4-trimethyl-1,2-dihydroquinoline,
5-(5-Fluoro-2-methylphenoxymethyl)-6-[5-(furan-2-ylcarbonyloxy)-2-methoxyphenyl]-2,2,4-trimethyl-1,2-dihydroquinoline,
5-(5-Fluoro-2-methylphenoxymethyl)-6-(2-methoxy-5-propionyloxyphenyl)-2,2,4-trimethyl-1,2-dihydroquinoline,
5-(5-Fluoro-2-methylphenoxymethyl)-6-[2-methoxy-5-(pyridin-3-ylcarbonyloxy)phenyl]-2,2,4-trimethyl-1,2-dihydroquinoline,
5-(5-Fluoro-2-methylphenoxymethyl)-6-[4-(furan-3-ylcarbonyloxy)-2-methoxyphenyl]-2,2,4-trimethyl-1,2-dihydroquinoline,
5-(5-Fluoro-2-methylphenoxymethyl)-6-[2-methoxy-4-(pyridin-4-ylcarbonyloxy)phenyl]-2,2,4-trimethyl-1,2-dihydroquinoline,
6-[4-(2-Acetoxybenzoyloxy)-2-methoxyphenyl]-5-(5-fluoro-2-methylphenoxymethyl)-2,2,4-trimethyl-1,2-dihydroquinoline, 5-(5-Fluoro-2-methylphenoxymethyl)-6-[2-methoxy-4-(2-methylthiobenzoyloxy)phenyl]-2,2,4-trimethyl-1,2-dihydroquinoline, 5-(5-Fluoro-2-methylphenoxymethyl)-6-[2-methoxy-4-(thiazol-4-ylcarbonyloxy)phenyl]-2,2,4-trimethyl-1,2-dihydroquinoline, 6-[4-(2-Fluorobenzoyloxy)-2-methoxyphenyl]-5-(5-fluoro-2-methylphenoxymethyl)-2,2,4-trimethyl-1,2-dihydroquinoline, 5-(5-Fluoro-2-methylphenoxymethyl)-6-[2-methoxy-4-(5-methylfuran-2-ylcarbonyloxy)phenyl]-2,2,4-trimethyl-1,2-dihydroquinoline, 5-(5-Fluoro-2-methylphenoxymethyl)-6-[2-methoxy-4-(2-methylpyridin-3-ylcarbonyloxy)phenyl]-2,2,4-trimethyl-1,2-dihydroquinoline, 5-(5-Fluoro-2-methylphenoxymethyl)-6-[2-methoxy-4-(3-methoxycarbonylbenzoyloxy)phenyl]-2,2,4-trimethyl-1,2-dihydroquinoline, 5-(5-Fluoro-2-methylphenoxymethyl)-6-[2-methoxy-4-(6-methylpyridin-3-ylcarbonyloxy)phenyl]-2,2,4-trimethyl-1,2-dihydroquinoline, 5-(5-Fluoro-2-methylphenoxymethyl)-6-[2-methoxy-4-(3-methylfuran-2-ylcarbonyloxy)phenyl]-2,2,4-trimethyl-1,2-dihydroquinoline, 6-(4-t-Butylcarbonyloxy-2-methoxyphenyl)-5-(5-fluoro-2-methylphenoxymethyl)-2,2,4-trimethyl-1,2-dihydroquinoline, 6-[4-(2-Chloropyridin-4-ylcarbonyloxy)-2-methoxyphenyl]-5-(5-fluoro-2-methylphenoxymethyl)-2,2,4-trimethyl-1,2-dihydroquinoline, 5-(5-Fluoro-2-methylphenoxymethyl)-6-[4-(3-fluoropyridin-4-ylcarbonyloxy)-2-methoxyphenyl]-2,2,4-trimethyl-1,2-dihydroquinoline, 6-[2-Methoxy-4-(pyridin-3-ylcarbonyloxy)phenyl]-5-(2-methyl-5-nitrophenoxymethyl)-2,2,4-trimethyl-1,2-dihydroquinoline, 5-(2-Methoxy-5-nitrophenoxymethyl)-6-[2-methoxy-4-(thiophen-3-ylcarbonyloxy)phenyl]-2,2,4-trimethyl-1,2-dihydroquinoline, 6-[2-Methoxy-4-(2-methylpyridin-3-ylcarbonyloxy)phenyl]-5-(2-methoxyphenylaminomethyl)-2,2,4-trimethyl-1,2-dihydroquinoline, 6-(4-Benzoyloxy-2-methoxyphenyl)-5-(2-methoxyphenylaminomethyl)-2,2,4-trimethyl-1,2-dihydroquinoline, 6-[4-(Furan-3-ylcarbonyloxy)-2-methoxyphenyl]-5-(2-methoxyphenylaminomethyl)-2,2,4-trimethyl-1,2-dihydroquinoline, 5-(2-Methoxyphenylaminomethyl)-6-[2-methoxy-4-(pyridin-3-ylcarbonyloxy)phenyl]-2,2,4-trimethyl-1,2-dihydroquinoline, 6-[4-(2-Chlorobenzoyloxy)-2-methoxyphenyl]-5-(5-fluoro-2-methylphenylaminomethyl)-2,2,4-trimethyl-1,2-dihydroquinoline, 6-[4-(2-Chlorobenzoyloxy)-2-methoxyphenyl]-5-(2-methoxyphenylaminomethyl)-2,2,4-trimethyl-1,2-dihydroquinoline, 6-[4-(2-Fluorobenzoyloxy)-2-methoxyphenyl]-5-(2-methoxyphenylaminomethyl)-2,2,4-trimethyl-1,2-dihydroquinoline, 5-(2-Methoxyphenylaminomethyl)-6-[2-methoxy-4-(pyridin-4-ylcarbonyloxy)phenyl]-2,2,4-trimethyl-1,2-dihydroquinoline, 5-(2-Methoxyphenylaminomethyl)-6-[2-methoxy-4-(thiophen-2-ylcarbonyloxy)phenyl]-2,2,4-trimethyl-1,2-dihydroquinoline, 5-(5-Fluoro-2-methylphenylaminomethyl)-6-[2-methoxy-4-(pyridin-3-ylcarbonyloxy)phenyl]-2,2,4-trimethyl-1,2-dihydroquinoline, 5-(5-Fluoro-2-methylphenylaminomethyl)-6-[4-(furan-2-ylcarbonyloxy)-2-methoxyphenyl]-2,2,4-trimethyl-1,2-dihydroquinoline, 6-[2-Methoxy-4-(3-methoxycarbonylbenzoyloxy)phenyl]-5-(2-methoxyphenylaminomethyl)-2,2,4-trimethyl-1,2-dihydroquinoline, 6-[4-(4-Fluorobenzoyloxy)-2-methoxyphenyl]-5-(2-methoxyphenylaminomethyl)-2,2,4-trimethyl-1,2-dihydroquinoline, 6-[2-Methoxy-4-(2-methylthiobenzoyloxy)phenyl]-5-(2-methoxyphenylaminomethyl)-2,2,4-trimethyl-1,2-dihydroquinoline, 6-[2-Methoxy-4-(3-methylfuran-2-ylcarbonyloxy)phenyl]-5-(2-methoxyphenylaminomethyl)-2,2,4-trimethyl-1,2-dihydroquinoline, 6-[2-Methoxy-4-(2-methoxypyridin-3-ylcarbonyloxy)phenyl]-5-(2-methoxyphenylaminomethyl)-2,2,4-trimethyl-1,2-dihydroquinoline, 5-(5-Fluoro-2-methylphenylaminomethyl)-6-[2-methoxy-4-(pyridin-4-ylcarbonyloxy)phenyl]-2,2,4-trimethyl-1,2-dihydroquinoline, 5-(5-Fluoro-2-methylphenylaminomethyl)-6-[2-methoxy-4-(2-methylpyridin-3-ylcarbonyloxy)phenyl]-2,2,4-trimethyl-1,2-dihydroquinoline, 5-(5-Fluoro-2-methylphenylaminomethyl)-6-[2-methoxy-4-(2-methoxypyridin-3-ylcarbonyloxy)phenyl]-2,2,4-trimethyl-1,2-dihydroquinoline, 5-(5-Fluoro-2-methylphenylaminomethyl)-6-[2-methoxy-4-(3-methylfuran-2-ylcarbonyloxy)phenyl]-2,2,4-trimethyl-1,2-dihydroquinoline, 6-[2-Methoxy-4-(6-methylpyridin-3-ylcarbonyloxy)phenyl]-5-(5-methylthiophen-2-ylcarbonyloxymethyl)-2,2,4-trimethyl-1,2-dihydroquinoline, 5-(4-Methylbenzoyloxymethyl)-6-[2-methoxy-4-(pyridin-3-ylcarbonyloxy)phenyl]-2,2,4-trimethyl-1,2-dihydroquinoline, 6-[2-Methoxy-4-(2-methoxybenzoyloxy)phenyl]-5-(5-methylthiophen-2-ylcarbonyloxymethyl)-2,2,4-trimethyl-1,2-dihydroquinoline, 6-[2-Methoxy-4-(pyridin-3-ylcarbonyloxy)phenyl]-5-(5-methylthiophen-2-ylcarbonyloxymethyl)-2,2,4-trimethyl-1,2-dihydroquinoline, 6-[4-(Furan-2-ylcarbonyloxy)-2-methoxyphenyl]-5-(5-methylthiophen-2-ylcarbonyloxymethyl)-2,2,4-trimethyl-1,2-dihydroquinoline, 6-[4-(2-Chlorobenzoyloxy)-2-methoxyphenyl]-5-(5-methylthiophen-2-ylcarbonyloxymethyl)-2,2,4-trimethyl-1,2-dihydroquinoline, 6-[4-(4-Chlorobenzoyloxy)-2-methoxyphenyl]-5-(5-methylthiophen-2-ylcarbonyloxymethyl)-2,2,4-trimethyl-1,2-dihydroquinoline, 6-(4-Benzoyloxy-2-methoxyphenyl)-5-(5-methylthiophen-2-ylcarbonyloxymethyl)-2,2,4-trimethyl-1,2-dihydroquinoline, 6-[2-Methoxy-4-(2-methylbenzoyloxy)phenyl]-5-(5-methylthiophen-2-ylcarbonyloxymethyl)-2,2,4-trimethyl-1,2-dihydroquinoline, 6-[4-(2-Fluorobenzoyloxy)-2-methoxyphenyl]-5-(5-methylthiophen-2-ylcarbonyloxymethyl)-2,2,4-trimethyl-1,2-dihydroquinoline, 6-[2-Methoxy-4-(thiophen-3-ylcarbonyloxy)phenyl]-5-(5-methylthiophen-2-ylcarbonyloxymethyl)-2,2,4-trimethyl-1,2-dihydroquinoline, 6-[4-(Furan-3-ylcarbonyloxy)-2-methoxyphenyl]-5-(5-methylthiophen-2-ylcarbonyloxymethyl)-2,2,4-trimethyl-1,2-dihydroquinoline, 6-[2-Methoxy-4-(2-methylthiobenzoyloxy)phenyl]-5-(5-methylthiophen-2-ylcarbonyloxymethyl)-2,2,4-trimethyl-1,2-dihydroquinoline, 6-[2-Methoxy-4-(2-methylpyridin-3-ylcarbonyloxy)phenyl]-5-(5-methylthiophen-2-ylcarbonyloxymethyl)-2,2,4-trimethyl-1,2-dihydroquinoline, 6-[2-Methoxy-4-(thiazol-4-ylcarbonyloxy)phenyl]-5-(5-methylthiophen-2-ylcarbonyloxymethyl)-2,2,4-trimethyl-1,2-dihydroquinoline, 6-[2-Methoxy-4-(pyridin-4-ylcarbonyloxy)phenyl]-5-(5-methylthiophen-2-ylcarbonyloxymethyl)-2,2,4-trimethyl-1,2-dihydroquinoline, 5-(4-Methoxybenzoyloxymethyl)-6-[2-methoxy-4-(pyridin-3-ylcarbonyloxy)phenyl]-2,2,4-trimethyl-1,2-dihydroquinoline, 5-(5-Bromothiophen-2-ylcarbonyloxymethyl)-6-[2-methoxy-4-(pyridin-3-ylcarbonyloxy)phenyl]-2,2,4-trimethyl-1,2-dihydroquinoline, 5-(5-Bromothiophen-2-ylcarbonyloxymethyl)-6-[4-(furan-2-ylcarbonyloxy)-2-methoxyphenyl]-2,2,4-trimethyl-1,2-dihydroquinoline, 6-(4-Isopropylcarbonyloxy-2-methoxyphenyl)-5-(5-methylthiophen-2-ylcarbonyloxymethyl)-2,2,4-trimethyl-1,2-dihydroquinoline, 6-[4-(2-Acetoxybenzoyloxy)-2-methoxyphenyl]-5-(5-methylthiophen-2-ylcarbonyloxymethyl)-2,2,4-trimethyl-1,2-dihydroquinoline, 6-[2-Methoxy-4-(2-methoxypyridin-3-ylcarbonyloxy)phenyl]-5-(5-methylthiophen-2-ylcarbonyloxymethyl)-2,2,4-trimethyl-1,2-dihydroquinoline, 6-[4-(4-Fluorobenzoyloxy)-2-methoxyphenyl]-5-(5-methylthiophen-2-ylcarbonyloxymethyl)-2,2,4-trimethyl-1,2-dihydroquinoline, 6-[2-Methoxy-4-(2-nitrobenzoyloxy)phenyl]-5-(5-methylthiophen-2-ylcarbonyloxymethyl)-2,2,4-trimethyl-1,2-dihydroquinoline, 6-[2-Methoxy-4-(3-methylfuran-2-ylcarbonyloxy)phenyl]-5-(5-methylthiophen-2-ylcarbonyloxymethyl)-2,2,4-trimethyl-1,2-dihydroquinoline, 5-(5-Fluoro-2-methylphenoxymethyl)-6-(2-methoxy-4-propylsulfonyloxyphenyl)-2,2,4-trimethyl-1,2-dihydroquinoline, 6-(4-Ethylsulfonyloxy-2-methoxyphenyl)-5-(5-fluoro-2-methylphenoxymethyl)-2,2,4-trimethyl-1,2-dihydroquinoline, 5-(5-Fluoro-2-methylphenoxymethyl)-6-(4-isopropylsulfonyloxy-2-methoxyphenyl)-2,2,4-trimethyl-1,2-dihydroquinoline, 6-(4-Butylsulfonyloxy-2-methoxyphenyl)-5-(5-fluoro-2-methylphenoxymethyl)-2,2,4-trimethyl-1,2-dihydroquinoline, 6-(4-Cyclopropylsulfonyloxy-2-methoxyphenyl)-5-(2-methoxy-5-nitrophenoxymethyl)-2,2,4-trimethyl-1,2-dihydroquinoline, 6-(4-Ethylsulfonyloxy-2-methoxyphenyl)-5-(2-methyl-5-nitrophenoxymethyl)-2,2,4-trimethyl-1,2-dihydroquinoline, 6-(2-Methoxy-4-propylsulfonyloxyphenyl)-5-(2-methyl-5-nitrophenoxymethyl)-2,2,4-trimethyl-1,2-dihydroquinoline, 6-(4-Cyclopropylsulfonyloxy-2-methoxyphenyl)-5-(5-fluoro-2-methylphenoxymethyl)-2,2,4-trimethyl-1,2-dihydroquinoline, 5-(2-Methoxyphenylaminomethyl)-6-(2-methoxy-4-propylsulfonyloxyphenyl)-2,2,4-trimethyl-1,2-dihydroquinoline, 6-(2-Methoxy-4-methylsulfonyloxyphenyl)-5-(2-methoxyphenylaminomethyl)-2,2,4-trimethyl-1,2-dihydroquinoline, 5-(5-Fluoro-2-methylphenylaminomethyl)-6-(2-methoxy-4-propylsulfonyloxyphenyl)-2,2,4-trimethyl-1,2-dihydroquinoline, 6-[2-Methoxy-4-(3,3,3-trifluoropropylsulfonyloxy)phenyl]-5-(5-methylthiophen-2-ylcarbonyloxymethyl)-2,2,4-trimethyl-1,2-dihydroquinoline, 6-(2-Methoxy-4-propylsulfonyloxyphenyl)-5-(5-methylthiophen-2-ylcarbonyloxymethyl)-2,2,4-trimethyl-1,2-dihydroquinoline, 6-(4-Isopropylsulfonyloxy-2-methoxyphenyl)-5-(5-methylthiophen-2-ylcarbonyloxymethyl)-2,2,4-trimethyl-1,2-dihydroquinoline, 6-(4-Cyclopentylsulfonyloxy-2-methoxyphenyl)-5-(5-methylthiophen-2-ylcarbonyloxymethyl)-2,2,4-trimethyl-1,2-dihydroquinoline, 6-(4-Ethylsulfonyloxy-2-methoxyphenyl)-5-(5-methylthiophen-2-ylcarbonyloxymethyl)-2,2,4-trimethyl-1,2-dihydroquinoline, 6-(4-Cyclopropylsulfonyloxy-2-methoxyphenyl)-5-(5-methylthiophen-2-ylcarbonyloxymethyl)-2,2,4-trimethyl-1,2-dihydroquinoline, 6-(4-Dimethylaminocarbonyloxy-2-methoxyphenyl)-5-(5-fluoro-2-methylphenoxymethyl)-2,2,4-trimethyl-1,2-dihydroquinoline, 6-[4-[N-(2-Dimethylaminoethyl)-N-ethylaminocarbonyloxy]-2-methoxyphenyl]-5-(5-fluoro-2-methylphenoxymethyl)-2,2,4-trimethyl-1,2-dihydroquinoline, 6-[2-Methoxy-4-(morpholin-4-ylcarbonyloxy)phenyl]-5-(5-methylthiophen-2-ylcarbonyloxymethyl)-2,2,4-trimethyl-1,2-dihydroquinoline, 6-[4-(4-Chlorophenylaminocarbonyloxy)-2-methoxyphenyl]-5-(5-methylthiophen-2-ylcarbonyloxymethyl)-2,2,4-trimethyl-1,2-dihydroquinoline, 5-(5-Fluoro-2-methylphenoxymethyl)-6-[2-methoxy-4-(morpholin-4-ylcarbonyloxy)phenyl]-2,2,4-trimethyl-1,2-dihydroquinoline, 6-(4-Dimethylaminocarbonyloxy-2-methoxyphenyl)-5-(2-methyl-5-nitrophenoxymethyl)-2,2,4-trimethyl-1,2-dihydroquinoline, 6-[2-Methoxy-4-(morpholin-4-ylcarbonyloxy)phenyl]-5-(2-methoxyphenylaminomethyl)-2,2,4-trimethyl-1,2-dihydroquinoline, and 6-(4-Dimethylaminocarbonyloxy-2-methoxyphenyl)-5-(5-methylthiophen-2-ylcarbonyloxymethyl)-2,2,4-trimethyl-1,2-dihydroquinoline.

11. The method according to claim 1, wherein the inflammatory disease or immune disease is an ocular inflammatory disease or dermatitis.

12. The method according to claim 11, wherein the ocular inflammatory disease is an inflammatory disease of anterior segment of eyeball.

13. The method according to claim 12, wherein the inflammatory disease of anterior segment of eyeball is dry eye syndrome or allergic conjunctivitis.

14. The method according to claim 11, wherein the ocular inflammatory disease is an inflammatory disease of posterior segment of eyeball.

15. The method according to claim 14, wherein the inflammatory disease of posterior segment of eyeball is age-related macular degeneration, diabetic retinopathy or diabetic macular edema.

16. The method according to claim 11, wherein the dermatitis is atopic dermatitis.

17. A method of treating an autoimmune disease, which comprises administering to a patient in need thereof a therapeutically effective amount of a compound represented by formula (1) or a salt thereof:

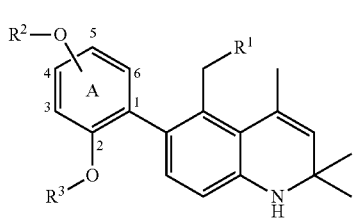
(1)

wherein $R^1$ represents formula (2a), (3a), (4a) or (5a);

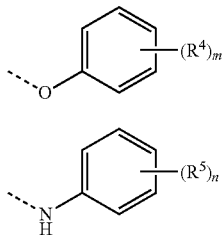
(2a)

(3a)

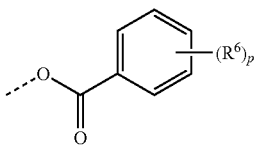
(4a)

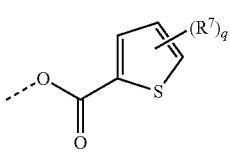
(5a)

$R^2$ represents —(CO)—$R^8$, —(CO)O—$R^9$, —(SO)—$R^{10}$, —(SO$_2$)—$R^{11}$ or —(CO)NR$^{12}$R$^{13}$;

$R^2$—O— is substituted at the 4- or -5-position of benzene ring A;

$R^3$ represents a lower alkyl group;

$R^4$, $R^5$, $R^6$ or $R^7$ represents a halogen atom, a lower alkyl group which may have a substituent, a lower alkenyl group, a lower alkynyl group, a lower alkoxy group, a nitro group or a formyl group;

m, n, p or q represents 0, 1 or 2;

in the case where m, n, p or q is 2, each $R^4$, $R^5$, $R^6$ or $R^7$ may be the same or different;

$R^8$, $R^9$, $R^{19}$ or $R^{11}$ represents a lower alkyl group which may have a substituent, a lower alkenyl group, a lower cycloalkyl group, an aryl group which may have a substituent or a heterocyclic group which may have a substituent;

$R^{12}$ and $R^{13}$ may be the same or different and represent a hydrogen atom, a lower alkyl group which may have a substituent, an aryl group which may have a substituent or a heterocyclic group.

* * * * *